(12) United States Patent
Horiguchi et al.

(10) Patent No.: US 7,608,627 B2
(45) Date of Patent: Oct. 27, 2009

(54) 6-AZAINDOLE COMPOUND

(75) Inventors: Yoshiaki Horiguchi, Yokohama (JP); Hiroshi Imoto, Osaka (JP); Mark A. Wolf, Delanson, NY (US)

(73) Assignee: Takeda Pharmaceutical Company Limited, Osaka (JP)

( * ) Notice: Subject to any disclaimer, the term of this patent is extended or adjusted under 35 U.S.C. 154(b) by 162 days.

(21) Appl. No.: 11/547,308

(22) PCT Filed: Apr. 4, 2005

(86) PCT No.: PCT/US2005/011531

§ 371 (c)(1),
(2), (4) Date: Dec. 7, 2006

(87) PCT Pub. No.: WO2005/097129

PCT Pub. Date: Oct. 20, 2005

(65) Prior Publication Data

US 2008/0064715 A1 Mar. 13, 2008

(51) Int. Cl.
*A61K 31/407* (2006.01)
*A61P 3/10* (2006.01)
*A61P 37/06* (2006.01)
*C07D 471/04* (2006.01)

(52) U.S. Cl. .................... 514/300; 546/113
(58) Field of Classification Search ............ 546/113; 514/300
See application file for complete search history.

(56) References Cited

U.S. PATENT DOCUMENTS 5,919,783 A 7/1999 Chambers et al.
2004/0266823 A1* 12/2004 Cumming et al. .......... 514/317

OTHER PUBLICATIONS

Donadelli Roberta et al., Journal of the American Society of Nephrology : JASN, (Oct. 2003) vol. 14, No. 10, pp. 2436-2446.*
Frydman et al., Journal of Organic Chemistry (1968), 33(10), 3762-6.*
Frydman et al., Journal of the American Chemical Society (1965), 87(15), 3530-1.*
Frydman et al., Journal of the American Chemical Society (1969), 91(9), 2338-42.*
Fisher et al., Journal of Heterocyclic Chemistry (1969), 6(5), 775-6.*
Clark et al., Journal of the Chemical Society [Section] C: Organic (1970), (3), 498-501. C.*
Chambers et al. "Preparation of N-(indolinylakyl)piperazines as 5-HT1Dα receptor agonists", Chemical Abstracts No. 125:33675.
F. J. Leeper et al., "Synthesis of Analogues of Porphobilinogen", J. Chem. Soc., Perkin Trans 1., pp. 2633-2642, 1996 & CA 126:103943 (Abstract).
A. R. Battersby et al., "Biosynthesis of Porphyrins and Related Macrocytes. Part I. Synthesis of $^{14}$C-Labelled Pyrromethaness", J. Chem. Soc., Perkin 1, pp. 1546-1556, 1973.
F. J. Leeper et al., "Synthesis of Analogues Porphobilinogen", Chemical Abstracts No. 126:103943 (1996).

* cited by examiner

*Primary Examiner*—D. Margaret Seaman
*Assistant Examiner*—Niloofar Rahmani
(74) *Attorney, Agent, or Firm*—Wenderoth, Lind & Ponack, L.L.P.

(57) ABSTRACT

A compound represented by the formula

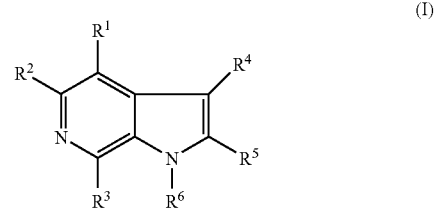

(I)

wherein $R^1$, $R^2$, $R^3$ and $R^6$ are the same or different and each is a hydrogen atom or a substituent; one of $R^4$ and $R^5$ is a hydrogen atom and the other is a group represented by the formula: —C(=X)—$R^7$ wherein X is N—O—$R^8$ or N—NH—$R^9$ wherein $R^8$ and $R^9$ are the same or different and each is a hydrogen atom or a group bonded via a carbon atom; and $R^7$ is a hydrogen atom or a substituent, and the like and a salt thereof have a superior IκB kinase inhibitory activity, and useful as pharmaceutical agents such as agents for preventing or treating diabetes and the like.

8 Claims, No Drawings

SEQUENCE LISTING

<160> NUMBER OF SEQ ID NOS: 4

<210> SEQ ID NO 1
<211> LENGTH: 33
<212> TYPE: DNA
<213> ORGANISM: Artificial Sequence
<220> FEATURE:
<223> OTHER INFORMATION: Designed oligonucleotide primer to amplify DNA
      encoding human IKKbeta

<400> SEQUENCE: 1
caaagctagc atgagctggt caccttccct gac                                33

<210> SEQ ID NO 2
<211> LENGTH: 62
<212> TYPE: DNA
<213> ORGANISM: Artificial Sequence
<220> FEATURE:
<223> OTHER INFORMATION: Designed oligonucleotide primer to amplify DNA
      encoding human IKKbeta

<400> SEQUENCE: 2
caaaggtacc ttacttgtcg tcatcgtctt tgtagtcgga ggcttgctcc aggcagctgt    60
gc                                                                  62

<210> SEQ ID NO 3
<211> LENGTH: 33
<212> TYPE: DNA
<213> ORGANISM: Artificial Sequence
<220> FEATURE:
<223> OTHER INFORMATION: Designed oligonucleotide primer to amplify DNA
      encoding human IkappaBalpha

<400> SEQUENCE: 3
aaagaattca tgttccaggc ggccgagcgc ccc                                33

<210> SEQ ID NO 4
<211> LENGTH: 36
<212> TYPE: DNA
<213> ORGANISM: Artificial Sequence
<220> FEATURE:
<223> OTHER INFORMATION: Designed oligonucleotide primer to amplify DNA
      encoding human IkaapaBalpha

<400> SEQUENCE: 4
aaacccgggt cagaggcgga tctcctgcag ctcctt                             36

6-AZAINDOLE COMPOUND

This application is a U.S. national stage of International Application No. PCT/US2005/011531 filed Apr. 4, 2005.

TECHNICAL FIELD

The present invention relates to a 6-azaindole compound having a superior IκB kinase inhibitory activity and useful as a pharmaceutical agent such as an agent for preventing or treating diabetes and the like.

BACKGROUND ART

IκB kinase (sometimes to be abbreviated as IKK in the specification) is a kinase complex having a molecular weight of not less than 900 kilodaltons that phosphorylates IκB. This complex includes kinase subunits such as IKKα (IKK-1), IKKβ (IKK-2), regulatory subunit IKKγ (NEMO) and the like.

IKK phosphorylates serine 312 of IRS-1, which is an insulin receptor substrate, and the like, and induces insulin resistance by inhibiting the phosphorylation of tyrosine of IRS-1 that should originally occur (J. Biol. Chem., 277, p. 48115 (2002)). Therefore, an IKK inhibitor is expected to improve insulin resistance observed in type II diabetes and obesity.

In addition, IKK is known to significantly con-tribute as one factor in the signal transduction pathway of NF-κB transcription factor. NF-κB is generally bound with inhibitory protein IκB and present as an inactive type in cytoplasm. Once IKK phosphorylates IκB, this triggers ubiquitination of IκB and degradation of IκB proceeds. NF-κB liberated by the degradation of IκB is translocated into the nucleus, where it activates transcription of the target gene and accelerates production of inflammatory cytokines such as tumor necrosis factor (TNF), IL-1 etc.; cell adhesion factors such as ICAM-1 (Intercellular Adhesion Molecule-1) etc.; and enzymes such as cyclooxygenase COX2 (Cyclooxygenase-2) and the like. In this way, NF-κB is deeply involved in inflammation and immune responses. IKK is also known to activate NF-κB by phosphorylation of NF-κB subunits and histone. Therefore, an IKK inhibitor is expected to suppress activation of NF-κB and be useful as an agent for preventing or treating autoimmune diseases (e.g., rheumatoid arthritis, systemic lupus erythematosus, systemic sclerosis), inflammatory diseases (e.g., osteoarthrosis, atherosclerosis, atopic dermatitis, chronic obstructive pulmonary disease, endotoxin shock, sepsis), ischemic diseases and the like or as an immunosuppressant. Moreover, since NF-κB acts as an anti-apoptosis factor or growth factor in cancer cells, an IKK inhibitor that suppresses activation of NF-κB is expected to be useful as an agent for preventing or treating cancer (J. Clin. Invest., 107, pp. 241-246 (2001)).

In the meantime, as 6-azaindole compounds, the following compounds have been reported.

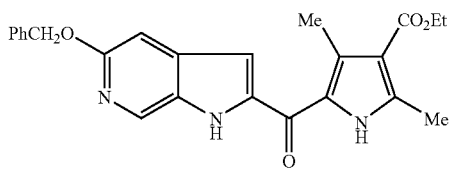

(J. Chem. Soc., Perkin 1, 1973, pp. 1546-1556)

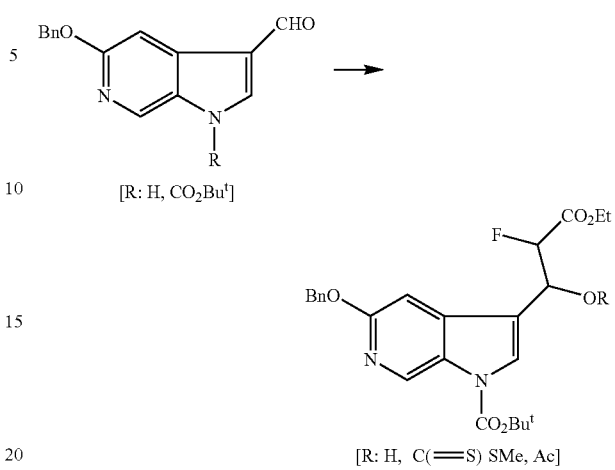

[R: H, CO$_2$Bu$^t$]

[R: H, C(=S) SMe, Ac]

(J. Chem. Soc., Perkin Trans. 1, 1996, pp. 2633-2642).

DISCLOSURE OF THE INVENTION

An object of the present invention is to provide a 6-azaindole compound having a superior IκB kinase inhibitory activity and useful as a pharmaceutical agent such as an agent for preventing or treating diabetes and the like.

The present invention relates to
(1) a compound represented by the formula

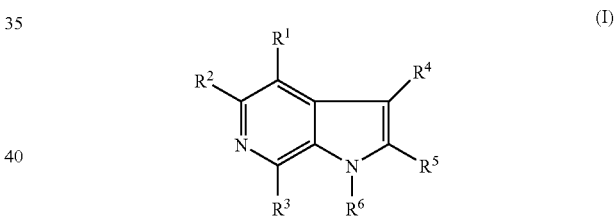

(I)

wherein
$R^1$, $R^2$, $R^3$ and $R^6$
    are the same or different and each is a hydrogen atom or a substituent;
one of $R^4$ and $R^5$
    is a hydrogen atom and the other is
    1) a group represented by the formula: —C(=X)—R$^7$ wherein X is N—O—R$^8$ or N—NH—R$^9$ wherein R$^8$ and R$^9$ are the same or different and each is a hydrogen atom or a group bonded via a carbon atom, and R$^7$ is a hydrogen atom or a substituent,
    2) a group represented by the formula: —C(=O)—R$^{10}$ wherein R$^{10}$ is a hydrogen atom or a group bonded via a carbon atom;
    3) a group represented by the formula: —CH(OH)—R$^{10}$ wherein R$^{10}$ is a hydrogen atom or a group bonded via a carbon atom;
    4) a group represented by the formula: —C(=O)—NH—(CH$_2$)n-Ar wherein n is 0, 1 or 2, and Ar is an aromatic group;
    5) a group represented by the formula: —C(=O)-Het wherein Het is an optionally substituted heterocyclic group bonded via a nitrogen atom; or

3

6) a group represented by the formula: —CH($R^{12}$)—N$R^{13}R^{14}$ wherein $R^{12}$ is a hydrogen atom or a hydrocarbon group, $R^{13}$ and $R^{14}$ are the same or different and each is a hydrogen atom, an optionally substituted hydrocarbon group, an optionally substituted heterocyclic group or an optionally substituted acyl group, or $R^{13}$ and $R^{14}$ form, together with the adjacent nitrogen atom, a nitrogen-containing heterocyclic group optionally having substituents (provided that the nitrogen-containing heterocyclic group is not an oxopyrrolidinyl group or an oxopiperazinyl group) except when $R^4$ is a group represented by the formula: —C(=O)—$R^{10}$ wherein $R^{10}$ is as defined above, and $R^5$ is a hydrogen atom;

except tert-butyl 5-(benzyloxy)-3-(3-ethoxy-2-fluoro-1-hydroxy-3-oxopropyl)-1H-pyrrolo[2,3-c]pyridine-1-carboxylate;
[5-(benzyloxy)-1H-pyrrolo[2,3-c]pyridin-3-yl]methanol;
ethyl 3-(hydroxymethyl)-1H-pyrrolo[2,3-c]pyridine-5-carboxylate;
1H-pyrrolo[2,3-c]pyridine-3-carbaldehyde oxime;
ethyl 5-{[5-(benzyloxy)-1H-pyrrolo[2,3-c]pyridin-2-yl]carbonyl}-2,4-dimethyl-1H-pyrrole-3-carboxylate;
5-(benzyloxy)-1H-pyrrolo[2,3-c]pyridine-2-carbaldehyde;
5-methoxy-1H-pyrrolo[2,3-c]pyridine-2-carbaldehyde;
[5-(benzyloxy)-1H-pyrrolo[2,3-c]pyridin-2-yl]methanol;
(5-methoxy-1H-pyrrolo[2,3-c]pyridin-2-yl)methanol; and
[2-({[4-(4-chloro-2,5-dimethoxyphenyl)-5-(2-cyclohexylethyl)-1,3-thiazol-2-yl]amino}carbonyl)-5-methoxy-1H-pyrrolo[2,3-c]pyridin-1-yl]acetic acid, or a salt thereof [sometimes to be abbreviated as compound (I) in the specification];

(2) a prodrug of compound (I);

(3) compound (I) wherein one of $R^4$ and $R^5$ is a hydrogen atom, and the other is a group represented by the formula: —C(=X)—$R^7$ wherein X and $R^7$ are as defined in the aforementioned (1);

(4) compound (I) wherein $R^4$ is a hydrogen atom, and $R^5$ is a group represented by the formula: —C(=O)—$R^{10}$ wherein $R^{10}$ is as defined in the aforementioned (1);

(5) compound (I) wherein $R^1$, $R^2$ and $R^3$ are each a hydrogen atom;

(6) a pharmaceutical agent comprising compound (I) or a prodrug thereof and a pharmacologically acceptable carrier;

(7) a method for inhibiting IκB kinase in a mammal, which comprises administering an effective amount of a compound represented by the formula

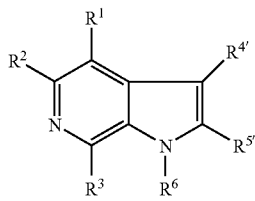

(I')

wherein
$R^1$, $R^2$, $R^3$ and $R^6$
are the same or different and each is a hydrogen atom or a substituent;
one of $R^{4'}$ and $R^{5'}$
is a hydrogen atom and the other is
1) a group represented by the formula: —C(=X)—$R^7$ wherein X is N—O—$R^8$ or N—NH—$R^9$ wherein $R^8$ and

4

$R^9$ are the same or different and each is a hydrogen atom or a group bonded via a carbon atom, and $R^7$ is a hydrogen atom or a substituent, 2) a group represented by the formula: —C(=O)—$R^{10}$ wherein $R^{10}$ is a hydrogen atom or a group bonded via a carbon atom;

3) a group represented by the formula: —CH(OH)—$R^{10}$ wherein $R^{10}$ is a hydrogen atom or a group bonded via a carbon atom;

4) a group represented by the formula: —C(=O)—NH—(CH$_2$)n-Ar wherein n is 0, 1 or 2, and Ar is an aromatic group;

5) a group represented by the formula: —C(=O)-Het wherein Het is an optionally substituted heterocyclic group bonded via a nitrogen atom; or 6) a group represented by the formula: —CH($R^{12}$)—N$R^{13'}R^{14'}$ wherein $R^{12}$ is a hydrogen atom or a hydrocarbon group; $R^{13'}$ and $R^{14'}$ are the same or different and each is a hydrogen atom, an optionally substituted hydrocarbon group, an optionally substituted heterocyclic group or an optionally substituted acyl group, or $R^{13'}$ and $R^{14'}$ form, together with the adjacent nitrogen atom, a nitrogen-containing heterocyclic group optionally having substituents, or a salt thereof [sometimes to be abbreviated as compound (I') in the specification] or a prodrug thereof to said mammal;

(8) a method for preventing or treating diabetes in a mammal, which comprises administering an effective amount of compound (I') or a prodrug thereof to said mammal;

(9) a method for preventing or treating an inflammatory disease in a mammal, which comprises administering an effective amount of compound (I') or a prodrug thereof to said mammal;

(10) an agent for inhibiting IκB kinase, which comprises compound (I') or a prodrug thereof;

(11) an agent for preventing or treating diabetes, which comprises compound (I') or a prodrug thereof;

(12) an agent for preventing or treating an inflammatory disease, which comprises compound (I') or a prodrug thereof;

(13) use of compound (I') or a prodrug thereof, for the production of an agent for inhibiting IκB kinase;

(14) use of compound (I') or a prodrug thereof, for the production of an agent for preventing or treating diabetes;

(15) use of compound (I') or a prodrug thereof, for the production of an agent for preventing or treating an inflammatory disease; and the like.

The definition of each symbol used in the present specification is explained in detail in the following.

As the substituent for $R^1$, $R^2$, $R^3$ or $R^6$, for example, a halogen atom, a cyano group, a nitro group, an amidino group, an optionally substituted hydrocarbon group, an optionally substituted heterocyclic group, an optionally substituted acyl group, an optionally substituted amino group, an optionally substituted carbamoyl group, an optionally substituted sulfamoyl group, an optionally substituted hydroxy group, an optionally substituted mercapto group and the like can be mentioned.

Here, as the "halogen atom", for example, fluorine, chlorine, bromine and iodine can be mentioned.

As the "hydrocarbon group" of the "optionally substituted hydrocarbon group", for example, a) $C_{1-6}$ alkyl groups (e.g., methyl, ethyl, propyl, isopropyl, butyl, isobutyl, sec-butyl, tert-butyl, pentyl, hexyl);

b) $C_{2-6}$ alkenyl groups (e.g., vinyl, allyl, isopropenyl, 2-butenyl);

c) $C_{2-6}$ alkynyl groups (e.g., ethynyl, propargyl, 2-butynyl);

d) $C_{3-8}$ cycloalkyl groups optionally substituted by the above-mentioned $C_{1-6}$ alkyl group and optionally condensed with a benzene ring (e.g., cyclopropyl, cyclobutyl, cyclopentyl, cyclohexyl, cycloheptyl, cyclooctyl, dihydroindenyl);

e) $C_{3-8}$ cycloalkenyl groups optionally substituted by the above-mentioned $C_{1-6}$ alkyl group and optionally condensed with a benzene ring (e.g., cyclopropenyl, cyclobutenyl, cyclopentenyl, cyclohexenyl, cycloheptenyl, cyclooctenyl);

f) $C_{6-14}$ aryl groups optionally substituted by the above-mentioned $C_{1-6}$ alkyl group (e.g., phenyl, 1-naphthyl, 2-naphthyl, 2-indenyl, 2-anthryl, biphenyl);

g) $C_{7-19}$ aralkyl groups optionally substituted by the above-mentioned $C_{1-6}$ alkyl group (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl); and the like can be mentioned.

As the substituent of the "optionally substituted hydrocarbon group", for example, halogen atoms (e.g., fluorine, chlorine, bromine, iodine), $C_{1-3}$ alkylenedioxy groups (e.g., methylenedioxy, ethylenedioxy), a nitro group, a cyano group, a hydroxy group, an optionally halogenated $C_{1-6}$ alkoxy group, an optionally halogenated $C_{1-6}$ alkylthio group, $C_{6-14}$ aryloxy groups (e.g., phenoxy, naphthoxy), 5- to 7-membered heterocyclic oxy groups (e.g., tetrahydropyranyloxy), an amino group, mono- or di-$C_{1-6}$ alkylamino groups (e.g., methylamino, ethylamino, propylamino, isopropylamino, butylamino, dimethylamino, diethylamino, dipropylamino, dibutylamino, N-ethyl-N-methylamino), an optionally substituted 5- to 7-membered heterocyclic group, a formyl group, a carboxyl group, a carbamoyl group, a thiocarbamoyl group, an optionally halogenated $C_{1-6}$ alkyl-carbonyl group, a $C_{1-6}$ alkoxy-carbonyl group, $C_{6-14}$ aryl-carbonyl groups (e.g., benzoyl, 1-naphthoyl, 2-naphthoyl), an optionally substituted heterocyclic carbonyl group, $C_{6-14}$ aryloxy-carbonyl groups (e.g., phenyloxycarbonyl, 1-naphthyloxycarbonyl, 2-naphthyloxycarbonyl), $C_{7-19}$ aralkyloxy-carbonyl groups (e.g., benzyloxycarbonyl, phenethyloxycarbonyl), mono- or di-$C_{1-6}$ alkyl-carbamoyl groups (e.g., methylcarbamoyl, ethylcarbamoyl, dimethylcarbamoyl, diethylcarbamoyl, N-ethyl-N-methylcarbamoyl), carbamoyl-$C_{1-6}$ alkyl-carbamoyl groups (e.g., carbamoylmethylcarbamoyl, carbamoylethylcarbamoyl), $C_{6-14}$ aryl-carbamoyl groups (e.g., phenylcarbamoyl), an optionally substituted heterocyclic carbamoyl group, an optionally halogenated $C_{1-6}$ alkylsulfonyl group, $C_{6-14}$ arylsulfonyl groups (e.g., phenylsulfonyl, 1-naphthylsulfonyl, 2-naphthylsulfonyl), a formylamino group, an optionally halogenated $C_{1-6}$ alkyl-carboxamido group, $C_{6-14}$ aryl-carboxamido groups (e.g., phenylcarboxamido, naphthylcarboxamido), $C_{1-6}$ alkoxy-carboxamido groups (e.g., methoxycarboxamido, ethoxycarboxamido, propoxycarboxamido, butoxycarboxamido, tert-butoxycarboxamido), $C_{1-6}$ alkylsulfonylamino groups (e.g., methylsulfonylamino, ethylsulfonylamino), $C_{1-6}$ alkyl-carbonyloxy groups (e.g., acetoxy, propanoyloxy), $C_{6-14}$ aryl-carbonyloxy groups (e.g., benzoyloxy, 1-naphthoyloxy, 2-naphthoyloxy), $C_{1-6}$ alkoxy-carbonyloxy groups (e.g., methoxycarbonyloxy, ethoxycarbonyloxy, propoxycarbonyloxy, butoxycarbonyloxy), mono- or di-$C_{1-6}$ alkyl-carbamoyloxy groups (e.g., methylcarbamoyloxy, ethylcarbamoyloxy, dimethylcarbamoyloxy, diethylcarbamoyloxy), $C_{6-14}$ aryl-carbamoyloxy groups (e.g., phenylcarbamoyloxy, naphthylcarbamoyloxy), 5 or 6-membered heterocyclic carbonyloxy groups (e.g., nicotinoyloxy) and the like can be mentioned. The number of substituents is, for example, 1 to 5, preferably 1 to 3. When the number of substituents is 2 or more, respective substituents may be the same or different.

As the aforementioned "optionally halogenated $C_{1-6}$ alkoxy group", for example, a $C_{1-6}$ alkoxy group optionally having 1 to 5, preferably 1 to 3, halogen atoms (e.g., fluorine, chlorine, bromine, iodine), such as methoxy, ethoxy, propoxy, butoxy, pentyloxy and the like can be mentioned. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

As the aforementioned "optionally halogenated $C_{1-6}$ alkylthio group", for example, a $C_{1-6}$ alkylthio group optionally having 1 to 5, preferably 1 to 3, halogen atoms (e.g., fluorine, chlorine, bromine, iodine), such as methylthio, ethylthio, propylthio, isopropylthio, butylthio, sec-butylthio, tert-butylthio and the like can be mentioned. Specific examples thereof include methylthio, difluoromethylthio, trifluoromethylthio, ethylthio, propylthio, isopropylthio, butylthio, 4,4,4-trifluorobutylthio, pentylthio, hexylthio and the like.

As the "5- to 7-membered heterocyclic group" of the aforementioned "optionally substituted 5- to 7-membered heterocyclic group", for example, a 5- to 7-membered heterocyclic group containing, as a ring-constituting atom besides carbon atom, 1 to 4 heteroatoms selected from nitrogen atom, sulfur atom and oxygen atom and the like can be mentioned. Preferable examples of the 5- to 7-membered heterocyclic group include 5- to 7-membered non-aromatic heterocyclic groups such as pyrrolidinyl (e.g., 1-, 2- or 3-pyrrolidinyl); imidazolidinyl (e.g., 1-, 2-, 4- or 5-imidazolidinyl); imidazolinyl (e.g., 2- or 4-imidazolinyl); pyrazolidinyl (e.g., 2-, 3- or 4-pyrazolidinyl); piperidinyl (e.g., 1-, 2-, 3- or 4-piperidinyl); piperazinyl (e.g., 1- or 2-piperazinyl); tetrahydropyranyl; morpholinyl; thiomorpholinyl and the like; and 5- to 7-membered aromatic heterocyclic groups such as thienyl (e.g., 2- or 3-thienyl); furyl (e.g., 2- or 3-furyl); pyrrolyl (e.g., 1-, 2- or 3-pyrrolyl); imidazolyl (e.g., 1-, 2- or 4-imidazolyl); thiazolyl (e.g., 2-, 4- or 5-thiazolyl); oxazolyl (e.g., 2-, 4- or 5-oxazolyl); isothiazolyl (e.g., 3-isothiazolyl); isoxazolyl (e.g., 3-isoxazolyl); pyridyl (e.g., 2-, 3- or 4-pyridyl); pyrazolyl (e.g., 1-, 3- or 4-pyrazolyl); pyrazinyl (e.g., 2-pyrazinyl); pyrimidinyl (e.g., 2-, 4- or 5-pyrimidinyl); pyridazinyl (e.g., 3- or 4-pyridazinyl); oxadiazolyl (e.g., 1,2,4-oxadiazol-5-yl; 1,2,4-oxadiazol-3-yl); thiadiazolyl (e.g., 1,2,4-thiadiazol-5-yl; 1,2,4-thiadiazol-3-yl); triazolyl (e.g., 1,2,3-triazol-1-yl; 1,2,3-triazol-4-yl; 1,2,4-triazol-1-yl; 1,2,4-triazol-3-yl); tetrazolyl (e.g., 1- or 5-tetrazolyl); pyranyl (e.g., 2-, 3- or 4-pyranyl) and the like.

As the aforementioned "optionally halogenated $C_{1-6}$ alkyl-carbonyl group", for example, a $C_{1-6}$ alkyl-carbonyl group optionally having 1 to 5, preferably 1 to 3, halogen atoms (e.g., fluorine, chlorine, bromine, iodine), such as acetyl, propanoyl, butanoyl, pentanoyl, hexanoyl and the like can be mentioned. Specific examples thereof include acetyl, monochloroacetyl, trifluoroacetyl, trichloroacetyl, propanoyl, butanoyl, pentanoyl, hexanoyl and the like.

As the aforementioned "$C_{1-6}$ alkoxy-carbonyl group", for example, methoxycarbonyl, ethoxycarbonyl, propoxycarbonyl, tert-butoxycarbonyl and the like can be mentioned.

As the "heterocyclic carbonyl group" of the aforementioned "optionally substituted heterocyclic carbonyl group", for example, nicotinoyl, isonicotinoyl, thenoyl (e.g., 2-thenoyl, 3-thenoyl), furoyl (e.g., 2-furoyl, 3-furoyl), morpholinocarbonyl, piperidinocarbonyl, pyrrolidin-1-ylcarbonyl, indolylcarbonyl and the like can be mentioned.

As the "heterocyclic carbamoyl group" of the aforementioned "optionally substituted heterocyclic carbamoyl group", for example, morpholinocarbamoyl, piperidinocarbamoyl, pyridylcarbamoyl (e.g., 2-pyridylcarbamoyl, 3-pyridylcarbamoyl, 4-pyridylcarbamoyl), thienylcarbamoyl (e.g., 2-thienylcarbamoyl, 3-thienylcarbamoyl), indolylcarbamoyl and the like can be mentioned.

As the aforementioned "optionally halogenated $C_{1-6}$ alkylsulfonyl group", for example, a $C_{1-6}$ alkylsulfonyl group optionally having 1 to 5, preferably 1 to 3, halogen atoms (e.g., fluorine, chlorine, bromine, iodine), such as methylsulfonyl, ethylsulfonyl, propylsulfonyl, isopropylsulfonyl, butylsulfonyl, sec-butylsulfonyl, tert-butylsulfonyl and the like can be mentioned. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl and the like.

As the aforementioned "optionally halogenated $C_{1-6}$ alkyl-carboxamido group", for example, a $C_{1-6}$ alkyl-carboxamido group optionally having 1 to 5, preferably 1 to 3, halogen atoms (e.g., fluorine, chlorine, bromine, iodine), such as acetamido, propanamido, butanamido and the like can be mentioned. Specific examples thereof include acetamido, trifluoroacetamido, propanamido, butanamido and the like.

As the substituent of the aforementioned "optionally substituted 5- to 7-membered heterocyclic group", "optionally substituted heterocyclic carbonyl group" and "optionally substituted heterocyclic carbamoyl group", for example, halogen atoms (e.g., fluorine, chlorine, bromine, iodine), $C_{1-3}$ alkylenedioxy groups (e.g., methylenedioxy, ethylenedioxy), a nitro group, a cyano group, an oxo group, an optionally halogenated $C_{1-6}$ alkyl group, carbamoyl-$C_{1-6}$ alkyl groups (e.g., carbamoylmethyl), an optionally halogenated $C_{3-6}$ cycloalkyl group, $C_{6-14}$ aryl groups (e.g., phenyl, naphthyl), $C_{7-19}$ aralkyl groups (e.g., benzyl, phenethyl), an optionally halogenated $C_{1-6}$ alkoxy group, an optionally halogenated $C_{1-6}$ alkylthio group, a hydroxy group, an amino group, mono- or di-$C_{1-6}$ alkylamino groups (e.g., methylamino, ethylamino, propylamino, isopropylamino, butylamino, dimethylamino, diethylamino, dipropylamino, dibutylamino, N-ethyl-N-methylamino), a formyl group, a carboxyl group, a carbamoyl group, a thiocarbamoyl group, an optionally halogenated $C_{1-6}$ alkyl-carbonyl group, a $C_{1-6}$ alkoxy-carbonyl group, $C_{6-14}$ aryl-carbonyl groups (e.g., benzoyl, 1-naphthoyl, 2-naphthoyl), mono- or di-$C_{1-6}$ alkyl-carbamoyl groups (e.g., methylcarbamoyl, ethylcarbamoyl, dimethylcarbamoyl, diethylcarbamoyl, N-ethyl-N-methylcarbamoyl), mono- or di-$C_{7-19}$ aralkyl-carbamoyl groups (e.g., benzylcarbamoyl), an optionally halogenated $C_{1-6}$ alkylsulfonyl group, $C_{6-14}$ arylsulfonyl groups (e.g., phenylsulfonyl), a sulfamoyl group, mono- or di-$C_{1-6}$ alkyl-sulfamoyl groups (e.g., methylsulfamoyl, ethylsulfamoyl, dimethylsulfamoyl, diethylsulfamoyl, N-ethyl-N-methylsulfamoyl), a formylamino group, an optionally halogenated $C_{1-6}$ alkyl-carboxamido group, $C_{1-6}$ alkoxy-carboxamido groups (e.g., methoxycarboxamido, ethoxycarboxamido, propoxycarboxamido, butoxycarboxamido), $C_{1-6}$ alkylsulfonylamino groups (e.g., methylsulfonylamino, ethylsulfonylamino), $C_{1-6}$ alkyl-carbonyloxy groups (e.g., acetoxy, propanoyloxy), $C_{1-6}$ alkoxy-carbonyloxy groups (e.g., methoxycarbonyloxy, ethoxycarbonyloxy, propoxycarbonyloxy, butoxycarbonyloxy), 5 or 6-membered aromatic heterocyclic groups (e.g., tetrazolyl, thiazolyl, oxazolyl) and the like can be mentioned. The number of substituents is, for example, 1 to 3. When the number of substituents is 2 or more, respective substituents may be the same or different.

As the aforementioned "optionally halogenated $C_{1-6}$ alkyl group", for example, a $C_{1-6}$ alkyl group optionally having 1 to 5, preferably 1 to 3, halogen atoms (e.g., fluorine, chlorine, bromine, iodine), such as methyl, ethyl, propyl, isopropyl, butyl, isobutyl, sec-butyl, tert-butyl, pentyl and hexyl can be mentioned. Specific examples thereof include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

As the aforementioned "optionally halogenated $C_{3-6}$ cycloalkyl group", for example, a $C_{3-6}$ cycloalkyl group optionally having 1 to 5, preferably 1 to 3, halogen atoms (e.g., fluorine, chlorine, bromine, iodine), such as cyclopropyl, cyclobutyl, cyclopentyl, cyclohexyl and the like can be mentioned. Specific examples thereof include cyclopropyl, cyclobutyl, cyclopentyl, cyclohexyl, 4,4-dichlorocyclohexyl, 2,2,3,3-tetrafluorocyclopentyl, 4-chlorocyclohexyl and the like.

As the "optionally halogenated $C_{1-6}$ alkoxy group", "optionally halogenated $C_{1-6}$ alkylthio group", "optionally halogenated $C_{1-6}$ alkyl-carbonyl group", "$C_{1-6}$alkoxy-carbonyl group", "optionally halogenated $C_{1-6}$ alkylsulfonyl group" and "optionally halogenated $C_{1-6}$ alkyl-carboxamido group", those respectively recited as the "substituent" of the aforementioned "optionally substituted hydrocarbon group" can be mentioned.

As the "heterocyclic group" of the "optionally substituted heterocyclic group" exemplified as the substituent for $R^1$ and the like, for example, (i) an aromatic heterocyclic group, (ii) a non-aromatic heterocyclic group and (iii) a 7 to 10-membered bridged heterocyclic group, each containing, as a ring-constituting atom besides carbon atom, 1 to 4 heteroatoms selected from nitrogen atom, sulfur atom and oxygen atom can be mentioned.

Here, as the "aromatic heterocyclic group", for example, 4 to 14-membered (preferably 4 to 10-membered) aromatic heterocyclic groups containing, as a ring-constituting atom besides carbon atom, 1 to 4 heteroatoms selected from nitrogen atom, sulfur atom and oxygen atom and the like can be mentioned. Preferable examples of the "aromatic heterocyclic group" include monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, furazanyl, pyranyl and the like; and condensed polycyclic (preferably bi- or tri-cyclic) aromatic heterocyclic groups such as benzothiophenyl, benzofuranyl, benzimidazolyl, benzoxazolyl, benzothiazolyl, benzisothiazolyl, naphtho[2,3-b]thiophenyl, phenoxathiinyl, indolyl, isoindolyl, 1H-indazolyl, purinyl, 4H-quinolizinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl, phthalimido and the like.

As the "non-aromatic heterocyclic group", for example, a 4 to 14-membered (preferably 4 to 10-membered) non-aromatic heterocyclic group containing, as a ring-constituting atom besides carbon atom, 1 to 4 heteroatoms selected from nitrogen atom, sulfur atom and oxygen atom and the like can be mentioned. Preferable examples of the "non-aromatic heterocyclic group" include monocyclic non-aromatic heterocyclic groups such as azetidinyl, tetrahydrothiophenyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydrothiazolyl, tetrahydroisothiazolyl, tetrahydrooxazolyl, tetrahydroisoxazolyl, piperidinyl, piperazinyl, tetrahydropyridinyl, dihydropyridinyl, tetrahydropyrimidinyl, tetrahydropyridazinyl, tetrahydropyranyl, azepanyl, morpholinyl, thiomorpholinyl, diazepanyl, azepinyl, azocanyl, diazocanyl and the like; and condensed polycyclic (preferably bi- or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thiophenyl, tetrahydroisoquinolyl, tetrahydroquinolyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl and the like.

Of the above-mentioned "non-aromatic heterocyclic groups", nitrogen-containing non-aromatic heterocyclic groups (preferably monocyclic nitrogen-containing non-aromatic heterocyclic groups), such as azetidinyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydrothiazolyl, tetrahydroisothiazolyl, tetrahydrooxazolyl, tetrahydroisoxazolyl, piperidinyl, piperazinyl, tetrahydropyridinyl, dihydropyridinyl, tetrahydropyrimidinyl, tetrahydropyridazinyl, azepanyl, morpholinyl, thiomorpholinyl, diazepanyl, azepinyl, azocanyl, diazocanyl and the like are preferable.

Preferable examples of the "7 to 10-membered bridged heterocyclic group" include quinuclidinyl, 7-azabicyclo[2.2.1]heptanyl and the like.

As the substituent of the "optionally substituted heterocyclic group", those exemplified as the substituent of the aforementioned "optionally substituted 5- to 7-membered heterocyclic group" can be mentioned. The number of substituents is, for example, 1 to 3. When the number of substituents is 2 or more, respective substituents may be the same or different.

As the acyl group of the "optionally substituted acyl group" exemplified as the substituent for $R^1$ and the like, for example, —$COR^{15}$, —CO—$OR^{15}$, —$SO_2R^{15}$, —$SOR^{15}$, —$PO(OR^{15})(OR^{16})$ [$R^{15}$ and $R^{16}$ are the same or different and each is a hydrogen atom, a hydrocarbon group or a heterocyclic group] and the like can be mentioned.

As the "hydrocarbon group" for $R^{15}$ or $R^{16}$, the "hydrocarbon group" exemplified for "optionally substituted hydrocarbon group" exemplified as the substituent for $R^1$ and the like can be mentioned. The hydrocarbon group is preferably a $C_{1-6}$ alkyl group, a $C_{2-6}$ alkenyl group, a $C_{3-8}$ cycloalkyl group, a $C_{3-8}$ cycloalkenyl group, a $C_{6-14}$ aryl group, a $C_{7-19}$ aralkyl group and the like.

As the "heterocyclic group" fox $R^{15}$ or $R^{16}$, the "heterocyclic group" exemplified for the "optionally substituted heterocyclic group" exemplified as the substituent for $R^1$ and the like can be mentioned. The heterocyclic group is preferably, thiazolyl, oxazolyl, isothiazolyl, isoxazolyl, pyrazolyl, pyridyl, pyrazinyl, benzoxazolyl, benzothiazolyl, quinolyl, isoquinolyl, pyrrolidinyl, piperidinyl, piperazinyl and the like.

The acyl group may have 1 to 3 substituents at substitutable position(s), and such substituent includes, for example, optionally halogenated $C_{1-6}$ alkyl groups (e.g., methyl, ethyl); optionally halogenated $C_{1-6}$ alkoxy groups (e.g., methoxy, ethoxy); halogen atoms (e.g., fluorine, chlorine, bromine, iodine); nitro group; hydroxy group; amino group optionally mono- or di-substituted by $C_{1-6}$ alkyl groups (e.g., methyl, ethyl); $C_{1-6}$ alkoxy-carboxamido groups (e.g., tert-butoxycarboxamido) and the like.

Preferable examples of acyl group include a formyl group, carboxyl group, $C_{1-6}$ alkyl-carbonyl groups (e.g., acetyl, propionyl, butyryl, isobutyryl, valeryl, isovaleryl, pivaloyl, hexanoyl), $C_{2-6}$ alkenyl-carbonyl groups (e.g., crotonoyl), $C_{3-8}$ cycloalkyl-carbonyl groups (e.g., cyclobutanecarbonyl, cyclopentanecarbonyl, cyclohexanecarbonyl, cycloheptanecarbonyl), $C_{3-8}$ cycloalkenyl-carbonyl groups (e.g., 2-cyclohexenecarbonyl), $C_{6-14}$ aryl-carbonyl groups (e.g., benzoyl, 1-naphthoyl, 2-naphthoyl), $C_{7-19}$ aralkyl-carbonyl groups (e.g., benzylcarbonyl, phenethylcarbonyl), aromatic heterocyclic carbonyl groups (e.g., nicotinoyl, isonicotinoyl), non-aromatic heterocyclic carbonyl groups (e.g., pyrrolidinylcarbonyl, piperidinylcarbonyl), $C_{1-6}$ alkoxy-carbonyl groups (e.g., methoxycarbonyl, ethoxycarbonyl, propoxycarbonyl, butoxycarbonyl, tert-butoxycarbonyl), $C_{6-14}$ aryloxy-carbonyl groups (e.g., phenyloxycarbonyl, naphthyloxycarbonyl), $C_{7-19}$ aralkyloxy-carbonyl groups (e.g., benzyloxycarbonyl, phenethyloxycarbonyl), $C_{1-6}$ alkylsulfinyl groups (e.g., methylsulfinyl, ethylsulfinyl), $C_{1-6}$ alkylsulfonyl groups (e.g., methylsulfonyl, ethylsulfonyl), $C_{6-14}$ arylsulfonyl groups (e.g., phenylsulfonyl), phosphono group, mono- or di-$C_{1-6}$ alkylphosphono groups (e.g., dimethylphosphono, diethylphosphono, diisopropylphosphono, dibutylphosphono) and the like.

As the "optionally substituted amino group", "optionally substituted carbamoyl group" and "optionally substituted sulfamoyl group" exemplified as the substituent for $R^1$ and the like, for example, amino group, carbamoyl group and sulfamoyl group each optionally substituted by 1 or 2 substituents selected from (1) "optionally substituted hydrocarbon group", "optionally substituted acyl group" and "optionally substituted heterocyclic group" recited as examples of the substituent for $R^1$ and the like; and (2) carbamoyl group optionally having 1 or 2 substituents selected from $C_{1-6}$ alkyl groups (e.g., methyl, ethyl), $C_{3-8}$ cycloalkyl groups (e.g., cyclopropyl, cyclohexyl), $C_{6-14}$ aryl groups (e.g., phenyl) and $C_{7-19}$ aralkyl groups (e.g., benzyl) can be mentioned. When nitrogen atom constituting these amino group, carbamoyl group and sulfamoyl group is substituted by 2 substituents, these substituents may form a nitrogen-containing heterocycle together with the adjacent nitrogen atom. As the "nitrogen-containing heterocycle", for example, a 5- to 7-membered nitrogen-containing heterocycle containing at least one nitrogen atom as a ring constituting atom besides carbon atom, and further, 1 or 2 heteroatoms selected from oxygen atom, sulfur atom and nitrogen atom can be mentioned. Preferable examples of the nitrogen-containing heterocycle include pyrrolidine, imidazolidine, pyrazolidine, piperidine, piperazine, morpholine, thiomorpholine and the like.

The "optionally substituted amino group", "optionally substituted carbamoyl group" and "optionally substituted sulfamoyl group" are preferably amino group, carbamoyl group and sulfamoyl group each optionally substituted by 1 or 2 substituents selected from $C_{1-6}$ alkyl group, $C_{2-6}$ alkenyl group, $C_{3-8}$ cycloalkyl group, $C_{6-14}$ aryl group, $C_{7-19}$ aralkyl group, $C_{1-6}$ alkyl-carbonyl group, $C_{6-14}$ aryl-carbonyl group, $C_{7-19}$ aralkyl-carbonyl group, aromatic heterocyclic carbonyl group, non-aromatic heterocyclic carbonyl group, $C_{1-6}$ alkoxy-carbonyl group, aromatic heterocyclic group, carbamoyl group, mono- or di-$C_{1-6}$ alkyl-carbamoyl group and mono- or di-$C_{7-19}$ aralkyl-carbamoyl group, each of which may have 1 to 3 substituents selected from halogen atoms (e.g., fluorine, chlorine, bromine, iodine), optionally halogenated $C_{1-6}$ alkoxy group, hydroxy group, nitro group, amino group and carbamoyl group.

Preferable examples of the optionally substituted amino group include amino group, mono- or di-$C_{1-6}$ alkylamino groups (e.g., methylamino, dimethylamino, ethylamino, diethylamino, propylamino, dibutylamino), mono- or di-$C_{2-6}$ alkenylamino groups (e.g., diallylamino), mono- or di-$C_{3-8}$ cycloalkylamino groups (e.g., cyclopropylamino, cyclohexylamino), mono- or di-$C_{6-14}$ arylamino groups (e.g., phenylamino), mono- or di-$C_{7-19}$ aralkylamino groups (e.g., benzylamino, dibenzylamino), mono- or di-(optionally halogenated $C_{1-6}$ alkyl)-carbonylamino groups (e.g., acetylamino, propionylamino), mono- or di-$C_{6-14}$ aryl-carbonylamino groups (e.g., benzoylamino), mono- or di-$C_{7-19}$ aralkyl-carbonylamino groups (e.g., benzylcarbonylamino), mono- or di-aromatic heterocyclic carbonylamino groups (e.g., nicotinoylamino, isonicotinoylamino), mono- or di-non-aromatic heterocyclic carbonylamino groups (e.g., piperidinylcarbonylamino), mono- or di-$C_{1-6}$ alkoxy-carbonylamino groups (e.g., tert-butoxycarbonylamino), aromatic heterocyclic amino groups (e.g., pyridylamino), carbamoylamino groups, (mono- or di-$C_{1-6}$ alkyl-carbamoyl)amino groups (e.g., methylcarbamoylamino, (mono- or di-$C_{7-19}$ aralkyl-carbamoyl)amino groups (e.g., benzylcarbamoylamino) and the like.

Preferable examples of the optionally substituted carbamoyl group include carbamoyl group, mono- or di-$C_{1-6}$ alkyl-carbamoyl groups (e.g., methylcarbamoyl, ethylcarbamoyl, dimethylcarbamoyl, diethylcarbamoyl, N-ethyl-N-methylcarbamoyl), mono- or di-$C_{2-6}$ alkenyl-carbamoyl groups (e.g., diallylcarbamoyl), mono- or di-$C_{3-8}$ cycloalkyl-carbamoyl groups (e.g., cyclopropylcarbamoyl, cyclohexylcarbamoyl), mono- or di-$C_{6-14}$ aryl-carbamoyl groups (e.g., phenylcarbamoyl), mono- or di-$C_{7-19}$ aralkyl-carbamoyl groups (e.g., benzylcarbamoyl, phenethylcarbamoyl), mono- or di-$C_{1-6}$ alkyl-carbonyl-carbamoyl groups (e.g., acetylcarbamoyl, propionylcarbamoyl), mono- or di-$C_{6-14}$ aryl-carbonyl-carbamoyl groups (e.g., benzoylcarbamoyl), aromatic heterocyclic carbamoyl groups (e.g., pyridylcarbamoyl), morpholinocarbonyl group and the like.

Preferable examples of the optionally substituted sulfamoyl group include sulfamoyl group, mono- or di-$C_{1-6}$ alkyl-sulfamoyl groups (e.g., methylsulfamoyl, ethylsulfamoyl, dimethylsulfamoyl, diethylsulfamoyl, N-ethyl-N-methylsulfamoyl), mono- or di-$C_{2-6}$ alkenyl-sulfamoyl groups (e.g., diallylsulfamoyl), mono- or di-$C_{3-8}$ cycloalkyl-sulfamoyl groups (e.g., cyclopropylsulfamoyl, cyclohexylsulfamoyl), mono- or di-$C_{6-14}$ aryl-sulfamoyl groups (e.g., phenylsulfamoyl), mono- or di-$C_{7-19}$ aralkyl-sulfamoyl groups (e.g., benzylsulfamoyl, phenethylsulfamoyl), mono- or di-$C_{1-6}$ alkyl-carbonyl-sulfamoyl groups (e.g., acetylsulfamoyl, propionylsulfamoyl), mono- or di-$C_{6-14}$ aryl-carbonyl-sulfamoyl groups (e.g., benzoylsulfamoyl), aromatic heterocyclic sulfamoyl groups (e.g., pyridylsulfamoyl) and the like.

As the "optionally substituted hydroxy group" and "optionally substituted mercapto group" exemplified as the substituent for $R^1$ and the like, for example, hydroxy group and mercapto group each optionally substituted by the substituent selected from the "optionally substituted hydrocarbon group", "optionally substituted acyl group" and "optionally substituted heterocyclic group" exemplified as the substituent for $R^1$ and the like can be mentioned.

The "optionally substituted hydroxy group" and "optionally substituted mercapto group" are preferably hydroxy group and mercapto group each optionally substituted by a "substituent selected from $C_{1-6}$ alkyl group, $C_{2-6}$ alkenyl group, $C_{3-8}$ cycloalkyl group, $C_{6-14}$ aryl group, $C_{7-19}$ aralkyl group, $C_{1-6}$ alkyl-carbonyl group, $C_{6-14}$ aryl-carbonyl group and aromatic heterocyclic group, each of which may have 1 to 3 substituents selected from halogen atoms (e.g., fluorine, chlorine, bromine, iodine), optionally halogenated $C_{1-6}$ alkoxy group, hydroxy group, nitro group, amino group and carbamoyl group".

Preferable examples of the optionally substituted hydroxy group include hydroxy group, $C_{1-6}$ alkoxy groups (e.g., methoxy, ethoxy, propoxy, isopropoxy, butoxy, isobutoxy, sec-butoxy, tert-butoxy, pentyloxy, isopentyloxy, neopentyloxy, hexyloxy), $C_{2-6}$ alkenyloxy groups (e.g., allyloxy, crotyloxy, 2-pentenyloxy, 3-hexenyloxy), $C_{3-8}$ cycloalkyloxy groups (e.g., cyclohexyloxy), $C_{6-14}$ aryloxy groups (e.g., phenoxy, naphthyloxy), $C_{7-19}$ aralkyloxy groups (e.g., benzyloxy, phenethyloxy), $C_{1-6}$ alkyl-carbonyloxy groups (e.g., acetyloxy, propionyloxy, butyryloxy, isobutyryloxy, pivaloyloxy), $C_{6-14}$ aryl-carbonyloxy groups (e.g., benzoyloxy), aromatic heterocyclic oxy groups (e.g., pyridyloxy) and the like.

Preferable examples of the optionally substituted mercapto group include mercapto group, $C_{1-6}$ alkylthio groups (e.g., methylthio, ethylthio, propylthio, isopropylthio, butylthio, isobutylthio, sec-butylthio, tert-butylthio, pentylthio, isopentylthio, neopentylthio, hexylthio), $C_{2-6}$ alkenylthio groups (e.g., allylthio, crotylthio, 2-pentenylthio, 3-hexenylthio), $C_{3-8}$ cycloalkylthio groups (e.g., cyclohexylthio), $C_{6-14}$ arylthio groups (e.g., phenylthio, naphthylthio), $C_{7-19}$ aralkylthio groups (e.g., benzylthio, phenethylthio), $C_{1-6}$ alkyl-carbonylthio groups (e.g., acetylthio, propionylthio, butyrylthio, isobutyrylthio, pivaloylthio), $C_{6-14}$ aryl-carbonylthio groups (e.g., benzoylthio), aromatic heterocyclic thio groups (e.g., pyridylthio) and the like.

The substituent for $R^1$, $R^2$, $R^3$ or $R^6$ is preferably a halogen atom, an optionally substituted amino group and the like. Here, as the optionally substituted amino group, an amino group, a mono- or di-$C_{7-19}$ aralkylamino group and the like are preferable.

$R^1$, $R^2$, $R^3$ and $R^6$ are preferably hydrogen atoms.

One of $R^4$ and $R^5$ is a hydrogen atom and the other is 1) a group represented by the formula: —C(=X)—$R^7$ wherein X is N—O—$R^8$ or N—NH—$R^9$ wherein $R^8$ and $R^9$ are the same or different and each is a hydrogen atom or a group bonded via a carbon atom; and $R^7$ is a hydrogen atom or a substituent, 2) a group represented by the formula: —C(=O)—$R^{10}$ wherein $R^{10}$ is a hydrogen atom or a group bonded via a carbon atom;

3) a group represented by the formula: —CH(OH)—$R^{10}$ wherein $R^{10}$ is a hydrogen atom or a group bonded via a carbon atom;

4) a group represented by the formula: —C(=O)—NH—(CH$_2$)n-Ar wherein n is 0, 1 or 2, and Ar is an aromatic group;

5) a group represented by the formula: —C(=O)-Het wherein Het is an optionally substituted heterocyclic group bonded via a nitrogen atom; or 6) a group represented by the formula: —CH($R^{12}$)—N$R^{13}R^{14}$ wherein $R^{12}$ is a hydrogen atom or a hydrocarbon group; $R^{13}$ and $R^{14}$ are the same or different and each is a hydrogen atom, an optionally substituted hydrocarbon group, an optionally substituted heterocyclic group or an optionally substituted acyl group, or $R^{13}$ and $R^{14}$ form, together with the adjacent nitrogen atom, a nitrogen-containing heterocyclic group optionally having substituents (provided that the nitrogen-containing heterocyclic group is not an oxopyrrolidinyl group or an oxopiperazinyl group).

As the substituent for $R^7$, those exemplified for the aforementioned $R^1$ and the like can be used. Of these, an optionally substituted hydrocarbon group, an optionally substituted heterocyclic group and the like are preferable. The substituent for $R^7$ is preferably a $C_{1-6}$ alkyl group, a $C_{6-14}$ aryl group (preferably, phenyl), a $C_{7-19}$ aralkyl group or a monocyclic aromatic heterocyclic group (preferably thienyl, furyl), each of which may have 1 to 3 substituents selected from a halogen atom, a $C_{1-6}$ alkyl group, an optionally halogenated $C_{1-6}$ alkoxy group and the like.

As the "group bonded via a carbon atom" for $R^8$, $R^9$ or $R^{10}$, for example, cyano group, amidino group, optionally substituted hydrocarbon group, optionally substituted heterocyclic group, optionally substituted acyl group, optionally substituted carbamoyl group and the like exemplified as the aforementioned $R^1$ and the like can be mentioned. However, the "optionally substituted heterocyclic group" is limited to a group bonded via a carbon atom. Moreover, the "optionally substituted acyl group" is limited to —$COR^{15}$ or —CO—$OR^{15}$ ($R^{15}$ is as defined above).

The "group bonded via a carbon atom" for $R^8$ or $R^9$ is preferably, (1) an amidino group;
(2) a $C_{1-6}$ alkyl group optionally having 1 to 3 substituents selected from a hydroxy group, an optionally halogenated $C_{1-6}$ alkoxy group, a carboxyl group, an amino group, a mono- or di-$C_{1-6}$ alkylamino group, a 5- to 7-membered heterocyclic group (preferably pyrrolidinyl, imidazolyl, morpholinyl), a $C_{1-6}$ alkoxy-carbonyl group, a carbamoyl group, a mono- or di-$C_{1-6}$ alkyl-carbamoyl group, a $C_{6-14}$ aryl-carbamoyl group (preferably phenylcarbamoyl), a $C_{1-6}$ alkoxy-carboxamido group, a 5- to 7-membered heterocyclic oxy group (preferably tetrahydropyranyloxy) and the like;
(3) a $C_{7-19}$ aralkyl group;
(4) a heterocyclic group (preferably 2- or 3-pyrrolidinyl; 2-, 3- or 4-piperidinyl) bonded via a carbon atom and optionally having 1 to 3 substituents selected from a $C_{1-6}$ alkoxy-carbonyl group and the like;
(5) a carbamoyl group; and the like.

The "group bonded via a carbon atom" for $R^{10}$ is preferably
(1) a $C_{1-6}$ alkyl group;
(2) $C_{6-14}$ aryl group (preferably phenyl) optionally having 1 to 3 substituents selected from a halogen atom, a $C_{1-6}$ alkyl group, an optionally halogenated $C_{1-6}$ alkoxy group and the like;
(3) a $C_{7-19}$ aralkyl group;
(4) a heterocyclic group (preferably 2- or 3-thienyl; 2- or 3-furyl; 2-, 3- or 4-pyridyl) bonded via a carbon atom; and the like.

As the aromatic group for Ar, for example, a $C_{6-14}$ aryl group (preferably phenyl), an aromatic heterocyclic group and the like can be mentioned. As the aromatic heterocyclic group, those exemplified as the "optionally substituted heterocyclic group" exemplified for the aforementioned $R^1$ and the like can be used.

Of these, a $C_{6-14}$ aryl group (preferably phenyl), a 5 or 6-membered aromatic heterocyclic group (preferably thienyl, furyl, pyridyl) and the like are preferable.

As the "optionally substituted heterocyclic group bonded via a nitrogen atom" for Het, for example, a group bonded via a nitrogen atom from the "optionally substituted heterocyclic groups" exemplified as the aforementioned $R^1$ and the like can be mentioned.

Of these, 1-pyrrolidinyl, 1-piperazinyl, 4-morpholinyl or 4-thiomorpholinyl optionally having 1 to 3 substituents selected from an optionally halogenated $C_{1-6}$ alkyl group, an optionally halogenated $C_{1-6}$ alkyl-carbonyl group and the like is preferable.

As the hydrocarbon group for $R^{12}$, for example, those exemplified as the "optionally substituted hydrocarbon group" exemplified as the aforementioned $R^1$ and the like are used.

Of these, a $C_{1-6}$ alkyl group, a $C_{6-14}$ aryl group (preferably phenyl) and the like are preferable.

As the "optionally substituted hydrocarbon group", "optionally substituted heterocyclic group" and "optionally substituted acyl group" for $R^{13}$ or $R^{14}$, those exemplified for the aforementioned $R^1$ and the like are used.

Here, the "optionally substituted hydrocarbon group" is preferably a $C_{1-6}$ alkyl group, a $C_{3-8}$ cycloalkyl group or a $C_{7-19}$ aralkyl group each optionally having 1 to 3 substituents selected from 5- to 7-membered heterocyclic groups (preferably thienyl, furyl, pyridyl, morpholinyl, thiomorpholinyl).

The "optionally substituted heterocyclic group" is preferably a monocyclic non-aromatic heterocyclic group (preferably piperidinyl) optionally having 1 to 3 substituents selected from a $C_{7-19}$ aralkyl group and the like.

The "optionally substituted acyl group" is preferably a $C_{1-6}$ alkyl-carbonyl group, a $C_{6-14}$ aryl-carbonyl group (preferably benzoyl) or an aromatic heterocyclic carbonyl group (preferably nicotinoyl, isonicotinoyl) each optionally having 1 to 3 substituents selected from a $C_{1-6}$ alkoxy-carboxamido group and the like.

The nitrogen-containing heterocyclic group of the "nitrogen-containing heterocyclic group optionally having substituents (provided that the nitrogen-containing heterocyclic group is not an oxopyrrolidinyl group or an oxopiperazinyl group)" formed by $R^{13}$ and $R^{14}$ together with the adjacent nitrogen atom is, for example, a 5- to 7-membered nitrogen-containing heterocyclic group containing at least one nitrogen atom as a ring constituting atom besides carbon atom, and optionally having 1 or 2 heteroatoms selected from oxygen atom, sulfur atom and nitrogen atom can be mentioned. Preferable examples of the nitrogen-containing heterocyclic group include 1-pyrrolidinyl, 1-imidazolidinyl, 1-pyrazolidinyl, 1-piperidinyl, 1-piperazinyl, 4-morpholinyl, 4-thiomorpholinyl and the like.

The nitrogen-containing heterocyclic group may have 1 to 3 substituents at substitutable position(s) and as such substituent, a halogen atom, an optionally halogenated $C_{1-6}$ alkyl group, an optionally halogenated $C_{1-6}$ alkoxy group and the like can be mentioned.

The "nitrogen-containing heterocyclic group optionally having substituents" is preferably 1-piperidinyl and the like.

In the formula (I), (1) a compound wherein one of $R^4$ and $R^5$ is a hydrogen atom, the other is a group represented by the formula: —C(=X)—$R^7$ wherein X and $R^7$ are as defined above; and (2) a compound wherein $R^4$ is a hydrogen atom, and $R^5$ is a group represented by the formula: —C(=O)—$R^{10}$ wherein $R^{10}$ is as defined above are preferable.

In the formula (I'), $R^{13'}$ and $R^{14'}$ are the same as $R^{13}$ and $R^{14}$, except that the nitrogen-containing heterocyclic group of the "nitrogen-containing heterocyclic group optionally having substituents" formed by these together with the adjacent nitrogen atom may be an oxopyrrolidinyl group or an oxopiperazinyl group.

The compound (I') is preferably compound (I).

As an example of preferable compound (I), the following compound can be mentioned.

[Compound A]

A compound wherein $R^1$, $R^2$, $R^3$ and $R^6$ are hydrogen atoms;

one of $R^4$ and $R^5$ is a hydrogen atom, and the other is a group represented by the formula: —C(=X)—$R^7$;

X is N—O—$R^8$ or N—NH—$R^9$;

$R^8$ and $R^9$ are the same or different and each is (1) a hydrogen atom; (2) an amidino group; (3) a $C_{1-6}$ alkyl group optionally having 1 to 3 substituents selected from a hydroxy group, an optionally halogenated $C_{1-6}$ alkoxy group, a carboxyl group, an amino group, a mono- or di-$C_{1-6}$ alkylamino group, a 5- to 7-membered heterocyclic group (preferably pyrrolidinyl, imidazolyl, morpholinyl), a $C_{1-6}$ alkoxy-carbonyl group, a carbamoyl group, a mono- or di-$C_{1-6}$ alkyl-carbamoyl group, a $C_{6-14}$ aryl-carbamoyl group, a $C_{1-6}$ alkoxy-carboxamido group, a 5- to 7-membered heterocyclic oxy group (preferably tetrahydropyranyloxy) and the like; (4) a $C_{7-19}$ aralkyl group; (5) a heterocyclic group (preferably 2- or 3-pyrrolidinyl; 2-, 3- or 4-piperidinyl) bonded via a carbon atom and optionally having 1 to 3 substituents selected from a $C_{1-6}$ alkoxy-carbonyl group and the like; or (6) a carbamoyl group; and $R^7$ is (1) a hydrogen atom; or (2) a $C_{1-6}$ alkyl group, a $C_{6-14}$ aryl group (preferably phenyl), a $C_{7-19}$ aralkyl group or a monocyclic aromatic heterocyclic group (preferably thienyl, furyl) each optionally having 1 to 3 substituents selected from a halogen atom, a $C_{1-6}$ alkyl group, an optionally halogenated $C_{1-6}$ alkoxy group and the like.

[Compound B]

A compound wherein $R^1$, $R^2$, $R^3$ and $R^6$ are hydrogen atoms;

$R^4$ is a hydrogen atom;

$R^5$ is a group represented by the formula: —C(=O)—$R^{10}$; and $R^{10}$ is (1) a hydrogen atom; (2) a $C_{1-6}$ alkyl group; (3) a $C_{6-14}$ aryl group (preferably phenyl) optionally having 1 to 3 substituents selected from a halogen atom, a $C_{1-6}$ alkyl group, an optionally halogenated $C_{1-6}$ alkoxy group and the like; (4) a $C_{7-19}$ aralkyl group; or (5) a heterocyclic group (preferably 2- or 3-thienyl; 2- or 3-furyl; 2-, 3- or 4-pyridyl) bonded via a carbon atom.

The salt of compound (I) or (I') is preferably a pharmacologically acceptable salt, and is exemplified by salts with inorganic bases, salts with organic bases, salts with inorganic acids, salts with organic acids, and salts with basic or acidic amino acids.

Preferable examples of the salts with inorganic bases include alkali metal salts such as sodium salts and potassium salts; alkaline earth metal salts such as calcium salts and magnesium salts; and aluminum salts and ammonium salts.

Preferable examples of the salts with organic bases include salts with trimethylamine, triethylamine, pyridine, picoline, ethanolamine, diethanolamine, triethanolamine, dicyclohexylamine, N,N-dibenzylethylenediamine, etc.

Preferable examples of the salts with inorganic acids include salts with hydrochloric acid, hydrobromic acid, nitric acid, sulfuric acid, phosphoric acid, etc.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferable examples of the salts with basic amino acids include salts with arginine, lysine, ornithine, etc.

Examples of preferable salts with acidic amino acids include salts with aspartic acid, glutamic acid, etc.

A prodrug of compound (I) refers to a compound capable of being converted to compound (I) by the actions of an enzyme, gastric juice, or the like, under physiological conditions in vivo, specifically a compound capable of being converted to compound (I) upon enzymatic oxidation, reduction, hydrolysis, or the like, or a compound capable of being converted to compound (I) upon hydrolysis or the like by gastric juice or the like. Examples of the prodrugs of compound (I) include compounds derived by acylation, alkylation or phosphorylation of the amino group of compound (I) (e.g., compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of compound (I)); compounds derived by acylation, alkylation, phosphorylation or boration of the hydroxy group of compound (I) (e.g., compounds derived by acetylation, palmitoylation, propanoylation, pivaloylation, succinylation, fumarylation, alanylation or dimethylaminomethylcarbonylation of the hydroxy group of compound (I)); and compounds derived by esterification or amidation of the carboxy group of compound (I) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxy group of compound (I)). These compounds can be produced from compound (I) by methods known per se.

The prodrug of compound (I) may be one capable of being converted to compound (I) under physiological conditions, as described in "Iyakuhin No Kaihatsu (Development of Drugs)", vol. 7, Molecular Designing, published by Hirokawa Shoten, 1990, pages 163-198.

As the prodrug of compound (I'), the same as the prodrug of compound (I) is used.

Compounds (I), compounds (I') and prodrug thereof (hereinafter also referred to as "compound of the present invention") are of low toxicity and can be used as an agent for preventing or treating the various diseases mentioned below in mammals (e.g., humans, mice, rats, rabbits, dogs, cats, bovines, horses, swine, monkeys), as such or in the form of pharmaceutical compositions prepared by admixing with a pharmacologically acceptable carrier, etc.

Examples of the dosage forms of the pharmaceutical composition include oral preparations such as tablets (including sublingual tablet, orally disintegrating tablet), capsules (including soft capsules and microcapsules), granules powders, troches, syrups, emulsions, suspensions; and non-oral preparations such as injections (e.g., subcutaneous injections, intravenous injections, intramuscular injections, intraperitoneal injections, drip infusions), external preparations (e.g., dermal preparations, ointments), suppositories (e.g., rectal suppositories, vaginal suppositories), pellets, preparations for nasal administration, preparations for transpulmonary administration (inhalant) and eye drops. These can be orally or parenterally administered safely.

These preparations may be controlled-release preparations (e.g., sustained-release microcapsules) such as rapid release preparations, sustained-release preparations and the like.

The pharmaceutical composition can be prepared by conventional methods in the fields of pharmaceutical manufacturing techniques, for example, methods described in the Japanese Pharmacopoeia While the content of the compound of the present invention in a pharmaceutical composition varies depending on the dosage form, dose of the compound the present invention and the like, it is, for example, about 0.1-100 weight %.

The compound of the present invention has a superior IκB kinase inhibitory activity and can be used as an agent for preventing or treating various diseases in mammals (e.g., humans, mice, rats, rabbits, dogs, cats, bovines, horses, swine, monkeys). Furthermore, since the compound of the present invention has a selective IκB kinase inhibitory activity, it shows low toxicity (e.g., acute toxicity, chronic toxicity, cardiotoxicity, cancinogenecity, genetic toxicity) and causes a fewer side effects.

As used herein, as IκB kinase, IKKα (IKK-1), IKKβ (IKK-2), regulatory subunit IKKγ (NEMO) and the like can be mentioned.

The compound of the present invention also has a NF-κB inhibitory (transcription inhibitory) activity, TNF-α inhibitory (production inhibitory) activity and the like.

The compound of the present invention can be used as, for example, an agent for preventing or treating diabetes (e.g., type I diabetes, type II diabetes, gestational diabetes etc.); an agent for preventing or treating hyperlipidemia (e.g., hypertriglyceridemia, hypercholesterolemia, hypo-high-density-lipoproteinemia, postprandial hyperlipemia etc.); an agent for preventing or treating arteriosclerosis; an agent for preventing or treating impaired glucose tolerance (IGT); an insulin secretagogue; and an agent for preventing progress from impaired glucose tolerance to diabetes.

The compound of the present invention can be used as an agent for preventing or treating, for example, diabetic complications [e.g., neuropathy, nephropathy, retinopathy, cataract, macroangiopathy, osteopenia, diabetic hyperosmolar coma, infectious disease (e.g., respiratory infectious disease, urinary tract infectious disease, gastrointestinal infectious disease, skin/soft tissue infectious disease, inferior limb infectious disease), diabetic gangrene, xerostomia, lowered sense of hearing, cerebrovascular disorder, peripheral blood circulation disorder], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, renal disease (e.g., diabetic nephropathy, glomerulonephritis, glomerulosclerosis, nephrotic syndrome, hypertensive nephrosclerosis, end stage renal disease), muscular dystrophy, cardiac infarction, angina pectoris, cerebrovascular disorder (e.g., cerebral infarction, stroke), insulin resistance syndrome, syndrome X, metabolic syndrome (a condition associated with at least one of type II diabetes, impaired glucose tolerance and insulin resistance and at least two of obesity, lipid metabolism abnormality, hypertension and microalbuminuria in combination), Cushing's syndrome, hyperinsulinemia, sensory disorder in hyperinsulinemia, tumors (e.g., leukemia, breast cancer, prostate cancer, skin cancer), irritable bowel syndrome, acute or chronic diarrhea, inflammatory diseases (e.g., spondylitis deformans, osteoarthritis, atopic dermatitis, chronic obstructive pulmonary disease, endotoxin shock, sepsis, low back pain, gout, postoperative or posttraumatic inflammation, swelling, neuralgia, pharyngolaryngitis, cystitis, hepatitis (including nonalcoholic fatty hepatitis), pneumonia, pancreatitis, inflammatory bowel disease, ulcerative colitis, gastric mucosal injury (including gastric mucosal injury caused by aspirin)), autoimmune diseases (e.g., rheumatoid arthritis, systemic lupus erythematosus, systemic sclerosis), viral diseases (e.g., cytomegalovirus pneumonia, common cold by adenovirus, conjunctivitis, acquired immunodeficiency syndrome, uveitis), endotherial hypertrophy, multiple sclerosis, atherosclerosis, Alzheimer's disease, diseases associated with abnormal vascular proliferation such as retinopathy and the like, anorexia, malaise, chronic fatigue syndrome, metabolic bone diseases such as bone cancer pain and the like, deterioration of organ during pretransplantation preservation, visceral fat syndrome and the like. In addition, the compound of the present invention is used an immunosuppressant.

The compound of the present invention is also used for the secondary prophylaxis and suppression of progression of the above-mentioned various diseases (e.g., cardiovascular event such as cardiac infarction and the like).

While the dose of the compound of the present invention varies depending on administration subject, administration route, target disease, clinical condition, etc., it is, for instance, about 0.01 to 100 mg/kg body weight, preferably 0.05 to 30 mg/kg body weight, more preferably 0.1 to 10 mg/kg body weight, as a usual dosage per administration for oral administration to an adult diabetic patient. This dose is desirably administered 1 to 3 times a day.

The compound of the present invention can be used in combination with a drug such as a therapeutic agent for diabetes, a therapeutic agent for diabetic complications, an anti-hyperlipidemic agent, a hypotensive agent, an antiobesity agent, a chemotherapeutic agent, an immunotherapeutic agent, antithrombotic agent and the like (hereinafter abbreviated as a combination drug). On such occasions, the timing of administration of the compound of the present invention and that of the combination drug is not limited. They may be administered simultaneously or at staggered times to the administration subject. Moreover, the compound of the present invention and a combination drug may be administered as two kinds of preparations respectively containing an active ingredient, or as a single preparation containing both active ingredients.

The dose of the combination drug can be appropriately selected based on the dose which is clinically employed. The proportion of the compound of the present invention and the combination drug can be appropriately selected according to the administration subject, administration route, target disease, clinical condition, combination, and other factors. In cases where the administration subject is human, for instance, the combination drug may be used in an amount of 0.01 to 100 parts by weight per part by weight of the compound of the present invention.

Examples of the therapeutic agent for diabetes include insulin preparations (e.g., animal insulin preparations extracted from the bovine or swine pancreas; human insulin preparations synthesized by a genetic engineering technique using *Escherichia coli* or a yeast, insulin zinc; protamine zinc insulin; fragment or derivative of insulin (e.g., INS-1 and the like); oral insulin preparations), insulin sensitizers (e.g., pioglitazone or its salt (preferably hydrochloride), rosiglitazone or its salt (preferably maleate), Reglixane, GI-262570, Netoglitazone, DRF-2593, BM-13.1258, KRP-297, R-119702, CS-011, FK-614, compounds described in WO99/58510 (e.g., (E)-4-[4-(5-methyl-2-phenyl-4-oxazolyl-methoxy)benzyloxyimino]-4-phenylbutyric acid), compounds described in WO01/38325, Tesaglitazar, BMS-298585, BM-13-1258, LM-4156, MBX-102, LY-519818, MX-6054, LY-510929, Balaglitazone, T-131 or its salt, THR-0921), PPARγ agonists, PPARγ antagonists, PPARγ/α dual agonists, α-glucosidase inhibitors (e.g., voglibose, acarbose, miglitol, emiglitate), biguanides (e.g., phenformin, metformin, buformin or their salts (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or its calcium salt hydrate], GPR40 agonist, GLP-1 receptor agonists [e.g., GLP-1, GLP-1MR agent, NN-2211, AC-2993 (exendin-4), BIM-51077, Aib(8,35) hGLP-1(7,37)NH$_2$, CJC-1131], amylin agonists (e.g., pramlintide), phosphotyrosine phosphatase inhibitors (e.g., sodium vanadate), dipeptidylpeptidase IV inhibitors (e.g., NVP-DPP-278, PT-100, P32/98, LAF237, P93/01, TS-021), β3 agonists (e.g., CL-316243, SR-58611-A, UL-TG-307, SB-226552, AJ-9677, BMS-196085, AZ40140), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-HSD1 inhibitors (e.g., BVT-3498), adiponectin or its agonist, IKK inhibitors (e.g., AS-2868), leptin resistance improving drug, somatostatin receptor agonist (e.g., compounds described in WO01/25228, WO03/42204, WO98/44921, WO98/45285, WO99/22735 etc.), glucokinase activator (e.g., Ro-28-1675) and the like.

Examples of the therapeutic agent for diabetic complications include aldose reductase inhibitors (e.g., tolrestat, epalrestat, zenarestat, zopolrestat, minalrestat, fidarestat (SNK-860), AS-3201, CT-112), neurotrophic factors and its increasing agents (e.g., NGF, NT-3, BDNF, neurotrophin production secretion promoters (e.g., 4-(4-chlorophenyl)-2-(2-methyl-1-imidazolyl)-5-[3-(2-methylphenoxy)propyl]oxazole) described in WO01/14372), neuranegenesis promoters (e.g., Y-128), PKC inhibitors (e.g., LY-333531), AGE inhibitors (e.g., ALT946, pimagedine, pyratoxathine, N-phenacylthiazolium bromide (ALT766), ALT-711, EXO-226, Pyridorin, Pyridoxamine), active oxygen scavengers (e.g. thioctic acid), cerebral vasodilators (e.g., tiapuride, mexiletine), somatostatin receptor agonist (e.g., BIM23190) and apoptosis signal regulating kinase-1 (ASK-1) inhibitor.

Examples of the antihyperlipidemic agent include HMG-CoA reductase inhibitors (e.g., pravastatin, simvastatin, lovastatin, atorvastatin, fluvastatin, itavastatin pitavastatin, rosuvastatin or their salts (e.g., sodium salt, calcium salt)), squalene synthase inhibitors (e.g., compound described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), ACAT inhibitors (e.g. Avasimibe, Eflucimibe), anion exchange resins (e.g., cholestylamine), probuchol, nicotinic pharmaceutical agents (e.g., nicomol, niceritrol), ethyl icosapentate, phytosterol (e.g., soysterol, γ-oryzanol) and the like.

Examples of the hypotensive agent include angiotensin converting enzyme inhibitors (e.g., captopril, enalapril, delapril), angiotensin II antagonists (e.g., candesartan cilexetil, losartan, eprosartan, valsartan, termisartan, irbesartan, olmesartan medoxomil, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121) and clonidine.

Examples of the anti obesity agent include antiobesity drugs acting on the central nervous system (e.g. dexfenfluramine, fenfluramine, phentermine, sibutramine, anfepramon, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonists; 11β-HSD1 inhibitors (e.g., BVT-3498)), pancreatic lipase inhibitors (e.g. orlistat, ALT-962), β3 agonists (e.g. CL-316243, SR-58611-A, UL-TG-307, SB-226552, AJ-9677, BMS-196085, AZ-40140), anorectic peptides (e.g. leptin, CNTF (Ciliary Neurotrophic Factor)), cholecystokinin agonists (e.g. lintitript, FPL-15849), feeding deterrent (e.g., P-57) and the like.

Examples of the chemotherapeutic agent include alkylating agents (e.g., cyclophosphamide, ifosamide), metabolic antagonists (e.g., methotrexate, 5-fluorouracil or derivative thereof), antitumor antibiotics (e.g., mitomycin, adriamycin), plant-derived antitumor agents (e.g., vincristine, vindesine, Taxol), cisplatin, carboplatin, etoposide. Among these, 5-fluorouracil derivatives such as Furtulon and Neo-Furtulon are preferable.

Examples of the immunotherapeutic agent include microorganism- or bacterium-derived components (e.g., muramyl dipeptide derivatives, Picibanil), immunopotentiator polysaccharides (e.g., lentinan, schizophyllan, krestin), genetically engineered cytokines (e.g., interferons, interleukins (IL)), colony stimulating factors (e.g., granulocyte colony stimulating factor, erythropoietin), etc. Among these, interleukins such as IL-1, IL-2, IL-12 and the like are preferable.

As the antithrombotic agent, for example, heparin (e.g., heparin sodium, heparin calcium, dalteparin sodium), warfarin (e.g., warfarin potassium), antithrombin agents (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like can be mentioned.

Furthermore, drugs confirmed to exhibit a cachexia ameliorating effect in animal models and clinical applications, namely, cyclooxygenase inhibitors (e.g., indomethacin), progesterone derivatives (e.g., megestrol acetate), glucocorticoids (e.g. dexamethasone), metoclopramide pharmaceuticals, tetrahydrocannabinol pharmaceuticals, fat metabolism ameliorating agents (e.g., eicosapentanoic acid), growth hormones, IGF-1, and antibodies to the cachexia-inducing factor TNF-α, LIF, IL-6 or oncostatin M and the like, can be also used in combination with the compound of the present invention.

The above combination drugs can be used as a mixture of two or more species in an appropriate ratio.

The combination drug is preferably an insulin preparation, an insulin sensitizer, an α-glucosidase inhibitor, a biguanide, an insulin secretagogue (preferably sulfonylurea), and the like.

By combining the compound of the present invention and a combination drug, a superior effect such as (1) the dose of the compound of the present invention and/or a combination drug can be reduced as compared to single administration of the compound of the present invention or a combination drug, (2) a sustained treatment effect can be designed by selecting a combination drug having different action and mechanism from the compound of the present invention, (3) a synergistic effect can be afforded by a combined use of the compound of the present invention and a combination drug, and the like, can be achieved.

The production methods of compound (I) are explained in the following.

Compounds (I) can be produced by a method known per se, such as Method A-Method I shown below or a method analogous thereto. In each of the following production methods, a starting compound may be used in the form of a salt and as such salt, those exemplified for the salts of compound (I) can be used.

A compound obtained in each Step can be isolated and purified by well-known separation and purification methods, such as concentration, concentration under reduced pressure, solvent extraction, crystallization, recrystallization, phase transfer, chromatography and the like.

The compound obtained in each Step can be directly used for the next reaction without isolation and in the form of a reaction mixture containing the compound.

Compound (I-1) which is compound (I) wherein $R^4$ is a hydrogen atom and $R^5$ is a hydroxymethyl group; compound (I-2) which is compound (I) wherein $R^4$ is a hydrogen atom and $R^5$ is a formyl group; compound (I-3) which is compound (I) wherein $R^4$ is a hydrogen atom and $R^5$ is $R^{10}CH(OH)$—; compound (I-4) which is compound (I) wherein $R^4$ is a hydrogen atom and $R^5$ is $R^{10}CO$—; compound (I-5) which is compound (I) wherein $R^4$ is a hydrogen atom and $R^5$ is $R^{10}C(=NOR^8)$—; and compound (I-6) which is compound (I) wherein $R^4$ is a hydrogen atom and $R^5$ is $R^{10}C(=NNHR^9)$— can be produced by, for example, Method A below or a method analogous thereto.

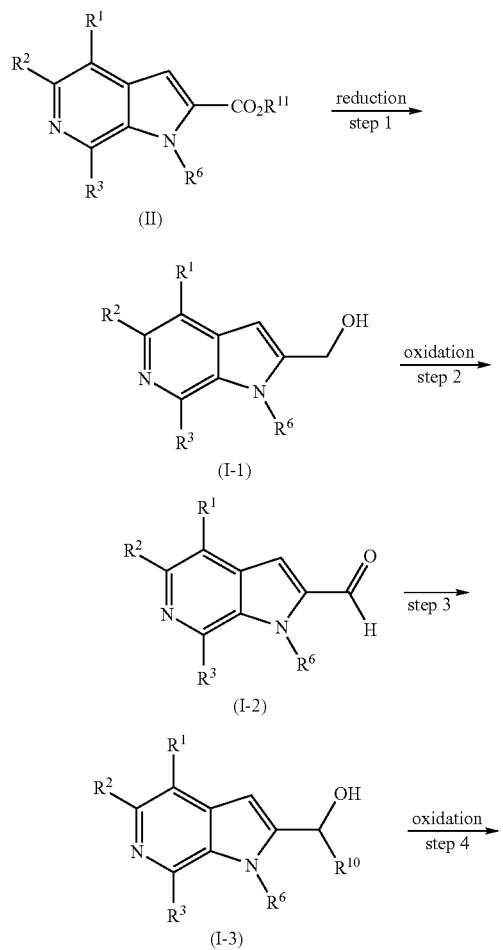

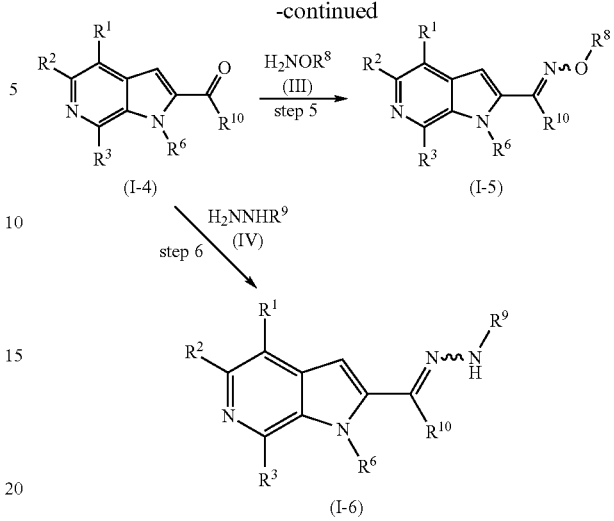

wherein $R^{11}$ is a hydrogen atom or a $C_{1-6}$ alkyl group (e.g., methyl, ethyl) and other symbols are as defined above.

In this method, compound (II) is subjected to reduction reaction to give compound (I-1), compound (I-1) is subjected to an oxidation reaction to give compound (I-2), compound (I-2) is reacted with an organic metal reagent to give compound (I-3), compound (I-3) is subjected to an oxidation reaction to give compound (I-4), and compound (I-4) is reacted with compound (III) to give compound (I-5). Alternatively, compound (I-4) is reacted with compound (IV) to give compound (I-6)

(Step 1)

In this Step, compound (II) is subjected to reduction reaction to give compound (I-1). This reaction is carried out by a method known per se. That is, this reaction is carried out according to a conventional method in the presence of a reducing agent in a solvent that does not adversely affect the reaction or without solvent.

As the reducing agent, for example, sodium borohydride, lithium borohydride, lithium aluminum hydride, diisobutylaluminum hydride and the like can be mentioned.

The amount of the reducing agent to be used is generally about 0.5 to about 20 molar equivalents, preferably about 1 to about 10 molar equivalents, relative to compound (II).

As the solvent that does not adversely affect the reaction, for example, aromatic hydrocarbons such as benzene, toluene, xylene and the like; halogenated hydrocarbons such as chloroform, dichloromethane and the like; ethers such as tetrahydrofuran, dioxane, diethyl ether and the like; water; alcohols such as methanol, ethanol, isopropanol and the like, and the like can be mentioned. Two or more kinds of these solvents may be mixed before use at an appropriate ratio.

The reaction temperature is generally about −50 to about 150° C., preferably about −10 to about 100° C.

The reaction time is generally about 0.5 to about 20 hrs.

(Step 2)

In this step, the compound (I-1) is subjected to an oxidation reaction to give compound (I-2). This reaction is carried out by a method known per se. That is, this reaction is carried out according to a conventional method in the presence of an oxidant in a solvent that does not adversely affect the reaction or without solvent.

As the oxidant, for example, metal oxidants such as manganese dioxide, pyridinium chlorochromate, pyridinium dichromate, ruthenium oxide and the like can be mentioned.

The amount of the oxidant to be used is generally about 0.5-about 20 molar equivalents, preferably about 1-about 10 molar equivalents, relative to compound (I-1).

As the solvent that does not adversely affect the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; and the like can be mentioned. Two or more kinds of these solvents may be mixed before use at an appropriate ratio.

The reaction temperature is generally about −50 to about 150° C., preferably about −10 to about 100° C.

The reaction time is generally about 0.5 to about 20 hrs.

(Step 3)

In this Step, compound (I-2) is reacted with an organic metal reagent to give compound (I-3). This reaction is carried out by a method known per se. That is, this reaction is carried out according to a conventional method in a solvent that does not adversely affect the reaction or without solvent.

As the organic metal reagent, Grignard reagents represented by the formula: HalMgR$^{10}$ (Hal is a halogen atom (e.g., chlorine, bromine) and R$^{10}$ is as defined above), organic lithium reagents represented by the formula: LiR$^{10}$ (the symbol is as defined above) and the like can be mentioned. The organic metal reagent can be produced according to a method known per se.

As the solvent that does not adversely affect the reaction, for example, aromatic hydrocarbons such as benzene, toluene, xylene and the like; ethers such as tetrahydrofuran, dioxane, diethyl ether and the like; and the like can be mentioned. Two or more kinds of these solvents may be mixed before use at an appropriate ratio.

The amount of the organic metal reagent to be used is generally about 0.5 to about 20 molar equivalents, preferably about 1 to about 10 molar equivalents, relative to compound (I-2).

The reaction temperature is generally about −100 to about 150° C., preferably about −80 to about 100° C.

The reaction time is generally about 0.5 to about 20 hrs.

(Step 4)

In this step, compound (I-3) is subjected to an oxidation reaction to give compound (I-4). This reaction is carried out in the same manner as in the aforementioned Step 2.

(Step 5)

In this step, compound (I-4) is reacted with compound (III) to give compound (I-5). This reaction is carried out by a method known per se. That is, this reaction is carried out according to a conventional method in a solvent that does not adversely affect the reaction or without solvent.

As compound (III), for example, hydroxylamine, N-alkylhydroxylamine or a salt thereof can be mentioned. As a salt here, for example, hydrochloride, oxalate and the like can be mentioned.

As the solvent that does not adversely affect the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; alcohols such as ethanol, methanol and the like; amides such as N,N-dimethylformamide and the like; sulfoxides such as dimethyl sulfoxide and the like; aliphatic carboxylic acids such as acetic acid and the like; water and the like can be mentioned. Two or more kinds of these solvents may be mixed before use at an appropriate ratio.

The amount of the compound (III) to be used is generally about 1 to about 20 molar equivalents, preferably about 2 to about 10 molar equivalents, relative to compound (I-4).

The reaction temperature is generally about −50 to about 150° C., preferably about −10 to about 100° C.

The reaction time is generally about 0.5 to about 20 hrs.

This reaction may be carried out in the presence of an acid or a neutralizing agent. As the acid, for example, hydrochloric acid, sulfuric acid, acetic acid and the like can be mentioned. As the neutralization agent, for example, bases such as pyridine, triethylamine, sodium carbonate, sodium acetate and the like can be mentioned.

(Step 6)

In this step, compound (I-4) is reacted with compound (IV) to give compound (I-6). This reaction is carried out by a method known per se. That is, this reaction is carried out according to a conventional method in a solvent that does not adversely affect the reaction or without solvent.

As compound (IV), for example, aminoguanidine, semicarbazide and a salt thereof can be mentioned. As a salt here, for example, hydrochloride, acetate and the like can be mentioned.

As the solvent that does not adversely affect the reaction, those exemplified in the aforementioned Step 5 are used.

The amount of the compound (IV) to be used is generally about 1 to about 20 molar equivalents, preferably about 1.2 to about 10 molar equivalents, relative to compound (I-4).

The reaction temperature is generally about −50 to about 150° C., preferably about −10 to about 100° C.

The reaction time is generally about 0.5 to about 20 hrs.

This reaction may be carried out in the presence of an acid or a neutralizing agent. As the acid, for example, hydrochloric acid, sulfuric acid, acetic acid and the like can be mentioned. As the neutralization agent, for example, bases such as pyridine, triethylamine, sodium carbonate, potassium carbonate, sodium acetate and the like can be mentioned.

The compound (II), compound (III) and compound (IV) used as starting compounds in the above-mentioned Method A can be produced by a method known per se.

For example, the compound (II'), which is a compound (II) wherein R$^{11}$ is a C$_{1-6}$ alkyl group and R$^6$ is a hydrogen atom, can be produced by the following Method B or a method analogous thereto.

[Method B]

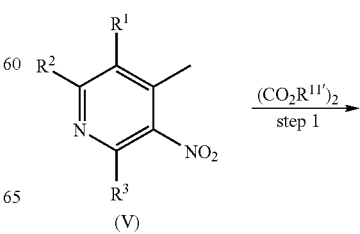

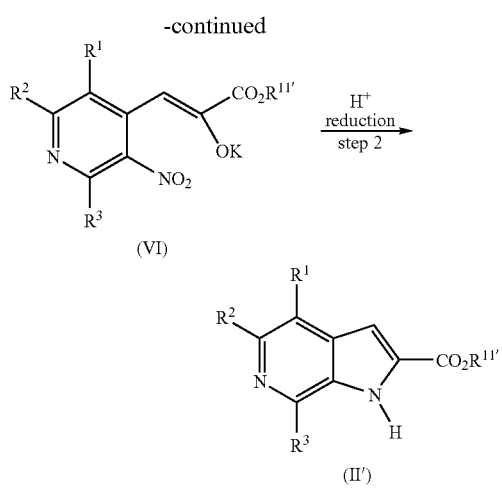

wherein $R^{11'}$ is a $C_{1-6}$ alkyl group and other symbols are as defined above.

In this method, compound (V) is reacted with an oxalic acid ester and a potassium salt to give compound (VI), and compound (VI) is subjected to reduction reaction under acidic conditions to give compound (II').

(Step 1)

In this step, compound (V) is reacted with an oxalic acid ester and a potassium salt to give compound (VI). This reaction is carried out by a method known per se. That is, this reaction is carried out according to a conventional method in the presence of a potassium salt in a solvent that does not adversely affect the reaction or without solvent.

As the oxalic acid ester, a compound represented by the formula $(CO_2R^{11'})_2$ wherein the symbol is as defined above is used. As concrete examples thereof, dimethyl oxalate, diethyl oxalate and the like can be mentioned.

As the potassium salt, for example, potassium tert-butoxide, potassium ethoxide and the like can be mentioned.

As the solvent that does not adversely affect the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; alcohols such as ethanol, methanol and the like; amides such as N,N-dimethylformamide and the like; sulfoxides such as dimethyl sulfoxide and the like; and the like can be mentioned. Two or more kinds of these solvents may be mixed before use at an appropriate ratio.

The amount of the oxalic acid ester to be used is generally about 1 to about 20 molar equivalents, preferably about 1.2 to about 10 molar equivalents, relative to compound (V).

The amount of the potassium salt to be used is generally about 1 to about 20 molar equivalents, preferably about 1 to about 10 molar equivalents, relative to compound (V).

The reaction temperature is generally about −50 to about 150° C., preferably about −10 to about 100° C.

The reaction time is generally about 0.5 to about 20 hrs.

(Step 2)

In this step, compound (VI) is subjected to reduction reaction under acidic conditions to give compound (II'). This reaction is carried out by a method known per se. That is, this reaction is carried out according to a conventional method in the presence of a reducing agent and an acid in a solvent that does not adversely affect the reaction or without solvent.

As the reducing agent, for example, iron, zinc and the like can be mentioned.

As the acid, for example, acetic acid, hydrochloric acid and the like can be mentioned.

As the solvent that does not adversely affect the reaction, those exemplified in the aforementioned Method A, step 5, are used.

The amount of the reducing agent to be used is generally about 1 to about 20 molar equivalents, preferably about 1 to about 10 molar equivalents, relative to compound (VI).

The amount of the acid to be used is generally about 1 to about 100 molar equivalents, preferably about 1 to about 20 molar equivalents, relative to compound (VI).

The reaction temperature is generally about 0 to about 150° C., preferably about 10 to about 100° C.

The reaction time is generally about 0.5 to about 20 hrs.

By further subjecting compound (II') obtained by the above-mentioned Method B to hydrolysis, compound (II) wherein $R^6$ and $R^{11}$ are hydrogen atoms can be produced. Here, hydrolysis is performed according to a method known per se.

The compound (V) and an oxalic acid ester which are used as starting compounds in the above-mentioned Method B can be produced according to a method known per se.

For example, compound (III) can be produced by means of the following Method C or a method analogous thereto.

[Method C]

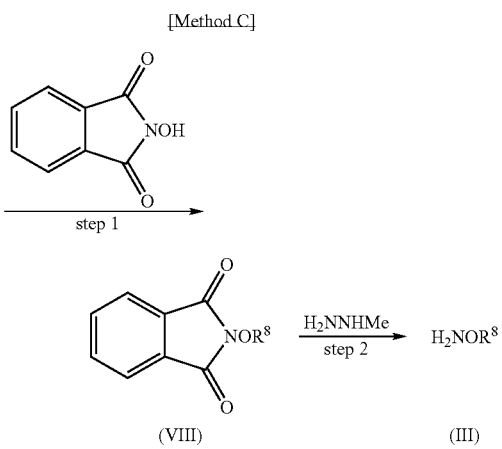

wherein the symbol in the formula is as defined above.

In this method, compound (VII) is reacted with N-hydroxyphthalimide to give compound (VIII) and compound (VIII) is reacted with methylhydrazine to give compound (III).

(Step 1)

In this step, compound (VII) is reacted with N-hydroxyphthalimide to give compound (VIII). This reaction is carried out by a method known per se. That is, this reaction is carried out in the presence of an organic phosphorus compound and an electrophilic agent in a solvent that does not adversely affect the reaction or without solvent.

As the organic phosphorus compound, for example, triphenylphosphine, tributylphosphine and the like can be mentioned.

As the electrophilic agent, for example, diethyl azodicarboxylate, diisopropyl azodicarboxylate, azodicarbonyldipiperidine and the like can be mentioned.

As the solvent that does not adversely affect the reaction, for example, ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like; and the like can be mentioned. Two or more kinds of these solvents may be mixed before use at an appropriate ratio.

The amount of N-hydroxyphthalimide to be used is generally about 1 to about 5 molar equivalents, preferably about 1 to about 3 molar equivalents, relative to compound (VII).

The amount of the organic phosphorus compound and electrophilic agent to be used is generally about 1 to about 10 molar equivalents, preferably about 1 to about 5 molar equivalents, relative to compound (VII).

The reaction temperature is generally about −50 to about 150° C., preferably about −10 to about 100° C.

The reaction time is generally about 0.5 to about 40 hrs.

(Step 2)

In this step, compound (VIII) is reacted with methylhydrazine to give compound (III). This reaction is carried out by a method known per se. That is, this reaction is carried out in a solvent that does not adversely affect the reaction or without solvent.

As the solvent that does not adversely affect the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; alcohols such as ethanol, methanol and the like; amides such as N,N-dimethylformamide and the like; sulfoxides such as dimethyl sulfoxide and the like; water and the like can be mentioned. Two or more kinds of these solvents may be mixed before use at an appropriate ratio.

The amount of methylhydrazine to be used is generally about 1 to about 5 molar equivalents, preferably about 1 to about 3 molar equivalents, relative to compound (VIII).

The reaction temperature is generally about −50 to about 150° C., preferably about −10 to about 100° C.

The reaction time is generally about 0.5 to about 40 hrs.

The compound (VII) used as a starting compound in the above-mentioned Method C can be produced according to a method known per se.

Compound (I-7) which is compound (I) wherein $R^4$ is a hydrogen atom and $R^5$ is Het-CO— and compound (I-7') which is compound (I) wherein $R^4$ is a hydrogen atom and $R^5$ is Ar—$(CH_2)$n-NH—CO— are produced by, for example, the following Method D or a method analogous thereto.

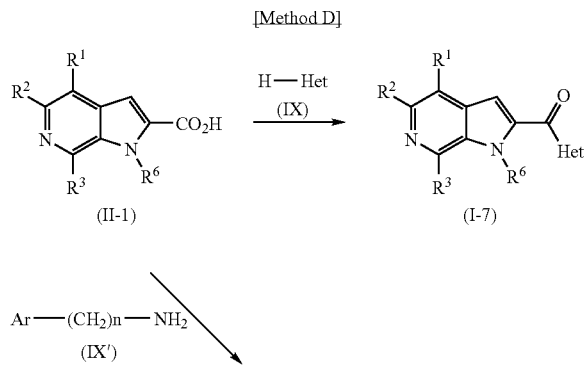

-continued

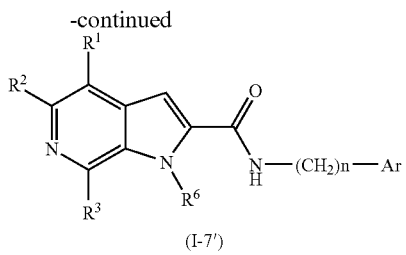

wherein the symbols in the formula are as defined above.

In this method, compound (II-1) which is compound (II) wherein $R^{11}$ is a hydrogen atom is reacted with compound (IX) to give compound (I-7), or compound (II-1) is reacted with compound (IX') to give compound (I-7'). This reaction is carried out by a method known per se. That is, this reaction is generally carried out in the presence of a condensation agent in a solvent that does not adversely affect the reaction or without solvent.

As the condensation agent, for example, carbodiimide condensation reagents such as dicyclohexylcarbodiimide, diisopropylcarbodiimide, 1-ethyl-3-dimethylaminopropylcarbodiimide, hydrochloride thereof and the like; phosphoric acid condensation reagents such as diethyl cyanophosphate, diphenyl phosphoryl azide and the like; carbonyldiimidazole, 2-chloro-1,3-dimethylimidazolium tetrafluoroborate and the like can be mentioned.

As the solvent that does not adversely affect the reaction, for example, amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate; water and the like can be mentioned. Two or more kinds of these solvents may be mixed before use at an appropriate ratio.

The amount of compound (IX) and compound (IX') to be used is generally about 1 to about 10 molar equivalents, preferably about 1 to about 3 molar equivalents, relative to compound (II-1).

The amount of condensation agent to be used is generally about 1 to about 10 molar equivalents, preferably about 1 to about 3 molar equivalents, relative to compound (II-1).

When the aforementioned carbodiimide condensation reagents are used as the condensation agent, the reaction efficiency can be improved by adding, where necessary, a suitable condensation promoter (e.g., 1-hydroxy-7-azabenzotriazole, 1-hydroxybenzotriazole, N-hydroxysuccinimide, N-hydroxyphthalimide). In addition, when the aforementioned phosphoric acid condensation reagents are used as the condensation agent, the reaction efficiency can be generally improved by adding an organic amine base such as triethylamine and the like.

The amount of the above-mentioned condensation promoter and the organic amine base to be used is generally about 0.1 to about 10 molar equivalents, preferably about 0.3 to about 3 molar equivalents, relative to compound (II-1).

The reaction temperature is generally, about −30° C. to about 100° C.

The reaction time is generally about 0.5 to about 60 hrs.

The compound (II-1), compound (IX) and compound (IX') used as starting compounds in the above-mentioned Method D can be produced according to a method known per se.

Compound (I-8) which is compound (I) wherein $R^4$ is a hydrogen atom and $R^5$ is $R^{13}R^{14}NCH_2$— can be produced by, for example, the following Method E or a method analogous thereto.

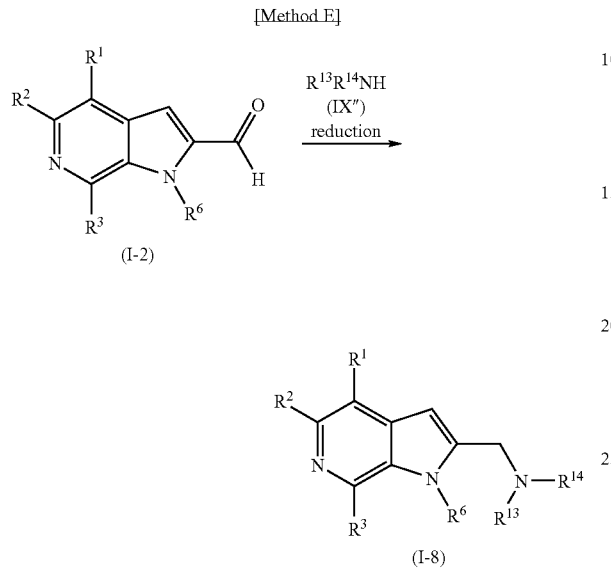

wherein the symbols in the formula are as defined above.

In this method, compound (I-2) is reacted with compound (IX″) to give compound (I-8). This reaction is carried out by a method known per se. That is, this reaction is generally carried out in the presence of a reducing agent in a solvent that does not adversely affect the reaction or without solvent.

As the reducing agent, for example, sodium borohydride, sodium triacetoxyborohydride, sodium cyanoborohydride and the like can be mentioned.

As the solvent that does not adversely affect the reaction, those exemplified in the aforementioned Method A, Step 1, can be used.

The amount of compound (IX″) to be used is generally about 1 to about 10 molar equivalents, preferably about 1 to about 3 molar equivalents, relative to compound (I-2).

The amount of the reducing agent to be used is generally about 0.5 to about 20 molar equivalents, preferably about 1 to about 10 molar equivalents, relative to compound (I-2).

The reaction temperature is generally, about −50° C. to about 150° C., preferably about −10° C. to about 100° C.

The reaction time is generally about 0.5 to about 20 hrs.

The compound (IX″) used as a starting compound in the above-mentioned Method E can be produced according to a method known per se.

Compound (I-10) which is compound (I) wherein $R^4$ is a hydrogen atom and $R^5$ is $R^7CH(NH_2)$—; and compound (I-11) which is compound (I) wherein $R^4$ is a hydrogen atom and $R^5$ is $R^7CH(NHCOR^{15})$— can be produced, for example, by the following Method F or a method analogous thereto.

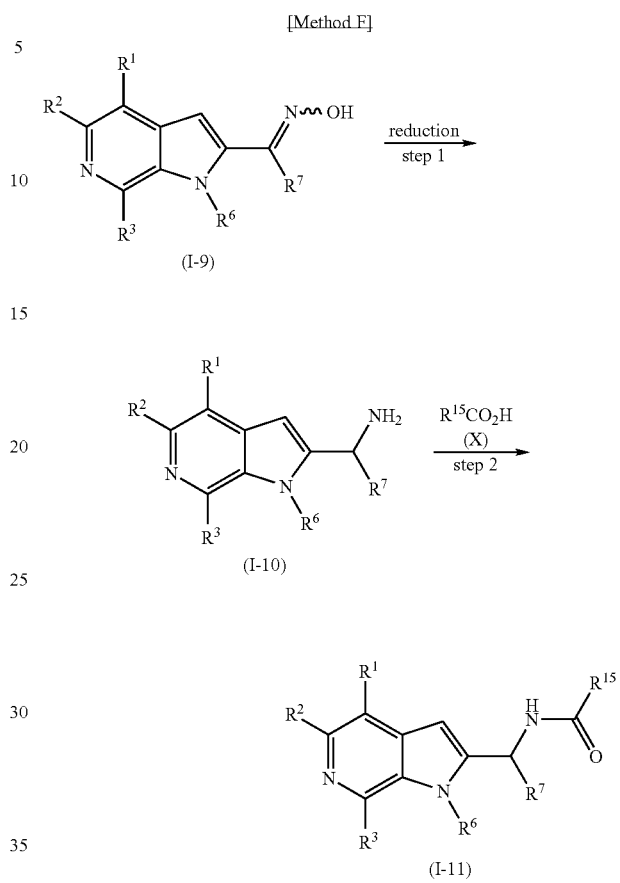

wherein the symbols in the formula are as defined above.

In this method, compound (I-9) which is compound (I) wherein $R^4$ is a hydrogen atom and $R^5$ is $R^7C(=NOH)$— is subjected to reduction reaction to give compound (I-10) and compound (I-10) is reacted with compound (X) to give compound (I-11).

(Step 1)

In this Step, compound (I-9) is subjected to reduction reaction to give compound (I-10). This reaction is carried out in the same manner as in the aforementioned Method A, Step 1.

(Step 2)

In this Step, compound (I-10) is reacted with compound (X) to give compound (I-11). This reaction is carried out in the same manner as in the aforementioned-Method D.

The compound (I-9) used as a starting compound in the above-mentioned Method F can be produced by, for example, the aforementioned Method A or a method analogous thereto. In addition, compound (X) can be produced according to a method known per se.

Compound (I-5') which is compound (I-5) wherein $R^8$ is a group bonded via a carbon atom, can be also produced by, for example, the following Method G or a method analogous thereto.

[Method G]

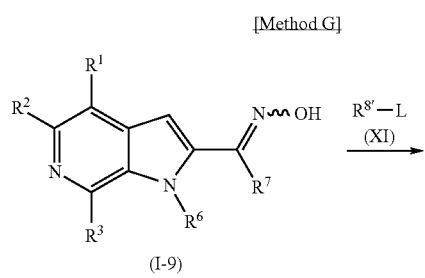

wherein L is a leaving group, $R^{8'}$ is a group bonded via a carbon atom, and other symbols are as defined above.

As the leaving group for L, halogen atoms (e.g., fluorine, chlorine, bromine, iodine); optionally halogenated $C_{1-6}$ alkylsulfonyloxy groups (e.g., methanesulfonyloxy, ethanesulfonyloxy, trichloromethanesulfonyloxy, trifluoromethanesulfonyloxy); $C_{6-10}$ arylsulfonyloxy group (e.g., phenylsulfonyloxy, naphthylsulfonyloxy) optionally having 1 to 3 substituents selected from $C_{1-6}$ alkyl groups (e.g., methyl, ethyl), $C_{1-6}$ alkoxy groups (e.g., methoxy, ethoxy) and nitro group; acyloxy groups (e.g., trichloroacetoxy, trifluoroacetoxy and the like) and the like can be mentioned.

In this method, compound (I-9) is reacted with compound (XI) to give compound (I-5'). This reaction is carried out by a method known per se. That is, this reaction is generally carried out in the presence of a base in a solvent that does not adversely affect the reaction or without solvent.

As the base, for example, alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like can be mentioned.

As the solvent that does not adversely affect the reaction, for example, aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like; and the like can be mentioned. Two or more kinds of these solvents may be mixed before use at an appropriate ratio.

The amount of compound (XI) and the base to be used is generally about 1 to about 10 molar equivalents, preferably about 1 to about 5 molar equivalents, relative to compound (I-9).

The reaction temperature is generally about −50° C. to about 150° C., preferably about −10° C. to about 100° C.

The reaction time is generally about 0.5 to about 20 hrs.

The compound (XI) used as a starting compound in the above-mentioned Method G can be produced according to a method known per se.

Compound (I-12) which is compound (I) wherein $R^1$, $R^2$, $R^3$ and $R^4$ are each a hydrogen atom, $R^5$ is $R^{10}CH(OH)$— and $R^6$ is $R^{15}SO_2$—; and compound (I-13) which is compound (I) wherein $R^1$, $R^2$, $R^3$, $R^4$ and $R^6$ are each a hydrogen atom and $R^5$ is $R^{10}CH(OH)$— can be produced by, for example, the following Method H or a method analogous thereto.

[Method H]

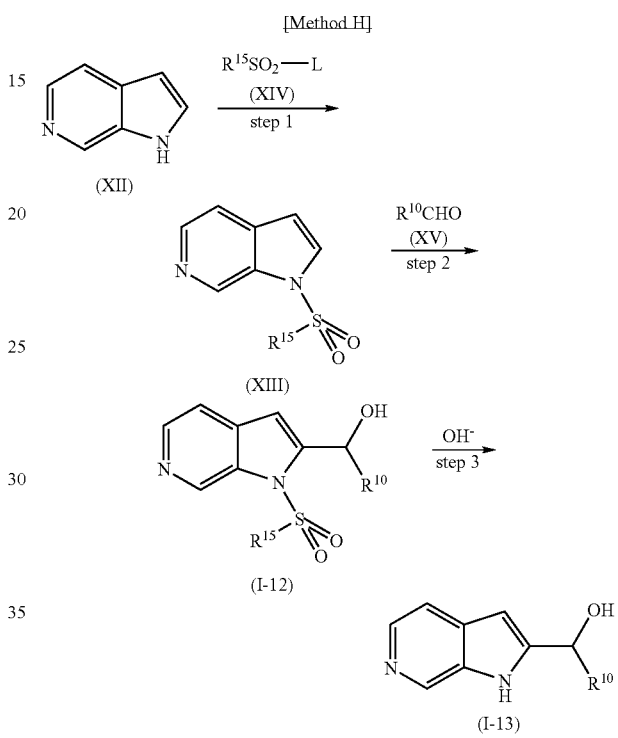

wherein the symbols in the formula are as defined above.

In this method, compound (XII) is reacted with compound (XIV) to give compound (XIII), and compound (XIII) is reacted with compound (XV) to give compound (I-12), and compound (I-12) is reacted with hydroxide ion to give compound (I-13).

(Step 1)

In this Step, compound (XII) is reacted with compound (XIV) to give compound (XIII). This reaction is carried out by a method known per se. That is, this reaction is generally carried out in the presence of a base in a solvent that does not adversely affect the reaction or without solvent.

As the base, for example, alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like; and alkali metal amides such as lithium diisopropylamide and the like can be mentioned.

As the solvent that does not adversely affect the reaction, those exemplified in the aforementioned Method G can be used.

The amount of compound (XIV) and the base to be used is generally about 1 to about 10 molar equivalents, preferably about 1 to about 5 molar equivalents, relative to compound (XII).

The reaction temperature is generally, about −100° C. to about 150° C., preferably about −80° to about 100° C.

The reaction time is generally about 0.5 to about 20 hrs.

(Step 2)

In this Step, compound (XIII) is reacted with compound (XV) to give compound (I-12). This reaction is carried out by a method known per se. That is, this reaction is generally carried out in the presence of a base in a solvent that does not adversely affect the reaction or without solvent.

As the base, for example, alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undec-7-ene, N,N,N',N'-tetramethylethylenediamine and the like; metal hydrides such as potassium hydride, sodium hydride and the like; alkali metal alkoxides such as sodium methoxide, sodium ethoxide, potassium tert-butoxide and the like; and alkali metal amides such as lithium diisopropylamide and the like can be mentioned. Two or more kinds of these bases may be mixed before use at an appropriate ratio.

As the solvent that does not adversely affect the reaction, those exemplified in the aforementioned Method G can be used.

The amount of compound (XV) and the base to be used is generally about 1 to about 10 molar equivalents, preferably about 1 to about 5 molar equivalents, relative to compound (XIII).

The reaction temperature is generally, about −100° C. to about 150° C., preferably about −80° C. to about 100° C.

The reaction time is generally about 0.5 to about 20 hrs.

(Step 3)

In this Step, compound (I-12) is reacted with hydroxide ion to give compound (I-13). This reaction is carried out by a method known per se. That is, this reaction is generally carried out in a solvent that does not adversely affect the reaction or without solvent.

As the hydroxide ion, for example, alkali metal hydroxides such as potassium hydroxide, sodium hydroxide, lithium hydroxide and the like; and the like can be mentioned.

As the solvent that does not adversely affect the reaction, those exemplified in the aforementioned Method A, Step 1, can be used.

The amount of the hydroxide ion to be used is generally about 1 to about 50 molar equivalents, preferably about 1 to about 10 molar equivalents, relative to compound (I-12).

The reaction temperature is generally about 0° C. to about 150° C., preferably about 10° C. to about 100° C.

The reaction time is generally about 0.5 to about 20 hrs.

The compound (XII), compound (XIV) and compound (XV) used as starting compounds in the above-mentioned Method H can be produced according to a method known per se.

Compound (I-15) which is compound (I) wherein $R^1$, $R^2$, $R^3$, $R^5$ and $R^6$ are each a hydrogen atom and $R^4$ is $R^{10}$CH(OH)—; compound (I-16) which is compound (I) wherein $R^1$, $R^2$, $R^3$, $R^5$ and $R^6$ are each a hydrogen atom and $R^4$ is $R^{10}$CO—; and compound (I-17) which is compound (I) wherein $R^1$, $R^2$, $R^3$, $R^5$ and $R^6$ are each a hydrogen atom and $R^4$ is $R^{10}$C(=NOR$^8$)—; and compound (I-18) which is compound (I) wherein $R^1$, $R^2$, $R^3$, $R^5$ and $R^6$ are each a hydrogen atom and $R^4$ is $R^{10}$C(=NNHR$^9$)— can be produced by, for example, the following Method I or a method analogous thereto.

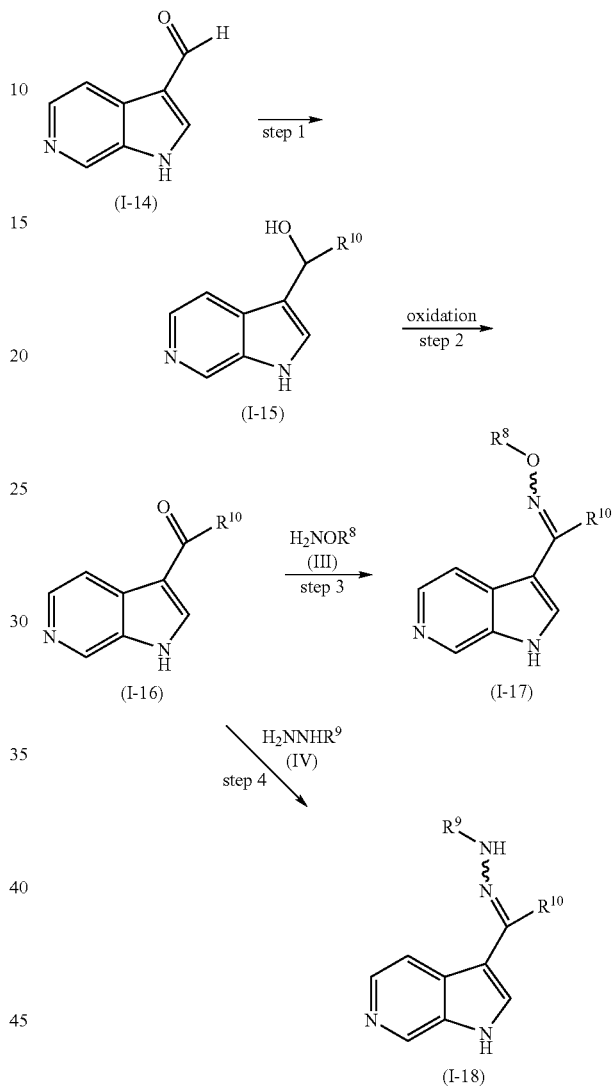

wherein the symbols in the formula are as defined above.

In this method, compound (I-14) is reacted with an organic metal reagent to give compound (I-15), compound (I-15) is subjected to oxidation reaction to give compound (I-16), and compound (I-16) is reacted with compound (III) to give compound (I-17). Alternatively, compound (I-16) is reacted with compound (IV) to give compound (I-18).

(Step 1)

In this Step, compound (I-14) is reacted with an organic metal reagent to give compound (I-15). This reaction is carried out in the same manner as in the aforementioned Method A, Step 3.

(Step 2)

In this Step, compound (I-15) is subjected to oxidation reaction to give compound (I-16). This reaction is carried out in the same manner as in the aforementioned Method A, Step 4.

(Step 3)

In this Step, compound (I-16) is reacted with compound (III) to give compound (I-17). This reaction is carried out in the same manner as in the aforementioned Method A, Step 5.

(Step 4)

In this Step, compound (I-16) is reacted with compound (IV) to give compound (I-18). This reaction is carried out in the same manner as in the aforementioned Method A, Step 6.

The compound (I-14) used as a starting compound in the above-mentioned Method I can be produced according to a method known per se.

In each of the aforementioned reactions, when a starting compound has an amino group, a carboxyl group, a hydroxy group or a carbonyl group as a substituent, a protecting group generally used for these groups in peptide chemistry and the like may be introduced. By removing the protecting group as necessary after the reaction, the object compound can be obtained.

As the amino-protecting group, for example, formyl group, $C_{1-6}$ alkyl carbonyl groups (e.g., acetyl, propionyl), $C_{1-6}$ alkoxy-carbonyl groups (e.g., methoxycarbonyl, ethoxycarbonyl, tert-butoxycarbonyl), benzoyl group, $C_{7-11}$ aralkyl-carbonyl groups (e.g., benzylcarbonyl), $C_{7-14}$ aralkyloxy-carbonyl groups (e.g., benzyloxycarbonyl, 9-fluorenylmethoxycarbonyl), trityl group, phthaloyl group, N,N-dimethylaminomethylene group, silyl groups (e.g., trimethylsilyl, triethylsilyl, dimethylphenylsilyl, tert-butyldimethylsilyl, tert-butyldiethylsilyl), $C_{2-6}$ alkenyl groups (e.g., 1-allyl) and the like can be mentioned. These groups may be substituted by 1 to 3 substituents selected from halogen atoms (e.g., fluorine, chlorine, bromine, iodine), $C_{1-6}$ alkoxy groups (e.g., methoxy, ethoxy, propoxy), nitro group and the like.

As the carboxyl-protecting group, for example, $C_{1-6}$ alkyl groups (e.g., methyl, ethyl, propyl, isopropyl, butyl, tert-butyl), $C_{7-11}$ aralkyl groups (e.g., benzyl), phenyl group, trityl group, silyl groups (e.g., trimethylsilyl, triethylsilyl, dimethylphenylsilyl, tert-butyldimethylsilyl, tert-butyldiethylsilyl, tert-butyldiphenylsilyl), $C_{2-6}$ alkenyl groups (e.g., 1-allyl) and the like can be mentioned. These groups may be substituted by 1 to 3 substituents selected from halogen atoms (e.g., fluorine, chlorine, bromine, iodine), $C_{1-6}$ alkoxy groups (e.g., methoxy, ethoxy, propoxy), nitro group and the like.

As the hydroxy-protecting group, for example, $C_{1-6}$ alkyl groups (e.g., methyl, ethyl, propyl, isopropyl, butyl, tert-butyl), phenyl group, trityl group, $C_{7-11}$ aralkyl groups (e.g., benzyl), formyl group, $C_{1-6}$ alkyl-carbonyl groups (e.g., acetyl, propionyl), benzoyl group, $C_{7-11}$ aralkyl-carbonyl groups (e.g., benzylcarbonyl), 2-tetrahydropyranyl group, 2-tetrahydrofuranyl group, silyl groups (e.g., trimethylsilyl, triethylsilyl, dimethylphenylsilyl, tert-butyldimethylsilyl, tert-butyldiethylsilyl), $C_{2-6}$ alkenyl groups (e.g., 1-allyl) and the like can be mentioned. These groups may be substituted by 1 to 3 substituents selected from halogen atoms (e.g., fluorine, chlorine, bromine, iodine), $C_{1-6}$ alkoxy groups (e.g., methoxy, ethoxy, propoxy), nitro group and the like.

As the carbonyl-protecting group, for example, cyclic acetals (e.g., 1,3-dioxane), non-cyclic acetals (e.g., di-$C_{1-6}$ alkyl acetals) and the like can be mentioned.

In addition, these protective groups can be removed by a method known per se, e.g., the method described in Protective Groups in Organic Synthesis, published by John Wiley and Sons (1980). For example, there may be used methods employing an acid, a base, ultraviolet rays, hydrazine, phenylhydrazine, sodium N-methyldithiocarbamate, tetrabutylammonium fluoride, palladium acetate, a trialkylsilyl halide (e.g., trimethylsilyl iodide, trimethylsilyl bromide), or the like, the reduction method, and the like.

When compound (I) contains an optical isomer, a stereoisomer, a position isomer, or a rotation isomer, these isomers are also contained as compound (I) and can each be obtained as a single substance by means of a method known per se of synthesis or separation. For example, when an optical isomer is present in compound (I), the optical isomer separated from said compound is also included in compound (I). These isomers can be produced by a method known per se.

The compound (I) may be a crystal and both single crystal and mixtures of crystals are encompassed in compound (I). The crystal of compound (I) (hereinafter sometimes to be abbreviated as crystal of the present invention) can be produced by crystallization, by applying a crystallization method known per se to compound (I).

The compound (I) may also be in the form of solvate (e.g., hydrate) or non-solvates, which are also encompassed in compound (I).

The compound (I) may be labeled with an isotope (e.g., $^{3}H$, $^{14}C$, $^{35}S$, $^{125}I$ and the like) and the like, which are also encompassed in compound (I).

The present invention is explained in detail by referring to the following Reference Examples, Examples, Experimental Examples and Formulation Examples, which are not to be construed as limitative. The present invention may be modified without deviating from the scope of the invention.

The abbreviations in Reference Examples and Examples mean the following.

s: singlet, d: doublet, t: triplet, q: quartet, m: multiplet, brs: broad singlet, J: coupling constant In Reference Examples and Examples, room temperature means a temperature of 1° C. to 30° C., and % means percent by weight, unless otherwise indicated particularly.

The gene manipulation methods described in the following Reference Examples followed a method described in a book (Maniatis et al., Molecular Cloning, Cold Spring Harbor Laboratory, 1989) or a method described in the attached protocol of the reagent.

The SEQ ID NOs of the sequence listing in the present specification show the following sequences.

[SEQ ID NO: 1]
A base sequence of primer used for PCR in Reference Example 1A below.
[SEQ ID NO: 2]
A base sequence of primer used for PCR in Reference Example 1A below.
[SEQ ID NO: 3]
A base sequence of primer used for PCR in Reference Example 2A below.
[SEQ ID NO: 4]
A base sequence of primer used for PCR in Reference Example 2A below.

REFERENCE EXAMPLE 1A

Cloning of Human IKKβ Gene and Preparation of Recombinant Baculovirus

Cloning of human IKKβ gene was performed by a PCR method using a primer set:

```
IKKB-U:
                                       (SEQ ID NO: 1)
5'- CAAAGCTAGCATGAGCTGGT CACCTTCCCT GAC- 3'
and IKKB-L:
                                       (SEQ ID NO: 2)
5'- CAAAGGTACCTTACTTGTCGTCATCGTCTTTGTAGTCGGAGGCTTG

CTCCAGGCAGCTGTGC- 3'
``` prepared by reference to the base sequence of IKKβ gene reported by Mercurio F. et al. (Science, 278, 860-866 (1997)) and employing human leukocyte cDNA (Clontech; trade name: QUICK-Clone cDNA) as a template.

A PCR was performed according to a protocol attached to LA Taq DNA polymerase (TAKARA SHUZO CO., LTD.). The obtained PCR product was electrophoresed on an agarose gel (1%) and a 2.3 kb DNA fragment containing IKKβ gene was recovered from the gel and digested with restriction enzymes Nhe I and Kpn I. The DNA after the restriction enzyme treatment was electrophoresed on an agarose gel (1%) and the resulting DNA fragment was recovered and ligated to plasmid pFASTBAC1 (Invitrogen) digested with restriction enzymes Nhe I and Kpn I to give an expression plasmid pFB-IKKB. The base sequence of the insertion fragment was confirmed and found to match the object sequence. Using BAC-TO-BAC Baculovirus Expression System (Invitrogen), virus stock BAC-IKKB of the recombinant baculovirus was prepared.

REFERENCE EXAMPLE 2A

Cloning of Human IκBα Gene

Cloning of human IκBα gene was performed by amplifying a gene encoding 54 amino acids on N terminal of IκBα by a PCR method using a primer set:

```
IKB-U:
                                    (SEQ ID NO: 3)
5'- AAAGAATTCATGTTCCAGGCGGCCGAGCGCCCC -3'
and IKB-L:
                                    (SEQ ID NO: 4)
5'- AAACCCGGGTCA GAGGCGGATCTCCTGCAGCTCCTT -3'
``` prepared by reference to the base sequence of IκBα gene reported by Haskill, S. et al. (Cell, 65, 1281-1289, (1991)) and using human spleen cDNA (Clontech, trade name: QUICK-Clone cDNA) as a template.

A PCR was performed according to a protocol attached to Pfu DNA polymerase (Stratagene). The obtained PCR product was electrophoresed on an agarose gel (1%) and a 183 bp DNA fragment containing IκBα gene was recovered from the gel and digested with restriction enzymes EcoRI and SmaI, after which inserted into a 4.9 kb EcoRI-SmaI fragment of plasmid pGEX4T-1 (Amersham Pharmacia Biotech) to give a plasmid PGEIKB.

REFERENCE EXAMPLE 3A

Preparation of Active IKKβ

Sf-21 cells (Invitrogen) were sown in 150 ml of Sf-900 II SFM medium (Invitrogen) containing 10% fetal calf serum to $1 \times 10^6$ cells/ml and cultured at 27° C. for 24 hrs. To the obtained culture medium were added 150 µl of virus stock BAC-IKKB of recombinant baculovirus obtained in Reference Example 1A and the cells were further cultured for 60 hrs. The culture medium was centrifuged (3000 rpm, 10 min) to separate the cells, and the cells were washed once with PBS. The cells were suspended in 10 ml of a cytolysis buffer (25 mM HEPES (pH 7.5), 1% Triton X, 130 mM sodium chloride, 1 mM EDTA, 1 mM Dithiothreitol, 25 mM β-glycerophosphate, Protease inhibitor Complete (Boeringer), 1 mM Sodium orthovanadate), and treated 4 times in a homogenizer (POLYTRON) at 20000 rpm for 30 sec to rupture the cells. The cell rupture suspension was centrifuged (40000 rpm, 45 min.), and active IKKβ was purified from the obtained supernatant using Anti-FLAG M2 Affinity Gel (Sigma).

REFERENCE EXAMPLE 4A

Preparation of Recombinant IκBα

The plasmid pGEIKB obtained in Reference Example 2A was transformed into *Escherichia coli* JM109 (TOYOBO) to give an ampicillin resistant strain pGEIKB/JM109. The pGEIKB/JM109 strain was cultured in 150 ml of LB medium (10 g/l tryptone, 5 g/l yeast extract, 10 g/l sodium chloride) supplemented with 50 µg/ml ampicillin overnight at 200 rpm, 37° C. The culture medium (15 ml) was added to a fresh LB medium (150 ml) and cultured at 37° C. for 2 hrs at 200 rpm. 1 mM IPTG (Wako Pure Chemical Industries, Ltd.) was added and the medium was further cultured for 6 hrs. The culture medium was centrifuged at 8000 rpm for 10 min. The cells were recovered, washed with PBS and frozen at −80° C. The cells were suspended in 15 ml of a cytolysis buffer (1% Triton X-containing PBS, 1 mM APMSF) and the suspension was ultrasonicated in iced water using SONIFIER450 (BRANSON) to rupture the cells. The cell rupture suspension was centrifuged (14000 rpm, 15 min., 4° C.) and GST-IκBα fused protein was purified from the obtained supernatant using Redipack GST Purification Module (Amersham Pharmacia Biotech) and desalted using a NAP-25 column (Amersham Pharmacia Biotech).

EXAMPLES

Unless otherwise noted, reagents and solvents were used as received from commercial suppliers. Proton and carbon nuclear magnetic resonance spectra were obtained on a Bruker AC 300 or a Bruker AV 300 spectrometer at 300 MHz for proton and 75 MHz for carbon. Spectra are given in ppm (δ) and coupling constants, J, are reported in Hertz. Tetramethylsilane was used as an internal standard for proton spectra and the solvent peak was used as the reference peak for carbon spectra. Infrared spectra were obtained on a Nicolet Nexus 470 (ATR) spectrometer. Mass spectra were obtained on a Perkin Elmer Sciex 100 atmospheric pressure ionization (APCI) mass spectrometer, a Shimadzu QP-5000 mass spectrometer (CI), or a Finnigan LCQ Duo LCMS ion trap electrospray ionization (ESI) mass spectrometer. Thin-layer chromatography (TLC) was performed using Analtech silica gel plates and visualized by ultraviolet (UV) light, iodine, or 20 wt % phosphomolybdic acid in ethanol. HPLC analyses were obtained using a Phenomenex Synergi Hydro-RP column (250×4.6 mm) with UV detection at 223 nm (Methods A, B and D). Preparative HPLC was performed using a Phenomenex Luna C18(2) column (250×21.2 mm) with Luna C18(2) guard column (60×21.2 mm) and UV detection at 223 nm (Method C).

Method A [Phenomenex Synergi Hydro-RP Column]

| Time (min) | Flow (mL/min) | % A | % B |
|---|---|---|---|
| B0.0 | 1.0 | 90.0 | 10.0 |
| 20.0 | 1.0 | 0.0 | 100.0 |

-continued

| Time (min) | Flow (mL/min) | % A | % B |
|---|---|---|---|
| 40.0 | 1.0 | 0.0 | 100.0 |
| 41.0 | 1.0 | 90.0 | 10.0 |

A = Water with 0.05% v/v Trifluoroacetic Acid
B = Acetonitrile with 0.05% v/v Trifluoroacetic Acid Method B [Phenomenex Synergi Hydro-RP Column]

| Time (min) | Flow (mL/min) | % A | % B |
|---|---|---|---|
| 0.0 | 1.0 | 90.0 | 10.0 |
| 30.0 | 1.0 | 0.0 | 100.0 |
| 35.0 | 1.0 | 0.0 | 100.0 |
| 36.0 | 1.0 | 90.0 | 10.0 |

A = Water with 0.05% v/v Trifluoroacetic Acid
B = Acetonitrile with 0.05% v/v Trifluoroacetic Acid Method C [Phenomenex Luna C18 (2) Column]

| Time (min) | Flow (mL/min) | % A | % B |
|---|---|---|---|
| 0.0 | 15.0 | 90.0 | 10.0 |
| 35.0 | 15.0 | 0.0 | 100.0 |
| 40.0 | 15.0 | 0.0 | 100.0 |
| 45.0 | 15.0 | 90.0 | 10.0 |

A = Water with 0.05% v/v Trifluoroacetic Acid
B = Acetonitrile with 0.05% v/v Trifluoroacetic Acid Method D [Phenomenex Synergi Hydro-RP Column]

| Time (min) | Flow (mL/min) | % A | % B |
|---|---|---|---|
| 0.0 | 1.0 | 90.0 | 10.0 |
| 20.0 | 1.0 | 0.0 | 100.0 |
| 35.0 | 1.0 | 0.0 | 100.0 |

A = Water with 0.05% v/v Trifluoroacetic Acid
B = Acetonitrile with 0.05% v/v Trifluoroacetic Acid Reference Example 1

7-Chloro-1H-pyrrolo[2,3-c]pyridine-2-carboxylic acid

To a heterogeneous solution of potassium ethoxide (6.56 g, 77.9 mmol) in diethyl ether (55 mL), was slowly added diethyl oxalate (10.6 mL, 77.9 mmol). A slight exotherm resulted. After stirring 5 min, a homogeneous yellow solution resulted, but after 10 min, a heterogeneous yellow slurry was observed. Addition of 2-chloro-4-methyl-3-nitropyridine (13.45 g, 77.9 mmol) as a solid, with a diethyl ether rinse (23 mL), resulted in a dark violet solution with a dark precipitate. The mixture was stirred at room temperature overnight (21 h). The solid precipitate was filtered, rinsed thoroughly with diethyl ether, and air-dried to give potassium (1Z)-1-(2-chloro-3-nitropyridin-4-yl)-3-ethoxy-3-oxoprop-1-en-2-olate (19.8 g, 63.6 mmol, yield 81%) as an orange solid. The crude product was used directly without further purification or identification.

Potassium (1Z)-1-(2-chloro-3-nitropyridin-4-yl)-3-ethoxy-3-oxoprop-1-en-2-olate (19.8 g, 63.6 mmol) was dissolved in acetic acid (908 mL) and the solution was treated with iron powder (14.6 g, 280.9 mmol). The reaction mixture was warmed to 60° C. and stirred overnight (18.5 h). TLC analysis indicated consumption of the starting material, therefore the reaction mixture was filtered through diatomaceous earth to remove the catalyst. The filtrate was concentrated to dryness. The residue was treated with methylene chloride (ca. 400 mL) and filtered through a plug of silica. Eluting with methylene chloride removed insolubles, and further elution with methylene chloride/ethyl acetate (50:50) provided ethyl 7-chloro-1H-pyrrolo[2,3-c]pyridine-2-carboxylate (10.3 g, 45.8 mmol, yield 72%) as a yellow solid after concentration: $R_f$ 0.80 (silica gel, 50:50 hexanes/ethyl acetate); mp 152-157° C.; $^1$H NMR (300 MHz, CD$_3$OD) δ1.43 (3H, t, J=7.0 Hz), 4.44 (2H, q, J=7.1 Hz), 7.27 (1H, s), 7.65 (1H, d, J=5.7 Hz), 7.95 (1H, d, J=5.4 Hz); ESI MS m/z 224 [C$_{10}$H$_9$ClN$_2$O$_2$+H]$^+$; HPLC (Method A) >99% (AUC), $t_R$=16.6 min.

Ethyl 7-chloro-1H-pyrrolo[2,3-c]pyridine-2-carboxylate (0.64 g, 2.85 mmol) was dissolved in tetrahydrofuran (5.7 mL) and methanol (6.8 mL). To the mixture was added 3 N KOH (2.85 mL). After stirring overnight (15.5 h) at room temperature, the reaction mixture was concentrated to dryness. The residue was dissolved in water. This aqueous solution was made acidic (pH 3) using 6 N HCl. The precipitate was collected by filtration. The precipitate was dissolved in methanol and concentrated to dryness to afford 7-chloro-1H-pyrrolo[2,3-c]pyridine-2-carboxylic acid (0.53 g, 2.7=mmol, 94%) as a yellow powder: mp 210-214° C.; $^1$H NMR (300 MHz, CD$_3$OD) δ7.25 (1H, s), 7.65 (1H, d, J=5.4 Hz), 7.94 (1H, d, J=5.4 Hz); ESI MS m/z 195 [C$_8$H$_5$ClN$_2$O$_2$—H]$^-$; HPLC (Method A) >99% (AUC), $t_R$=12.2 min.

Reference Example 2

N-Cyclohexyl-1H-pyrrolo[2,3-c]pyridine-2-carboxamide

Ethyl 7-chloro-1H-pyrrolo[2,3-c]pyridine-2-carboxylate (preparation described in Reference Example 1) (240 mg, 1.07 mmol), phenol (500 mg, 5.35 mmol) and cyclohexylamine (1.1 mL, 10.7 mmol) were combined in a sealed tube and heated at 100° C. for 6 h. The reaction tube was cooled to room temperature. The reaction mixture was diluted with ethyl acetate (10 mL), washed with 2 N sodium hydroxide (10 mL) and brine (10 mL), dried over magnesium sulfate, and evaporated to provide 538 mg of dark brown viscous oil. The viscous oil was purified by chromatography (SiO$_2$; 3:1 hexanes/ethyl acetate) to give 7-chloro-N-cyclohexyl-1H-pyrrolo[2,3-c]pyridine-2-carboxamide as an off-white powder (218 mg, 0.785 mmol, 74%): $^1$H NMR (300 MHz, CD$_3$OD) δ1.20-1.55 (6H, m), 1.65-2.10 (4H, m), 3.90 (1H, m), 7.21 (1H, s), 7.61 (1H, d, J=5.4 Hz), 7.93 (1H, d, J=5.4 Hz); ESI MS m/z 278 [C$_{14}$H$_{16}$ClN$_3$O+H]$^+$.

7-Chloro-N-cyclohexyl-1H-pyrrolo[2,3-c]pyridine-2-carboxamide (230 mg, 0.828 mmol), triethylamine (0.25 mL) and palladium(II)chloride (3 mg, 2 mol %) were combined in N,N-dimethylformamide (5 mL) under an atmosphere of hydrogen. The reaction mixture was heated at 60° C. for 3 h.

The reaction mixture was cooled to room temperature and the catalyst was removed by filtration through a pad of diatomaceous earth and washed with ethyl acetate. Evaporation of the solvents provided crude product (169 mg, 84%) as an off-white solid. Purification by chromatography (SiO$_2$; 0-10% methanol in methylene chloride, 1400 mL) afforded N-cyclohexyl-1H-pyrrolo[2,3-c]pyridine-2-carboxamide (101 mg, 0.414 mmol, 50%) as fine, white needles: mp 298-301° C., $^1$H NMR (300 MHz, CD$_3$OD) δ 1.20-1.55 (6H, m), 1.65-2.10 (4H, m), 3.90 (1H, m), 7.21 (1H, s), 7.15 (1H, s), 7.65 (1H, d, J=5.7 Hz), 8.09 (1H, d, J=5.7 Hz), 8.77 (1H, s); ESI MS m/z 244 [C$_{14}$H$_{17}$N$_3$O+H]$^+$; HPLC (Method A) >99% (AUC), t$_R$=13.2 min.

Reference Example 3

Ethyl 7-(dibenzylamino)-1H-pyrrolo[2,3-c]pyridine-2-carboxylate

To a stirred solution of 2-chloro-4-methyl-3-nitropyridine (1.06 g, 6.14 mmol) in tetrahydrofuran (12 mL) under an atmosphere of nitrogen were added dibenzylamine (2.4 mL, 13 mmol) and sodium carbonate (684 mg, 6.45 mmol). The mixture was warmed to reflux for 48 h and cooled to room temperature. The mixture was diluted with dichloromethane (100 mL) and water (100 mL), and the layers were separated. The aqueous layer was extracted with dichloromethane (2×50 mL). The combined organic extracts were washed with 1 N HCl (100 mL) and brine (100 mL), dried (Na$_2$SO$_4$), filtered, and concentrated in vacuo. The residue was purified by chromatography (silica gel, 10% ethyl acetate/hexanes) to provide 2-(dibenzylamino)-4-methyl-3-nitropyridine (1.53 g, 4.59 mmol, 75%) as a bright yellow oil which solidified upon standing. R$_f$ 0.52 (67:33 hexanes/ethyl acetate); $^1$H NMR (300 MHz, CDCl$_3$) δ2.32 (3H, s), 4.45 (4H, s), 6.70 (1H, d, J=4.9 Hz), 7.16-7.19 (4H, m), 7.21-7.34 (6H, m), 8.16 (1H, d, J=4.9 Hz); ESI MS m/z 334 [C$_{20}$H$_{19}$N$_3$O$_2$+H]$^+$.

A slurry of potassium ethoxide (391 mg, 4.64 mmol) in diethyl ether (4 mL) under N$_2$ was cooled to 0° C. under vigorous stirring. Diethyl oxalate (0.63 mL, 4.65 mmol) was added, and the mixture was stirred for 5 min. A solution of 2-(dibenzylamino)-4-methyl-3-nitropyridine (1.52 g, 4.56 mmol) in diethyl ether (3 mL) was added, and the mixture was stirred for 16 h while slowly warming to room temperature, during which time a precipitate formed. The solid was collected on a sintered glass frit and rinsed several times with additional diethyl ether. The solid was transferred to a vial and dried under vacuum at 30° C. for 2 h to provide potassium (1Z)-1-[2-(dibenzylamino)-3-nitropyridin-4-yl]-3-ethoxy-3-oxoprop-1-en-2-olate (1.63 g, 3.46 mmol, 76%) as a light orange solid. This product was immediately used without purification or identification.

Potassium (1Z)-1-[2-(dibenzylamino)-3-nitropyridin-4-yl]-3-ethoxy-3-oxoprop-1-en-2-olate (1.63 g, 3.46 mmol) was dissolved in glacial acetic acid (21 mL) and treated with iron powder (851 mg, 15.2 mmol). This mixture was warmed to 60° C. for 3.5 h and cooled to room temperature. The slurry was filtered through diatomaceous earth to remove the catalyst, and the filtrate was concentrated in vacuo. The residue was purified by chromatography (silica gel, gradient 0-50% ethyl acetate/dichloromethane) to provide ethyl 7-(dibenzylamino)-1H-pyrrolo[2,3-c]pyridine-2-carboxylate (902 mg, 68%) as a tan solid: R$_f$ 0.55 (silica gel, 67:33 hexanes/ethyl acetate); mp 120-123° C.; $^1$H NMR (300 MHz, CDCl$_3$) δ1.27 (3H, t, J=7.1 Hz), 4.28 (2H, q, J=7.0 Hz), 4.91 (4H, s), 7.03 (1H, J=5.9 Hz), 7.06 (1H, d, J=1.8 Hz), 7.27-7.38 (10H, m), 7.89 (1H, d, J=5.7 Hz), 8.67 (1H, br s); APCI MS m/z 386 [C$_{24}$H$_{23}$N$_3$O$_2$+H]$^+$; HPLC (Method A) >99% (AUC), t$_R$=17.7 min.

Reference Example 4

7-(Dibenzylamino)-1H-pyrrolo[2,3-c]pyridine-2-carboxylic acid

A mixture of ethyl 7-(dibenzylamino)-1H-pyrrolo[2,3-c]pyridine-2-carboxylate (Reference Example 3) (500 mg, 1.30 mmol), 2 M sodium hydroxide solution (6 mL), tetrahydrofuran (3 mL) and ethanol (3 mL) was refluxed for 2 h. The mixture was neutralized by addition of 1 M hydrochloric acid and extracted with ethyl acetate. The organic extract was washed with brine, dried over sodium sulfate, and concentrated in vacuo. The residue was crystallized from ethyl acetate to give 7-(dibenzylamino)-1H-pyrrolo[2,3-c]pyridine-2-carboxylic acid (100 mg, 22%) as pale brown amorphous solid. Additional material (348 mg, 75%; 97% overall yield) was obtained from the mother liquid: R$_f$ 0.01 (silica gel, ethyl acetate); mp 114-120° C.; $^1$H NMR (300 MHz, DMSO-d$_6$) δ4.82 (4H, br s), 7.18-7.35 (12H, m), 7.68 (1H, d, J=6.0 Hz); ESI MS m/z 358 [C$_{22}$H$_{19}$N$_3$O$_2$+H]$^+$; HPLC (Method A) 98.8% (AUC), t$_R$=17.7 min.

Reference Example 5

Ethyl 5-(dibenzylamino)-1H-pyrrolo[2,3-c]pyridine-2-carboxylate

To a mixture of 2-chloro-4-methyl-5-nitropyridine (5.44 g, 26.3 mmol) and dibenzylamine (5.04 mL, 26.3 mmol) in toluene (13.1 mL) was added sodium carbonate (5.58 g, 52.6 mmol). After stirring under a nitrogen atmosphere under reflux for 36 h, the reaction mixture was filtered to remove the sodium carbonate. The filtrate was concentrated to provide the crude material as a light orange oil. The crude oil was dissolved in methylene chloride and treated with 2 N HCl. The resulting precipitate was filtered off and discarded. The filtrate was washed with 2 N HCl and the acidic layers were back-extracted with methylene chloride. The combined extracts were washed with saturated NaHCO$_3$, dried over Na$_2$SO$_4$, filtered and concentrated to provide 2-(dibenzylamino)-5-nitro-4-methylpyridine (8.97 g, 102% theoretical) as a light yellow solid: $^1$H NMR (300 MHz, CDCl$_3$) δ2.53 (3H, s), 4.85 (4H, s), 6.27 (1H, s), 7.19-7.37 (10H, m), 9.05 (1H, s).

To a suspension of potassium ethoxide (2.21 g, 26.3 mmol) in diethyl ether (20 mL) was added diethyl oxalate (3.57 mL, 26.3 mmol) under a nitrogen atmosphere. The reaction exhibited a slight exotherm and the reaction mixture was stirred for 20 min. The heterogeneous mixture became a homogeneous orange solution and then became a heterogeneous thick slurry and the stirring was ceased. In a separate container 2-(dibenzylamino)-5-nitro-4-methylpyridine (8.76 g, 26.3 mmol) was diluted with diethyl ether (14.3 mL) to give a suspension. The suspension was added to the slurry obtained above. The mixture was manually stirred using a glass rod, then sonicated for 20 min resulting in a thick black heterogeneous solution. The reaction mixture was allowed to stand under a nitrogen atmosphere overnight. The resulting solid was collected by filtration and rinsed with diethyl ether to give potassium (1Z)-1-[2-(dibenzylamino)-5-nitropyridin-4-yl]-3-ethoxy-3-oxoprop-1-en-2-olate (9.5 g, 76%) as a deep red solid: $^1$H NMR (300 MHz, CD$_3$OD) δ1.17 (3H, t, J=7.0 Hz), 3.58 (2H, q, J=6.9 Hz), 4.82 (4H, s), 7.22-7.32 (11H, m), 8.74 (1H, s), 8.80 (1H, s).

To a solution of potassium (1Z)-1-[2-(dibenzylamino)-5-nitropyridin-4-yl]-3-ethoxy-3-oxoprop-1-en-2-olate (5.0 g, 10.6 mmol) in acetic acid (151.4 mL) was added iron powder (2.43 g, 43.5 mmol) under a nitrogen atmosphere. The mixture was warmed to 60° C. and stirred for 2 h. The reaction mixture was filtered through diatomaceous earth, and the filtrate was concentrated to ca. 100 mL in volume. The concentrate was poured into rapidly stirring water (ca. 200 mL). The precipitate was observed. Ethyl acetate (150 mL) was added and the mixture was stirred until the solid was dissolved. The layers were separated, and the aqueous layer was extracted with ethyl acetate (2×). The combined extracts were washed with dilute $NaHCO_3$ and saturated NaCl, and dried over $Na_2SO_4$. The solution was dark red. Consequently, activated charcoal (Darco G-60, 1.20 g) was added to the solution. After filtration through diatomaceous earth, the filtrate was concentrated to dryness to afford a dark brown solid. The solid was sonicated in toluene (ca. 75 mL) for 30 min. After standing at room temperature overnight, the solid was collected by filtration and rinsed with toluene to give ethyl 5-(dibenzylamino)-1H-pyrrolo[2,3-c]pyridine-2-carboxylate (0.80 g, 19%) as a yellow solid. Further manipulation of the mother liquors provided additional material (0.19 g, 5%): mp 169-174° C.; $^1$H NMR (300 MHz, $CD_3OD$) δ1.38 (3H, t, J=7.0 Hz), 4.37 (2H, q, T=7.0 Hz), 4.75 (4H, s), 6.64 (1H, d, J=0.9 Hz), 6.85 (1H, d, J=0.9 Hz), 7.21-7.27 (10H, m), 8.48 (1H, s); ESI MS m/z 386 $[C_{24}H_{23}N_3O_2+H]^+$; HPLC (Method A) >99% (AUC), $t_R$=20.1 min.

Reference Example 6

N-Cyclopentyl-1H-pyrrol[2,3-c]pyridine-2-carboxamide

N-Cyclopentyl-1H-pyrrolo[2,3-c]pyridine-2-carboxamide (20 mg, 43%) was prepared as an off-white solid following the procedure described for Example 27 using 7-chloro-N-cyclopentyl-1H-pyrrolo[2,3-c]pyridine-2-carboxamide and ethanol as a solvent: mp 220-224° C.; $^1$H NMR (300 MHz, $CD_3OD$) δ1.22-2.18 (8H, m), 4.28-4.42 (1H, m), 7.27 (1H, s), 7-82 (1H, d, J=5.8 Hz), 8.15 (1H, d, J=5.8 Hz), 8.85 (1H, s); ESI MS m/z 230 $[C_{13}H_{15}N_3O+H]^+$; HPLC (Method A) >99% (AUC), $t_R$=12.1 min.

Reference Example 7

2-Benzyl-1H-pyrrolo[2,3-c]pyridine

N-Benzyl-AT-[(7-chloro-1H-pyrrolo[2,3-c]pyridin-2-yl)(phenyl)methyl]amine dihydrochloride (103 mg, 286 μmol), ammonium formate (108 mg, 1.72 mmol) and palladium-on-carbon (30 mg, 10 mol % Pd) were combined in methanol (3 mL). The reaction mixture was heated under reflux under an atmosphere of nitrogen for 2 h. The reaction mixture was cooled to room temperature. The catalyst was removed by filtration through a pad of diatomaceous earth and washed with methanol followed by methylene chloride. Evaporation of the solvents provided 102 mg of crude, off-white solid. Purification by chromatography ($SiO_2$; 93:7 methylene chloride/methanol) afforded 2-benzyl-1H-pyrrolo[2,3-c]pyridine (41 mg, 194 μmol, 68%) as an off-white powder: mp 142-146° C.; $^1$H NMR (300 MHz, $CD_3OD$) δ 4.17 (2H, s), 6.29 (1H, s), 7.15-7.35 (5H, m), 7.46 (1H, d, J=5.1 Hz), 7.95 (1H, d, J=5.1 Hz), 8.52 (1H, s); ESI MS m/z 209 $[C_{14}H_{12}N_2+H]^+$; HPLC (Method A) 98.0% (AUC), $t_R$=15.5 min.

Reference Example 8

Phenyl(1H-pyrrolo[2,3-c]pyridin-3-yl)methanone

Phenyl(1H-pyrrolo[2,3-c]pyridin-3-yl)methanone (379 mg, 78%) was prepared using phenyl(1H-pyrrolo[2,3-c]pyridin-3-yl)methanol (Example 97) as a yellow solid following the procedure described for Reference Example 13: $R_f$ 0.48 (90:10 methylene chloride/methanol); mp 218-220° C.; $^1$H NMR (300 MHz, DMSO-$d_6$) δ7.55-7.58 (2H, m), 7.62-7.65 (1H, m), 7.81-7.83 (2H, m), 8.09-8.10 (1H, d, J=5.4 Hz), 8.19 (1H, s), 8.33-8.34 (1H, d, J=5.4 Hz), 8.88 (1H, s), 12.50 (1H, br s); ESI MS m/z 223 $[C_{14}H_{10}N_2O+H]^+$; HPLC (Method A) 96.6% (AUC), $t_R$=13.2 min.

Reference Example 9 tert-Butyl 3-(aminooxy)pyrrolidine-1-carboxylate

A mixture of 3-hydroxypyrrolidine (2.0 g, 23 mmol), triethylamine (3.8 mL, 28 mmoL), di-tert-butyl dicarbonate (5.2 g, 24 mmol) and N,N-dimethylaminopyridine (140 mg, 1.1 mmol) in $CH_2Cl_2$ (180 mL) was stirred at ambient temperature. After 5 h, the reaction mixture was diluted with $H_2O$ (50 mL). The aqueous layer was separated and extracted with $CH_2Cl_2$ (25 mL). The combined organic layers were washed with saturated NaCl (40 mL), dried ($Na_2SO_4$) and concentrated under reduced pressure. Purification by column chromatography (silica gel, 90:10 $CH_2Cl_2$/MeOH) gave tert-butyl 3-hydroxypyrrolidine-1-carboxylate (4.1 g, 95%): $^1$H NMR (300 MHz, $CDCl_3$) δ1.46 (9H, s), 1.92-2.04 (2H, s), 2.11-2.17 (1H, s), 3.30-3.49 (4H, s), 4.44-4.45 (1H, m).

To an ice-cold solution of tert-butyl 3-hydroxypyrrolidine-1-carboxylate (1.0 g, 5.5 mmol), N-hydroxyphthalimide (0.90 g, 5.5 mmol) and triphenylphosphine (1.4 g, 5.5 mmol) in THF (30 mL) was added a solution of diethyl azodicarboxylate (0.96 mL, 6.1 mmol) in THF (5 mL) dropwise. The stirred reaction mixture was allowed to warm to ambient temperature. After 3 days, most of the THF was removed under reduced pressure. The residue was partitioned between $CH_2Cl_2$ (40 mL) and $H_2O$ (30 mL). The organic layer was separated and washed with saturated NaCl (20 mL), dried ($Na_2SO_4$) and concentrated under reduced pressure. Purification by column chromatography (silica gel, 75:25 hexanes/EtOAc to 50:50 hexanes/EtOAc) gave tert-butyl 3-[(1,3-dioxo-1,3-dihydro-2H-isoindol-2-yl)oxy]pyrrolidine-1-carboxylate (0.96 g, 52%): $^1$H NMR (300 MHz, $CDCl_3$) δ1.49 (9H, s), 1.97-2.20 (1H, s), 2.25-2.31 (1H, m), 3.53-3.78 (4H, m), 4.95-5.00 (1H, m), 7.75-7.87 (4H, m).

To an ice-cold solution of tert-butyl 3-[(1,3-dioxo-1,3-dihydro-2H-isoindol-2-yl)oxy]pyrrolidine-1-carboxylate (0.96 g, 2.8 mmol) in $CH_2Cl_2$ (16 mL) and MeOH (4 mL) was added methylhydrazine (0.70 mL, 13 mmol) dropwise. The stirred reaction mixture was allowed to slowly warm to ambient temperature. After 2 h, the reaction mixture was concentrated under reduced pressure. To the residue was added $CH_2Cl_2$ (20 mL) and with the aid of sonication a solid formed and was collected by vacuum filtration. The filtrate was concentrated and purified by column chromatography (silica gel, 75:25 hexanes/EtOAc to 25:75 hexanes/EtOAc) to afford tert-butyl 3-(aminooxy)pyrrolidine-1-carboxylate (440 mg, 76%): $^1$H NMR (500 MHz, $CDCl_3$) δ 1.46 (9H, s), 1.82-1.98 (1H, m), 2.04-2.10 (1H, m), 3.31-3.65 (4H, m), 4.24-4.27 (1H, m), 5.37.

Reference Examples 10 tert-Butyl 4-(aminooxy)piperidine-1-carboxylate

Reaction of tert-butyl 4-hydroxypiperidine-1-carboxylate with N-hydroxyphthalimide following the procedure described for the preparation of Reference Example 9 gave tert-butyl 4-[(1,3-dioxo-1,3-dihydro-2H-isoindol-2-yl)oxy] piperidine-1-carboxylate (3.0 g, 72%) as a yellow oil: $^1$H NMR (500 MHz, CDCl$_3$) δ 1.46 (9H, s), 1.82-1.85 (2H, m), 1.92-1.96 (2H, m), 3.20-3.25 (2H, m), 3.86-3.90 (2H, m), 4.41-4.44 (1H, m), 7.74-7.78 (2H, m), 7.82-7.86 (2H, m).

Deprotection of tert-butyl 4-[(1,3-dioxo-1,3-dihydro-2H-isoindol-2-yl)oxy]piperidine-1-carboxylate with methylhydrazine following the procedure described for the preparation of Reference Example 9 gave tert-butyl 4-(aminooxy)piperidine-1-carboxylate (1.3 g, 73%) as an amber oil: $^1$H NMR (500 MHz, CDCl$_3$) δ 1.47 (9H, s), 1.48-1.54 (2H, m), 1.86-1.88 (2H, m), 3.04-3.10 (2H, m), 3.66-3.69 (2H, m), 4.20 (1H, br s), 5.30 (2H, br s).

Reference Example 11 tert-Butyl 3-(aminooxy)piperidine-1-carboxylate

Reaction of tert-butyl 3-hydroxypiperidine-1-carboxylate with N-hydroxyphthalimide following the procedure described for the preparation of Reference Example 9 gave tert-butyl 3-[(1,3-dioxo-1,3-dihydro-2H-isoindol-2-yl)oxy] piperidine-1-carboxylate (2.3 g, 57%) as a yellow oil: $^1$H NMR (500 MHz, CDCl$_3$) δ 1.42 (9H, s), 1.47-1.58 (1H, m), 1.74-1.76 (1H, m), 1.90-1.92 (1H, m), 2.08-2.11 (1H, m), 3.04-3.40 (2H, m), 3.66-3.68 (1H, m), 3.70-4.14 (1H, m) 4.24-4.27 (1H, m), 7.74-7.76 (2H, m), 7.82-7.86 (2H, m).

Deprotection of tert-butyl 3-[(1,3-dioxo-1,3-dihydro-2H-isoindol-2-yl)oxy]piperidine-1-carboxylate with methylhydrazine following the procedure described for the preparation of Reference Example 9 gave tert-butyl 3-(aminooxy)piperidine-1-carboxylate (1.0 g, 73%) as an off-white, waxy solid: $^1$H NMR (500 MHz, CDCl$_3$) δ 1.34-1.39 (1H, m), 1.47 (9H, s), 1.69-1.76 (3H, m), 3.12-3.26 (1.5H, m), 3.45-3.60 (3H, m), 3.77-3.83 (0.5H, m), 3.37-5.47 (2H, m).

Reference Example 12

1-(Phenylsulfonyl)-1H-pyrrolo[2,3-c]pyridine

To a suspension of 1H-pyrrolo[2,3-c]pyridine (700 mg, 5.9 mmol) in tetrahydrofuran (14.0 mL) was added lithium diisopropylamide (2.9 mL of a 2 M solution in THF/heptane, 5.9 mmol) at −78° C. After 0.5 h, benzenesulfonyl chloride (0.79 mL, 6.2 mmol) was added dropwise. The mixture was allowed to slowly warm to ambient temperature overnight. The reaction mixture was poured into 2% aq NaHCO$_3$ (30 mL) and extracted with EtOAc (2×25 mL). The combined extracts were washed with H$_2$O (20 mL) and saturated NaCl (20 mL), dried (Na$_2$SO$_4$) and concentrated under reduced pressure. Purification by column chromatography (silica gel, 1:1 hexanes/EtOAc) gave 1-(phenylsulfonyl)-1H-pyrrolo[2, 3-c]pyridine (1.2 g, 80%): $^1$H NMR (500 MHz, DMSO-d$_6$) δ 6.94 (1H, d, J=6.0 Hz), 7.59-7.66 (3H, m), 7.70-7.75 (1H, m), 8.07-8.10 (3H, m), 8.38 (1H, d, J=8.8 Hz), 9.23 (1H, s); ESI MS m/z 259 [C$_{13}$H$_{10}$N$_2$O$_2$S+H]$^+$.

Reference Example 13

Phenyl[1-(phenylsulfonyl)-1H-pyrrolo[2,3-c]pyridin-2-yl]methanone

To a solution of lithium diisopropylamide (1.2 mL of a 2 M solution in THF/heptane, 2.3 mmol) in THF (3 mL) was added a solution of 1-(phenylsulfonyl)-1H-pyrrolo[2,3-c]pyridine (300 mg, 1.2 mmol) and N,N,N',N'-tetramethylethylenediamine (0.18 mL, 1.2 mmol) in THF (5 mL), dropwise at −25° C. After 0.5 h, a solution of benzaldehyde (0.24 mL, 2.3 mmol) in THF (6 mL) was added dropwise. After 1 h, the reaction mixture was warmed to 10° C. and quenched by the addition of saturated NH$_4$Cl (5 mL). The reaction mixture was diluted with H$_2$O (20 mL) and extracted with EtOAc (2×40 mL). The combined extracts were dried (Na$_2$SO$_4$) and concentrated under reduced pressure. Purification by column chromatography (silica gel, 9:1 hexanes/EtOAc to EtOAc) gave phenyl[1-(phenylsulfonyl)-1H-pyrrolo[2,3-c]pyridin-2-yl]methanol (155 mg, 37%) as a mixture of enantiomers: $^1$H NMR (500 MHz, DMSO-d$_6$) δ 6.36 (1H, d, J=5.5 Hz), 6.43 (1H, d, J=5.5 Hz), 6.75 (1H, s), 7.32-7.36 (5H, m), 7.53 (2H, dd, J=8.4, 7.6 Hz), 7.59 (1H, d, J=5.2 Hz), 7.66-7.70 (1H, m), 7.82-7.85 (2H, m), 8.35 (1H, d, J=5.2 Hz), 9.22 (1H, s); ESI MS m/z 365 [C$_{20}$H$_{16}$N$_2$O$_3$S+H]$^+$; HPLC (Method A) 91.9% (AUC), t$_R$=16.5 min.

A mixture of phenyl[1-(phenylsulfonyl)-1H-pyrrolo[2,3-c]pyridin-2-yl]methanol (2.6 g, 7.1 mmol) and MnO$_2$ (9.3 g, 110 mmol) in THF (125 mL) was heated to reflux. After 20 h, the reaction mixture was filtered through a pad of diatomaceous earth. The filtrate was concentrated under reduced pressure. Purification by column chromatography (silica gel, CH$_2$Cl$_2$ to 99:1 CH$_2$Cl$_2$/MeOH) gave phenyl[1-(phenylsulfonyl)-1H-pyrrolo[2,3-c]pyridin-2-yl]methanone (1.7 g, 68%) as an off-white solid: mp 145-146° C.; $^1$H NMR (500 MHz, DMSO-d$_6$) δ7.32 (1H, s), 7.60-7.63 (2H, m), 7.66-7.69 (2H, m), 7.73-7.77 (3H, m), 7.93-7.95 (2H, m), 8.07-8.09 (2H, m), 8.50 (1H, d, J=5.3 Hz), 9.35 (1H, s); ESI MS m/z 363 [C$_{20}$H$_{14}$N$_2$O$_3$S+H]$^+$; HPLC (Method A) 99.0% (AUC), t$_R$=18.2 min.

Reference Example 14 tert-Butyl[2-(aminooxy)ethyl]methylcarbamate

A mixture of 2-(methylamino)ethanol (2.0 g, 27 mmol), triethylamine (4.4 mL, 33 mmol), di-tert-butyl dicarbonate (6.1 g, 28 mmol) and 4-dimethylaminopyridine (160 mg, 1.3 mmol) in CH$_2$Cl$_2$ (200 mL) was stirred at ambient temperature. After 17 h, the reaction mixture was diluted with H$_2$O (50 mL). The aqueous layer was separated and extracted with CH$_2$Cl$_2$ (25 mL). The combined organic layers were washed with saturated NaCl (25 mL), dried (Na$_2$SO$_4$) and concentrated under reduced pressure. Purification by column chromatography (silica gel, 75:25 CH$_2$Cl$_2$/MeOH) gave tert-butyl (2-hydroxyethyl)methylcarbamate (3.1 g, 66%) as a colorless oil: $^1$H NMR (300 MHz, DMSO-d$_6$) δ1.38 (9H, s), 2.80 (3H, br s), 3.17 (2H, t, J=8.8 Hz), 3.42-3.48 (2H, m), 4.65 (1H, br s).

To an ice-cold solution of tert-butyl (2-hydroxyethyl)methylcarbamate (3.0 g, 17 mmol), N-hydroxyphthalimide (2.8 g, 17 mmol) and triphenylphosphine (4.5 g, 17 mmol) in THF (90 mL) was added a solution of diethyl azodicarboxylate (3.0 mL, 19 mmol) in THF (15 mL) dropwise. The stirred reaction mixture was allowed to warm to ambient temperature. After 2 days, most of the THF was removed under reduced pressure. The residue was partitioned between CH$_2$Cl$_2$ (40 ml) and H$_2$O (30 mL). The organic layer was separated and washed with saturated NaCl (20 ml), dried (Na$_2$SO$_4$) and concentrated under reduced pressure. Purification by column chromatography (silica gel, 50:50 hexanes/EtOAc) gave tert-butyl[2-[(1,3-dioxo-1,3-dihydro-2H-isoindol-2-yl)oxy]ethyl]methylcarbamate (4.3 g, 79%) as a yellow oil: $^1$H NMR (300 MHz, CDCl$_3$) δ1.46 (9H, s), 3.03 (3H, br s), 3.62 (2H, br s), 4.34 (2H, br s), 7.74-7.85 (4H, m).

To an ice-cold solution of tert-butyl[2-[(1,3-dioxo-1,3-dihydro-2H-isoindol-2-yl)oxy]ethyl]methylcarbamate (4.3 g, 13=mmol) in CH$_2$Cl$_2$/MeOH (8:2, 90 mL) was added methylhydrazine (3.2 mL, 60 mmol) dropwise. The stirred reaction mixture was allowed to warm to ambient temperature. After 1.5 h, the reaction mixture was concentrated under reduced pressure. To the residue was added CH$_2$Cl$_2$ (35 mL) and the resulting white solid was collected by vacuum filtration. The filtrate was concentrated and purified by column chromatography (silica gel, 50:50 hexanes/EtOAc to 35:65 hexanes/EtOAc) to afford tert-butyl[2-(aminooxy)ethyl]methylcarbamate (2.3 g, 90%) as a yellow oil: $^1$H NMR (500 MHz, CDCl$_3$) δ 1.46 (9H, s), 1.82-1.98 (1H, m), 2.88 (3H, br s), 3.44-3.46 (2H, m), 3.74 (2H, t, J=5.3 Hz), 5.44-5.77 (2H, m).

Reference Example 15

4-[(Aminooxy)methyl]-1H-imidazole

To an ice-cold solution of 4-(hydroxymethyl)imidazole hydrochloride (2.0 g, 15 mmol), N-hydroxyphthalimide (2.4 g, 15 mmol) and triphenylphosphine (4.0 g, 15 mmol) in THF (65 mL) was added a solution of diethyl azodicarboxylate (2.6 mL, 16 mmol) in THF (10 mL) dropwise. The stirred reaction mixture was allowed to warm to ambient temperature. After 18 h, the resultant precipitate was collected by vacuum filtration. The solid was partitioned between EtOAc (75 ml) and saturated NaHCO$_3$ (75 mL). The aqueous layer was separated and extracted again with EtOAc (75 mL). The combined organic layers were dried (Na$_2$SO$_4$) and concentrated under reduced pressure. Purification by column chromatography (silica gel, CH$_2$Cl$_2$ to 90:10 CH$_2$Cl$_2$/MeOH) gave 2-(1H-imidazol-4-ylmethoxy)-1,3-dihydro-2H-isoindole-1,3-dione (800 mg, 22%) as a yellow oil: $^1$H NMR (300 MHz, DMSO-d$_6$) δ5.03 (2H, s), 7.30 (1H, s), 7.55 (1H, s), 7.81-7.86 (4H, m), 12.08 (1H, br s).

Deprotection of 2-(1H-imidazol-4-ylmethoxy)-1,3-dihydro-2H-isoindole-1,3-dione with methylhydrazine following the procedure described for Reference Example 14, except purification by column chromatography (silica gel, 98:2 CH$_2$Cl$_2$/MeOH to 90:10 CH$_2$Cl$_2$/MeOH), gave 4-[(aminooxy)methyl]-1H-imidazole (189 mg, 50%) as a colorless oil: $^1$H NMR (300 MHz, DMSO-d$_6$) δ 4.45 (2H, s), 5.98 (2H, br s), 6.99 (1H, br s), 7.57 (1H, s), 11.96 (1H, br s).

Reference Example 16

2-[(Aminooxy)methyl]-1H-imidazole

To an ice-cold solution of (1H-imidazol-2-yl)methanol hydrochloride (2.0 g, 15 mmol), N-hydroxyphthalimide (2.4 g, 15 mmol) and triphenylphosphine (4.0 g, 15 mmol) in THF (65 mL) was added a solution of diethyl azodicarboxylate (2.6 mL, 16 mmol) in THF (10 mL) dropwise. The stirred reaction mixture was allowed to warm to ambient temperature. After 1 day, most of the THF was removed under reduced pressure. The residue was partitioned between CH$_2$Cl$_2$ (75 ml) and H$_2$O (30 mL). The organic layer was separated and washed with saturated NaHCO$_3$ (75 mL) and saturated NaCl (20 ml), dried (Na$_2$SO$_4$) and concentrated under reduced pressure. Purification by column chromatography (silica gel, CH$_2$Cl$_2$ to 95:5 CH$_2$Cl$_2$/MeOH) gave 2-(1H-imidazol-2-ylmethoxy)-1,3-dihydro-2H-isoindole-1,3-dione (240 mg, 6.5%) which was used directly in the next reaction.

Deprotection of 2-(1H-imidazol-2-ylmethoxy)-1,3-dihydro-2H-isoindole-1,3-dione with methylhydrazine following the procedure described for the preparation of Reference Example 14, except purification by ion-exchange chromatography (SCX-2, 1:3 7 N NH$_4$OH in MeOH/MeOH), gave 2-[(aminooxy)methyl]-1H-imidazole (51 mg, 45%) as an amber oil: $^1$H NMR (300 MHz, DMSO-d$_6$) δ 4.53 (2H, s), 6.95 (2H, s).

Reference Example 17 tert-Butyl[2-(aminooxy)ethyl]isopropylcarbamate

Reaction of 2-(isopropylamino)ethanol with di-tert-butyl dicarbonate following the procedure described for Reference Example 14, except purification by column chromatography (silica gel, CH$_2$Cl$_2$), gave (2-hydroxyethyl)isopropylcarbamic acid tert-butyl ester (970 mg, 25%) as a colorless oil: $^1$H NMR (300 MHz, CDCl$_3$) δ 1.12 (6H, d, J=6.8 Hz), 1.47 (9H, s), 3.30-3.32 (2H, m), 3.68-3.74 (2H, m), 4.17 (1H, br s).

Reaction of (2-hydroxyethyl)isopropylcarbamic acid tert-butyl ester with N-hydroxyphthalimide following the procedure described for Reference Example 14, except purification by column chromatography (silica gel, 75:25 hexanes/EtOAc to 50:50 hexanes/EtOAc), gave tert-butyl[2-[(1,3-dioxo-1,3-dihydro-2H-isoindol-2-yl)oxy]ethyl]isopropylcarbamate (960 mg, 57%) as a colorless oil: $^1$H NMR (300 MHz, CDCl$_3$) δ 1.15-1.20 (6H, br s), 1.43 (9H, s), 3.48-3.50 (2H, s), 4.08-4.15 (1H, m), 4.25-4.28 (2H, m), 7.74-7.85 (4H m).

Deprotection of tert-butyl[2-[(1,3-dioxo-1,3-dihydro-2H-isoindol-2-yl)oxy]ethyl]isopropylcarbamate with methylhydrazine following the procedure described for Reference Example 14, except purification by column chromatography (silica gel, CH$_2$Cl$_2$ to 98:2 CH$_2$Cl$_2$/MeOH), gave tert-butyl[2-(aminooxy)ethyl]isopropylcarbamate (422 mg, 72%) as a yellow oil: $^1$H NMR (300 MHz, DMSO-d$_6$) δ 1.07 (6H, d, J=6.3 Hz), 1.39 (9H, s), 3.15-3.21 (2H, m), 3.54 (2H, t, J=6.7 Hz), 3.8-4.15 (1H, m), 6.00 (2H, br s).

Reference Example 18

2-(Aminooxy)acetamide

Potassium carbonate (2.67 g, 19.31 mmol) was added to a solution of N-hydroxyphthalimide (3.0 g, 18.39 mmol) in anhydrous DMF (37 mL) at 0° C. The reaction mixture was stirred at 0° C. for 10 min and then at room temperature for 1 h. The reaction mixture was cooled to 0° C. and 2-bromoacetamide (2.79 g, 20.23 mmol) was added. The reaction mixture was stirred at 0° C. for 10 min and then at room temperature overnight. The reaction mixture was poured into rapidly stirring water and the precipitated solid was collected by filtration and dried to afford 2-[(1,3-dioxo-1,3-dihydro-2H-isoindol-2-yl)oxy]acetamide (2.0 g, 49%) as a yellow solid: $^1$H NMR (300 MHz, CD$_3$OD) δ4.63 (2H, s), 7.85-7.88 (4H, m); ESI MS m/z 221 [C$_{10}$H$_8$N$_2$O$_4$+H]$^+$.

Methylhydrazine (2.16 ml, 40.68 mmol) was added dropwise to a suspension of 2-[(1,3-dioxo-1,3-dihydro-2H-isoindol-2-yl)oxy]acetamide (2.0 g, 9.04 mmol) in MeOH/CH$_2$Cl$_2$ (2:8, 100 mL) at 0° C. The reaction mixture was stirred at 0° C. for 10 min and then at room temperature for 6 h. The solvent was removed in vacuo. The solid was triturated with methylene chloride and filtered. The filtrate was concentrated and the solid obtained was purified using SCX-2 to afford 2-(aminooxy)acetamide (220 mg, 27%) as a pale yellow solid: $^1$H NMR (500 MHz, DMSO-d$_6$) δ 3.90 (2H, s), 6.37 (2H, s), 7.18-7.34 (2H, br s).

Reference Example 19

2-(Aminooxy)-N-methylacetamide

2-[(1,3-Dioxo-1,3-dihydro-2H-isoindol-2-yl)oxy]-N-methylacetamide (470 mg, 11%) was prepared as a yellow solid following the procedure described for Reference Example 18 using 2-chloro-N-methylacetamide: $^1$H NMR (300 MHz, CD$_3$OD) δ2.85 (3H, s), 4.69 (2H, s), 7.80-7.88 (4H, m).

2-(Aminooxy)-N-methylacetamide (147 mg, 71%) was prepared as a yellow solid from 2-[(1,3-dioxo-1,3-dihydro-2H-isoindol-2-yl)oxy]-N-methylacetamide following the procedure described for Reference Example 18: $^1$H NMR (300 MHz, DMSO-d$_6$) δ2.61-2.63 (3H, d, J=4.7 Hz), 3.91 (2H, s), 6.33 (2H, s), 7.71 (1H, br s).

Reference Example 20

2-(Aminooxy)-N-phenylacetamide

2-[(1,3-Dioxo-1,3-dihydro-2H-isoindol-2-yl)oxy]-N-phenylacetamide (2.9 g, 53%) was prepared as a yellow solid following the procedure described for Reference Example 18 using 2-chloro-N-phenylacetamide: 1H NMR (300 MHz, CDCl$_3$) δ4.89 (2H, s), 7.13-7.18 (1H, t, J=7.4 Hz), 7.35-7.40 (2H, m) 7.75-7.93 (6H, m), 9.69 (1H, br s); ESI MS m/z 297 [C$_{16}$H$_{12}$N$_2$O$_4$+H]$^+$.

2-(Aminooxy)-N-phenylacetamide (570 mg, 35%) was prepared as a yellow solid from 2-[(1,3-dioxo-1,3-dihydro-2H-isoindol-2-yl)oxy]-N-phenylacetamide following the procedure described for Reference Example 18: $^1$H NMR (300 MHz, CDCl$_3$) δ4.29 (2H, s), 5.79 (2H, s), 7.10-7.16 (1H, m), 7.31-7.37 (2H, m), 7.55-7.58 (2H, m), 8.08 (1H, br s); ESI MS m/z 167 [C$_8$H$_{10}$N$_2$O$_2$+H]$^+$.

Reference Example 21

7-Chloro-N-[2-hydroxy-1,1-bis(hydroxymethyl)ethyl]-1H-pyrrolo[2,3-c]pyridine-2-carboxamide 7-Chloro-N-[2-hydroxy-1,1-bis(hydroxymethyl)ethyl]-1H-pyrrolo[2,3-c]pyridine-2-carboxamide (11.3 mg, 7%) was prepared as an off-white solid following the procedure described for Example 2 using 2-amino-2-(hydroxymethyl)-1,3-propanediol: mp 218-220° C.; $^1$H NMR (300 MHz, CD$_3$OD) δ3.89 (6H, s), 7.22 (1H, s), 7.63 (1H, d, J=5.6 Hz), 7.94 (1H, d, J=5.6 Hz); ESI MS m/z 300 [C$_{12}$H$_{14}$ClN$_3$O$_4$+H]$^+$; HPLC (Method B) 97.5% (AUC), t$_R$=11.6 min.

Reference Example 22

[1-(Phenylsulfonyl)-1H-pyrrolo[2,3-c]pyridin-2-yl](pyridin-4-yl)methanol

[1-(Phenylsulfonyl)-1H-pyrrolo[2,3-c]pyridin-2-yl](pyridin-4-yl)methanol (269 mg, 48%) was prepared as a tan solid following the procedure described for Example 137 using commercially available 4-pyridine carboxaldehyde. Purification was achieved using Biotage chromatography (silica, 1 to 18% methanol in methylene chloride): $^1$H NMR (500 MHz, CD$_3$OD) δ 6.60 (1H, s), 6.77 (1H, s), 7.48-7.67 (6H, m), 7.88-7.90 (2H, m), 8.31-8.32 (1H, m), 8.46-8.52 (2H, m), 9.30 (1H, s); ESI MS m/z 366 [C$_{19}$H$_{15}$N$_3$O$_3$S+H]$^+$.

Example 1

(7-Chloro-1H-pyrrolo[2,3-c]pyridin-2-yl)methanol

To a solution of ethyl 7-chloro-1H-pyrrolo[2,3-c]pyridine-2-carboxylate (preparation described in Reference Example 1) (230 mg, 1.02 mmol) in tetrahydrofuran (4 mL) at 0° C. under an atmosphere of nitrogen was added portionwise lithium aluminum hydride (94 mg, 2.0 mmol). The reaction mixture was maintained at 0° C. for 4 h then quenched by adding water (100 µL), 15% aqueous sodium hydroxide (100 µL), and water (250 µL) successively. The mixture was filtered through a pad of diatomaceous earth, washing well with ethyl acetate. Solvent evaporation provided 184 mg of crude yellow solid. Purification by column chromatography (silica gel, 60:40 hexanes/ethyl acetate) afforded (7-chloro-1H-pyrrolo[2,3-c]pyridin-2-yl)methanol (157 mg, 0.860 mmol, 84%) as an off-white powder: R$_f$ 0.30 (silica gel, 70:30 hexanes/ethyl acetate); mp 185-187° C.; $^1$H NMR (300 MHz, CD$_3$OD) δ4.94 (2H, s), 6.56 (1H, s), 7.49 (1H, d, J=5.5 Hz), 7.84 (1H, d, J=5.5 Hz); ESI MS m/z 183 [C$_8$H$_7$ClN$_2$O+H]$^+$; HPLC (H$_2$O/CH$_3$CN 100:0 to 0:100 over 20 min, hold for 10 min, 0.05% TFA added to solvents) 95.4% (AUC), t$_R$=11.1 min.

Example 2

N-Benzyl-7-chloro-1H-pyrrolo[2,3-c]pyridine-2-carboxamide

A mixture of 7-chloro-1H-pyrrolo[2,3-c]pyridine-2-carboxylic acid (Reference Example 1) (0.10 g, 0.51 mmol) and 1,1'-carbonyldiimidazole (0.09 g, 0.53 mmol) in N,N-dimethylformamide (3.4 mL) was stirred at 50° C. for 1 h. To the stirring solution was added benzylamine (0.11 mL, 1.02 mmol) and the reaction mixture was stirred at 65° C. until the reaction was complete by TLC analysis. The crude reaction mixture was poured into rapidly stirring water, and extracted with ethyl acetate (3×). The combined organic extracts were washed with water (3×) and saturated NH$_4$Cl, and dried over Na$_2$SO$_4$. The organic extract was filtered and concentrated to provide N-benzyl-7-chloro-1H-pyrrolo[2,3-c]pyridine-2-carboxamide (0.04 g, 0.14 mmol, 27%) as an off-white solid: mp 217-220° C.; $^1$H NMR (300 MHz, CDCl$_3$) δ4.70 (2H, d, J=5.7 Hz), 6.45-6.61 (1H, m), 6.85 (1H, s), 7.31-7.39 (5H, m), 7.47 (1H, d, J=5.7 Hz), 8.06 (1H, d, J=5.7 Hz), 9.55 (1H, br s); APCI MS m/z 286 [C$_{15}$H$_{12}$ClN$_3$O+H]$^+$; HPLC (Method A) >99% (AUC), t$_R$=16.3 min.

Example 3

7-Chloro-2-(4-morpholinylcarbonyl)-1H-pyrrolo[2,3-c]pyridine

7-Chloro-2-(4-morpholinylcarbonyl)-1H-pyrrolo[2,3-c]pyridine (70 mg, 50%) was prepared as an off-white solid following the procedure described for Example 2 using morpholine: mp 170-171° C.; $^1$H NMR (300 MHz, CDCl$_3$) δ3.73-3.93 (8H, m), 6.78 (1H, d, J=2.1 Hz), 7.48 (1H, d, J=5.4 Hz), 8.07 (1H, d, J=5.4 Hz), 9.55 (1H, br s); APCI MS m/z 266 $[C_{12}H_{12}ClN_3O_2+H]^+$; HPLC (Method A) >99% (AUC), $t_R$=11.7 min.

Example 4

7-Chloro-N-(2-pyridinylmethyl)-1H-pyrrolo[2,3-c]pyridine-2-carboxamide

7-Chloro-N-(2-pyridinylmethyl)-1H-pyrrolo[2,3-c]pyridine-2-carboxamide (91 mg, 62%) was prepared as a yellow solid following the procedure described for Example 2 using 2-(aminomethyl)pyridine: mp 177-183° C.; $^1$H NMR (300 MHz, CD$_3$OD) δ4.74 (2H, s), 7.26 (1H, s), 7.28-7.32 (1H, m), 7.46 (1H, d), 7.64 (1H, d, J=5.7 Hz), 7.81-7.88 (1H, m), 7.95 (1H, d, J=5.7 Hz), 8.53 (1H, d); APCI MS m/z 287 $[C_{14}H_{11}ClN_4O+H]^+$; HPLC (Method A) >99% (AUC), $t_R$=12.9 min.

Example 5

7-Chloro-N-(3-pyridinylmethyl)-1H-pyrrolo[2,3-c]pyridine-2-carboxamide

7-Chloro-N-(3-pyridinylmethyl)-1H-pyrrolo[2,3-c]pyridine-2-carboxamide (49 mg, 33%) was prepared as a yellow solid following the procedure described for Example 2 using 3-picolylamine: mp 189-191° C.; $^1$H NMR (300 MHz, CD$_3$OD) δ4.65 (2H, s), 7.20 (1H, d, J=1.5 Hz), 7.40-7.48 (1H, m), 7.62 (1H, d, J=5.7 Hz), 7.84-7.95 (2H, m), 8.47 (1H, d), 8.59 (1H, s); APCI MS m/z 287 $[C_{14}H_{11}ClN_4O+H]^+$; HPLC (Method A) >99% (AUC), $t_R$=11.9 min.

Example 6

7-Chloro-N-(4-pyridinylmethyl)-1H-pyrrolo[2,3-c]pyridine-2-carboxamide

7-Chloro-N-(4-pyridinylmethyl)-1H-pyrrolo[2,3-c]pyridine-2-carboxamide (68 mg, 46%) was prepared as a yellow solid following the procedure described for Example 2 using 4-(aminomethyl)pyridine: mp>340° C., no clear melt was observed; $^1$H NMR (300 MHz, CD$_3$OD) δ4.67 (2H, s), 7.22 (1H, s), 7.44 (2H, d, J=5.6 Hz), 7.63 (1H, d, J=5.5 Hz), 7.94 (1H, d, J=5.5 Hz), 8.48-8.50 (2H, m); APCI MS m/z 287 $[C_{14}H_{11}ClN_4O+H]^+$; HPLC (Method A) >99% (AUC), $t_R$=11.1 min.

Example 7

7-Chloro-N-(2-furylmethyl)-1H-pyrrolo[2,3-c]pyridine-2-carboxamide

7-Chloro-N-(2-furylmethyl)-1H-pyrrolo[2,3-c]pyridine-2-carboxamide (64 mg, 45%) was prepared as a brown solid following the procedure described for Example 2 using furfurylamine: mp 205-209° C.; $^1$H NMR (300 MHz, CD$_3$OD) δ4.60 (2H, s), 6.23-6.38 (2H, m), 7.20 (1H, s), 7.42-7.43 (1H, m), 7.60 (1H, d, J=5.5 Hz), 7.92 (1H, d, J=5.5 Hz); APCI MS m/z 276 $[C_{13}H_{10}ClN_3O_2+H]^+$; HPLC (Method A) >99% (AUC), $t_R$=15.4 min.

Example 8

7-Chloro-N-(2-thienylmethyl)-1H-pyrrolo[2,3-c]pyridine-2-carboxamide

7-Chloro-N-(2-thienylmethyl)-1H-pyrrolo[2,3-c]pyridine-2-carboxamide (46 mg, 30%) was prepared as a yellow solid following the procedure described for Example 2 using 2-thiophenemethylamine: mp 179-181° C.; $^1$H NMR (300 MHz, CD$_3$OD) δ4.78 (2H, s), 6.89-6.99 (1H, m), 7.07-7.09 (1H, m), 7.19 (1H, s), 7.29-7.32 (1H, m), 7.61 (1H, d, J=5.5 Hz), 7.93 (1H, d, J=5.5 Hz); APCI MS m/z 292 $[C_{13}H_{10}ClN_3OS+H]^+$; HPLC (Method A) >99% (ACU), $t_R$=16.3 min.

Example 9

N-[(7-Chloro-1H-pyrrolo[2,3-c]pyridin-2-yl)methyl]-N-ethylamine hydrochloride

7-Chloro-1H-pyrrolo[2,3-c]pyridine-2-carboxaldehyde (Example 138) (75 mg, 0.42 mmol) was dissolved in methanol (3 mL). Ethylamine (0.23 mL, 2 M in tetrahydrofuran) was added. After 2 h, sodium borohydride (25 mg, 0.67 mmol) was added. After an additional 2 h, the reaction mixture was quenched by addition of 5% aqueous sodium bicarbonate. The reaction mixture was extracted with diethyl ether, dried (magnesium sulfate), and evaporated to dryness (50 mg, 52% crude). The crude material was dissolved in acetonitrile and treated with hydrochloric acid (0.24 mL, 1 M in diethyl ether) to give N-[(7-chloro-1H-pyrrolo[2,3-c]pyridin-2-yl)methyl]-N-ethylamine hydrochloride (47 mg, 0.19 mmol, 42%) as an off-white powder: mp 242-245° C. dec.; $^1$H NMR (300 MHz, CD$_3$OD) δ1.40 (3H, t, J=7.3 Hz), 3.24 (2H, q, J=7.3 Hz), 4.57 (2H, s), 7.09 (1H, s), 7.92 (1H, d, J=6.1 Hz), 8.1 (1H, d, J=6.1 Hz); ESI MS m/z 210 $[C_{10}H_{12}ClN_3+H]^+$; HPLC (H$_2$O/CH$_3$CN 75:25 to 0:100 over 20 min, hold for 10 min) 94.5%, $t_R$=8.0 min.

Example 10

N-[(7-Chloro-1H-pyrrolo[2,3-c]pyridin-2-yl)methyl]-N-methylamine hydrochloride

7-Chloro-1H-pyrrolo[2,3-c]pyridine-2-carboxaldehyde (Example 138) (75 mg, 0.42 mmol) was dissolved in methanol (3 mL). Methylamine (0.23 mL, 2 M in tetrahydrofuran) was added. After 2 h, sodium borohydride (25 mg, 0.67 mmol) was added. After an additional 2 h, the reaction mixture was quenched by addition of 5% aqueous sodium bicarbonate. The reaction mixture was extracted with diethyl ether, dried (magnesium sulfate), and evaporated to dryness (29 mg, 32% crude). The crude material was dissolved in acetonitrile and treated with hydrochloric acid (0.15 mL, 1 M in diethyl ether) to give A-[(7-chloro-1H-pyrrolo[2,3-c]pyridin-2-yl)methyl]A-N-methylamine hydrochloride (21 mg, 9.3 μmol, 20%) as an off-white powder: mp 264-266° C. dec.; $^1$H NMR (300 MHz, CD$_3$OD) δ2.85 (3H, s), 4.57 (2H, s), 7.10 (1H, s), 7.97 (1H, d, J=6.2 Hz), 8.15 (1H, d, J=6.6 Hz); ESI MS m/z 196 $[C_9H_{10}ClN_3+H]^+$; HPLC (H$_2$O/CH$_3$CN 75:25 to 0:100 over 20 min, hold for 10 min) 88.2%, $t_R$=8.0 min.

Example 11

N-Benzyl-N-[(7-chloro-1H-pyrrolo[2,3-c]pyridin-2-yl)methyl]amine hydrochloride

7-Chloro-1H-pyrrolo[2,3-c]pyridine-2-carboxaldehyde (Example 138) (102 mg, 0.565 mmol) was dissolved in methanol (2.5 mL). Benzylamine (70 μL, 0.62 mmol) was added. After 2 h, sodium borohydride (35 mg, 0.90 mmol) was added. After an additional 2 h, the reaction mixture was quenched by addition of 59% aqueous sodium bicarbonate. The reaction mixture was extracted with diethyl ether, dried (magnesium sulfate), and evaporated to dryness (124 mg, 81% crude). The crude material was dissolved in acetonitrile and treated with hydrochloric acid (0.46 mL, 1 M in diethyl ether) to give N-benzyl-N-[(7-chloro-1H-pyrrolo[2,3-c]pyridin-2-yl)methyl]amine hydrochloride (107 mg, 0.347 mmol, 61%) as an off-white powder: mp 201-204° C.; $^1$H NMR (300 MHz, CD$_3$OD) δ4.35 (2H, s), 4.52 (2H, s), 6.87 (1H, s), 7.45-7.60 (5H, m), 7.60 (1H, d, J=5.6 Hz), 7.94 (1H, d, J=5.6 Hz); ESI MS m/z 272 [C$_{15}$H$_{14}$ClN$_3$+H]$^+$; HPLC (H$_2$O/CH$_3$CN 90:10 to 0:100 over 20 min, hold for 15 min, 0.05% TFA added to solvents) >99%, t$_R$=11.1 min.

Example 12

2-[(4-Acetyl-1-piperazinyl)carbonyl]-7-chloro-1H-pyrrolo[2,3-c]pyridine

2-[(4-Acetyl-1-piperazinyl)carbonyl]-7-chloro-1H-pyrrolo[2,3-c]pyridine (20 mg, 12%) was prepared as an off-white solid following the procedure described for Example 2 using 1-acetylpiperazine: mp 179-184° C.; $^1$H NMR (300 MHz, CD$_3$OD) δ2.15 (3H, s), 3.65-3.87 (8H, m), 6.92 (1H, s), 7.63 (1H, d, J=5.7 Hz), 7.95 (1H, d, J=5.7 Hz); ESI MS m/z 307 [C$_{14}$H$_{15}$ClN$_4$O$_2$+H]$^+$; HPLC (Method A) >99% (AUC), t$_R$=11.6 min.

Example 13

7-Chloro-2-(1-pyrrolidinylcarbonyl)-1H-pyrrolo[2,3-c]pyridine

7-Chloro-2-(1-pyrrolidinylcarbonyl)-1H-pyrrolo[2,3-c]pyridine (79 mg, 60%) was prepared as an off-white solid following the procedure described for Example 2 using pyrrolidine: mp 152-154° C.; $^1$H NMR (300 MHz, CD$_3$OD) δ1.98-2.07 (4H, m), 3.65-3.69 (2H, m), 3.82-3.86 (2H, m), 7.08 (1H, s), 7.64 (1H, d, J=5.7 Hz), 7.94 (1H, d, J=5.4 Hz); ESI MS m/z 250 [C$_{12}$H$_{12}$ClN$_3$O+H]$^+$; HPLC (Method A) 93.1% (AUC), t$_R$=14.4 min.

Example 14

7-Chloro-2-(4-thiomorpholinylcarbonyl)-1H-pyrrolo[2,3-c]pyridine

7-Chloro-2-(4-thiomorpholinylcarbonyl)-1H-pyrrolo[2,3-c]pyridine (76 mg, 54%) was prepared as an off-white solid following the procedure described for Example 2 using thiomorpholine: mp 62-72° C.; $^1$H NMR (300 MHz, CD$_3$OD) δ2.67-2.81 (4H, m), 3.91-4.13 (4H, m), 6.85 (1H, s), 7.61 (1H, d, J=5.4 Hz), 7.94 (1H, d, J=5.7 Hz); ESI MS m/z 282 [C$_{12}$H$_{12}$ClN$_3$OS+H]$^+$; HPLC (Method A) 94.5% (AUC), t$_R$=15.0 min.

Example 15

N-[(7-Chloro-1H-pyrrolo[2,3-c]pyridin-2-yl)methyl]-N-cyclopentylamine hydrochloride 7-Chloro-1H-pyrrolo[2,3-c]pyridine-2-carboxaldehyde (Example 138) (75 mg, 0.42 mmol) and cyclopentylamine (45 μL, 0.46 mmol) were dissolved in methanol (3 mL). After 4 h, sodium borohydride (25 mg, 0.67 mmol) was added in one portion. After an additional 2 h, the reaction mixture was quenched by addition of 2 N aqueous sodium hydroxide and extracted with diethyl ether. The organic layer was dried over sodium sulfate and evaporated. The residue was dissolved in acetonitrile and salted with 1 N ethereal hydrochloric acid. The precipitate was collected by filtration and crystallized from acetonitrile to give N-[(7-chloro-1H-pyrrolo[2,3-c]pyridin-2-yl)methyl]-N-cyclopentylamine hydrochloride (35 mg, 30%) as a white solid: mp 241-244° C.; $^1$H NMR (300 M-z, CD$_3$OD) δ1.70-1.95 (6H, m), 2.25 (2H, m), 3.75 (1H, m), 4.57 (2H, s), 7.09 (1H, s), 7.93 (1H, d, J=6.0 Hz), 8.12 (1H, J=6.0 Hz); ESI MS m/z 250 [C$_{13}$H$_{16}$ClN$_3$+H]$^+$; HPLC (Method C) >99% (AUC), t$_R$=12.9 min.

Example 16

N-[(7-Chloro-1H-pyrrolo[2,3-c]pyridin-2-yl)methyl]-N-(2-furylmethyl)amine hydrochloride N-[(7-Chloro-1H-pyrrolo[2,3-c]pyridin-2-yl)methyl]-N-(2-furylmethyl)amine hydrochloride (56 mg, 41%) was prepared as an off-white powder following the procedure described for Example 15 using furfurylamine: mp 98-101° C.; $^1$H NMR (300 MHz, CD$_3$OD) δ4.44 (2H, s), 4.53 (2H, s), 6.53 (1H, m), 6.70 (1H, m), 6.96 (1H, s), 7.68 (1H, m), 7.76 (1H, d, J=5.8 Hz), 8.03 (1H, J=5.8 Hz); ESI MS m/z 262 [C$_{13}$H$_{12}$ClN$_3$O+H]$^+$; HPLC (Method C) >99% (AUC), t$_R$=12.9 min.

Example 17

N-[(7-Chloro-1H-pyrrolo[2,3-c]pyridin-2-yl)methyl]-N-[2-(4-morpholinyl)ethyl]amine hydrochloride N-[(7-Chloro-1H-pyrrolo[2,3-c]pyridin-2-yl)methyl]-N-[2-(4-morpholinyl)ethyl]amine hydrochloride (22 mg, 16%) was prepared as an off-white powder following the procedure described for Example 15 using N-(2-aminoethyl)morpholine: mp 146-150° C.; ESI MS m/z 295 [C$_{14}$H$_{19}$ClN$_4$O+H]$^+$; HPLC (Method C) >99% (AUC), t$_R$=11.1 min.

Example 18

N-[(7-Chloro-1H-pyrrolo[2,3-c]pyridin-2-yl)methyl]-N-(2-pyridinylmethyl)amine hydrochloride N-[(7-Chloro-1H-pyrrolo[2,3-c]pyridin-2-yl)methyl]-N-(2-pyridinylmethyl)amine hydrochloride (12 mg, 8%) was prepared as a white powder following the procedure described for Example 15 using 2-(aminomethyl)pyridine: mp 176-179° C.; $^1$H NMR (300 MHz, CD$_3$OD) δ4.46 (2H, s), 4.59 (2H, s), 6.87 (1H, s), 7.44 (2H, m), 7.60 (1H, d, J=5.5 Hz), 7.86 (1H, m), 7.94 (1H, d, J=5.5 Hz), 8.65 (1H, m); ESI MS m/z 273 [C$_{14}$H$_{13}$ClN$_4$+H]$^+$; HPLC (Method C) >99% (AUC), t$_R$=12.7 min.

Example 19

7-Chloro-2-[(4-methyl-1-piperazinyl)carbonyl]-1H-pyrrolo[2,3-c]pyridine

7-Chloro-2-[(4-methyl-1-piperazinyl)carbonyl]-1H-pyrrolo[2,3-c]pyridine (13.4 mg, 9%) was prepared as a yellow solid following the procedure described for Example 2 using 1-methylpiperazine: mp 230-232° C.; $^1$H NMR (300 MHz, CD$_3$OD) δ2.34 (3H, s), 2.47-2.59 (4H, m), 3.72-3.87 (4H, m), 6.87 (1H, s), 7.61 (1H, d, J=5.4 Hz), 7.94 (1H, d, J=5.7 Hz); ESI MS m/z 279 [C$_{13}$H$_{15}$ClN$_4$O+H]$^+$; HPLC (Method B) 88.1% (AUC), t$_R$=10.9 min.

Example 20

7-Chloro-N-(2-pyridinyl)-1H-pyrrolo[2,3-c]pyridine-2-carboxamide

7-Chloro-N-(2-pyridinyl)-1H-pyrrolo[2,3-c]pyridine-2-carboxamide (11.5 mg, 8%) was prepared as an off-white solid following the procedure described for Example 2 using 2-aminopyridine: mp 94-102° C.; $^1$H NMR (300 MHz, CD$_3$OD) δ7.16-7.46 (1H, m), 7.67 (1H, s), 7.81 (1H, d, J=5.6 Hz), 7.82-7.87 (1H, m), 7.97 (1H, d, J=5.6 Hz), 8.26-8.28 (1H, m), 8.35-8.45 (1H, m); ESI MS m/z 273 [C$_{13}$H$_9$ClN$_4$O+H]$^+$; HPLC (Method B) >99% (AUC), t$_R$=13.4 min.

Example 21

7-Chloro-N-(3-pyridinyl)-1H-pyrrolo[2,3-c]pyridine-2-carboxamide

7-Chloro-N-(3-pyridinyl)-1H-pyrrolo[2,3-c]pyridine-2-carboxamide (49 mg, 35%) was prepared as an off-white solid following the procedure described for Example 2 using 3-aminopyridine: mp>320° C. (no melt was observed); $^1$H NMR (300 MHz, CD$_3$OD) δ7.42-7.49 (2H, m), 7.65-7.68 (1H, m), 7.95-7.97 (1H, m), 8.30-8.33 (2H, m), 8.94-8.95 (1H, m); ESI MS m/z 273 [C$_{13}$H$_9$ClN$_4$O+H]$^+$; HPLC (Method B) >99% (AUC), t$_R$=12.2 min.

Example 22

7-Chloro-N-(4-pyridinyl)-1H-pyrrolo[2,3-c]pyridine-2-carboxamide

7-Chloro-N-(4-pyridinyl)-1H-pyrrolo[2,3-c]pyridine-2-carboxamide (24 mg, 17%) was prepared as an off-white solid following the procedure described for example 2 using 4-aminopyridine: mp>320° C. (no melt was observed); $^1$H NMR (300 MHz, CD$_3$OD) δ7.46 (1H, s), 7.68 (1H, d, J=5.4 Hz), 7.87-7.89 (2H, m), 7.97 (1H, d, J=5.4 Hz), 8.45-8.47 (2H, m); ESI MS m/z 273 [C$_{13}$H$_9$ClN$_4$O+H]$^+$; HPLC (Method B) 99.0% (AUC), t$_R$=12.4 min.

Example 23

1-Benzyl-4-[N-[(7-chloro-1H-pyrrolo[2,3-c]pyridin-2-yl)methyl]amino]piperidine hydrochloride 1-Benzyl-4-[N-[(7-chloro-1H-pyrrolo[2,3-c]pyridin-2-yl)methyl]amino]piperidine hydrochloride (30 mg, 17%) was prepared as a white crystalline solid following the procedure described for Example 15 using 1-benzyl-4-aminopiperidine: mp 295-310° C. dec.; $^1$H NMR (300 MHz, CD$_3$OD) δ2.07 (2H, m), 2.46 (2H, m), 3.16 (2H, m), 3.50-3.70 (3H, m), 4.35 (2H, s), 4.54 (2H, s), 6.88 (1H, s), 7.45-7.65 (6H, m), 7.95 (1H, d, J=5.5 Hz); ESI MS m/z 355 [C$_{20}$H$_{23}$ClN$_4$+H]$^+$; HPLC (Method D) >99% (AUC), t$_R$=12.6 min.

Example 24

7-Chloro-2-(1-piperidinylmethyl)-1H-pyrrolo[2,3-c]pyridine hydrochloride

7-Chloro-2-(1-piperidinylmethyl)-1H-pyrrolo[2,3-c]pyridine hydrochloride (53 mg, 40%) was prepared as an off-white crystalline solid following the procedure described for Example 15 using piperidine: mp 240-244° C.; $^1$H NMR (300 MHz, CD$_3$OD) δ1.40-2.05 (6H, m), 3.07 (2H, m), 3.51 (2H, m), 4.51 (2H, s), 6.91 (1H, s), 7.62 (1H, d, J=5.6 Hz), 7.96 (1H, d, J=5.6 Hz); ESI MS m/z 250 [C$_{13}$H$_{16}$ClN$_3$+H]$^+$; HPLC (Method D) >99% (AUC), t$_R$=11.9 min.

Example 25

N-Phenyl-2-[[[phenyl (1H-pyrrolo[2,3-c]pyridin-2-yl)methylene]amino]oxy]acetamide N-Phenyl-2-[[[phenyl (1H-pyrrolo[2,3-c]pyridin-2-yl)methylene]amino]oxy]acetamide (25 mg, 8%) was prepared using 2-(aminooxy)-N-phenylacetamide (Reference Example 20) as a white solid following the procedure described for Example 128: R$_f$ 0.45 (90:10 methylene chloride/methanol); ESI MS m/z 371 [C$_{22}$H$_{18}$N$_4$O$_2$+H]$^+$; HPLC (Method A) >99% (AUC), t$_R$=17.7 min and 17.8 min.

Example 26

(7-Chloro-1H-pyrrolo[2,3-c]pyridin-2-yl)(phenyl)methanol

To a solution of 7-chloro-1H-pyrrolo[2,3-c]pyridine-2-carboxaldehyde (Example 138) (1.0 g, 5.5 mmol) in THF (27.7 mL) was added 3.0 M phenylmagnesium bromide in Et$_2$O (3.8 mL, 11.3 mmol) at −78° C. under a nitrogen atmosphere. After stirring for ca. 2 h, additional 3.0 M phenylmagnesium bromide in Et$_2$O (0.92 mL, 2.7 mmol) was added. The reaction mixture was stirred for another 1.5 h. The reaction mixture was poured into a saturated NH$_4$Cl solution and extracted with EtOAc (3×). The combined organic extracts were washed with saturated NaCl, and dried over Na$_2$SO$_4$. Filtration and concentration provided the crude material, which was purified by flash chromatography to provide (7-chloro-1H-pyrrolo[2,3-c]pyridin-2-yl)(phenyl)methanol (0.97 g, 67%) as an off-white solid: $^1$H NMR (300 MHz, CD$_3$OD) δ5.99 (1H, s), 6.42 (1H, s), 7.25-7.48 (6H, m), 7.82 (1H, d, J=5.4 Hz); ESI MS m/z 259 [C$_{14}$H$_{11}$ClN$_2$O+H]$^+$; HPLC (Method A) >99% (AUC), t$_R$=13.8 min.

Example 27

N-(2-Pyridinylmethyl)-1H-pyrrolo[2,3-c]pyridine-2-carboxamide

7-Chloro-N-(2-pyridinylmethyl)-1H-pyrrolo[2,3-c]pyridine-2-carboxamide (Example 4) (0.06 g, 0.21 mmol) in N,N-dimethylformamide (4.2 mL) was warmed to 60° C. under a nitrogen atmosphere. To the stirring solution were added triethylamine (0.06 mL, 0.43 mmol) and palladium dichloride (spatula tip, catalytic amount), and the reaction mixture was placed under a hydrogen atmosphere. The formation of palladium black was observed within 15 min. After stirring at 60° C. for 2 h, the heating bath was removed and the reaction mixture was stirred at room temperature overnight under a hydrogen atmosphere. The crude reaction mixture was filtered through a pad of diatomaceous earth, and the filtrate was concentrated. The residue was dissolved in ethyl acetate and washed with saturated NH$_4$Cl and saturated NaCl, and dried over Na$_2$SO$_4$. Filtration and concentration provided N-(2-pyridinylmethyl)-1H-pyrrolo[2,3-c]pyridine-2-carboxamide (0.015 g, 25%) as an off-white solid: mp 230-236 C; $^1$H NMR (300 MHz, CD$_3$OD) δ4.73 (2H, s), 7.20 (1H, s), 7.31-7.35 (1H, m), 7.46 (1H, d, J=7.9 Hz), 7.67 (1H, d, J=5.6 Hz), 7.79-7.83 (1H, m), 8.12 (1H, d, J=5.6 Hz), 8.50-8.52 (1H, m), 8.79 (1H, s); ESI MS m/z 253 [C$_{14}$H$_{12}$N$_4$O+H]$^+$; HPLC (Method A) 95.5% (AUC), t$_R$=16.7 min.

Example 28

N-(4-Pyridinylmethyl)-1H-pyrrolo[2,3-c]pyridine-2-carboxamide

N-(4-Pyridinylmethyl)-1H-pyrrolo[2,3-c]pyridine-2-carboxamide (10 mg, 30%) was prepared as a yellow solid following the procedure described for Example 27 using 7-chloro-N-(4-pyridinylmethyl)-1H-pyrrolo[2,3-c]pyridine-2-carboxamide (Example 6): $^1$H NMR (300 MHz, CD$_3$OD) δ 4.66 (2H, s), 7.18 (1H, s), 7.43-7.48 (2H, m), 7.67-7.73 (1H, m), 8.12-8.18 (1H, m), 8.49-8.53 (2H, m), 8.80 (1H, s); ESI MS m/z 253 [C$_{14}$H$_{12}$N$_4$+H]$^+$; HPLC (Method A) 92.0% (AUC), $t_R$=16.2 min.

Example 29

(7-Chloro-1H-pyrrolo[2,3-c]pyridin-2-yl)(phenyl)methanone

A mixture of (7-chloro-1H-pyrrolo[2,3-c]pyridin-2-yl)(phenyl)methanol (Example 26) (0.83 g, 3.2 mmol) and MnO$_2$ (3.35 g, 38.5 mmol) in methylene chloride (64 mL) was stirred under a nitrogen atmosphere at room temperature overnight (20 h). The crude reaction mixture was filtered through diatomaceous earth and rinsed with methylene chloride. Concentration afforded (7-chloro-1H-pyrrolo[2,3-c]pyridin-2-yl)(phenyl)methanone (0.68 g, 82%) as an off-white solid: mp 152-153° C.; $^1$H NMR (300 MHz, CDCl$_3$) δ 7.18 (1H, d, J=2.1 Hz), 7.55-7.71 (4H, m), 7.99-8.05 (2H, m), 8.11 (1H, d, J=5.7 Hz), 9.55 (1H, br s); ESI MS m/z 257 [C$_{14}$H$_9$ClN$_2$O+H]$^+$; HPLC (Method A) >99% (AUC), $t_R$=25.0 min.

Example 30

N-(3-Pyridinyl)-1H-pyrrolo[2,3-c]pyridine-2-carboxamide

N-(3-Pyridinyl)-1H-pyrrolo[2,3-c]pyridine-2-carboxamide (10 mg, 60%) was prepared as an off-white solid following the procedure described for Example 27 using 7-chloro-N-(3-pyridinyl)-1H-pyrrolo[2,3-c]pyridine-2-carboxamide (Example 21): mp 270-290° C.; $^1$H NMR (300 MHz, DMSO-d$_6$) δ 7.43-7.48 (1H, m), 7.58 (1H, d, J=2.9 Hz), 7.90 (1H, d, J=5.6 Hz), 8.22-8.25 (2H, m), 8.36-8.40 (1H, m), 8.94 (1H, s), 8.99 (1H, s), 10.79 (1H, d, J=6.6 Hz), 12.83 (1H, br s); ESI MS m/z 239 [C$_{13}$H$_{10}$N$_4$O+H]$^+$; HPLC (Method A) 95.2% (AUC), $t_R$=16.1 min.

Example 31

Phenyl(1H-pyrrolo[2,3-c]pyridin-2-yl)methanone O-(1H-imidazol-2-ylmethyl)oxime dihydrochloride Phenyl(1H-pyrrolo[2,3-c]pyridin-2-yl)methanone O-(1H-imidazol-2-ylmethyl)oxime dihydrochloride (79.5 mg, 51%) was prepared from 2-[(aminooxy)methyl]-1H-imidazole (Reference Example 16) following the procedure described for Example 128, but without basic treatment, as a mixture of isomers (74.6:24.7 by HPLC analysis): $^1$H NMR (500 MHz, DMSO-d$_6$) δ 5.47 (0.6H, s), 5.61 (1.4H, s), 6.72 (0.3H, s), 7.08 (0.7H, s), 7.50-7.57 (5H, m), 7.73 (2H, m), 8.10 (0.3H, d, J=6.3 Hz), 8.19 (0.7H, d, J=6.3 Hz), 8.31 (0.3H, d, J=6.3 Hz), 8.37 (0.7H, d, J=6.3 Hz), 9.08 (0.3H, s), 9.29 (0.7H, s), 13.73 (1H, br s), 15.07 (3H, br s); ESI MS m/z 318 [C$_{18}$H$_{15}$N$_5$O+H]$^+$; HPLC (Method A) >99% (AUC), $t_R$=13.3 and 13.4 min.

Example 32

(1H-Pyrrolo[2,3-c]pyridin-2-yl)(thien-3-yl)methanone

[1-(Phenylsulfonyl)-1H-pyrrolo[2,3-c]pyridin-2-yl](thien-3-yl)methanol (121 mg, 47%) was prepared as a tan solid following the procedure described for Example 137 using commercially available 3-thiophenecarboxaldehyde. Purification was achieved by Biotage chromatography (silica gel; 20 to 100% ethyl acetate in hexanes): mp 157-160° C. dec.; $^1$H NMR (500 MHz, CD$_3$OD) δ 6.66 (1H, br s), 6.86 (1H, br s), 7.08 (1H, m), 7.29-7.75 (8H, m), 8.30 (1H, d, J=5.3 Hz), 9.27 (1H, br s); ESI MS m/z 371 [C$_{18}$H$_{14}$N$_2$O$_3$S$_2$+H]$^+$; HPLC (Method A) >99% (AUC), $t_R$=16.1 min.

(1H-Pyrrolo[2,3-c]pyridin-2-yl)(thien-3-yl)methanol (149 mg, 98%) was prepared as a tan solid following the procedure described for Example 137 from [1-(phenylsulfonyl)-1H-pyrrolo[2,3-c]pyridin-2-yl](thien-3-yl)methanol:
$^1$H NMR (500 MHz, CD$_3$OD) δ 6.07 (1H, s), 6.39 (1H, s) 7.11-7.12 (1H, m), 7.36-7.39 (2H, m), 7.48-7.50 (1H, m), 7.99-8.03 (1H, m), 8.59 (1H, s).

(1H-Pyrrolo[2,3-c]pyridin-2-yl)(thien-3-yl)methanone (90 mg, 61%) was prepared as a tan solid following the procedure described for Example 137 from (1H-pyrrolo[2,3-c]pyridin-2-yl)(thien-3-yl)methanol: mp 178-181° C. dec.; $^1$H NMR (300 MHz, CD$_3$OD) δ 7.48 (1H, s), 7.61-7.65 (1H, m), 7.71-7.74 (1H, m), 7.94-7.96 (1H, m), 8.21 (1H, d, J=6.0 Hz), 8.51-8.53 (1H, m), 8.96 (1H, s); ESI MS m/z 229 [C$_{12}$H$_8$N$_2$OS+H]$^+$; HPLC (Method A) 96.2% (AUC), $t_R$=14.1 min.

Example 33

2-(1-Pyrrolidinylcarbonyl)-1H-pyrrolo[2,3-c]pyridine 2-(1-Pyrrolidinylcarbonyl)-1H-pyrrolo[2,3-c]pyridine (22 mg, 46%) was prepared as an off-white solid following the procedure described for Example 27 using 7-chloro-2-(1-pyrrolidinylcarbonyl)-1H-pyrrolo[2,3-c]pyridine (Example 13) and ethanol as a solvent: mp 260-275° C. dec.; $^1$H NMR (300 MHz, CD$_3$OD) δ 1.98-2.10 (4H, m), 3.66-3.71 (2H, m), 3.89-3.94 (2H, m), 7.10 (1H, s), 7.74 (1H, d, J=5.4 Hz), 8.13 (1H, d, J=5.7 Hz), 8.82 (1H, s); ESI MS m/z 216 [C$_{12}$H$_{13}$N$_3$O+H]$^+$; HPLC (Method A) 93.3% (AUC), $t_R$=10.3 min.

Example 34

N-Benzyl-N-[(7-chloro-1H-pyrrolo[2,3-c]pyridin-2-yl)(phenyl)methyl]amine dihydrochloride A mixture of (7-chloro-1H-pyrrolo[2,3-c]pyridin-2-yl)(phenyl)methanone (Example 29) (1.0 g, 3.9 mmol), molecular sieves and benzylamine (0.42 g, 3.90 mmol) in toluene (4.7 mL) was heated under reflux overnight (19 h). The reaction mixture was hot filtered to remove the molecular sieves, and the sieves were rinsed with ethyl acetate. The filtrate was concentrated to provide the intermediate imine (1.3 g, 94%) as a viscous orange oil: ESI MS m/z 346 [C$_{21}$H$_{16}$ClN$_3$+H]$^+$.

The crude imine intermediate (1.3 g, 3.6 mmol) was dissolved in methanol (18.3 mL), cooled to 0° C. and placed under a nitrogen atmosphere, and sodium borohydride (0.14 g, 3.6 mmol) was carefully added. Upon complete addition of sodium borohydride, the ice/water bath was removed and the reaction mixture was stirred overnight (18 h). The reaction mixture was quenched with water and concentrated to remove methanol. The residue was diluted with ethyl acetate, and the product was extracted with 2 N HCl (3×). The combined extracts were washed with ethyl acetate. The acidic extracts were made basic (pH 10) with 6 N NaOH then extracted with ethyl acetate (3×). The combined organic extracts were dried over $Na_2SO_4$, filtered and concentrated to give a yellow foam. The crude foam was dissolved in methanol and ethereal HCl was added. This mixture was concentrated to dryness, and then triturated with ethyl acetate. The solid was collected by filtration to give N-benzyl-N-[(7-chloro-1H-pyrrolo[2,3-c]pyridin-2-yl)(phenyl)methyl]amine dihydrochloride (0.80 g, 52%) as an off-white solid: mp 170-185° C. dec.; $^1$H NMR (300 MHz, $CD_3OD$) δ4.21-4.41 (2H, m), 5.91 (1H, s), 7.31 (1H, s), 7.45-7.71 (10H, m), 7.97-8.14 (2H, m); ESI MS 348 $[C_{21}H_{18}ClN_3+H]^+$; HPLC (Method A) 88.3% (AUC), $t_R$=14.6 min.

Example 35

Phenyl(1H-pyrrolo[2,3-c]pyridin-2-yl)methanone (7-Chloro-1H-pyrrolo[2,3-c]pyridin-2-yl)(phenyl)methanone (Example 29) (1.09 g, 4.25 mmol), palladium(II)chloride (15.4 mg, 3 mol %) and triethylamine (1.3 mL) were combined in N,N-dimethylformamide (25 mL). The reaction mixture was heated at 60° C. under an atmosphere of hydrogen for 8 h, then at room temperature for an additional 16 h. The reaction mixture was diluted with methylene chloride (25 mL) and filtered through a pad of diatomaceous earth. Evaporation of the solvents provided 1.3 g of crude orange solid. Purification by chromatography ($SiO_2$; 0-10% methanol in methylene chloride, 1400 mL) afforded phenyl(1H-pyrrolo[2,3-c]pyridin-2-yl)methanone (196 mg, 0.893 mmol, 21%) as an off-white solid: mp 245-247° C.; $^1$H NMR (300 MHz, $CD_3OD$) δ 7.18 (1H, s), 7.55-7.63 (2H, m), 7.65-7.77 (2H, m), 7.95-8.04 (2H, m), 8.17 (1H, d, J=5.7 Hz), 8.87 (1H, s); ESI MS m/z 223 $[C_{14}H_{10}N_2O+H]^+$; HPLC (Method A) >99% (AUC), $t_R$=13.4 min.

Phenyl(1H-pyrrolo[2,3-c]pyridin-2-yl)methanone was prepared in an alternative method.

Phenyl[1-(phenylsulfonyl)-1H-pyrrolo[2,3-c]pyridin-2-yl]methanone (Reference Example 13) (2.2 g, 6.1 mmol) and 10% aq NaOH (70 mL) in EtOH (135 mL) was heated to reflux. After 4 h, the mixture was concentrated under reduced pressure to remove most of the EtOH. The mixture was diluted with $H_2O$ (50 mL) and extracted with EtOAc (2×100 mL). The combined extracts were washed with saturated NaCl (25 mL), dried ($Na_2SO_4$) and concentrated under reduced pressure. Trituration in EtOAc/diethyl ether gave phenyl(1H-pyrrolo[2,3-c]pyridin-2-yl)methanone (1.14 g, 83%).

Example 36

3-Furyl(1H-pyrrolo[2,3-c]pyridin-2-yl)methanone O-(2-aminoethyl)oxime dihydrochloride 3-Furyl(1H-pyrrolo[2,3-c]pyridin-2-yl)methanone (Example 137) (63 mg, 0.30 mmol) and tert-butyl[2-(aminooxy)ethyl]carbamate (55 mg, 0.31 mmol) were combined in ethanol (5 mL). The pH of the mixture was adjusted to ca. 4 using 1 M ethereal hydrogen chloride and the reaction mixture was refluxed for 12 h. The solvent was removed under vacuum. The residue was dissolved in ethyl acetate, washed with saturated sodium bicarbonate solution and then brine, dried over sodium sulfate, and concentrated to a solid. Purification by Biotage chromatography (silica gel, 2 to 18% methanol in dichloromethane) produced tert-butyl 2-[[[(3-furyl)(1H-pyrrolo[2,3-c]pyridin-2-yl)methylene]amino]oxy]ethylcarbamate (50 mg, 45%) as a yellow solid.

tert-Butyl 2-[[[(3-furyl)(1H-pyrrolo[2,3-c]pyridin-2-yl)methylene]amino]oxy]ethylcarbamate (50 mg, 0.13 mmol) was dissolved in trifluoroacetic acid (5 mL) and the solution was stirred at room temperature for 1 h. The solvent was removed under vacuum. The residue was taken up in ethyl acetate, washed with saturated sodium bicarbonate solution, dried over sodium sulfate, and concentrated to an oil. Purification by column chromatography (silica gel, 95:5 dichloromethane; methanol followed by 89:9:1 dichloromethane: methanol:ammonium hydroxide) produced the amine as an oil. The amine (46 mg) was taken up in dichloromethane (3 mL) and cooled to 0° C. Ethereal hydrogen chloride (1 mL of a 1 M solution) was added dropwise and the reaction mixture was stirred for 45 min at ambient temperature. The solvent was removed under vacuum and the product was dried in a vacuum oven at 45° C. for 12 h to give 3-furyl(1H-pyrrolo[2,3-c]pyridin-2-yl)methanone O-(2-aminoethyl)oxime dihydrochloride (18 mg, 51% yield) as a brown solid: $^1$H NMR (500 MHz, $CD_3OD$) δ3.43-3.50 (2H, m), 4.57-4.64 (2H, m), 6.87 (0.60H, s), 6.96 (0.40H, s), 7.23-7.31 (2H, m), 7.66-7.73 (1H, m), 7.87 (0.60H, s), 8.15-8.37 (2.4H, m), 9.06 (0.40H, s), 9.23 (0.60H, s); ESI MS m/z=271 $[C_{14}H_{14}N_4O_2+H]^+$; HPLC (Method A) 93.4% (AUC), $t_R$=12.3 min.

Example 37

7-(Dibenzylamino)-N-(3-pyridinylmethyl)-1H-pyrrolo[2,3-c]pyridine-2-carboxamide

A mixture of ethyl 7-(dibenzylamino)-1H-pyrrolo[2,3-c]pyridine-2-carboxylate (Reference Example 3) (634 mg, 1.64 mmol) and 3-(aminomethyl)pyridine (3.8 mL, 37 mmol) was heated neat at 100° C. for 72 h under $N_2$. The mixture was cooled to room temperature and diluted with dichloromethane (150 mL) and water (100 mL). The layers were separated, and the aqueous layer was extracted with dichloromethane (2×50 mL). The combined organic extracts were dried ($Na_2SO_4$), filtered, and concentrated in vacuo. The residue was purified by chromatography (silica gel, gradient 50-70% ethyl acetate/hexanes) to provide 7-(dibenzylamino)-N-(3-pyridinylmethyl)-1H-pyrrolo[2,3-c]pyridine-2-carboxamide (364 mg, 49%) as an orange solid: $R_f$ 0.08 (75:25 ethyl acetate/hexanes); mp 105-108° C.; $^1$H NMR (300 MHz, $CDCl_3$) δ4.60 (2H, d, J=6.0 Hz), 4.89 (4H, s), 6.50 (1H, t, J=5.4 Hz), 6.71 (1H, s), 6.99 (1H, d, J=5.6 Hz), 7.28-7.31 (2H, m), 7.34-7.42 (9H, m), 7.64 (1H, d, J=7.8 Hz), 7.89 (1H, d, J=5.6 Hz), 8.55 (2H, s), 8.97 (1H, s); ESI MS m/z 448 $[C_{28}H_{25}N_5O+H]^+$; HPLC (Method A) >99% (AUC), $t_R$=13.02 min.

Example 38

7-(Dibenzylamino)-N-(2-thienylmethyl)-1H-pyrrolo[2,3-c]pyridine-2-carboxamide

A mixture of ethyl 7-(dibenzylamino)-1H-pyrrolo[2,3-c]pyridine-2-carboxylate (Reference Example 3) (634 mg, 1.64 mmol) and 2-(thienylmethyl)amine (2.0 mL, 19 mmol) was heated neat at 100° C. for 24 h under $N_2$. The mixture was cooled to room temperature and diluted with dichloromethane (150 mL) and water (100 mL). The layers were separated, and the aqueous layer was extracted with dichloromethane (2×50 mL). The combined organic extracts were dried (Na$_2$SO$_4$), filtered, and concentrated in vacuo. The residue was purified by chromatography (silica gel, gradient 5-15% ethyl acetate/hexanes) to provide 7-(dibenzylamino)-N-(2-thienylmethyl)-1H-pyrrolo[2,3-c]pyridine-2-carboxamide (22 mg, 3%) as a white solid: mp 152-154° C.; $^1$H NMR (300 MHz, CDCl$_3$) δ4.76 (2H, d, J=5.6 Hz), 4.88 (4H, s), 6.32 (1H, t, J=5.1 Hz), 6.68 (1H, d, J=1.9 Hz), 6.95-7.01 (3H, m), 7.25-7.31 (4H, m), 7.32-7.38 (7H, m), 7.89 (1H, d, J=5.6 Hz), 8.95 (1H, br s); ESI MS m/z 453 [C$_{27}$H$_{24}$N$_5$OS+H]$^+$; HPLC (Method A) >99% (AUC), t$_R$=13.96 min.

Example 39

Phenyl(1H-pyrrolo[2,3-c]pyridin-2-yl)methanone oxime

To a mixture of phenyl(1H-pyrrolo[2,3-c]pyridin-2-yl)methanone (Example 35) (161 mg, 0.72 mmol) and hydroxylamine hydrochloride (100 mg, 1.45 mmol) in ethanol (3.6 mL) were added LiOH.H$_2$O (120 mg, 2.16 mmol) and water (1.0 mL). The reaction mixture was heated under reflux until TLC analysis indicated consumption of the ketone. The mixture was concentrated to dryness. The residue was treated with water, and the residual solid was collected by filtration to give predominately one isomer of phenyl(1H-pyrrolo[2,3-c]pyridin-2-yl)methanone oxime (75.8 mg, 0.31 mmol, 44%) as a yellow solid. The aqueous filtrate was extracted with methylene chloride (3×). The combined extracts were washed with saturated NaCl, dried over Na$_2$SO$_4$, filtered, and concentrated to give ca. 1:1 mixture of isomers of the oxime (72 mg, 0.30 mmol, 42%) as a yellow solid:

Isomer A: $^1$H NMR (300 MHz, CDCl$_3$) δ6.55 (1H, s), 7.48-7.65 (7H, m), 8.29 (1H, d, J=5.4 Hz), 8.96 (1H, s), 10.90 (1H, br s).

Isomer B: mp 132-142° C.; $^1$H NMR (300 MHz, CDCl$_3$) δ6.24 (1H, s), 7.34-7.63 (7H, m), 8.90 (1H, d), 9.89 (1H, br s), 10.83 (1H, br s); ESI MS m/z 238 [C$_{14}$H$_{11}$N$_3$O+H]$^+$; HPLC (Method A) >99% (AUC), t$_R$=14.93, 15.24 min.

Example 40

1-Phenyl-1-(1H-pyrrolo[2,3-c]pyridin-2-yl)methylamine dihydrochloride

To a solution of phenyl(1H-pyrrolo[2,3-c]pyridin-2-yl)methanone oxime (Example 39) (100 mg, 0.42 mmol) in THF (4.2 mL) was added LiAlH$_4$ (80 mg, 2.11 mmol) under a nitrogen atmosphere. The reaction mixture was heated to reflux and stirred until TLC analysis indicated the starting oxime was consumed. The reaction mixture was cooled to room temperature and water (0.80 mL) was carefully added followed by 15% NaOH (0.80 mL), and water (2.4 mL). After stirring for 1 h, a wet slurry formed instead of filterable solid. Consequently, solid Na$_2$SO$_4$ was added and the mixture was filtered through diatomaceous earth. The filtrate was concentrated to give an off-white foam (60 mg). The crude material was dissolved in EtOAc (10 mL) and 2 N HCl in Et$_2$O (0.70 mL) was added. The resulting precipitate was collected by filtration and rinsed with EtOAc and Et$_2$O to give 1-phenyl-1-(1H-pyrrolo[2,3-c]pyridin-2-yl)methylamine dihydrochloride (71 mg, 0.24 mmol, 57%) as an off-white solid: mp 240-250° C.; 1H NMR (300 MHz, CD$_3$OD) δ6.09 (1H, s), 7.22 (1H, s), 7.53 (5H, br s), 8.21 (1H, d, J=6.4 Hz), 8.30 (1H, d, J=6.5 Hz), 9.01 (1H, s); ESI MS m/z 224 [C$_{14}$H$_{13}$N$_3$+H]$^+$; HPLC (Method A) 97.7% (AUC), t$_R$=11.76 min.

Example 41

7-(Dibenzylamino)-N-(4-pyridinylmethyl)-1H-pyrrolo[2,3-c]pyridine-2-carboxamide A mixture of 7-(dibenzylamino)-1H-pyrrolo[2,3-c]pyridine-2-carboxylic acid (Reference Example 4) (398 mg, 1.11 mmol), 4-(aminomethyl)pyridine (169 mg, 1.56 mmol), 1-ethyl-3-dimethylaminopropylcarbodiimide (EDCI) (299 mg, 1.56 mmol), 1-hydroxybenzotriazole (HOBt) (211 mg, 1.56 mol) and N,N-dimethylformamide (5 mL) was stirred at room temperature for 18 h. The mixture was diluted with water and extracted with ethyl acetate. The organic extract was washed with aqueous sodium hydrogen carbonate, dried over sodium sulfate, and concentrated in vacuo. The residue was purified by column chromatography (silica gel, 0:10 to 1:10 methanol/ethyl acetate). Recrystallization from hexanes/ethyl acetate gave 7-(dibenzylamino)-N-(4-pyridinylmethyl)-1H-pyrrolo[2,3-c]pyridine-2-carboxamide (419 mg, 84%) as colorless crystals: R$_f$ 0.20 (silica gel, ethyl acetate); mp 119-120° C.; $^1$H NMR (300 MHz, CDCl$_3$) δ4.62 (2H, d, J=6.0 Hz), 4.90 (4H, s), 6.40-6.52 (1H, m), 6.75 (1H, s), 7.01 (1H, d, J=5.6 Hz), 7.21 (2H, d, J=5.9 Hz), 7.25-7.38 (10H, m), 7.91 (1H, d, J=5.6 Hz), 8.57 (2H, d, J=5.9 Hz), 8.98 (1H, br s); ESI MS m/z 448 [C$_{28}$H$_{25}$N$_5$O+H]$^+$; HPLC (Method A) >99% (AUC), t$_R$=15.7 min.

Example 42

7-(Benzylamino)-N-(4-pyridinylmethyl)-1H-pyrrolo[2,3-c]pyridine-2-carboxamide Hydrogen (1 atm, balloon) was applied to a slurry of 7-(dibenzylamino)-N-(4-pyridinylmethyl)-1H-pyrrolo[2,3-c]pyridine-2-carboxamide (Example 41) (69 mg, 0.15 mmol), 10% palladium on carbon (wet, 100 mg) and HCl (saturated solution in 2-propanol, 5 M, 0.5 mL) in ethanol (4.5 mL) at room temperature for 3 h. The slurry was filtered to remove the catalyst, and the filtrate was concentrated in vacuo. The residue was partitioned between ethyl acetate and aqueous sodium hydrogen carbonate. The two layers were separated. The organic layer was dried over sodium sulfate and concentrated in vacuo. The residue was purified by column chromatography (silica gel, 2:1 to 1:2 hexanes/ethyl acetate). Recrystallization from hexanes/ethyl acetate gave 7-(benzylamino)-N-(4-pyridinylmethyl)-1H-pyrrolo[2,3-c]pyridine-2-carboxamide (13.2 mg, 24%) as colorless crystals: R$_f$ 0.42 (silica gel, 20:80 methanol/ethyl acetate); mp 199-200° C. (recrystallized from hexanes/ethyl acetate); $^1$H NMR (300 MHz, CD$_3$OD) δ4.63 (2H, s), 4.69 (2H, s), 6.91 (1H, d, J=6.0 Hz), 7.05 (1H, s), 7.22-7.43 (7H, m), 7.55 (1H, d, J=6.0 Hz), 8.48 (2H, d, J=6.0 Hz); ESI MS m/z 358 [C$_{21}$H$_{19}$N$_5$O+H]$^+$; HPLC (Method A) >99% (AUC), t$_R$=13.2 min.

Example 43

N-[Phenyl(1H-pyrrolo[2,3-c]pyridin-2-yl)methyl]nicotinamide

To a solution of 1-phenyl-1-(1H-pyrrolo[2,3-c]pyridin-2-yl)methylamine dihydrochloride (Example 40) (51 mg, 0.17 mmol), N,N-diisopropylethylamine (DIPEA) (0.15 mL, 0.85 mmol) and nicotinic acid (22 mg, 0.18=mmol) in methylene chloride (2.0 mL) was added 1-ethyl-3-dimethylaminopropylcarbodiimide hydrochloride (EDC-HCl) (30 mg, 0.20 mmol) followed by a catalytic amount of 4-dimethylaminopyridine (DMAP). The reaction mixture was stirred at room temperature overnight (20 h) under a $N_2$ atmosphere. TLC analysis showed the starting amine, therefore the reaction mixture was heated to reflux. After refluxing overnight, the reaction mixture was concentrated to dryness. The residue was dissolved in EtOAc and water. The organic layer was washed with water, 1 M citric acid, saturated $NaHCO_3$, and saturated NaCl. TLC analysis showed that the majority of desired product was extracted into the 1 M citric acid washing. The citric acid extracts were made basic with 15% NaOH solution and extracted with methylene chloride. The organic extracts were dried over $Na_2SO_4$, filtered and concentrated to dryness. Trituration with $Et_2O/CH_2Cl_2$ (1:1) provided N-[phenyl(1H-pyrrolo[2,3-c]pyridin-2-yl)methyl]nicotinamide (18 mg, 32%) as a light yellow solid after drying: mp 178-188° C.; $^1$H NMR (300 MHz, $CD_3OD$) δ6.30 (1H, s), 6.67 (1H, s), 7.35-7.55 (7H, m), 8.03 (1H, d, J=5.5 Hz), 8.30-8.38 (1H, m), 8.61 (1H, s), 8.69-8.71 (1H, m), 9.05-9.07 (1H, m); ESI MS m/z 329 $[C_{20}H_{16}N_4O+H]^+$; HPLC (Method A) >99% (AUC) $t_R$=13.3 min.

Example 44

1H-Pyrrolo[2,3-c]pyridine-2-carboxaldehyde oxime

To a solution of 1H-pyrrolo[2,3-c]pyridine-2-carboxaldehyde (0.83 g, 5.7 mmol) and hydroxylamine hydrochloride (0.49 g, 7.1 mmol) in ethanol (57 mL), was added pyridine (0.57 mL, 7.1 mmol). After refluxing for 6.5 h, the reaction mixture was cooled to room temperature and concentrated under reduced pressure. The residue was dissolved in water, and extractions were attempted with EtOAc and $CH_2Cl_2$. However, the desired product remained in the aqueous layer. The aqueous layer was concentrated to give a solid residue that was triturated with EtOAc. The solid was collected by filtration to provide a mixture of oxime isomers of 1H-pyrrolo[2,3-c]pyridine-2-carboxaldehyde oxime (1.0 g, 111% theoretical yield) as a tan solid after drying: $^1$H NMR (300 MHz, $CD_3OD$) major isomer δ7.07 (1H, s), 8.20-8.27 (2H, m), 8.31 (1H, s), 8.98 (1H, s).

Example 45

[[Phenyl (1H-pyrrolo[2,3-c]pyridin-2-yl)methylene]amino]guanidine dihydrochloride To a solution of phenyl(1H-pyrrolo[2,3-c]pyridin-2-yl) methanone (Example 35) (0.15 g, 0.67 mmol) in ethanol (6.7 mL) were added aminoguanidine hydrochloride (0.09 g, 0.81 mmol) and 6 N HCl (0.56 mL). The reaction mixture was heated to reflux under $N_2$. After 3 h, heating was terminated and the reaction mixture was slowly cooled to room temperature overnight. The reaction mixture was concentrated to dryness. The residue was dissolved in water and washed with diethyl ether. The aqueous layer was made basic with 15% NaOH solution and extracted with ethyl acetate (2×). The organic extracts were combined and washed with water and saturated NaCl, and dried over $Na_2SO_4$. Filtration and concentration provided the crude residue, which was dissolved in methanol. To the methanol solution was added 2 N HCl in $Et_2O$ (0.67 mL, 1.34 mmol). The mixture was concentrated to dryness and the resulting solid was crystallized from EtOH/$Et_2O$ (9:1) to provide [[phenyl (1H-pyrrolo[2,3-c]pyridin-2-yl)methylene]amino]guanidine dihydrochloride (0.22 g, 93%) as an off-white solid: mp 306-310° C.; $^1$H NMR (300 MHz, $CD_3OD$) δ6.71 (1H, s), 7.57-7.74 (5H, m), 8.07 (1H, d, J=6.5 Hz), 8.24 (1H, d, J=6.4 Hz), 9.10 (1H, s); ESI MS m/z 279 $[C_{15}H_{14}N_6+H]^+$; HPLC (Method A) >99% (AUC) $t_R$=12.9 min.

Example 46

[7-(Dibenzylamino)-1H-pyrrolo[2,3-c]pyridin-2-yl](phenyl)methanol

To a solution of 7-(dibenzylamino)-1H-pyrrolo[2,3-c]pyridine-2-carboxaldehyde (Example 141) (1.7 g, 5.1 mmol) in tetrahydrofuran (25 mL) was added 3.0 M phenylmagnesium bromide in $Et_2O$ (2.0 mL, 6 mmol) dropwise at −78° C. under a nitrogen atmosphere. After stirring for ca. 2 h, additional 3.0 M phenylmagnesium bromide in $Et_2O$ (2.0 mL, 6 mmol) was added. The reaction mixture was stirred for another 1.5 h warming to −15° C. The reaction mixture was poured into a saturated ammonium chloride solution, and extracted with ethyl acetate (3×). The combined organic extracts were washed with saturated sodium chloride, and dried over sodium sulfate. Filtration and concentration provided the crude material, which was purified by Biotage chromatography (10-30% ethyl acetate in hexanes) to provide [7-(dibenzylamino)-1H-pyrrolo[2,3-c]pyridin-2-yl](phenyl)methanol (1.32 g, 62%) as a yellow foam: mp 53-61° C.; $^1$H NMR (500 MHz, $CD_3OD$) δ4.60 (4H, q, J=23.2, 15.4 Hz), 5.95 (1H, s), 6.25 (1H, s), 7.05 (1H, d, J=5.7 Hz), 7.15-7.40 (15H, m), 7.62 (1H, d, J=5.7 Hz); ESI MS m/z 420 $[C_{28}H_{25}N_3O+H]^+$; HPLC (Method A) >99% (AUC), $t_R$=19.2 min.

Example 47

[7-(Dibenzylamino)-1H-pyrrolo[2,3-c]pyridin-2-yl](phenyl)methanone

A mixture of [7-(dibenzylamino)-1H-pyrrolo[2,3-c]pyridin-2-yl](phenyl)methanol (Example 46) (1.13 g, 2.69 mmol) and $MnO_2$ (2.35 g, 27.0 mmol) in methylene chloride (75 mL) was stirred under a nitrogen atmosphere at room temperature overnight (17 h). The crude reaction mixture was filtered through diatomaceous earth, rinsing with methylene chloride. The filtrate was concentrated to give a dark oil. Purification by Biotage chromatography (10-30% ethyl acetate in hexanes) provided [7-(dibenzylamino)-1H-pyrrolo[2,3-c]pyridin-2-yl](phenyl)methanone as a yellow solid: mp 122-124° C.; $^1$H NMR (300 MHz, $CD_3OD$) δ4.76 (4H, s), 5.49 (1H, s), 6.25 (1H, s), 7.11 (1H, s) 7.15-7.30 (10H, m), 7.56-7.72 (4H, m), 7.94-7.97 (2H, m); ESI MS m/z 418 $[C_{28}H_{23}N_3O+H]^+$; HPLC (Method A) >99% (AUC), $t_R$=20.2 min.

Example 48

[5-(Dibenzylamino)-1H-pyrrolo[2,3-c]pyridin-2-yl] methanol

To a solution of ethyl 5-(dibenzylamino)-1H-pyrrolo[2,3-c]pyridine-2-carboxylate (Reference Example 5) (12.9 g, 33.6 mmol) in THF (135 mL) under a $N_2$ atmosphere, was carefully added $LiAlH_4$ (1.92 g, 50.5 mmol) portionwise. After stirring at room temperature for 2 h, TLC analysis showed the starting ester was consumed. The reaction mixture was carefully quenched with water (1.92 mL), 15% NaOH (1.92 mL), followed by more water (5.76 mL) and diluted with diethyl ether. After stirring for 5 h, the solid was removed by filtration through diatomaceous earth. The filtrate was concentrated to provide a dark oil (13.3 g). The crude oil was purified by chromatography on silica gel to provide [5-(dibenzylamino)-1H-pyrrolo[2,3-c]pyridin-2-yl]methanol (9.76 g, 84%) as a green foam: $^1$H NMR (300 MHz, CDCl$_3$) δ4.72 (2H, s), 4.78 (4H, s), 6.04 (1H, s), 6.90 (1H, s), 7.20-7.30 (10H, m), 8.34 (1H, s), 8.63 (1H, br s); ESI MS m/z 344 [C$_{22}$H$_{21}$N$_3$O+H]$^+$; HPLC (Method A) >99% (AUC) t$_R$=17.7 min.

Example 49

N-[Phenyl (1H-pyrrolo[2,3-c]pyridin-2-yl)methyl] isonicotinamide

Using the procedure described for Example 43 with isonicotinic acid at room temperature, the reaction was stopped once 1-phenyl-1-(1H-pyrrolo[2,3-c]pyridin-2-yl)methylamine was consumed as judged by TLC analysis. Upon addition of water a solid precipitated. The solid was collected by filtration and dried to provide N-[phenyl(1H-pyrrolo[2,3-c]pyridin-2-yl)methyl]isonicotinamide (58 mg, 44%) as an off-white solid: mp 182-192° C.; $^1$H NMR (300 MHz, CD$_3$OD) δ6.34 (1H, s), 6.67 (1H, s), 7.30-7.55 (7H, m), 7.84-7.87 (2H, m), 8.04 (1H, d, J=5.7 Hz), 8.63 (1H, s), 8.69-8.71 (1H, m); ESI MS m/z 329 [C$_{20}$H$_{16}$N$_4$O+H]+; HPLC (Method A) >99% (AUC) t$_R$=14.1 min.

Example 50

N-[Phenyl (1H-pyrrolo[2,3-c]pyridin-2-yl)methyl]-2-pyridinecarboxamide

Using the procedure described for Example 43 with picolinic acid at room temperature, the reaction was stopped once 1-phenyl-1-(1H-pyrrolo[2,3-c]pyridin-2-yl)methylamine was consumed as judged by TLC analysis. Purification by Biotage chromatography provided N-[phenyl(1H-pyrrolo[2,3-c]pyridin-2-yl)methyl]-2-pyridinecarboxamide (8 mg, 6%) as an off-white solid: mp 102-110° C.; $^1$H NMR (300 MHz, CD$_3$OD) δ 6.42 (1H, s), 6.64 (1H, s), 7.36-7.62 (7H, m), 7.98-8.03 (2H, m), 8.13-8.16 (1H, m), 8.59 (1H, s), 8.63-8.67 (1H, m); ESI MS m/z 329 [C$_{20}$H$_{16}$N$_4$O+H]$^+$; HPLC (Method A) >99% (AUC) t$_R$=15.8 min.

Example 51

N-[Phenyl(1H-pyrrolo[2,3-c]pyridin-2-yl)methyl] benzamide

Using the procedure described for Example 43 with benzoic acid at room temperature, the reaction was stopped once 1-phenyl-1-(1H-pyrrolo[2,3-c]pyridin-2-yl)methylamine was consumed as judged by TLC analysis. Upon addition of water a solid precipitated. The solid was collected by filtration and dried to provide N-[phenyl(1H-pyrrolo[2,3-c]pyridin-2-yl)methyl]benzamide (9 mg, 9%) as an off-white solid: mp 206-208° C.; $^1$H NMR (300 MHz, CD$_3$OD) δ6.31 (1H, s), 6.67 (1H, s), 7.43-7.51 (9H, m), 7.89-7.92 (2H, m), 8.02 (1H, d, J=5.6 Hz), 8.60 (1H, s); ESI MS m/z 328 [C$_{21}$H$_{17}$N$_3$O+H]$^+$; HPLC (Method A) >99% (AUC) t$_R$=16.2 min.

Example 52

Phenyl(1H-pyrrolo[2,3-c]pyridin-2-yl)methanol

To a solution of (7-chloro-1H-pyrrolo[2,3-c]pyridin-2-yl)(phenyl)methanol (Example 26) (2.10 g, 8.12 mmol) and ammonium formate (3.07 g, 48.7 mmol) in methanol (28 mL) was added 10% Pd/C (0.21 g). The reaction mixture was refluxed for 1.5 h. TLC analysis showed the starting material was consumed. The reaction mixture was filtered through diatomaceous earth. The filtrate was concentrated to dryness. The crude mixture was dissolved in EtOAc and water. The aqueous layer was extracted with EtOAc (2×) and CH$_2$Cl$_2$. The combined organic extracts were dried over Na$_2$SO$_4$. After filtration and concentration, the crude material was purified by Biotage chromatography to provide phenyl(1H-pyrrolo[2,3-c]pyridin-2-yl)methanol (0.79 g, 43%) as an off-white solid: mp 178-180° C.; $^1$H NMR (300 MHz, CD$_3$OD) δ5.99 (1H, s), 6.35 (1H, s), 7.20-7.49 (6H, m), 7.99 (1H, d, J=5.6 Hz), 8.58 (1H, s); ESI MS m/z 224 [C$_{14}$H$_{12}$N$_2$O+H]$^+$; HPLC (Method A) >99% (AUC) t$_R$=14.5 min.

Example 53

1-[5-(Dibenzylamino)-1H-pyrrolo[2,3-c]pyridin-2-yl]ethanol

To a solution of 5-(dibenzylamino)-1H-pyrrolo[2,3-c]pyridine-2-carboxaldehyde (Example 139) (2.89 g, 8.46 mmol) in tetrahydrofuran (42 mL) was added 3.0 M methylmagnesium bromide in diethyl ether (7.05 mL, 21.2 mmol). The reaction mixture was stirred overnight (16 h) under a nitrogen atmosphere at room temperature. The reaction mixture was poured into a stirring saturated NH$_4$Cl solution. The layers were separated and the aqueous layer was extracted with EtOAc (2×). The combined organic extracts were dried over Na$_2$SO$_4$. After filtration and concentration, a small amount of the desired product was obtained by trituration with CH$_2$Cl$_2$. Additional material was obtained by purification using Biotage chromatography on silica (eluting with Hex/EtOAc 90:10 to 0:100) to provide 1-[5-(dibenzylamino)-1H-pyrrolo[2,3-c]pyridin-2-yl]ethanol (1.74 g, 57%) as an off-white solid: $^1$H NMR (300 MHz, CD$_3$OD) δ1.53 (3H, d, J=6.6 Hz), 4.69 (4H, s), 4.90-4.99 (1H, m), 6.08 (1H, s), 6.58 (1H, s), 7.17-7.29 (10H, m), 8.26 (1H, s); ESI MS m/z 358 [C$_{23}$H$_{23}$N$_3$O+H]$^+$; HPLC (Method A) 98.5% (AUC), t$_R$=18.2 min.

Example 54

[5-(Dibenzylamino)-1H-pyrrolo[2,3-c]pyridin-2-yl] (phenyl)methanol

Following the procedure described above for Example 53, using phenylmagnesium bromide, [5-(dibenzylamino)-1H-pyrrolo[2,3-c]pyridin-2-yl](phenyl)methanol was prepared (1.45 g, 42%) as a light red foam followed by purification by Biotage chromatography: $^1$H NMR (300 MHz, CD$_3$OD) δ4.68 (4H, s), 5.87 (1H, s), 6.02 (1H, s), 6.57 (1H, s), 7.12-7.43 (15H, m), 8.24 (1H, s); ESI m/z 420 [C$_{28}$H$_{25}$N$_3$O+H]$^+$; HPLC (Method A) >99% (AUC), t$_R$=19.9 min.

Example 55

[5-(Dibenzylamino)-1H-pyrrolo[2,3-c]pyridin-2-yl] (phenyl)methanone

[5-(Dibenzylamino)-1H-pyrrolo[2,3-c]pyridin-2-yl](phenyl)methanol (Example 54) was oxidized using manganese dioxide to provide [5-(dibenzylamino)-1 h-pyrrolo[2,3-c]pyridin-2-yl](phenyl)methanone following the procedure described for Example 139 using methylene chloride as a solvent. Trituration of the crude material with Et$_2$O provided

[5-(dibenzylamino)-1H-pyrrolo[2,3-c]pyridin-2-yl](phenyl)methanone (220 mg, 44%) as a yellow solid: $^1$H NMR (300 MHz, CD$_3$OD) δ4.77 (4H, s), 6.69 (1H, s), 6.82 (1H, s), 7.19-7.27 (10H, m), 7.53-7.65 (3H, m), 7.92-7.95 (2H, m), 8.57 (1H, s); ESI MS m/z 418 [C$_{28}$H$_{23}$N$_3$O+H]$^+$; HPLC (Method A) >99% (AUC), t$_R$=20.9 min.

Example 56

1-[5-(Dibenzylamino)-1H-pyrrolo[2,3-c]pyridin-2-yl]ethanone

1-[5-(Dibenzylamino)-1H-pyrrolo[2,3-c]pyridin-2-yl]ethanol (Example 53) was oxidized using manganese dioxide to provide 1-[5-(dibenzylamino)-1H-pyrrolo[2,3-c]pyridin-2-yl]ethanone following the procedure described for Example 139 using tetrahydrofuran as a solvent. Purification by Biotage chromatography provided 1-[5-(dibenzylamino)-1H-pyrrolo[2,3-c]pyridin-2-yl]ethanone (200 mg, 40%) as a yellow solid: $^1$H NMR (300 MHz, CD$_3$OD) δ2.54 (3H, s), 4.76 (4H, s), 6.67 (1H, s), 6.97 (1H, s), 7.12-7.30 (10H, m), 8.50 (1H, s); ESI m/z 356 [C$_{23}$H$_{21}$N$_3$O+H]$^+$; HPLC (Method A) >99% (AUC), t$_R$=18.8 min.

Example 57

(5-Amino-1H-pyrrolo[2,3-c]pyridin-2-yl)(phenyl)methanol

A mixture of [5-(dibenzylamino)-1H-pyrrolo[2,3-c]pyridin-2-yl](phenyl)methanone (Example 55) (674 mg, 1.61 mmol), ammonium formate (2.04 g, 32.3 mmol) and 10% palladium on carbon (350 mg, 50% by wt.) in methanol (40.2 mL) and ethanol (40.2 mL) was heated under reflux for 1 h. The reaction mixture was filtered through diatomaceous earth to remove the catalyst. After concentration to dryness, the residue was treated with a small amount of methanol (ca. 3 mL) and a precipitate formed. The solid was filtered, rinsed with a small amount of methanol, and collected. Additional material was obtained from Biotage chromatography of the filtrate. This provided (5-amino-1H-pyrrolo[2,3-c]pyridin-2-yl)(phenyl)methanol (119 mg, 32%) as a white solid: $^1$H NMR (300 MHz, DMSO-d$_6$) δ5.81 (1H, s), 5.94 (1H, s), 6.44 (1H, s), 7.27-7.53 (5H, m), 8.06 (1H, s), 8.20 (1H, s), 10.9 (1H, br s); ESI MS m/z 240 [C$_{14}$H$_{13}$N$_3$O+H]$^+$; HPLC (Method A) 89.0% (AUC), t$_R$=14.0 min.

Example 58 tert-Butyl[[[phenyl(1H-pyrrolo[2,3-c]pyridin-2-yl)methylene]amino]oxy]acetate

A mixture of phenyl(1H-pyrrolo[2,3-c]pyridin-2-yl)methanone oxime (Example 39) (100 mg, 0.42 mmol) and sodium hydride (17 mg of a 60% in mineral oil, 0.43 mmol) in N,N-dimethylformamide (4 mL) was stirred for 0.5 h. tert-Butyl bromoacetate (60 μL, 0.41 mmol) was added dropwise and the reaction mixture was heated at 60° C. for 3 h. After stirring at room temperature for 12 h, the reaction mixture was quenched with water (10 mL) and extracted with diethyl ether (3×15 mL). The combined organic extracts were washed with water (1×25 mL) and brine (1×25 mL), dried over sodium sulfate and concentrated to an oil. Purification by Biotage chromatography (1-10% methanol in methylene chloride) provided tert-butyl [[[phenyl(1H-pyrrolo[2,3-c]pyridin-2-yl)methylene]amino]oxy]acetate as a tan solid: mp 47-52° C.; $^1$H NMR (500 MHz, CDCl$_3$) δ 1.46-1.61 (9H, m), 4.63 (0.66H, s), 4.85 (1.33H, s), 6.37 (0.33H, s), 6.53 (0.66H, s), 7.26-7.62 (6H, m), 8.23-8.28 (0.66H, m), 8.84 (0.33H, br s), 8.96 (1H, br s), 9.13 (0.33H, br s), 11.04 (0.66H, br s); ESI MS m/z 352 [C$_{20}$H$_{21}$N$_3$O$_3$+H]$^+$; HPLC (Method A) 97.8% (AUC), t$_R$=18.3 and 18.5 min.

Example 59

Phenyl(1H-pyrrolo[2,3-c]pyridin-2-yl)methanone O-[2-(dimethylamino)ethyl]oxime

Phenyl(1H-pyrrolo[2,3-c]pyridin-2-yl)methanone O-[2-(dimethylamino)ethyl]oxime was prepared as a yellow solid following the procedure described for Example 58 using commercially available dimethyl aminoethyl chloride: $^1$H NMR (500 MHz, CD$_3$OD) δ 2.99 (6H, s), 3.31 (3H, s), 3.68-3.72 (2H, m), 7.07 (1H, s), 7.47-7.63 (5H, m), 8.16-8.28 (2H, m), 9.25 (1H, s); ESI MS m/z 309 [C$_{18}$H$_{20}$N$_4$O+H]$^+$; HPLC (Method A) 96.8% (AUC), t$_R$=13.3 min.

Example 60 tert-Butyl 2-[[[phenyl(1H-pyrrolo[2,3-c]pyridin-2-yl)methylene]amino]oxy]ethylcarbamate tert-Butyl 2-[[[phenyl(1H-pyrrolo[2,3-c]pyridin-2-yl)methylene]amino]oxy]ethylcarbamate (a mixture of isomers) was prepared as an off white solid following the procedure described for Example 58 using Boc protected 2-aminoethyl chloride: mp 84-88° C.; $^1$H NMR (300 MHz, CDCl$_3$) δ 1.46 (9H, br s), 3.62-3.68 (2H, m), 4.37-4.40 (2H, m), 5.00-5.04 (1H, m), 6.45 (1H, s), 7.41-7.61 (6H, m), 8.24 (1H, d, J=5.5 Hz), 9.15 (1H, s), 11.55 (1H, br s); ESI MS m/z 381 [C$_{21}$H$_{24}$N$_4$O$_3$+H]$^+$; HPLC (Method A) 96.9% (AUC), t$_R$=18.5 min.

Example 61

Phenyl(1H-pyrrolo[2,3-c]pyridin-2-yl)methanone O-(2-methoxyethyl)oxime

Phenyl (1H-pyrrolo[2,3-c]pyridin-2-yl)methanone O-(2-methoxyethyl)oxime was prepared as an orange oil following the procedure described for Example 58 using commercially available 2-chloroethyl methyl ether: $^1$H NMR (300 MHz, CDCl$_3$) δ 3.38 (0.6H, s), 3.54 (2.4H, s), 3.70-3.83 (2H, m), 4.35-4.55 (2H, m), 6.38 (0.2H, s), 6.53 (0.8H, s), 7.40-7.69 (6H, m), 8.23-8.25 (1H, m), 8.86-8.91 (1H, m), 9.25 (0.2H, br s), 10.69 (0.8H, br s); ESI MS m/z 296 [C$_{17}$H$_{17}$N$_3$O$_2$+H]$^+$; HPLC (Method A) 90.5% (AUC), t$_R$=16.4 and 16.6 min.

Example 62 and Example 63

Phenyl(1H-pyrrolo[2,3-c]pyridin-2-yl)methanone semicarbazone

A mixture of phenyl(1H-pyrrolo[2,3-c]pyridin-2-yl)methanone (Example 35) (108 mg, 0.49 mmol), semicarbazide hydrochloride (57 mg, 0.51 mmol) and potassium carbonate (58 mg, 0.42 mmol) in ethanol (3.0 mL) was refluxed under a nitrogen atmosphere overnight (14 h). The reaction mixture was cooled to room temperature, water was added, and the reaction mixture was extracted with EtOAc (2×). The combined organic extracts were dried over Na$_2$SO$_4$. After filtration and concentration, the crude material was purified by Biotage chromatography to afford phenyl(1H-pyrrolo[2, 3-c]pyridin-2-yl)methanone semicarbazone as two isomers, Example 62 (5.3 mg, 4%) and Example 63 (5.9 mg, 4%), as a yellow solid:

Example 62: $^1$H NMR (300 MHz, CD$_3$OD) δ6.87 (1H, s), 7.39-7.42 (3H, m), 7.61-7.64 (2H, m), 7.72-7.74 (1H, m), 8.15 (1H, d, J=5.65 Hz), 8.75 (1H, s); ESI MS m/z 280 [C$_{15}$H$_{13}$N$_5$O+H]$^+$; HPLC (Method A) 92.1% (AUC), t$_R$=13.8 min.

Example 63: $^1$H NMR (300 MHz, CD$_3$OD) δ6.21 (1H, s), 7.45-7.50 (3H, m), 7.62-7.65 (3H, m), 8.04 (1H, d, J=5.61 Hz), 8.69 (1H, s); ESI MS m/z 280 [C$_{15}$H$_{13}$N$_5$O+H]$^+$; HPLC (Method A) >99% (AUC), t$_R$=13.8 min.

Example 64

[[1-[5-(Dibenzylamino)-1H-pyrrolo[2,3-c]pyridin-2-yl]ethylidene]amino]guanidine dihydrochloride A mixture of 1-[5-(dibenzylamino)-1H-pyrrolo[2,3-c]pyridin-2-yl]ethanone (Example 56) (91 mg, 0.26 mmol), aminoguanidine hydrochloride (30 mg, 0.27 mmol) and 6 N HCl (0.22 mL) in ethanol (10 mL) was heated to reflux under a nitrogen atmosphere for 1.5 h. The reaction mixture was cooled to room temperature, and the desired product precipitated from the solution. The solid was collected by filtration and rinsed with ethanol. After drying, [[1-[5-(dibenzylamino)-1H-pyrrolo[2,3-c]pyridin-2-yl]ethylidene]amino]guanidine dihydrochloride (82 mg, 65%) was obtained as a yellow solid: ESI MS m/z 412 [C$_{24}$H$_{25}$N$_7$+H]$^+$; HPLC (Method A) 94.9% (AUC), t$_R$=16.5 min.

Example 65

[[[5-(Dibenzylamino)-1H-pyrrolo[2,3-c]pyridin-2-yl](phenyl)methylene]amino]guanidine dihydrochloride A mixture of [5-(dibenzylamino)-1H-pyrrolo[2,3-c]pyridin-2-yl](phenyl)methanone (Example 55) (129 mg, 0.31 mmol), aminoguanidine hydrochloride (36 mg, 0.32 mmol) and 6 N HCl (0.26 mL) in ethanol (10 mL) was heated to reflux under a nitrogen atmosphere for 2.5 h. TLC analysis showed the remaining ketone, therefore additional aminoguanidine hydrochloride (10 mg, 0.09 mmol) was added. The reaction mixture was refluxed until TLC analysis showed the reaction was completed (2 h). After concentration to dryness, the crude material was triturated with EtOAc. The solid was collected by filtration and dried to provide [[[5-(dibenzylamino)-1H-pyrrolo[2,3-c]pyridin-2-yl](phenyl)methylene]amino]guanidine dihydrochloride (60.6 mg, 36%) as a yellow solid: ESI MS m/z 474 [C$_{29}$H$_{27}$N$_7$+H]$^+$; HPLC (Method A) 89.3% (AUC), t$_R$=17.5 min.

Example 66

[[[Phenyl(1H-pyrrolo[2,3-c]pyridin-2-yl)methylene]amino]oxy]acetic acid

[[[Phenyl(1H-pyrrolo[2,3-c]pyridin-2-yl)methylene]amino]oxy]acetic acid was prepared by treating tert-butyl [[[phenyl(1H-pyrrolo[2,3-c]pyridin-2-yl)methylene]amino]oxy]acetate (Example 58) (18 mg, 0.05 mmol) with trifluoroacetic acid (1 mL) as an off white solid after concentration: mp 68-73° C.; ESI MS m/z 296 [C$_{16}$H$_{13}$N$_3$O$_3$+H]$^+$; HPLC (Method A) 98.9% (AUC), t$_R$=15.7 min.

Example 67

Phenyl(1H-pyrrolo[2,3-c]pyridin-2-yl) methanone O-(2-aminoethyl)oxime hydrochloride Phenyl(1H-pyrrolo[2,3-c]pyridin-2-yl)methanone O-(2-aminoethyl)oxime hydrochloride was prepared by treating tert-butyl 2-[[[phenyl(1H-pyrrolo[2,3-c]pyridin-2-yl)methylene]amino]oxy]ethylcarbamate (Example 60) with ethereal hydrogen chloride as an off-white solid (a mixture of isomers): mp 176-184° C. dec.; $^1$H NMR (500 MHz, CD$_3$OD) δ 3.22 (2H, br s), 3.37 (2H, br s), 4.44-4.81 (2H, m), 6.68 (0.17H, s) 7.00 (0.83H, s), 7.37-7.54 (6H, m), 7.97-8.20 (1H, m), 8.96 (0.17H, br s), 9.14 (0.83H, br s); ESI MS m/z 281 [C$_{16}$H$_{16}$N$_4$O+H]$^+$; HPLC (Method A) 98.3% (AUC), t$_R$=13.0 and 13.2 min.

Example 68

1-(1H-Pyrrolo[2,3-c]pyridin-2-yl)ethanol

To a solution of 1H-pyrrolo[2,3-c]pyridine-2-carboxaldehyde (0.80 g, 5.47 mmol) in THF (27.4 mL) was slowly added methylmagnesium chloride (22% by weight in THF, 5.0 mL, 15.3 mmol) at 0° C. under a nitrogen atmosphere. The ice/water bath was removed, and the reaction mixture was stirred for 45 min. The reaction mixture was quenched with methanol and concentrated to dryness. The solid residue was treated with water (50 mL) and sonicated. The solids were filtered and collected, but they were shown to be undesired material. The water filtrate was concentrated to dryness, treated with 6 N HCl (2.55 mL) and concentrated to dryness again. The resulting orange solid was diluted with EtOAc and treated with saturated NaHCO$_3$. The aqueous layer was extracted with EtOAc (3×). The combined organic extracts were washed with saturated NaCl and dried over Na$_2$SO$_4$. The organic extract was filtered and concentrated to provide 1-(1H-pyrrolo[2,3-c]pyridin-2-yl)ethanol (0.67 g, 75%) as a tan solid: $^1$H NMR (300 MHz, CD$_3$OD) δ1.59 (3H, d, J=6.6 Hz), 5.05 (1H, q, J=6.6 Hz), 6.41 (1H, s), 7.49-7.51 (1H, m), 8.00 (1H, d, J=5.6 Hz), 8.60 (1H, s); ESI MS m/z 163 [C$_9$H$_{10}$N$_2$O+H]$^+$; HPLC (Method A) 89.0% (AUC), t$_R$=9.34 min.

Example 69

Phenyl(1H-pyrrolo[2,3-c]pyridin-2-yl)methanone O-[2-(4-morpholinyl)ethyl]oxime hydrochloride A mixture of phenyl(1H-pyrrolo[2,3-c]pyridin-2-yl)methanone oxime (Example 39) (100 mg, 0.42 mmol) and sodium hydride (17 mg of 60% in mineral oil, 0.43 mmol) in N,N-dimethyl formamide (2 mL) was stirred under a nitrogen atmosphere for 0.5 h. A mixture of N-(2-chloroethyl)morpholine hydrochloride (80 mg, 0.43 mmol) and sodium hydride (17 mg of 60% in mineral oil, 0.43 mmol) in N,N-dimethylformamide was added and the reaction mixture was stirred at room temperature for 38 h. The reaction mixture was poured into stirring cold water (25 mL) and extracted with ethyl acetate (3×10 mL). The combined organic extracts were washed with water and brine, dried over sodium sulfate, and concentrated. Purification by Biotage chromatography (1 to 10% methanol in methylene chloride) produced an oil. The oil was dissolved in ethyl acetate (5 mL) and ethereal hydrogen chloride (0.45 mL of a 1 M solution in diethyl ether) was added. The reaction mixture was stirred for 1 h and the precipitate formed. The solvent was decanted and the solid was dried to give phenyl(1H-pyrrolo[2,3-c]pyridin-2-yl)methanone O-[2-(4-morpholinyl)ethyl]oxime hydrochloride, a mixture of isomers, as a pale yellow solid: ESI MS m/z 351 $[C_{20}H_{22}N_4O_2+H]^+$; HPLC (Method A) >99% (AUC), $t_R$=13.3 and 13.7 min.

Example 70

1-(1H-Pyrrolo[2,3-c]pyridin-2-yl)ethanone

To a solution of 1-(1H-pyrrolo[2,3-c]pyridin-2-yl)ethanol (Example 68) (0.65 g, 4.0 mmol) in THF (80 mL) was added manganese dioxide (4.18 g, 48 mmol). After stirring 2 h at room temperature, TLC analysis indicated that the reaction was completed. The reaction mixture was filtered through diatomaceous earth and rinsed with EtOAc. The filtrate was concentrated and triturated with $Et_2O$ to provide 1-(1H-pyrrolo[2,3-c]pyridin-2-yl)ethanone as an off-white solid: mp 236-242° C. dec.; $^1$H NMR (300 MHz, $CD_3OD$) δ2.63 (3H, s), 7.34 (1H, s), 7.70-7.73 (1H, m), 8.13 (1H, d, J=5.7 Hz), 8.80 (1H, s); ESI MS m/z 161 $[C_9H_8N_2O+H]^+$; HPLC (Method A) 92.7% (AUC), $t_R$=7.75 min.

Example 71

[[1-(1H-Pyrrolo[2,3-c]pyridin-2-yl)ethylidene]amino]guanidine dihydrochloride A mixture of 1-(1H-pyrrolo[2,3-c]pyridin-2-yl)ethanone (Example 70) (90 mg, 0.56 mmol) and aminoguanidine hydrochloride (65 mg, 0.59 mmol) in ethanol (5.6 mL) and 6 N HCl (0.47 mL) was heated under reflux for 1.5 h. The reaction mixture was cooled to room temperature and the precipitate was filtered, rinsed with ethanol and diethyl ether, and dried under vacuum at 45° C. to provide [[1-(1H-pyrrolo[2,3-c]pyridin-2-yl)ethylidene]amino]guanidine dihydrochloride (138 mg, 86%) as a white solid: mp 314-318° C. dec.; $^1$H NMR (300 MHz, $CD_3OD$) δ2.50 (3H, s), 7.40 (1H, s), 8.10-8.27 (2H, m), 9.04 (1H, s); ESI MS m/z 217 $[C_{10}H_{12}N_6+H]^+$; HPLC (Method A) >99% (AUC), $t_R$=9.01 min.

Example 72

1-(1H-Pyrrolo[2,3-c]pyridin-2-yl)ethanone oxime

To a solution of 1-(1H-pyrrolo[2,3-c]pyridin-2-yl)ethanone (Example 70) (0.39 g, 2.42 mmol) and hydroxylamine.HCl (0.34 g, 4.84 mmol) in ethanol (12.1 mL) and water (3.4 mL) was added LiOH (0.31 g, 7.26 mmol). The reaction mixture was refluxed for 1.0 h, and then the heat was removed. After concentration under reduced pressure, the residue was triturated with water. The solid was collected by filtration, rinsed with water and $Et_2O$, and dried under vacuum at 45° C. to give 1-(1H-pyrrolo[2,3-c]pyridin-2-yl)ethanone oxime (0.20 g, 47%) as a yellow solid: $^1$H NMR (300 MHz, $CD_3OD$) δ2.26 (3H, s), 6.78 (1H, s), 7.54-7.57 (1H, m), 8.03 (1H, d, J=5.6 Hz), 8.64 (1H, s); ESI MS m/z 176 $[C_9H_9N_3O+H]^+$; HPLC (Method A) >99% (AUC, isomeric ratio=89.3:10.7), $t_R$=12.47 (major) and 12.25 (minor).

Example 73

(5-Chloro-1H-pyrrolo[2,3-c]pyridin-2-yl)(phenyl)methanone (5-Chloro-1H-pyrrolo[2,3-c]pyridin-2-yl)(phenyl)methanol (Example 140) (105 mg, 0.41 mmol) was dissolved in methylene chloride (10 mL). Manganese dioxide (358 mg, 4.1 mmol) was added and the reaction mixture was stirred for 60 h. The reaction mixture was filtered through diatomaceous earth and the filter cake was washed several times with methylene chloride. The filtered was concentrated to give a pink solid. Recrystallization from methylene chloride gave (5-chloro-1H-pyrrolo[2,3-c]pyridin-2-yl)(phenyl)methanone (73 mg, 70%) as a white solid: mp 194-197° C.; $^1$H NMR (300 MHz, $CDCl_3$) δ7.10 (1H, s), 7.51-7.75 (4H, m), 8.01 (2H, m), 8.79 (1H, s), 9.57 (1H, br s); ESI MS m/z 257 $[C_{14}H_9ClN_2O+H]^+$; HPLC (Method A) >99% (AUC), $t_R$=21.5 min.

Example 74

[[(5-Chloro-1H-pyrrolo[2,3-c]pyridin-2-yl)(phenyl)methylene]amino]guanidine dihydrochloride To a solution of (5-chloro-1H-pyrrolo[2,3-c]pyridin-2-yl)(phenyl)methanone (Example 73) (65 mg, 0.25 mmol) in ethanol (5 mL) was added aminoguanidine hydrochloride (55 mg, 0.85 mmol) and 6 N HCl (0.2 mL). The reaction mixture was heated to reflux under $N_2$. After 2 h, heating was terminated and the reaction mixture was cooled to room temperature forming a white precipitate. The precipitate was collected by filtration and dried under vacuum to provide [[(5-chloro-1H-pyrrolo[2,3-c]pyridin-2-yl)(phenyl)methylene]amino]guanidine dihydrochloride (78 mg, 100%) as a white solid: mp 274-278° C.; $^1$H NMR (300 MHz, $CD_3OD$) δ 6.62 (1H, s), 7.49-7.58 (2H, m), 7.68-7.79 (4H, m), 8.04 (1H, s), 8.98 (1H, s); ESI MS m/z 313 $[C_{15}H_{13}ClN_6+H]^+$; HPLC (Method A) >99% (AUC) $t_R$=16.5 min.

Example 75

1-(1H-Pyrrolo[2,3-c]pyridin-2-yl)ethylamine dihydrochloride

To a heterogeneous solution of 1-(1H-pyrrolo[2,3-c]pyridin-2-yl)ethanone oxime (Example 72) (0.31 g, 1.75 mmol) in THF (27.5 mL) was added lithium aluminum hydride (0.33 g, 8.79 mmol) at room temperature under a nitrogen atmosphere. The reaction mixture was refluxed for 1 h and then quenched by careful addition of hydrated $Na_2SO_4$. Ethyl acetate was added and the reaction mixture was stirred overnight. The solid was filtered off and thoroughly rinsed with EtOAc and EtOH. The filtrate was concentrated to give a yellow oil. The crude residue was dissolved in EtOAc and EtOH (100 mL; 1:1) and 2 M HCl in $Et_2O$ was added (1.85 mL). The precipitate was filtered off, rinsed with EtOAc and $Et_2O$, and dried to provide 1-(1H-pyrrolo[2,3-c]pyridin-2-yl)ethylamine dihydrochloride (0.29 g, 72%) as a light orange solid: mp 289-292° C.; $^1$H NMR (300 MHz, $CD_3OD$) δ1.82 (3H, d, J=6.9 Hz), 4.88-4.95 (1H, m), 7.09 (1H, s), 8.17 (1H, d, J=6.4 Hz), 8.29 (1H, d, J=64 Hz), 9.13 (1H, s); ESI MS m/z 162 $[C_9H_{11}N_3+H]^+$; HPLC (Method A) 97.7% (AUC), $t_R$=6.50 min.

Example 76 tert-Butyl 3-[[[phenyl(1H-pyrrolo[2,3-c]pyridin-2-yl)methylene]amino]oxy]propylcarbamate A mixture of 1-(1H-pyrrolo[2,3-c]pyridin-2-yl)ethanone oxime (Example 72) (100 mg, 0.42 mmol) and sodium hydride (18 mg of a 60% in mineral oil, 0.45 mmol) in N,N-dimethylformamide (4 mL) was stirred for 0.5 h. N-Boc chloropropylamine (86 mg, 0.44 mmol) was added dropwise and the reaction mixture was heated at 60° C. for 3 h. After stirring at room temperature for 12 h, the reaction mixture was quenched with water (10 mL) and extracted with ethyl acetate (3×15 mL). The combined organic extracts were washed with water and brine, dried over sodium sulfate, and concentrated to an oil. Purification by Biotage chromatography (30 to 100% ethyl acetate in hexanes) produced tert-butyl 3-[[[phenyl (1H-pyrrolo[2,3-c]pyridin-2-yl)methylene]amino]oxy]propylcarbamate (76 mg, 46%) as a white solid: mp 52-58° C.; ESI MS m/z 395 $[C_{22}H_{26}N_4O_3+H]^+$; HPLC (Method A) 98.6% (AUC), $t_R$=19.2 min.

Example 77

Phenyl(1H-pyrrolo[2,3-c]pyridin-2-yl)methanone O-(3-aminopropyl)oxime hydrochloride tert-Butyl 3-[[[phenyl(1H-pyrrolo[2,3-c]pyridin-2-yl)methylene]amino]oxy]propylcarbamate (Example 76) (60 mg, 0.15 mmol) was dissolved in methylene chloride (4 mL) and trifluoroacetic acid (1 mL) was added. The reaction mixture was stirred for 1 h. The solvents were removed under vacuum and the residue was dissolved in ethyl acetate. Saturated sodium bicarbonate solution was added and the mixture was stirred for 10 min. The layers were separated and the aqueous layer extracted with ethyl acetate (2×). The combined organic extracts were washed with water and brine, dried over sodium sulfate, and concentrated to an oil. The oil was dissolved in ethyl acetate (4 mL), 2 M ethereal hydrogen chloride (0.2 mL) was added and the precipitate formed. Removal of the solvents and drying under vacuum produced phenyl(1H-pyrrolo[2,3-c]pyridin-2-yl)methanone O-(3-aminopropyl)oxime hydrochloride, a mixture of isomers (39 mg, 71%) as an off-white solid: mp 168-174° C. dec.; $^1$H NMR (500 MHz, CD$_3$OD) δ2.02-2.31 (2H, m), 2.98-3.27 (2H, m), 4.47-4.59 (2H, m), 6.75 (0.24H, s) 7.12 (0.76H, s), 7.47-7.59 (5H, m), 8.05-8.27 (2H, m), 8.96 (0.24H, s), 9.13 (0.76H, br s); ESI MS m/z 295 $[C_{17}H_{18}N_4O+H]^+$; HPLC (Method A) 91.5% (AUC), $t_R$=14.0 min.

Example 78

2-Methyl-1-(1H-pyrrolo[2,3-c]pyridin-2-yl)-1-propanol

1H-Pyrrolo[2,3-c]pyridine-2-carboxaldehyde (125 mg, 0.86 mmol) was suspended in tetrahydrofuran (5 mL) at –30° C. under a nitrogen atmosphere. Isopropylmagnesium bromide in diethyl ether (0.87 mL, 1.74 mmol) was added dropwise. The reaction mixture was slowly warmed to room temperature. After stirring for ca. 3 h, the reaction mixture was cooled to –30° C. and additional 2.0 M isopropylmagnesium bromide in diethyl ether (0.22 mL, 0.44 mmol) was added. The reaction mixture was stirred for another 1 h, while warming to room temperature. The reaction mixture was poured into a 2:1 solution of saturated ammonium chloride and water, and extracted with ethyl acetate (3×). The combined organic extracts were washed with water and brine, dried over sodium sulfate, and concentrated. The crude product was purified by Biotage chromatography (2 to 10% methanol in methylene chloride) to provide 2-methyl-1-(1H-pyrrolo[2,3-c]pyridin-2-yl)-1-propanol (86 mg, 53%) as a white solid: mp 140-144° C.; $^1$H NMR (500 MHz, CD$_3$OD) δ0.99 (6H, m), 2.01-2.25 (1H, m), 4.57-4.65 (1H, m), 6.38 (1H, s), 7.51 (1H, s), 8.00 (1H, s), 8.63 (1H, s); ESI MS m/z 191 $[C_{11}H_{14}N_2O+H]^+$; HPLC (Method A) >99% (AUC), $t_R$=13.1 min.

Example 79

3-Methyl-1-(1H-pyrrolo[2,3-c]pyridin-2-yl)-1-butanol

3-Methyl-1-(1H-pyrrolo[2,3-c]pyridin-2-yl)-1-butanol (101 mg, 58%) was prepared as an off-white solid following the procedure described for Example 78 using commercially available 2 M isobutylmagnesium bromide in diethyl ether: mp 182-189° C. dec.; $^1$H NMR (300 MHz, CDCl$_3$) δ0.97-1.00 (6H, m), 1.72-1.89 (3H, m), 5.03-5.07 (1H, m), 6.35 (1H, s), 7.44 (1H, d, J=5.5 Hz), 8.16-88.18 (1H, d, J=5.5 Hz), 8.62 (1H, s); ESI MS m/z 205 $[C_{12}H_{16}N_2O+H]^+$; HPLC (Method A) >99% (AUC), $t_R$=14.4 min.

Example 80

2-Methyl-1-(1H-pyrrolo[2,3-c]pyridin-2-yl)-1-propanone

2-Methyl-1-(1H-pyrrolo[2,3-c]pyridin-2-yl)-1-propanol (Example 78) (75 mg, 0.39 mmol) was dissolved in methylene chloride (10 mL). Manganese dioxide (343 mg, 3.94 mmol) was added and the reaction mixture was stirred for ca. 14 h. The reaction mixture was filtered through diatomaceous earth and the filter cake was washed several times with hot methanol. The filtrate was concentrated to give a white solid. Drying under vacuum produced 2-methyl-1-(1H-pyrrolo[2,3-c]pyridin-2-yl)-1-propanone (64 mg, 88%) as a white solid: mp 224-228° C.; $^1$H NMR (500 MHz, CD$_3$OD) δ1.26 (6H, d, J=7.0 Hz), 3.45-3.62 (1H, m), 7.37 (1H, s), 7.72-7.74 (1H, m), 8.14 (1H, d, J=6.0 Hz), 8.82 (1H, s); ESI MS m/z 189 $[C_{11}H_{12}N_2O+H]^+$; HPLC (Method A) 95.4% (AUC), $t_R$=13.7 min.

Example 81

3-Methyl-1-(1H-pyrrolo[2,3-c]pyridin-2-yl)-1-butanone

3-Methyl-1-(1H-pyrrolo[2,3-c]pyridin-2-yl)-1-butanone (69 mg, 78%) was prepared as a yellow solid following the procedure described for Example 80 using 3-methyl-1-(1H-pyrrolo[2,3-c]pyridin-2-yl)-1-butanol (Example 79): mp 215-218° C.; $^1$H NMR (300 MHz, CD$_3$OD) δ1.03 (6H, d, J=6.6 Hz), 2.22-2.37 (1H, m), 2.88-2.91 (2H, m), 7.04 (1H, s), 7.71-7.73 (1H, m), 8.13 (1H, d, J=5.7 Hz), 9.91 (1H, s); ESI MS m/z 203 $[C_{12}H_{14}N_2O+H]^+$; HPLC (Method A) >99% (AUC), $t_R$=15.0 min.

Example 82

N-[1-(1H-Pyrrolo[2,3-c]pyridin-2-yl)ethyl]nicotinamide dihydrochloride

A mixture of 1-(1H-pyrrolo[2,3-c]pyridin-2-yl)ethylamine dihydrochloride (Example 75) (74 mg, 0.32 mmol), nicotinic acid (41 mg, 0.33 mmol), diisopropylethylamine (0.28 mL, 0.38 mmol), EDCI (73 mg, 0.38 mmol) and dimethylaminopyridine (catalytic amount) in methylene chloride (2.8 mL) was stirred under a nitrogen atmosphere overnight (18 h). The reaction mixture was diluted with EtOAc and extracted with 1 N HCl. The acidic extracts were washed with EtOAc, and then made basic with 15% NaOH. The aqueous layer was extracted with CH$_2$Cl$_2$ (3×). The combined extracts were dried over Na$_2$SO$_4$. Filtration and concentration gave a crude yellow oil. Initial purification by Biotage chromatography (KP-NH silica) provided an impure product. The mixture was dissolved in EtOH and 2.0 M HCl in Et$_2$O (0.34 mL) was added. The mixture was concentrated and then crystallized from acetone/methanol (9:1) to provide N-[1-(1H-pyrrolo[2,3-c]pyridin-2-yl)ethyl]nicotinamide dihydrochloride (12 mg, 11%) as a light yellow solid: $^1$H NMR (300 MHz, CD$_3$OD) δ3.64 (3H, d, J=7.1 Hz), 5.65 (1H, q, J=7.0 Hz), 6.98 (1H, s), 8.03-8.20 (3H, m), 8.94-9.02 (3H, m), 9.34 (1H, s); ESI MS m/z 267 [C$_{15}$H$_{14}$N$_4$O+H]$^+$; HPLC (Method A) >99% (AUC), t$_R$=9.19 min.

Example 83

3-Phenyl-1-(1H-pyrrolo[2,3-c]pyridin-2-yl)propan-1-ol

3-Phenyl-1-(1H-pyrrolo[2,3-c]pyridin-2-yl)propan-1-ol (150 mg, 69%) was prepared as a white solid following the procedure described for Example 78 using commercially available 1M phenethylmagnesium chloride in tetrahydrofuran: mp 162-166° C.; ESI MS m/z 253 [C$_{16}$H$_{16}$N$_2$O+H]$^+$; HPLC (Method A) 98.9% (AUC), t$_R$=16.2 min.

Example 84

(1H-Pyrrolo[2,3-c]pyridin-2-yl)methylamine dihydrochloride

Following the procedure described for Example 75, 1H-pyrrolo[2,3-c]pyridine-2-carboxaldehyde oxime (Example 44) was reduced to provide (1H-pyrrolo[2,3-c]pyridin-2-yl)methylamine dihydrochloride (1.0 g, 80%) as a tan solid: mp 302-303° C.; $^1$H NMR (300 MHz, CD$_3$OD) δ4.56 (2H, s), 7.12 (1H, s), 8.16 (1H, d, J=6.4 Hz), 8.28 (1H, d, J=6.4 Hz), 9.16 (1H, s); ESI MS m/z 148 [C$_8$H$_9$N$_3$+H]$^+$; HPLC (Method A) >99% (AUC), t$_R$=5.20 min.

Example 85

2-Phenyl-1-(1H-pyrrolo[2,3-c]pyridin-2-yl)ethanol

2-Phenyl-1-(1H-pyrrolo[2,3-c]pyridin-2-yl)ethanol (32 mg, 17%) was prepared as a yellow solid following the procedure described for Example 78 using commercially available 1M benzylmagnesium chloride in diethyl ether: mp 169-172° C. dec.; $^1$H NMR (500 MHz, CD$_3$OD) δ3.12-3.22 (2H, m), 5.08-5.10 (1H, m), 6.35 (1H, s), 7.15-7.23 (5H, m), 7.49 (1H, d, J=5.5 Hz), 7.99 (1H, d, J=5.3 Hz), 8.60 (1H, s); ESI MS m/z 239 [C$_{15}$H$_{14}$N$_2$O+H]$^+$; HPLC (Method A) 96.7% (AUC), t$_R$=14.8 min.

Example 86 tert-Butyl[2-[N-[1-(1H-pyrrolo[2,3-c]pyridin-2-yl)ethyl]carbamoyl]ethyl]carbamate A mixture of 1-(1H-pyrrolo[2,3-c]pyridin-2-yl)ethylamine dihydrochloride (Example 75) (108 mg, 0.46 mmol), N-Boc-β-alanine (71 mg, 0.37 mmol), diisopropylethylamine (0.31 mL, 1.85 mmol), EDCI (78 mg, 0.41 mmol) and HOBt (catalytic amount) in methylene chloride (2.2 mL) was stirred at room temperature under a nitrogen atmosphere overnight (22 h). The reaction mixture was concentrated to dryness under reduced pressure. The residue was dissolved in CH$_2$Cl$_2$, washed with water and saturated NaHCO$_3$, and dried over Na$_2$SO$_4$. Filtration and concentration provided tert-butyl[2-[N-[1-(1H-pyrrolo[2,3-c]pyridin-2-yl)ethyl]carbamoyl]ethyl]carbamate (70 mg, 58%) as a tan solid: $^1$H NMR (500 MHz, CD$_3$OD) δ1.45 (9H, s), 1.63 (3H, d), 2.37-2.51 (2H, m), 3.30-3.42 (2H, m), 5.26-5.35 (1H, m), 6.43 (1H, s), 7.48-7.51 (1H, m), 7.99-8.05 (1H, m), 8.60 (1H, s); ESI MS m/z 333 [C$_{17}$H$_{24}$N$_4$O$_3$+H]$^+$; HPLC (Method A) 95.9% (AUC), t$_R$=14.39 min.

Example 87 tert-Butyl[[N-[1-(1H-pyrrolo[2,3-c]pyridin-2-yl)ethyl]carbamoyl]methyl]carbamate Following the procedure described for Example 86, tert-butyl [[N-[1-(1H-pyrrolo[2,3-c]pyridin-2-yl)ethyl]carbamoyl]methyl]carbamate (0.15 g, quantitative) was prepared as a light yellow solid using N-Boc-glycine (81 mg, 0.46 mmol): $^1$H NMR (300 MHz, CD$_3$OD) δ1.45 (9H, s), 1.61 (3H, d, J=7.0 Hz), 3.75 (2H, s), 5.33 (1H, q, J=7.0 Hz), 6.45 (1H, s), 7.48-7.51 (1H, m), 8.00 (1H, d, J=5.6 Hz), 8.58 (1H, s); ESI MS m/z 319 [C$_{16}$H$_{22}$N$_4$O$_3$+H]$^+$; HPLC (Method A) 97.5% (AUC), t$_R$=14.08 min.

Example 88

N-(1H-Pyrrolo[2,3-c]pyridin-2-ylmethyl)nicotinamide dihydrochloride

A mixture of (1H-pyrrolo[2,3-c]pyridin-2-yl)methylamine dihydrochloride (Example 84) (110 mg, 0.50 mmol), nicotinic acid (62 mg, 0.50 mmol), diisopropylethylamine (0.44 mL, 2.5 mmol), EDCI (110 mg, 0.55 mmol) and HOBt (cat.) in methylene chloride (2.9 mL) and DMF (3 mL) was stirred at room temperature under a nitrogen atmosphere overnight (18 h). The reaction mixture was concentrated to dryness under reduced pressure. The residue was diluted with water. The water layer was concentrated to dryness. The residue was dissolved in ethanol (10 mL) and 2 N HCl in Et$_2$O (10 mL) was added. Methanol (ca. 5 mL) was added to dissolve the majority of material. The remaining brown precipitate was filtered off and discarded. The filtrate was concentrated, and the resulting solid was triturated with EtOH (ca. 4 mL), filtered, and dried to provide N-(1H-pyrrolo[2,3-c]pyridin-2-ylmethyl)nicotinamide dihydrochloride (31 mg, 19%) as a tan solid: $^1$H NMR (500 MHz, CD$_3$OD) δ4.99 (2H, s), 7.00 (1H, s), 8.03 (1H, d, J=6.0 Hz), 8.17-8.24 (3H, m), 8.77 (1H, s), 9.04-9.12 (3H, m), 9.38 (1H, s); ESI MS m/z 253 [C$_{14}$H$_{12}$N$_4$O+H]$^+$; HPLC (Method A) >99% (AUC), t$_R$=7.78 min.

Example 89

3-Phenyl-1-(1H-pyrrolo[2,3-c]pyridin-2-yl)propan-1-one

3-Phenyl-1-(1H-pyrrolo[2,3-c]pyridin-2-yl)propan-1-one (98 mg, 72%) was prepared as a yellow solid following the procedure described for Example 80 using 3-phenyl-1-(1H-pyrrolo[2,3-c]pyridin-2-yl)propan-1-ol (Example 83): mp 246-250° C.; $^1$H NMR (500 MHz, DMSO-d$_6$) δ3.00 (2H, t, J=7.6 Hz), 3.87 (2H, t, J=7.6 Hz), 7.16-7.19 (1H, m), 7.25-7.32 (4H, m), 7.43 (1H, s), 7.65 (1H, d, J=5.5 Hz), 8.17 (1H, d, J=5.5 Hz), 8.84 (1H, s), 12.18 (1H, s); ESI MS m/z 251 [$C_6H_{14}N_2O$+H]$^+$; HPLC (Method A) >99% (AUC), $t_R$=16.4 min.

Example 90 tert-Butyl 3-[[[phenyl(1H-pyrrolo[2,3-c]pyridin-2-yl)methylene]amino]oxy]pyrrolidine-1-carboxylate To a mixture of phenyl(1H-pyrrolo[2,3-c]pyridin-2-yl) methanone (Example 35) (90 mg, 0.40 mmol) and tert-butyl 3-(aminooxy)pyrrolidine-1-carboxylate (Reference Example 9) (82 mg, 0.40 mmol) in isopropanol (6 mL) was added 4 Å molecular sieves. The pH of the solution was adjusted to pH 4-5 with glacial acetic acid. The reaction mixture was heated to reflux. After 3 days, the reaction mixture was cooled to ambient temperature. The mixture was filtered through a pad of diatomaceous earth and the filtrate was concentrated under reduced pressure. Purification by column chromatography (silica gel, 9.75:0.25 $CH_2Cl_2$/MeOH to 9.5:0.5 $CH_2Cl_2$/MeOH) followed by ion-exchange chromatography (SCX-2, 1:3 7 N $NH_4OH$ in MeOH/MeOH) gave tert-butyl 3-[[[phenyl(1H-pyrrolo[2,3-c]pyridin-2-yl)methylene]amino]oxy] pyrrolidine-1-carboxylate (52.3 mg, 32%) as a mixture of isomers: mp 80-82° C.; $^1$H NMR (500 MHz, DMSO-$d_6$) major isomer δ 1.37-1.39 (9H, m), 2.08-2.10 (2H, m), 3.13-3.17 (1H, m), 3.31-3.50 (3H, m), 4.92 (1H, br s), 6.23 (1H, s), 7.41-7.53 (6H, m), 8.08 (1H, d, J=5.4 Hz), 8.79 (1H, s), 11.85 (1H, s); ESI MS m/z 407 [$C_{23}H_{26}N_4O_3$+H]$^+$; HPLC (Method A) 85.8% (AUC), $t_R$=18.0 min.

Example 91

Phenyl (1H-pyrrolo[2,3-c]pyridin-2-yl)methanone O-pyrrolidin-3-yloxime dihydrochloride Phenyl (1H-pyrrolo[2,3-c]pyridin-2-yl)methanone O-pyrrolidin-3-yloxime dihydrochloride (12.3 mg, 33%) was prepared as an off-white amorphous solid from tert-butyl 3-[[[phenyl (1H-pyrrolo[2,3-c]pyridin-2-yl)methylene] amino]oxy]pyrrolidine-1-carboxylate (Example 90) following the procedure described for Example 77, except 1:1 trifluoroacetic acid/$CH_2Cl_2$ was used: $^1$H NMR (500 MHz, $CD_3OD$) major isomer δ 0.94-0.92 (1H, m), 2.33-2.35 (1H, m), 3.26-3.27 (1H, m), 3.33-3.34 (1H, m), 3.45-3.46 (1H, m), 3.58-3.60 (1H, m), 3.70-3.72 (1H, m), 5.23-5.24 (1H, m), 6.78 (1H, s), 7.53-7.57 (5H, m), 8.08 (1H, d, J=6.4 Hz), 8.22 (1H, d, J=6.5 Hz), 9.01 (1H, s); ESI MS m/z 307 [$C_{18}H_{18}N_4O$+H]$^+$; HPLC (Method A) 96.6% (AUC), $t_R$=12.6 min.

Example 92

[[2-Methyl-1-(1H-pyrrolo[2,3-c]pyridin-2-yl)propylidene]amino]guanidine dihydrochloride To a solution of 2-methyl-1-(1H-pyrrolo[2,3-c]pyridin-2-yl)-1-propanone (Example 80) (100 mg, 0.53 mmol) in ethanol (5 mL) were added aminoguanidine hydrochloride (58 mg, 0.53 mmol) and 6 N HCl (0.2 mL). The reaction mixture was heated to reflux under $N_2$. After 2 h, heating was terminated and the reaction mixture was cooled to room temperature. Purification by column chromatography (silica gel, 5 to 20% methanol in methylene chloride) produced [[2-methyl-1-(1H-pyrrolo[2,3-c]pyridin-2-yl)propylidene]amino]guanidine dihydrochloride (28 mg, 26%) as a yellow solid: mp 242-245° C.; $^1$H NMR (500 MHz, $CD_3OD$) δ 1.49 (6H, d, J=7.1 Hz), 3.50-3.54 (1H, m), 7.15 (1H, s), 7.72 (1H, d, J=5.5 Hz), 8.11 (1H, d, J=5.6 Hz), 8.77 (1H, s); ESI MS m/z 245 [$C_{12}H_{16}N_6$+H]$^+$; HPLC (Method A) >99% (AUC) $t_R$=11.9 min.

Example 93

[[3-Phenyl-1-(1H-pyrrolo[2,3-c]pyridin-2-yl)propylidene]amino]guanidine dihydrochloride

[[3-Phenyl-1-(1H-pyrrolo[2,3-c]pyridin-2-yl)propylidene]amino]guanidine dihydrochloride (18 mg, 22%) was prepared as a yellow solid following the procedure described for Example 92 from 3-phenyl-1-(1H-pyrrolo[2,3-c]pyridin-2-yl)propan-1-one (Example 89) (60 mg, 0.24 mmol): $^1$H NMR (500 MHz, $CD_3OD$) δ 3.00-3.04 (2H, m), 3.19-3.22 (2H, m), 7.03 (1H, s), 7.14-7.17 (1H, m), 7.23-7.29 (4H, m), 7.77 (1H, m), 8.13 (1H, br s), 8.80 (1H, br s); ESI MS m/z 307 [$C_{17}H_{18}N_6$+H]$^+$; HPLC (Method A) >99% (AUC) $t_R$=13.4 min.

Example 94

[[3-Methyl-1-(1H-pyrrolo[2,3-c]pyridin-2-yl)butylidene]amino]guanidine dihydrochloride

[[3-Methyl-1-(1H-pyrrolo[2,3-c]pyridin-2-yl)butylidene] amino]guanidine dihydrochloride (27 mg, 34%) was prepared as a white solid following the procedure described for Example 92 from 3-methyl-1-(1H-pyrrolo[2,3-c]pyridin-2-yl)-1-butanone (Example 81) (54 mg, 0.27 mmol): mp 232-236° C.; $^1$H NMR (300 MHz, $CD_3OD$) δ 1.06 (6H, d, J=6.5 Hz), 2.14-2.23 (1H, m), 2.86 (2H, d, J=7.7 Hz), 7.40 (1H, s), 8.13-8.25 (2H, m), 9.06 (1H, s); ESI MS m/z 259 [$C_{13}H_{18}N_6$+H]$^+$; HPLC (Method A) >99% (AUC) $t_R$=13.4 min.

Example 95

Phenyl(1H-pyrrolo[2,3-c]pyridin-2-yl)methanone O-(2-aminoethyl)oxime hydrochloride One of the isomers of tert-butyl 2-[[[phenyl(1H-pyrrolo[2,3-c]pyridin-2-yl)methylene]amino]oxy]ethylcarbamate (Example 60) (81 mg, 0.21 mmol) was separated and dissolved in ethyl acetate (4 mL). Trifluoroacetic acid (4 mL) was added and the reaction mixture was stirred for 14 h. The solvent was removed under vacuum and the residue was dissolved in ethyl acetate. Saturated sodium bicarbonate solution was added to the stirring solution. After 15 min, the organic layer was separated and the aqueous layer was extracted with ethyl acetate (2×10 mL). The combined organic layers were washed with water and then brine, dried over sodium sulfate and the solvent was removed under vacuum to ca. 5 mL. Ethereal hydrogen chloride (0.9 mL of a 1 M solution) was added, and the solution was stirred under a nitrogen atmosphere. The solvent was removed under vacuum to give the isomerically pure phenyl(1H-pyrrolo[2,3-c]pyridin-2-yl) methanone O-(2-aminoethyl)oxime hydrochloride (geometry of the oxime double bond was not defined) (25 mg, 78% yield) as a white solid: mp 161-165° C. dec.; $^1$H NMR (500 MHz, $CD_3OD$) δ 3.46 (2H, t, J=5.1 Hz), 4.64 (2H, t, J=5.1 Hz), 7.12 (1H, s), 7.48-7.62 (5H, m), 8.17 (1H, d, J=6.5 Hz), 8.27 (1H, d, J=6.5 Hz), 9.19 (1H, s); ESI MS m/z 281 $[C_{16}H_{16}N_4O_3+H]^+$; HPLC (Method A) >99% (AUC) $t_R$=12.5 min.

Example 96

Phenyl(1H-pyrrolo[2,3-c]pyridin-2-yl)methanone O-(2-aminoethyl)oxime bis(hydrogen trifluoroacetate)

The other isomer of tert-butyl 2-[[[phenyl(1H-pyrrolo[2,3-c]pyridin-2-yl)methylene]amino]oxy]ethylcarbamate (Example 60) (27 mg, 0.07 mmol), containing a small amount of the isomer used in Example 95, was dissolved in methylene chloride (1 mL). Trifluoroacetic acid (1 mL) was added and the reaction mixture was stirred for 3 h. The solvent was removed under vacuum. Preparative HPLC [Synergi column, 10 to 100% acetonitrile in water (0.05% TFA added)] produced phenyl(1H-pyrrolo[2,3-c]pyridin-2-yl)methanone O-(2-aminoethyl)oxime bis(hydrogen trifluoroacetate) as an off-white solid with a 84:16 isomeric ratio: $^1$H NMR (500 MHz, CD$_3$OD) δ 3.40-3.44 (2H, m), 4.51-4.54 (2H, m), 6.79 (1H, s), 7.56 (5H, s), 8.06 (1H, d, J=6.4 Hz), 8.20-8.22 (1H, m), 8.98 (1H, s); ESI MS m/z 281 $[C_{16}H_{16}N_4O_3+H]^+$; HPLC (Method A) 83.4% (AUC) $t_R$=13.0 min.

Example 97

Phenyl(1H-pyrrolo[2,3-c]pyridin-3-yl)methanol

A mixture of 1H-pyrrolo[2,3-c]pyridine-3-carboxaldehyde (100 mg, 0.68 mmol) and THF (6.8 mL) was cooled to −40° C. and phenylmagnesium chloride (0.68 mL, 1.36 mmol) was added. The reaction mixture was warmed to room temperature and refluxed for 1 h. The reaction mixture was cooled to room temperature and quenched with saturated NH$_4$Cl and then water was added. The aqueous layer was extracted with EtOAc (1×), dried (MgSO$_4$) and filtered, and the solvent was removed. The crude material was purified by Biotage chromatography (90:10 to 85:15 methylene chloride/methanol) to give phenyl(1H-pyrrolo[2,3-c]pyridin-3-yl)methanol as a yellow solid (65.5 mg, 43%): $R_f$ 0.11 (90:10 methylene chloride/methanol); $^1$H NMR (300 MHz, CD$_3$OD) (6.09 (1H, s), 7.25-7.27 (1H, m), 7.32-7.35 (3H, m), 7.46-7.48 (3H, m), 7.96-7.97 (1H, d, J=5.6 Hz), 8.64 (1H, s); ESI MS m/z 225 $[C_{14}H_{12}N_2O+H]^+$; Estimated Purity: >90% by $^1$H NMR analysis.

Example 98

(4-Methylphenyl)(1H-pyrrolo[2,3-c]pyridin-2-yl)methanol 1H-pyrrolo[2,3-c]pyridine-2-carboxaldehyde (180 mg, 1.23 mmol) was dissolved in tetrahydrofuran (6 mL) under a nitrogen atmosphere. p-Tolylmagnesium bromide in tetrahydrofuran (2.48 mL, 2.48 mmol) was added dropwise. After stirring for 3 h, the reaction mixture was quenched by pouring into a 2:1 solution of saturated ammonium chloride and water, then extracted with ethyl acetate (2×20 mL). The combined organic extracts were washed with water and then brine, dried over sodium sulfate, and concentrated to provide the crude material. Purification by Biotage chromatography (silica, 0 to 18% methanol in methylene chloride) to provide (4-methylphenyl)(1H-pyrrolo[2,3-c]pyridin-2-yl)methanol (226 mg, 77%) as an off-white solid: mp 78-82° C.; $^1$H NMR (500 MHz, CD$_3$OD) δ2.32 (3H, s), 5.95 (1H, s), 6.36 (1H, s), 7.17 (2H, d, J=7.9 Hz), 7.34 (2H, d, 8.0 Hz), 7.51 (1H, m), 8.00 (1H, d, J=5.6 Hz), 8.59 (1H, s); ESI MS m/z 239 $[C_{15}H_{14}N_2+H]^+$; HPLC (Method A) >99% (AUC), $t_R$=15.1 min.

Example 99

(4-Methoxyphenyl)(1H-pyrrolo[2,3-c]pyridin-2-yl)methanol (4-Methoxyphenyl)(1H-pyrrolo[2,3-c]pyridin-2-yl)methanol (101 mg, 32%) was prepared as an off-white solid following the procedure described for Example 98 using commercially available 4-methoxyphenylmagnesium bromide in tetrahydrofuran: mp 183-185° C. dec.; $^1$H NMR (500 MHz, CD$_3$OD) δ3.78 (3H, s), 5.94 (1H, s), 6.35 (1H, s), 6.90-6.92 (2H, m), 7.35-7.38 (2H, m), 7.48-7.50 (1H, m), 7.95-8.00 (1H, m), 8.59 (1H, s); ESI MS m/z 255 $[C_{15}H_{14}N_2O_2+H]^+$; HPLC (Method A) >99% (AUC), $t_R$=14.6 min.

Example 100

(4-Methylphenyl)(1H-pyrrolo[2,3-c]pyridin-2-yl)methanone (4-Methylphenyl)(1H-pyrrolo[2,3-c]pyridin-2-yl)methanol (Example 98) (225 mg, 0.94 mmol) was dissolved in methylene chloride (15 mL). Manganese dioxide (817 mg, 9.40 mmol) was added and the reaction mixture was stirred for ca. 14 h. The reaction mixture was filtered through diatomaceous earth and the filter cake was washed several times with hot ethanol. The filtrate was concentrated to give a white solid. Drying under vacuum produced (4-methylphenyl)(1H-pyrrolo[2,3-c]pyridin-2-yl)methanone (149 mg, 67%) as a white solid: mp 264-268° C. dec.; $^1$H NMR (300 MHz, CD$_3$OD) δ2.47 (3H, s), 7.18 (1H, s), 7.41 (2H, d, J=7.9 Hz), 7.73-7.75 (1H, m), 7.92 (2H, d, J=8.1 Hz), 8.16 (1H, d, J=5.6 Hz), 8.87 (1H, s); ESI MS m/z 237 $[C_{15}H_{12}N_2O+H]^+$; HPLC (Method A) 93.4% (AUC), $t_R$=15.9 min.

Example 101

(4-Chlorophenyl)(1H-pyrrolo[2,3-c]pyridin-2-yl)methanol (4-Chlorophenyl)(1H-pyrrolo[2,3-c]pyridin-2-yl)methanol (174 mg, 55%) was prepared as a white solid following the procedure described for Example 98 using commercially available 4-chlorophenylmagnesium bromide in diethyl ether: mp 176-180° C.; $^1$H NMR (500 MHz, CD$_3$OD) δ5.99 (1H, s), 6.36 (1H, s), 7.35-7.37 (2H, m), 7.45-7.51 (3H, m), 8.00 (1H, d, J=5.6 Hz), 8.59 (1H, s); ESI MS m/z 259 $[C_{14}H_{11}ClN_2O+H]^+$; HPLC (Method A) 97.9% (AUC), $t_R$=15.5 min.

Example 102

(4-Methoxyphenyl)(1H-pyrrolo[2,3-c]pyridin-2-yl)methanone (4-Methoxyphenyl)(1H-pyrrolo[2,3-c]pyridin-2-yl)methanone (87 mg, 99%) was prepared as an off-white solid following the procedure described for Example 100 using (4-methoxyphenyl)(1H-pyrrolo[2,3-c]pyridin-2-yl)methanol (Example 99) and tetrahydrofuran as a solvent: mp 225-228° C.; $^1$H NMR (300 MHz, CD$_3$OD) δ3.92 (3H, s), 7.10-7.19 (3H, m), 7.75-7.76 (1H, m), 8.02-8.06 (2H, m), 8.16 (1H, d, J=5.6 Hz), 8.86 (1H, s); ESI MS m/z 253 [C$_{15}$H$_{12}$N$_2$O$_2$+H]$^+$; HPLC (Method A) >99% (AUC), t$_R$=15.3 min.

Example 103

(4-Chlorophenyl)(1H-pyrrolo[2,3-c]pyridin-2-yl)methanone (4-Chlorophenyl)(1H-pyrrolo[2,3-c]pyridin-2-yl)methanone (108 mg, 67%) was prepared as a yellow solid following the procedure described for Example 100 using (4-chlorophenyl)(1H-pyrrolo[2,3-c]pyridin-2-yl)methanol (Example 101) and tetrahydrofuran as a solvent: mp 274-277° C. dec.; $^1$H NMR (300 MHz, CD$_3$OD) δ7.21 (1H, s), 7.60-7.63 (2H, m), 7.73-7.76 (1H, m), 7.99-8.03 (2H, m), 8.16 (1H, d, J=5.6 Hz), 8.88 (1H, s); ESI MS m/z 257 [C$_{14}$H$_9$ClN$_2$O+H]$^+$; HPLC (Method A) >99% (AUC), t$_R$=16.3 min.

Example 104 and Example 105

Phenyl(1H-pyrrolo[2,3-c]pyridin-2-yl)methanone O-piperidin-4-yloxime dihydrochloride A mixture of phenyl(1H-pyrrolo[2,3-c]pyridin-2-yl)methanone (Example 35) (300 mg, 1.34 mmol) and tert-butyl 4-(aminooxy)piperidine-1-carboxylate (Reference Example 10) (289 mg, 1.34 mmol) in EtOH (30 mL) was adjusted to pH 4-5 with HCl (1.9 mL of a 1 N HCl solution in diethyl ether, 1.9 mmol). The reaction mixture was heated to reflux. After 3 h, the reaction mixture was concentrated under reduced pressure. The residue was partitioned between EtOAc and saturated NaHCO$_3$. The aqueous layer was separated and extracted with EtOAc. The combined organic layers were dried (Na$_2$SO$_4$) and concentrated under reduced pressure. Purification by column chromatography (silica gel, 98:2 CH$_2$Cl$_2$/MeOH to 95:5 CH$_2$Cl$_2$/MeOH) gave tert-butyl 4-[[[phenyl(1H-pyrrolo[2,3-c]pyridin-2-yl)methylene]amino]oxy]piperidine-1-carboxylate (120 mg, 23%) as a white amorphous solid (geometry of the oxime double bond undefined).

Isomer A (30 mg, 5%): $^1$H NMR (500 MHz, DMSO-d$_6$) δ 1.39 (9H, s), 1.52-1.61 (2H, m), 1.90-1.94 (2H, m), 3.18-3.26 (2H, m), 3.49-3.52 (2H, d), 4.41-4.44 (1H, m), 6.19 (1H, s), 7.44-7.64 (6H, m), 7.97 (1H, d, J=6.8 Hz), 8.78 (1H, s), 11.80 (1H, br s).

Isomer B (175 mg, 31%): $^1$H NMR (500 MHz, DMSO-d$_6$) δ 1.38 (9H, s), 1.70-1.77 (2H, m), 1.98-2.02 (2H, m), 3.10-3.12 (2H, m), 3.72-3.75 (2H, m), 4.43-4.46 (1H, m), 6.76 (1H, s), 7.45-7.62 (6H, m), 8.13 (1H, d, J=5.4 Hz), 8.86 (1H, s), 11.51 (1H, br s).

Phenyl(1H-pyrrolo[2,3-c]pyridin-2-yl)methanone O-piperidin-4-yloxime dihydrochloride was prepared from tert-butyl 4-[[[phenyl(1H-pyrrolo[2,3-c]pyridin-2-yl)methylene]amino]oxy]piperidine-1-carboxylate (Isomer A) following the procedure described for Example 95 (24.9 mg, 98%) as a white solid (geometry of the oxime double bond undefined).

Example 104: mp 240-245° C. dec.; $^1$H NMR (500 MHz, DMSO-d$_6$) δ1.90-1.98 (2H, m), 2.16-2.20 (2H, m), 3.00-3.10 (4H, m), 4.57-4.61 (1H, m), 6.69 (1H, s), 7.53-7.58 (5H, m), 8.07 (1H, d, J=6.3 Hz), 8.30 (1H, d, J=6.3 Hz), 8.88 (1H, br s), 9.02 (1H, s), 9.18 (1H, br s), 13.06 (1H, s), 15.33 (1H, br s); ESI MS m/z 321 [C$_{19}$H$_{20}$N$_4$O+H]$^+$; HPLC (Method A) 99.0% (AUC), t$_R$=13.6 min.

Phenyl(1H-pyrrolo[2,3-c]pyridin-2-yl)methanone O-piperidin-4-yloxime dihydrochloride was prepared from tert-butyl 4-[[[phenyl(1H-pyrrolo[2,3-c]pyridin-2-yl)methylene]amino]oxy]piperidine-1-carboxylate (Isomer B) following the procedure described for Example 95 (32.0 mg, 21%) as a white solid (isomer of Example 104, geometry of the oxime double bond undefined).

Example 105: mp 240-245° C. dec.; $^1$H NMR (500 MHz, DMSO-d$_6$) δ 2.00-2.05 (2H, m), 2.16-2.20 (2H, m), 3.04-3.07 (2H, m), 3.18-3.22 (2H, m), 4.58-4.61 (1H, m), 7.17 (1H, s), 7.48-7.56 (5H, m), 8.19 (1H, d, J=6.3 Hz), 8.35 (1H, d, J=6.4 Hz), 8.89 (1H, br s), 9.02 (1H, br s), 9.22 (1H, s), 13.11 (1H, s), 15.25 (1H, br s); ESI MS m/z 321 [C$_{19}$H$_{20}$N$_4$O+H]$^+$; HPLC (Method A) 94.1% (AUC), t$_R$=13.6 min.

Example 106

Phenyl(1H-pyrrolo[2,3-c]pyridin-2-yl)methanone O-[2-(isopropylamino)ethyl]oxime dihydrochloride Phenyl(1H-pyrrolo[2,3-c]pyridin-2-yl)methanone O-[2-(isopropylamino)ethyl]oxime dihydrochloride was prepared from tert-butyl[2-(aminooxy)ethyl]isopropylcarbamate (Reference Example 17) following the procedure described for Example 128 and Example 131 (318 mg, 33%) as a mixture of isomers (74.5:25.5 by HPLC analysis): $^1$H NMR (500 MHz, CD$_3$OD) δ 1.31 (1.5H, d, J=6.5 Hz), 1.37 (4.5H, d, J=6.5 Hz), 3.32-3.36 (3H, m), 4.61 (0.5H, t, J=5.0 Hz), 4.70 (1.5H, t, J=5.0 Hz), 6.78 (0.25H, s), 7.06 (0.75H, s), 7.48-7.63 (5H, m), 8.07 (0.25H, d, J=6.3 Hz), 8.17 (0.75H, d, J=6.3 Hz), 8.23 (0.25, d, J=6.3 Hz), 8.25 (0.75, d, J=6.3 Hz), 9.04 (0.25H, s), 9.27 (0.75H, s); ESI MS m/z 323 [C$_{19}$H$_{22}$N$_4$O+H]$^+$; HPLC (Method A) >99% (AUC), t$_R$=13.7 and 14.0 min.

Example 107 and Example 108

Phenyl(1H-pyrrolo[2,3-c]pyridin-2-yl)methanone O-piperidin-3-yloxime dihydrochloride tert-Butyl 3-[[[phenyl(1H-pyrrolo[2,3-c]pyridin-2-yl)methylene]amino]oxy]piperidine-1-carboxylate was prepared from phenyl(1H-pyrrolo[2,3-c]pyridin-2-yl)methanone (Example 35) and tert-butyl 3-(aminooxy)piperidine-1-carboxylate (Reference Example 11) following the procedure described for Example 104 (geometry of the oxime double bond undefined).

Isomer A (84 mg, 14%): $^1$H NMR (500 MHz, DMSO-d$_6$) δ 1.06-1.49 (12H, m), 1.74-1.88 (2H, m), 2.94-3.03 (0.5H, m), 2.49-2.50 (0.5H, m), 3.58-3.61 (1H, m), 3.71-3.73 (0.5H, m), 4.15-4.17 (0.5H, m), 4.29-4.30 (1H, m), 6.24 (1H, s), 7.45-7.49 (6H, m), 8.08 (1H, d, J=5.39 Hz), 8.79 (1H, s), 11.83 (1H, s).

Isomer B (170 mg, 30%): $^1$H NMR (500 MHz, DMSO-d$_6$) δ 1.28-1.47 (9H, m), 1.67-1.74 (2H, m), 1.94-1.98 (2H, m), 3.31-3.80 (4H, m), 4.30-4.32 (1H, m), 5.87 (1H, s), 6.83-6.86 (1H, m), 7.47-7.56 (5H, m), 8.13 (1H, d, J=5.5 Hz), 8.84 (1H, br s), 11.47 (1H, s).

Phenyl(1H-pyrrolo[2,3-c]pyridin-2-yl)methanone O-piperidin-3-yloxime dihydrochloride was prepared from tert-butyl 3-[[[phenyl (1H-pyrrolo[2,3-c]pyridin-2-yl)methylene]amino]oxy]piperidine-1-carboxylate (Isomer A) following the procedure described for Example 95 (28.9 mg, 38%) as a white solid (geometry of the oxime double bond undefined).

Example 107: mp 240-245° C. dec.; $^1$H NMR (500 MHz, DMSO-d$_6$) δ1.75-1.78 (3H, m), 1.98-2.02 (1H, m), 2.99-3.07 (2H, m), 3.46 (2H, br s), 4.57 (1H, br s), 6.71 (1H, s), 7.55-7.65 (5H, m), 8.08 (1H, d, J=6.3 Hz), 8.30 (1H, d, J=6.3 Hz), 8.92 (1H, br s), 9.05 (1H, s), 9.58 (1H, br s), 13.24 (1H, s) 15.21 (1H, br s); ESI MS m/z 321 [C$_{19}$H$_{20}$N$_4$O+H]$^+$; HPLC (Method A) 97.3% (AUC), t$_R$=13.8 min.

Phenyl (1H-pyrrolo[2,3-c]pyridin-2-yl)methanone O-piperidin-3-yloxime dihydrochloride was prepared from tert-butyl 3-[[[phenyl (1H-pyrrolo[2,3-c]pyridin-2-yl)methylene]amino]oxy]piperidine-1-carboxylate (Isomer B) following the procedure described for Example 95 (47-9 mg, 38%) as a white solid (isomer of Example 107, geometry of the oxime double bond undefined).

Example 108: mp 240-245° C. dec.; $^1$H NMR (500 MHz, DMSO-$d_6$) δ1.66-1.69 (1H, m), 1.90-1.98 (3H, m), 2.99-3.01 (1H, m), 3.03-3.14 (1H, m), 3.35-3.40 (1H, m), 3.48-3.53 (1H, m), 4.63 (1H, br s), 7.01 (1H, s), 7.49-7.59 (5H, m), 8.09 (1H, d, J=6.2 Hz), 8.32 (1H, d, J=6.2 Hz), 9.16-9.29 (3H, m), 13.20 (1H, br s), 15.11 (1H, br s); ESI MS m/z 321 $[C_{19}H_{20}N_4O+H]^+$; HPLC (Method A) 96.6% (AUC), $t_R$=13.9 min.

Example 109 and Example 110

Phenyl(1H-pyrrolo[2,3-c]pyridin-2-yl)methanone O-[2-(tetrahydro-2H-pyran-2-yloxy)ethyl]oxime and phenyl(1H-pyrrolo[2,3-c]pyridin-2-yl)methanone O-(2-hydroxyethyl)oxime To phenyl(1H-pyrrolo[2,3-c]pyridin-2-yl)methanone oxime (Example 39) (200 mg, 0.84 mmol) in N,N-dimethylformamide (5 mL) was added NaH (40 mg, 60% dispersion in mineral oil, 1.0 mmol). After 45 min, 2-(2-bromoethoxy)tetrahydro-2H-pyran (0.13 mL, 0.88 mmol) was added and the mixture was heated to 60° C. After 15 h, the reaction mixture was concentrated under reduced pressure. The residue was partitioned between $H_2O$ and EtOAc. The aqueous layer was separated and extracted with EtOAc. The combined organic layers were washed with $H_2O$ and saturated NaCl, dried ($Na_2SO_4$) and concentrated under reduced pressure. Purification by column chromatography (silica gel, 95:5 $CH_2Cl_2$/MeOH) gave an impure brown oil (87.8 mg, 28%). Further purification by ion-exchange chromatography (SCX-2, 1:3 7 N $NH_4OH$ in MeOH/MeOH) gave a mixture of phenyl(1H-pyrrolo[2,3-c]pyridin-2-yl)methanone O-[2-(tetrahydro-2H-pyran-2-yloxy)ethyl]oxime (Example 109) and phenyl(1H-pyrrolo[2,3-c]pyridin-2-yl)methanone O-(2-hydroxyethyl)oxime (Example 110). Separation was carried out by column chromatography (silica gel, 95:5 $CH_2Cl_2$/MeOH).

Example 109 (12.3 mg) as an amber oil: $^1$H NMR (500 MHz, DMSO-$d_6$) δ 1.55-1.98 (6H, m), 3.61-3.64 (1H, m), 3.95-3.99 (2H, m) 4.09-4.12 (1H, m), 4.55-4.58 (2H, m), 4.81-4.83 (1H, m), 6.73 (1H, s), 7.48-7.55 (6H, ma), 8.13 (1H, d, J=5.5 Hz), 8.86 (1H, s), 11.68 (1H, s); ESI MS m/z 366 $[C_{21}H_{23}N_3O_3+H]^+$; HPLC (Method A) 85.8% (AUC), $t_R$=16.6 min.

Example 110 (33.2 mg) as a brown oil: $^1$H NMR (500 MHz, DMSO-$d_6$) δ 3.77 (2H, d, J=4.4 Hz), 4.30-4.32 (2H, m), 4.86 (1H, br s), 6.68 (1H, s), 7.47-7.57 (6H, m), 8.14 (1H, d, J=5.5 Hz), 8.88 (1H, s), 11.68 (1H, br s); ESI MS m/z 282 $[C_{16}H_{15}N_3O_2+H]^+$; HPLC (Method A) 98.5% (AUC), $t_R$=14.5 min.

Example 111 tert-Butyl 2-[[[phenyl(1H-pyrrolo[2,3-c]pyridin-3-yl)methylene]amino]oxy]ethylcarbamate tert-Butyl 2-[[[phenyl(1H-pyrrolo[2,3-c]pyridin-3-yl)methylene]amino]oxy]ethylcarbamate (429.2 mg, 89%) was prepared as a white foam using phenyl(1H-pyrrolo[2,3-c]pyridin-3-yl)methanone (Reference Example 8) and tert-butyl[2-(aminooxy)ethyl]carbamate following the procedure described for Example 104: $R_f$ 0.42 (90:10 methylene chloride/methanol); $^1$H NMR (300 MHz, $CD_3OD$) δ1.38-1.39 (9H, s), 3.40-3.44 (2H, m), 3.17-3.20 (1H, t, J=5.7 Hz), 3.26-3.28 (1H, t, J=5.3 Hz), 6.50-6.80 (1H, m), 7.30-7.50 (5H, m), 7.86-8.32 (2H, m), 8.76 (1H, s); ESI MS m/z 381 $[C_{21}H_{24}N_4O_3+H]^+$; HPLC (Method A) 96.8% (AUC), $t_R$=17.7 min.

Example 112

Phenyl(1H-pyrrolo[2,3-c]pyridin-3-yl)methanone O-(2-aminoethyl)oxime

A mixture of tert-butyl 2-[[[phenyl(1H-pyrrolo[2,3-c]pyridin-3-yl)methylene]amino]oxy]ethylcarbamate (Example 111) (385.8 mg, 0.94 mmol), trifluoroacetic acid (4 mL) and methylene chloride (2 mL) was stirred at room temperature for 6 h. The solvent was removed in vacuo. The crude material was purified and free based using SCX-2 to give phenyl(1H-pyrrolo[2,3-c]pyridin-3-yl)methanone O-(2-aminoethyl)oxime (220 mg, 84%) as an off-white foam: $^1$H NMR (500 MHz, $CD_3OD$) δ2.97-3.02 (2H, m), 3.20-3.31 (2H, m), 6.75-6.77 (0.6H, m), 7.19 (0.4H, m), 7.40-7.49 (5H, m), 7.91-7.92 (0.6H, m), 8.07-8.20 (1.5H, m), 8.70-8.72 (1H, m); ESI MS m/z 281 $[C_{16}H_{16}N_4O+H]^+$; HPLC (Method A) >99% (AUC), Isomeric ratio 58:42, $t_R$=12.5 and 12.2 min.

Example 113

(3,4-Dichlorophenyl)(1H-pyrrolo[2,3-c]pyridin-2-yl)methanol (3,4-Dichlorophenyl)(1H-pyrrolo[2,3-c]pyridin-2-yl)methanol (83 mg, 23%) was prepared as a white solid following the procedure described for Example 98 using commercially available 3,4-dichlorophenylmagnesium bromide in tetrahydrofuran: mp 264-266° C. dec.; $^1$H NMR (500 MHz, $CD_3OD$) δ5.99 (1H, s), 6.13 (1H, s), 7.36-7.39 (1H, m), 7.41-7.58 (2H, m), 7.67 (1H, d, J=1.9 Hz), 8.01 (1H, d, J=5.6 Hz), 8.60 (1H, s); ESI MS m/z 293 $[C_{14}H_{10}Cl_2N_2O+H]^+$; HPLC (Method A) >99% (AUC), $t_R$=16.5 min.

Example 114

[[Phenyl(1H-pyrrolo[2,3-c]pyridin-3-yl)methylene]amino]guanidine bis(hydrogen trifluoroacetate)

[[Phenyl (1H-pyrrolo[2,3-c]pyridin-3-yl)methylene]amino]guanidine bis(hydrogen trifluoroacetate) (13.3 mg, 10%) was prepared as an off-white solid using phenyl(1H-pyrrolo[2,3-c]pyridin-3-yl)methanone (Reference Example 8) following the procedure described for Example 74, except additional treatment with aqueous $NaHCO_3$ followed by trifluoroacetic acid: $^1$H NMR (300 MHz, $CD_3OD$) δ7.48-7.51 (2H, m), 7.68-7.72 (3H, m), 8.01 (1H, s) 8.30-8.38 (2H, dd, J=6.5, 16.5), 9.15 (1H, s); ESI MS m/z 279 $[C_{15}H_{14}N_6+H]^+$; HPLC (Method A) 97.6% (AUC), $t_R$=11.8 min.

Example 115

Phenyl(1H-pyrrolo[2,3-c]pyridin-2-yl)methanone O-benzyloxime hydrochloride

A mixture of phenyl[1-(phenylsulfonyl)-1H-pyrrolo[2,3-c]pyridin-2-yl]methanone (Reference Example 13) (200 mg, 0.55 mmol), O-benzylhydroxylamine hydrochloride (97 mg, 0.92 mmol) and pyridine (74 μL, 0.92 mmol) in 1,2-dichloroethane (8 mL) was heated at 60° C. After 24 h, saturated NH$_4$Cl (10 mL) was added and the mixture was extracted with EtOAc (2×25 mL). The combined extracts were washed with saturated NaCl (20 mL), dried (Na$_2$SO$_4$) and concentrated under reduced pressure. Purification by column chromatography (silica gel, 1:1 hexanes/EtOAc) gave phenyl(1H-pyrrolo[2,3-c]pyridin-2-yl)methanone O-benzyloxime hydrochloride (84 mg, 47%) as a mixture of isomers: mp 153-155° C.; $^1$H NMR (500 MHz, DMSO-d$_6$) δ 5.35-5.40 (2H, m), 6.66 (0.5H, s), 7.12 (0.5H, s), 7.34-7.56 (10H, m), 8.07 (0.5H, d, J=6.3 Hz), 8.19 (0.5H, d, J=6.3 Hz), 8.29 (0.5H, d, J=6.3 Hz), 8.34 (0.5H, d, J=6.3 Hz), 8.99 (0.5H, s), 9.17 (0.5H, s), 13.04 (0.5H, s), 13.14 (0.5H, s), 15.14 (1H, br s); ESI MS m/z 328 [C$_{21}$H$_{17}$N$_3$O+H]$^+$; HPLC (Method A) 98.3% (AUC), t$_R$=19.1 and 19.3 min.

Example 116 tert-Butyl 2-[[[(4-chlorophenyl)(1H-pyrrolo[2,3-c]pyridin-2-yl)methylene]amino]oxy]ethylcarbamate tert-Butyl 2-[[[(4-chlorophenyl)(1H-pyrrolo[2,3-c]pyridin-2-yl)methylene]amino]oxy]ethylcarbamate was prepared from (4-chlorophenyl)(1H-pyrrolo[2,3-c]pyridin-2-yl)methanone (Example 103) and tert-butyl[2-(aminooxy)ethyl]carbamate following the procedure described for Example 104. Purification by Biotage chromatography (silica, 2 to 15% methanol in methylene chloride) provided tert-butyl 2-[[[(4-chlorophenyl)(1H-pyrrolo[2,3-c]pyridin-2-yl)methylene]amino]oxy]ethylcarbamate (geometry of the oxime double bond undefined).

Isomer A (81 mg, 53%) as a white solid: mp 166-169° C.; $^1$H NMR (500 MHz CD$_3$OD) δ 1.39 (9H, s), 3.42 (2H, t, T=5.5 Hz), 4.25 (2H, t, J=5.6 Hz), 6.29 (1H, s), 7.48-7.58 (5H, m), 8.05 (1H, d, J=5.5 Hz), 8.72 (1H, s); ESI MS m/z 415 [C$_{21}$H$_{23}$ClN$_4$O$_3$+H]$^+$; HPLC (Method A) 85.4% (AUC), t$_R$=17.5 min.

Isomer B (37 mg, 24%) as an oil: $^1$H NMR (500 MHz CD$_3$OD) δ 1.39 (9H, s), 3.52-3.55 (2H, m), 4.35 (2H, t, J=4.9 Hz), 6.58 (1H, s), 7.47-7.49 (2H, m), 7.57-7.62 (3H, m), 8.09 (1H, d, J=5.6 Hz), 8.93 (1H, s).

Example 117

(Pyridin-2-yl)(1H-pyrrolo[2,3-c]pyridin-2-yl)methanol

A solution of diisopropylamine (0.43 mL, 3.07 mmol) in tetrahydrofuran (4 mL) was cooled to −78° C. under a nitrogen atmosphere. n-Butyllithium (1.24 mL of a 2.5 M solution in hexanes) was added dropwise and the reaction mixture was stirred for 30 min at −78° C. and then warmed to −30° C. A solution of 1-(phenylsulfonyl)-1H-pyrrolo[2,3-c]pyridine (Reference Example 12) (400 mg, 1.55 mmol) and N,N,N',N'-tetramethylethylenediamine (0.24 mL, 1.59=mmol) in tetrahydrofuran (4 mL) was added and the reaction mixture was stirred for 30 min. A solution of 2-pyridinecarboxaldehyde (0.30 mL, 3.14 mmol) in tetrahydrofuran (3 mL) was added dropwise at −30° C. The reaction mixture was allowed to warm to ambient temperature over 1.5 h. Saturated ammonium chloride solution (7 mL) was added to quench the reaction mixture. The reaction mixture was diluted with water (10 mL) and extracted with ethyl acetate (2×25 mL). The combined organic extracts were washed successively with water and brine, dried over sodium sulfate and concentrated to dryness. Purification by Biotage chromatography (silica, 2 to 18% methanol in methylene chloride) produced (pyridin-2-yl)(1H-pyrrolo[2,3-c]pyridin-2-yl)methanol (67 mg, 12%) as an off-white solid: mp 166-169° C.; $^1$H NMR (500 MHz, CD$_3$OD) δ6.05 (1H, s), 6.39 (1H, s), 7.34-7.36 (1H, m), 7.50-7.52 (1H, m), 7.72 (1H, d, J=7.9 Hz), 7.87 (1H, d, J=6.0 Hz), 8.00 (1H, d, J=5.6 Hz), 8.52 (1H, d, J=4.8 Hz), 8.62 (1H, s); ESI MS m/z 226 [C$_{13}$H$_{11}$N$_3$O+H]$^+$; HPLC (Method A) 98.9% (AUC), t$_R$=13.1 min.

Example 118

(4-Methylphenyl)(1H-pyrrolo[2,3-c]pyridin-2-yl)methanone O-(2-aminoethyl)oxime bis(hydrogen trifluoroacetate)

(4-Methylphenyl)(1H-pyrrolo[2,3-c]pyridin-2-yl)methanone (Example 100) (130 mg, 0.55 mmol) and tert-butyl[2-(aminooxy)ethyl]carbamate (99 mg, 0.56 mmol) were combined in ethanol (8 mL). The pH of the mixture was adjusted to ca. 4 using 1 M ethereal hydrogen chloride and the reaction mixture was refluxed for 14 h. The solvent was removed under vacuum. The residue was dissolved in ethyl acetate, washed with saturated sodium bicarbonate solution and then brine, dried over sodium sulfate, and concentrated to a solid. Purification by column chromatography (silica gel, 75 to 100% ethyl acetate in hexanes) produced tert-butyl 2-[[[(4-methylphenyl)(1H-pyrrolo[2,3-c]pyridin-2-yl)methylene]amino]oxy]ethylcarbamate (geometry of the oxime double bond undefined).

Isomer A (22 mg, 10%) as a white solid: $^1$H NMR (500 MHz CD$_3$OD) δ 1.41 (9H, s), 3.11 (3H, s), 3.51-3.53 (2H, m), 4.32-4.34 (2H, m), 6.61 (1H, s), 7.20-7.22 (2H, m), 7.45-7.58 (3H, m), 8.08 (1H, d, J=5.6 Hz), 8.93 (1H, br s).

Isomer B (24 mg, 11%) as a clear oil: $^1$H NMR (300 MHz CD$_3$OD) δ 1.40 (9H, s), 2.42 (3H, s), 3.40-3.43 (2H, m), 4.21-4.24 (2H, m), 6.32 (1H, s), 7.28-7.52 (5H, m), 8.03 (1H, d, J=5.6 Hz), 8.71 (1H, s).

tert-Butyl 2-[[[(4-methylphenyl)(1H-pyrrolo[2,3-c]pyridin-2-yl)methylene]amino]oxy]ethylcarbamate (Isomer A) (22 mg, 0.06 mmol) was dissolved in trifluoroacetic acid (3 mL) at 0° C. and the reaction mixture was stirred for 3 h. The solvent was removed under vacuum and the excess trifluoroacetic acid was co-evaporated with toluene (3×10 mL). Drying in a vacuum oven at 50° C. produced (4-methylphenyl)(1H-pyrrolo[2,3-c]pyridin-2-yl)methanone O-(2-aminoethyl)oxime bis(hydrogen trifluoroacetate) (22 mg, 71%) as an off-white solid (geometry of the oxime double bond undefined).

Example 118: mp 179-182° C.; $^1$H NMR (500 MHz, CD$_3$OD) δ 2.42 (3H, s), 3.43 (2H, t, J=5.1 Hz), 4.59 (2H, t, J=5.1 Hz), 7.12 (1H, s), 7.31 (2H, d, J=7.9 Hz), 7.49 (2H, d, J=8.1 Hz), 8.15 (1H, d, J=6.3 Hz), 8.26 (1H, d, J=6.5 Hz), 9.11 (1H, s); ESI MS m/z 295 [C$_{17}$H$_{18}$N$_4$O+H]$^+$; HPLC (Method A) 98.4% (AUC) t$_R$=14.1 min.

Example 119

(4-Methylphenyl)(1H-pyrrolo[2,3-c]pyridin-2-yl)methanone O-(2-aminoethyl)oxime bis(hydrogen trifluoroacetate)

tert-Butyl 2-[[[(4-methylphenyl)(1H-pyrrolo[2,3-c]pyridin-2-yl)methylene]amino]oxy]ethylcarbamate (Example 118, Isomer B) (22 mg, 0.06 mmol) was dissolved in trifluoroacetic acid (3 mL) at 0° C. and the reaction mixture was stirred for 4 h. The solvent was removed under vacuum and the excess trifluoroacetic acid was co-evaporated with toluene (3×10 mL). Drying in a vacuum oven at 60° C. produced (4-methylphenyl)(1H-pyrrolo[2,3-c]pyridin-2-yl)methanone O-(2-aminoethyl)oxime bis(hydrogen trifluoroacetate) (24 mg, 77%) as a tan solid (geometry of the oxime double bond undefined, isomer of Example 118): mp 190-194° C.; $^1$H NMR (500 MHz, CD$_3$OD) δ 2.44 (3H, s), 3.41 (2H, t, J=5.0 Hz), 4.52 (2H, t, J=5.0 Hz), 6.81 (1H, s), 7.37 (2H, d, J=7.8 Hz), 7.47 (2H, d, J=8.0 Hz), 8.06 (1H, d, J=6.4 Hz), 8.21 (1H, d, J=6.3 Hz), 8.98 (1H, s); ESI MS m/z 295 [C$_{17}$H$_{18}$N$_4$O+H]$^+$; HPLC (Method A) 96.9% (AUC) t$_R$=14.0 min.

Example 120 and Example 121

Phenyl (1H-pyrrolo[2,3-c]pyridin-2-yl)methanone O-methyloxime hydrochloride

Phenyl (1H-pyrrolo[2,3-c]pyridin-2-yl)methanone O-methyloxime hydrochloride was prepared from phenyl(1H-pyrrolo[2,3-c]pyridin-2-yl)methanone (Example 35) and O-methylhydroxylamine hydrochloride following the procedure described for Example 104 (geometry of the oxime double bond undefined).

Example 120 (45.3 mg, 17%): mp 202-203° C.; $^1$H NMR (500 MHz, DMSO-d$_6$) δ4.11 (3H, s), 7.03 (1H, s), 7.48-7.56 (5H, m), 8.17 (1H, d, J=6.3 Hz), 8.34 (1H, d, J=6.3 Hz), 9.19 (1H, s), 13.13 (1H, s), 15.30 (1H, br s); ESI MS m/z 252 [C$_{15}$H$_{13}$N$_3$O+H]$^+$; HPLC (Method A) 96.9% (AUC), t$_R$=16.6 min.

Example 121 (geometry of the oxime double bond undefined, isomer of Example 120) (67.9 mg, 26%): mp 220-222° C.; $^1$H NMR (500 MHz, DMSO-d$_6$) δ4.05 (3H, s), 6.65 (1H, s), 7.48-7.56 (5H, m), 8.07 (1H, d, J=6.3 Hz), 8.29 (1H, d, J=6.3 Hz), 8.99 (1H, s), 13.08 (1H, s), 15.24 (1H, br s); ESI MS m/z 252 [C$_{15}$H$_{13}$N$_3$O+H]$^+$; HPLC (Method A) 98.3% (AUC), t$_R$=16.6 min.

Example 122

(Pyridin-2-yl)(1H-pyrrolo[2,3-c]pyridin-2-yl)methanone (Pyridin-2-yl)(1H-pyrrolo[2,3-c]pyridin-2-yl)methanol (Example 117) (55 mg, 0.24 mmol) was dissolved in tetrahydrofuran (4 mL). Manganese dioxide (210 mg, 2.42 mmol) was added and the reaction mixture was stirred at room temperature for 2 h. The reaction mixture was filtered through diatomaceous earth and the filter cake was washed thoroughly with tetrahydrofuran. The organic filtrate was concentrated to a yellow solid. Drying under vacuum at 40° C. produced (pyridin-2-yl)(1H-pyrrolo[2,3-c]pyridin-2-yl)methanone (60 mg, quant.): mp 219-222° C.; $^1$H NMR (500 MHz, CD$_3$OD) δ7.66-7.76 (2H, m), 7.85 (1H, m), 8.04-8.08 (1H, m), 8.14-8.21 (2H, m), 8.82-8.43 (1H, m), 8.92 (1H, s); ESI MS m/z=224 [C$_{13}$H$_9$N$_3$O+H]$^+$; HPLC (Method A) 95.4% (AUC), t$_R$=13.1 min.

Example 123

(4-Methoxyphenyl)(1H-pyrrolo[2,3-c]pyridin-2-yl)methanone O-(2-aminoethyl)oxime bis(hydrogen trifluoroacetate)

tert-Butyl 2-[[[(4-methyloxyphenyl)(1H-pyrrolo[2,3-c]pyridin-2-yl)methylene]amino]oxy]ethylcarbamate was prepared from (4-methoxyphenyl)(1H-pyrrolo[2,3-c]pyridin-2-yl)methanone (Example 102) following the procedure described for Example 118. Isomeric separation by Biotage chromatography (silica gel, 3→10% methanol in methylene chloride) produced tert-butyl 2-[[[(4-methyloxyphenyl)(1H-pyrrolo[2,3-c]pyridin-2-yl)methylene]amino]oxy]ethylcarbamate (geometry of the oxime double bond undefined).

Isomer A (63 mg, 48%) as a yellow solid: $^1$H NMR (500 MHz CD$_3$OD) δ 1.41 (9H, s), 3.51-3.53 (2H, m), 3.86 (3H, s), 4.32-4.34 (2H, m), 6.59 (1H, s), 7.00-7.02 (2H, m), 7.50-7.59 (3H, m), 8.08 (1H, d, J=5.6 Hz), 8.92 (1H, s).

Isomer B (20 mg, 15%) as an oil: $^1$H NMR (500 MHz CD$_3$OD) δ 1.40 (9H, s), 3.41-3.43 (2H, m), 3.87 (3H, s), 4.22-4.25 (2H, m), 6.36 (1H, s), 7.02 (2H, d, J=8.7 Hz)), 7.46-7.52 (3H, m), 8.04 (1H, d, J=5.6 Hz), 8.71 (1H, s).

tert-Butyl 2-[[[(4-methyloxyphenyl)(1H-pyrrolo[2,3-c]pyridin-2-yl)methylene]amino]oxy]ethylcarbamate (Isomer A) (58 mg, 0.14 mmol) was dissolved in 0° C. trifluoroacetic acid (3 mL) and the reaction mixture was stirred for 3 h. The solvent was removed under vacuum and the excess trifluoroacetic acid was co-evaporated with toluene (3×). Preparative HPLC [synergi column, 10→100% acetonitrile in water (0.05% TFA added to eluents) over 35 min] produced (4-methoxyphenyl)(1H-pyrrolo[2,3-c]pyridin-2-yl)methanone O-(2-aminoethyl)oxime bis(hydrogen trifluoroacetate) (49 mg, 64%) as an off-white solid (geometry of the oxime double bond undefined).

Example 123: mp 158-162° C.; $^1$H NMR (500 MHz, CD$_3$OD) δ 3.43 (2H, t, J=5.1 Hz), 3.86 (3H, s), 4.59 (2H, t, J=5.1 Hz), 7.03 (2H, d, J=8.8 Hz), 7.14 (1H, s), 7.53-7.55 (2H, m), 8.17 (1H, d, J=6.4 Hz), 8.26 (1H, d, J=6.4 Hz), 9.11 (1H, s); ESI MS m/z 311 [C$_{17}$H$_{18}$N$_4$O$_2$+H]$^+$; HPLC (Method A) 96.5% (AUC), t$_R$=14.0 min.

Example 124

(4-Methoxyphenyl)(1H-pyrrolo[2,3-c]pyridin-2-yl)methanone O-(2-aminoethyl)oxime dihydrochloride tert-Butyl 2-[[[(4-methyloxyphenyl)(1H-pyrrolo[2,3-c]pyridin-2-yl)methylene]amino]oxy]ethylcarbamate (Example 123, Isomer B) (22 mg, 0.06 mmol) was dissolved in trifluoroacetic acid (3 mL) and the reaction mixture was stirred for 1.5 h. The solvent was removed under vacuum and the excess trifluoroacetic acid was co-evaporated with toluene (3×). The trifluoroacetic acid salt was dissolved in ethyl acetate and washed with saturated sodium bicarbonate solution. The organic layer was separated, washed with water and brine, dried over sodium sulfate and concentrated. The residue was dissolved in ethyl acetate and ethereal hydrogen chloride (2 mL of a 1 M solution) was added. After 2 h, the solvent was removed under vacuum to produce (4-methoxyphenyl)(1H-pyrrolo[2,3-c]pyridin-2-yl)methanone O-(2-aminoethyl)oxime dihydrochloride (18 mg, 64%) as an off-white solid (geometry of the oxime double bond undefined, isomer of Example 123): mp 178-184° C.; $^1$H NMR (500 MHz, CD$_3$OD) δ 3.43 (2H, t, J=5.1 Hz), 3.88 (3H, s), 4.53 (2H, t, J=5.1 Hz), 6.85 (1H, s), 7.07-7.10 (2H, m), 7.56 (2H, d, J=8.7 Hz), 8.06-8.10 (1H, m), 8.22 (1H, d, J=6.3 Hz), 8.99 (1H, s); ESI MS m/z 311 [C$_{17}$H$_{18}$N$_4$O$_2$+H]$^+$; HPLC (Method A) 85.4% (AUC), Isomeric ratio 85:8, t$_R$=13.4 min.

Example 125

(4-Chlorophenyl)(1H-pyrrolo[2,3-c]pyridin-2-yl)methanone O-(2-aminoethyl)oxime bis(hydrogen trifluoroacetate)

tert-Butyl 2-[[[(4-chlorophenyl)(1H-pyrrolo[2,3-c]pyridin-2-yl)methylene]amino]oxy]ethylcarbamate (Example 116, Isomer A) (22 mg, 0.06 mmol) was dissolved in trifluoroacetic acid (3 mL) and the reaction mixture was stirred for 3 h. The solvent was removed under vacuum and the excess trifluoroacetic acid was co-evaporated with toluene (2×10 mL). The residue was triturated with ethyl acetate to give (4-chlorophenyl)(1H-pyrrolo[2,3-c]pyridin-2-yl)methanone O-(2-aminoethyl)oxime bis(hydrogen trifluoroacetate) (18 mg, 46%) as a tan solid (geometry of the oxime double bond undefined): $^1$H NMR (500 MHz, CD$_3$OD) δ 3.41-3.45 (2H, m), 4.62 (2H, t, J=5.0 Hz), 7.12 (1H, s), 7.50-7.62 (4H, m), 8.17 (1H, d, J=6.4 Hz), 8.28 (1H, d, J=6.4 Hz), 9.17 (1H, s); ESI MS m/z 315 [C$_{16}$H$_{15}$ClN$_4$O+H]$^+$; HPLC (Method A) 81.3% (AUC), Isomeric ratio 81:18, t$_R$=14.4 min.

Example 126

(4-Chlorophenyl)(1H-pyrrolo[2,3-c]pyridin-2-yl) methanone O-(2-aminoethyl)oxime bis(hydrogen trifluoroacetate)

tert-Butyl 2-[[[(4-chlorophenyl)(1H-pyrrolo[2,3-c]pyridin-2-yl)methylene]amino]oxy]ethylcarbamate (Example 116, Isomer B) (24 mg, 0.06 mmol) was dissolved in trifluoroacetic acid (3 mL) at 0° C. and the reaction mixture was stirred for 2 h. The solvent was removed under vacuum and the excess trifluoroacetic acid was co-evaporated with toluene (3×10 mL). Drying in a vacuum oven at 40° C. produced (4-chlorophenyl)(1H-pyrrolo[2,3-c]pyridin-2-yl)methanone O-(2-aminoethyl)oxime bis(hydrogen trifluoroacetate) (28 mg, 88%) as a tan solid (geometry of the oxime double bond undefined, isomer of Example 125): mp 146-150° C.; $^1$H NMR (500 MHz, CD$_3$OD) δ 3.41 (2H, m), 4.53 (2H, t, J=5.0 Hz), 6.83 (1H, s), 7.58 (4H, s), 8.09 (1H, d, J=6.4 Hz), 8.23 (1H, d, J=6.4 Hz), 8.99 (1H, s); ESI m/z 315 [C$_{16}$H$_{15}$ClN$_4$O+H]$^+$; HPLC (Method A) 93.9% (AUC), Isomeric ratio 94:4, t$_R$=14.2 min.

Example 127

(3,4-Dichlorophenyl)(1H-pyrrolo[2,3-c]pyridin-2-yl) methanone (3,4-Dichlorophenyl)(1H-pyrrolo[2,3-c]pyridin-2-yl) methanone (99 mg, 45%) was prepared as a yellow solid following the procedure described for Example 100 using (3,4-dichlorophenyl)(1H-pyrrolo[2,3-c]pyridin-2-yl)methanol (Example 113) and tetrahydrofuran as a solvent: mp 274-277° C. dec.; $^1$H NMR (500 MHz, DMSO-d$_6$) δ7.24 (1H, s), 7.70 (1H, d, J=5.5 Hz), 7.87-7.95 (2H, m), 8.14 (1H, d, J=1.9 Hz), 8.22 (1H, d, J=5.6 Hz), 8.93 (1H, s), 12.50 (1H, s); ESI MS m/z 291 [C$_{14}$H$_8$Cl$_2$N$_2$O+H]$^+$; HPLC (Method A) >99% (AUC), t$_R$=17.4 min.

Example 128 and Example 129 tert-Butyl methyl[2-[[[phenyl(1H-pyrrolo[2,3-c]pyridin-2-yl)methylene]amino]oxy]ethyl]carbamate A mixture of phenyl(1H-pyrrolo[2,3-c]pyridin-2-yl) methanone (Example 35) (200 mg, 90 mmol) and tert-butyl [2-(aminooxy)ethyl]methylcarbamate (Reference Example 14) (180 mg, 94 mmol) in EtOH (20 mL) was adjusted to pH 4-5 with HCl (1.2 mL of a 1 N HCl solution in diethyl ether, 1.2 mmol). The reaction mixture was heated to reflux. After 15.5 h, the reaction mixture was concentrated under reduced pressure. The residue was diluted with EtOAc (25 mL) and washed with saturated NaHCO$_3$ (2×10 mL). The combined organic layers were washed with saturated NaCl (10 mL), dried (Na$_2$SO$_4$) and concentrated under reduced pressure. Purification by column chromatography (silica gel, 99:1 CH$_2$Cl$_2$/MeOH to 95:5 CH$_2$Cl$_2$/MeOH) gave tert-butyl methyl[2-[[[phenyl(1H-pyrrolo[2,3-c]pyridin-2-yl)methylene]amino]oxy]ethyl]carbamate (geometry of the oxime double bond undefined).

Example 128 (105 mg, 30%) as an off-white amorphous solid: $^1$H NMR (500 MHz, DMSO-d$_6$) δ1.27-1.38 (9H, m), 2.79-2.86 (3H, m), 3.58-3.62 (2H, m), 4.39 (2H, s), 6.60-6.68 (1H, m), 7.48-7.55 (6H, m), 8.13 (1H, d, J=5.5 Hz), 8.87-8.91 (1H, m), 11.75 (1H, br s); ESI MS m/z 395 [C$_{22}$H$_{26}$N$_4$O$_3$+H]$^+$; HPLC (Method A) 98.1% (AUC), t$_R$=19.3 min.

Example 129 (40 mg, 11%) as an off-white amorphous solid: 1H NMR (500 MHz, DMSO-d$_6$) δ1.30-1.34 (9H, m), 2.72-2.77 (3H, m), 3.55 (2H, br s), 4.26 (2H, t, J=5.1 Hz), 6.20-6.22 (1H, m), 7.44-7.50 (6H, m), 8.08 (1H, d, J=5.5 Hz), 8.79 (1H, s), 11.78 (1H, br s); ESI MS m/z 395 [C$_{22}$H$_{26}$N$_4$O$_3$+H]$^+$; HPLC (Method A) 94.9% (AUC), t$_R$=19.0 min Example 130

2-[[[Phenyl(1H-pyrrolo[2,3-c]pyridin-2-yl)methylene]amino]oxy]acetamide

1 N HCl (0.67 mL, 0.67 mmol) was added to a solution of 2-(aminooxy)acetamide (Reference Example 18) (90.5 mg, 1.04 mmol) in EtOH (6.7 mL) followed by addition of phenyl (1H-pyrrolo[2,3-c]pyridin-2-yl)methanone (Example 35) (150 mg, 0.67 mmol). The reaction mixture was refluxed overnight. The reaction mixture was cooled to room temperature and the solvent was removed in vacuo. The residue was free based using an SCX-2 and purified by Biotage chromatography to isolate 2-[[[phenyl(1H-pyrrolo[2,3-c]pyridin-2-yl)methylene]amino]oxy]acetamide (72.9 mg, 37%) as a white solid (single isomer, geometry of the oxime double bond undefined): R$_f$ 0.13 (90:10 methylene chloride/methanol); $^1$H NMR (500 MHz, DMSO-d$_6$) δ4.65 (2H, s), 6.65 (1H, s), 7.41-7.58 (8H, m), 8.14-8.15 (1H, d, J=5.5 Hz), 8.89 (1H, s), 12.01 (1H, br s); ESI MS m/z 295 [C$_{16}$H$_{14}$N$_4$O$_2$+H]$^+$; HPLC (Method A) 98.9% (AUC), t$_R$=14.8 min.

Example 131

Phenyl(1H-pyrrolo[2,3-c]pyridin-2-yl)methanone O-[2-(methylamino)ethyl]oxime dihydrochloride tert-Butyl methyl[2-[[[phenyl (1H-pyrrolo[2,3-c]pyridin-2-yl)methylene]amino]oxy]ethyl]carbamate (Example 128) (100 mg, 0.25 mmol) in trifluoroacetic acid/CH$_2$Cl$_2$ (2:1, 5 mL) was stirred at ambient temperature. After 5 h, the reaction mixture was concentrated under reduced pressure. The residue was diluted with CH$_2$Cl$_2$ (35 mL) and washed with saturated NaHCO$_3$ (20 mL) and saturated NaCl (20 mL), dried (Na$_2$SO$_4$) and concentrated under reduced pressure. The residue was purified by column chromatography (silica gel, 89:10:1 CH$_2$Cl$_2$/MeOH/NH$_4$OH). The obtained product was dissolved in EtOAc, an excess of 1 N HCl in Et$_2$O was added and the mixture was concentrated under reduced pressure. The resulting solid was triturated with EtOAc and collected by vacuum filtration to give phenyl(1H-pyrrolo[2,3-c] pyridin-2-yl)methanone O-[2-(methylamino)ethyl]oxime dihydrochloride (46.8 mg, 51%) as an off-white solid (geometry of the oxime double bond undefined): $^1$H NMR (500 MHz, DMSO-d$_6$) δ 2.63 (3H, s), 3.39 (2H, br s), 4.59 (2H, t, J=4.5 Hz), 6.96 (1H, s), 7.50-7.61 (5H, m), 8.14 (1H, d, J=6.3

Hz), 8.34 (1H, d, J=6.3 Hz), 9.31-9.35 (3H, m), 13.56 (1H, s), 15.28 (1H, br s); ESI MS m/z 295 $[C_{17}H_{18}N_4O+H]^+$; HPLC (Method A) 96.6% (AUC), $t_R$=13.5 min.

Example 132

Phenyl(1H-pyrrolo[2,3-c]pyridin-2-yl)methanone O-[2-(methylamino)ethyl]oxime dihydrochloride Phenyl(1H-pyrrolo[2,3-c]pyridin-2-yl)methanone O-[2-(methylamino)ethyl]oxime dihydrochloride was prepared from tert-butyl methyl[2-[[[phenyl(1H-pyrrolo[2,3-c]pyridin-2-yl)methylene]amino]oxy]ethyl]carbamate (Example 129) following the procedure described for the Example 131 (21.4 mg, 86%) as an off-white amorphous solid (geometry of the oxime double bond undefined, isomer of Example 131): $^1$H NMR (500 MHz, DMSO-$d_6$) δ 2.60 (3H, s), 3.41 (2H, br s), 4.50 (2H, t, J=4.9 Hz), 6.68 (1H, s), 7.55-7.61 (5H, m), 8.05 (1H, d, J=6.3 Hz), 8.29 (1H, d, J=6.3 Hz), 9.03-9.07 (3H, m), 13.42 (1H, s), 15.20 (1H, br s); ESI MS m/z 295 $[C_{17}H_{18}N_4O+H]^+$; HPLC (Method A) 95.8% (AUC), $t_R$=13.3 min.

Example 133

N-Methyl-2-[[[phenyl (1H-pyrrolo[2,3-c]pyridin-2-yl)methylene]amino]oxy]acetamide N-Methyl-2-[[[phenyl (1H-pyrrolo[2,3-c]pyridin-2-yl)methylene]amino]oxy]acetamide (126 mg, 58%) was prepared using 2-(aminooxy)-N-methylacetamide (Reference Example 19) as an off-white foam following the procedure described for Example 130: $R_f$ 0.31 (90:10 methylene chloride/methanol); $^1$H NMR (300 MHz, CD$_3$OD) δ 2.82 (3H, s), 4.78 (2H, s), 6.66 (1H, s), 7.42-7.62 (7H, m), 8.09-8.11 (1H, d, J=5.7 Hz), 8.84 (1H, s); ESI MS m/z 309 $[C_{17}H_{16}N_4O_2+H]^+$; HPLC (Method A) >99% (AUC), $t_R$=15.0 min.

Example 134

(3,4-Dichlorophenyl)(1H-pyrrolo[2,3-c]pyridin-2-yl)methanone O-(2-aminoethyl)oxime bis(hydrogen trifluoroacetate)

(3,4-Dichlorophenyl)(1H-pyrrolo[2,3-c]pyridin-2-yl)methanone (Example 127) (92 mg, 0.32 mmol) and tert-butyl [2-(aminooxy)ethyl]carbamate (58 mg, 0.33 mmol) were combined in ethanol (5 mL). The pH was adjusted to ca. 4 using 1 M ethereal hydrogen chloride and the react ion mixture was refluxed for 14 h. The solvent was removed under vacuum. The residue was dissolved in ethyl acetate, washed with saturated sodium bicarbonate solution and then brine, dried over sodium sulfate, and concentrated to a solid. Purification by Biotage chromatography (silica gel, 97:3 CH$_2$Cl$_2$:CH$_3$OH) produced tert-butyl 2-[[[(3,4-dichlorophenyl)(1H-pyrrolo[2,3-c]pyridin-2-yl)methylene]amino]oxy] ethylcarbamate (74 mg, 51%) as a yellow foam: $^1$H NMR (300 MHz CD$_3$OD) δ 1.39 (9H, s), 3.50-3.54 (2H, m), 4.26-4.39 (2H, m), 6.35 (0.35H, s), 6.62 (0.65H, s), 7.38-7.77 (4H, m), 8.04-8.11 (1H, m), 8.72 (0.35H, s), 8.93 (0.65H, s); ESI MS m/z 449 $[C_{21}H_{22}Cl_2N_4O_3+H]^+$.

tert-Butyl 2-[[[(3,4-dichlorophenyl)(1H-pyrrolo[2,3-c]pyridin-2-yl)methylene]amino]oxy]ethylcarbamate (72 mg, 0.16 mmol) was dissolved in trifluoroacetic acid (3 mL) at 0° C. and the reaction mixture was stirred for 3 h. The solvent was removed under vacuum and the excess trifluoroacetic acid was co-evaporated with toluene (3×10 mL). Drying in a vacuum oven at 50° C. produced (3,4-dichlorophenyl)(1H-pyrrolo[2,3-c]pyridin-2-yl)methanone O-(2-aminoethyl)oxime bis(hydrogen trifluoroacetate) (48 mg, 52%) as a tan solid: mp 64-68° C.; $^1$H NMR (500 MHz, CD$_3$OD) δ3.43-3.45 (2H, m), 4.54-4.64 (2H, m), 6.85 (0.33H, s), 7.17 (0.67H, s), 7.52-7.83 (3H, m), 8.18-8.29 (2H, m), 9.02 (0.33H, s), 9.16 (0.67H, s); ESI MS m/z 349 $[C_{16}H_{14}Cl_2N_4O+H]^+$; HPLC (Method A) 90.6% (AUC) $t_R$=14.6 min and 14.8 min, Isomeric ratio 30.9:59.7.

Example 135

Phenyl(1H-pyrrolo[2,3-c]pyridin-2-yl)methanone O-(1H-imidazol-4-ylmethyl)oxime dihydrochloride Phenyl(1H-pyrrolo[2,3-c]pyridin-2-yl)methanone O-(1H-imidazol-4-ylmethyl)oxime dihydrochloride was prepared from 4-[(aminooxy)methyl]-1H-imidazole (Reference Example 15) following the procedure described for Example 128, but without basic treatment, (402 mg, 68%) as a mixture of isomers (64.5:34.7 by HPLC analysis): $^1$H NMR (500 MHz, DMSO-$d_6$) δ 5.31 (0.7H, s), 5.44 (1.3H, s), 6.67 (0.35H, s), 7.04 (0.65H, s), 7.50-7.56 (5H, m), 7.84 (0.65H, s), 7.92 (0.35H, s), 8.08 (0.35H, d, J=6.3 Hz), 8.18 (0.65H, d, J=6.3 Hz), 8.31 (0.35H, d, J=6.3 Hz), 8.36 (0.65H, d, J=6.3 Hz), 9.11 (0.35H, s), 9.16 (1H, s), 9.30 (0.65H, s), 13.48 (0.65H, s), 13.75 (0.35H, s), 15.07 (3H, br s); ESI MS m/z 318 $[C_{18}H_{15}N_5O+H]^+$; HPLC (Method A) >99% (AUC), $t_R$=13.4 and 13.6 min.

Example 136

(Pyridin-4-yl)(1H-pyrrolo[2,3-c]pyridin-2-yl)methanone

[1-(Phenylsulfonyl)-1H-pyrrolo[2,3-c]pyridin-2-yl](pyridin-4-yl)methanol (Reference Example 22, 217 mg, 0.59 mmol) was dissolved in ethanol (10 mL). A 10% solution of sodium hydroxide (6 mL) was added and the reaction mixture was refluxed for 4.5 hours and then stirred at ambient temperature for the weekend. The solvent was removed under vacuum. The residue was taken up in ethyl acetate, washed with water and brine, dried over sodium sulfate and concentrated to give (pyridin-4-yl)(1H-pyrrolo[2,3-c]pyridin-2-yl) methanone (air-oxidation product) (86 mg, 65%) as a yellow solid: $^1$H NMR (500 MHz, CD$_3$OD) δ 7.26 (1H, s), 7.75-7.77 (1H, m), 7.90-7.92 (2H, m), 8.18 (1H, d, J=5.6 Hz), 8.81-8.83 (2H, m), 8.90 (1H, s); ESI MS m/z=224 $[C_{13}H_9N_3O+H]^+$; HPLC (Method A) >99% (AUC), $t_R$=7.6 min.

Example 137

3-Furyl(1H-pyrrolo[2,3-c]pyridin-2-yl)methanone

A solution of diisopropylamine (0.43 mL, 3.07 mmol) in tetrahydrofuran (4 mL) was cooled to −78° C. under a nitrogen atmosphere. n-Butyllithium (1.24 mL of a 2.5 M solution in hexanes) was added dropwise and the reaction mixture was stirred for 30 minutes at −78° C. and then warmed to −30° C. A solution of 1-(phenylsulfonyl)-1H-pyrrolo[2,3-c]pyridine (Reference Example 12) (400 mg, 1.55 mmol) and N,N,N',N'-tetramethylethylenediamine (0.24 mL, 1.59 mmol) in tetrahydrofuran (4 mL) was added and the reaction mixture was stirred for 45 minutes. A solution of 3-furfural (0.27 mL, 3.12 mmol) in tetrahydrofuran (3 mL) was added dropwise. The reaction mixture was allowed to warm to ambient temperature over 2 h. Saturated ammonium chloride solution (5 mL)

was added to quench the reaction mixture. The reaction mixture was diluted with water (10 mL) and extracted with ethyl acetate (3×25 mL). The combined organic extracts were washed successively with water and brine, dried over sodium sulfate and concentrated to dryness. Recrystallization from methanol gave 3-furyl[1-(phenylsulfonyl)-1H-pyrrolo[2,3-c]pyridin-2-yl]methanol (208 mg, 38%) as an off-white solid: mp 168-171° C.; $^1$H NMR (500 MHz, DMSO-$d_6$) δ 6.24 (1H, d, J=5.8 Hz), 6.40 (1H, d, J=5.8 Hz), 6.48 (1H, d, J=1.1 Hz), 6.84 (1H, s), 7.55-7.62 (5H, m), 7.68-7.71 (1H, m), 7.92-7.94 (2H, m), 8.35 (1H, d, J=5.2 Hz), 9.23 (1H, s); ESI MS m/z 355 $[C_{18}H_{14}N_2O_4S+H]^+$; HPLC (Method A) >99% (AUC), $t_R$=15.4 min.

3-Furyl[1-(phenylsulfonyl)-1H-pyrrolo[2,3-c]pyridin-2-yl]methanol (186 mg, 0.51 mmol) was dissolved in ethanol (10 mL). A 10% solution of sodium hydroxide (6 mL) was added and the reaction mixture was refluxed for 3 hours. The solvent was removed under vacuum. The residue was taken up in ethyl acetate, washed with water and brine, dried over sodium sulfate and concentrated to give 3-furyl(1H-pyrrolo[2,3-c]pyridin-2-yl)methanol (134 mg, quant.) as a yellow foam: $^1$H NMR (500 MHz, DMSO-$d_6$) δ 5.87 (1H, d, J=4.7 Hz), 6.06 (1H, d, J=4.9 Hz), 6.29 (1H, s), 6.49 (1H, s), 7.42 (1H, d, J=5.4 Hz), 7.60 (2H, s), 8.03 (1H, d, J=5.4 Hz), 8.65 (1H, s), 11.49 (1H, s).

3-Furyl(1H-pyrrolo[2,3-c]pyridin-2-yl)methanol (130 mg, 0.61 mmol) was dissolved in tetrahydrofuran (8 mL). Manganese dioxide (530 mg, 6.10=mmol) was added and the reaction mixture was stirred at room temperature for 8 h. The reaction mixture was filtered through diatomaceous earth and the filter cake was washed thoroughly with ethyl acetate. The organic filtrate was concentrated to a tan solid. Drying under vacuum at 40° C. produced 3-furyl(1H-pyrrolo[2,3-c]pyridin-2-yl)methanone (78 mg, 60%): mp 232-236° C. dec.; $^1$H NMR (500 MHz, $CD_3OD$) δ 7.00-7.01 (1H, m), 7.42 (1H, s), 7.71-7.77 (2H, m), 8.16 (1H, d, J=5.6 Hz), 8.53 (1H, d, J=0.8 Hz), 8.85 (1H, s); ESI MS m/z=213 $[C_{12}H_8N_2O_2+H]^+$; HPLC (Method A) >99% (AUC), $t_R$=13.8 min.

Example 138

7-Chloro-1H-pyrrolo[2,3-c]pyridine-2-carboxaldehyde

A mixture of (7-chloro-1H-pyrrolo[2,3-c]pyridin-2-yl)methanol (Example 1) (2.81 g, 15.4 mmol), manganese(IV) oxide (16 g) and dichloromethane (250 mL) was stirred under an atmosphere of nitrogen for 16 h. The mixture was filtered through a pad of diatomaceous earth, washing generously with hot acetone. Evaporation of the solvents provided 7-chloro-1H-pyrrolo[2,3-c]pyridine-2-carboxaldehyde (2.40 g, 13.3 mmol, 84%) as a mixture of aldehyde and aldehyde hydrate: $^1$H NMR (300 MHz, $CD_3OD$) δ 5.79 (1H, s), 6.65 (1H, s), 7.44 (1H, s), 7.53 (1H, d, J=5.5 Hz), 7.72 (1H, d, J=5.5 Hz), 7.85 (1H, d, J=5.5 Hz), 7.99 (1H, d, J=5.5 Hz), 10.02 (1H, s); ESI MS m/z 181 $[C_8H_5ClN_2O+H]^+$.

Example 139

5-(Dibenzylamino)-1H-pyrrolo[2,3-c]pyridine-2-carboxaldehyde

A mixture of [5-(dibenzylamino)-1H-pyrrolo[2,3-c]pyridin-2-yl]methanol (Example 48) (9.74 g, 28.4 mmol) and manganese dioxide (24.6 g, 283.6 mmol) in methylene chloride (584 mL) was stirred at room temperature under a nitrogen atmosphere overnight (15 h). The reaction mixture was filtered through diatomaceous earth to remove the manganese dioxide. Concentration of the filtrate provided the crude material as a dark solid. The crude material was purified by trituration with toluene to give 5-(dibenzylamino)-1H-pyrrolo[2,3-c]pyridine-2-carboxaldehyde (6.36 g, 65%) as an orange solid: $^1$H NMR (300 MHz, $CDCl_3$) δ4.84 (4H, s), 6.60 (1H, s), 6.95 (1H, s), 7.21-7.33 (10H, m), 8.63 (1H, s), 9.75 (1H, br s), 9.86 (1H, s).

Example 140

(5-Chloro-1H-pyrrolo[2,3-c]pyridin-2-yl)(phenyl)methanol

Concentrated sulfuric acid (120 mL) was cooled in an ice bath at 0° C. 2-Amino-4-methylpyridine (25.0 g, 230=mol) was added portionwise. A mixture of concentrated sulfuric acid (18 mL) and concentrated nitric acid (17.5 mL) was added with addition funnel over 1 h, maintaining the temperature at 0° C. The reaction mixture was then warmed to room temperature over 4 h. After 15 h, the reaction mixture was heated at 60° C. for 1 h, and then at 100° C. for 1 h. The reaction mixture was poured over ice and adjusted to pH 4-5 with 6 N aqueous sodium hydroxide. The 3-regioisomer was removed by steam distillation (9.11 g, 26%). The remaining residue was extracted with methylene chloride and dried over sodium sulfate, and the solvent was evaporated. The dark yellow solid was crystallized from acetonitrile and methanol to give 2-amino-4-methyl-5-nitropyridine (9.53 g, 27%) as a dark yellow solid: $^1$H NMR (300 MHz, $CD_3OD$) δ2.53 (3H, s), 6.39 (1H, s), 8.76 (1H, s).

Copper(II)chloride (10.01 g, 74.5 mmol) was dissolved in N,N-dimethylformamide (75 mL) and the solution was warmed to 60° C. A solution of 2-amino-4-methyl-5-nitropyridine (9.50 g, 62.0 mmol) in N,N-dimethylformamide (145 mL) was added with addition funnel over 0.5 h. The reaction mixture was heated at 110° C. for 16 h. The reaction mixture was cooled to room temperature and poured into 3 N aqueous hydrochloric acid (300 mL), followed by extraction with diethyl ether. The organic extract was dried over sodium sulfate and adsorbed onto silica gel for purification by column chromatography ($SiO_2$, 20:3 hexanes/ethyl acetate). 2-Chloro-4-methyl-5-nitropyridine was obtained as a yellow solid (2.10 g, 20%): $^1$H NMR (300 MHz, $CD_3OD$) δ2.63 (3H, s), 7.60 (1H, s), 8.96 (1H, s); ESI MS m/z 173 $[C_6H_5ClN_2O_2+H]^+$.

Potassium ethoxide (1.17 g, 13.9 mmol) was suspended in diethyl ether (15 mL). Diethyl oxalate (1.9 mL, 13.9 mmol) was added in one portion. 2-Chloro-4-methyl-5-nitropyridine (2.40 g, 13.9 mmol) was added in one portion. The mixture was stirred 16 h. The solid was collected by filtration and washed generously with diethyl ether. Potassium (1Z)-1-(2-chloro-5-nitropyridin-4-yl)-3-ethoxy-3-oxoprop-1-era-2-olate (2.86 g, 66%) was obtained as a dark brown powder: $^1$H NMR (300 MHz, $CD_3OD$) δ1.33 (3H, t, J=7.1 Hz), 4.20 (2H, q, J=7.1 Hz), 6.67 (1H, s), 8.60 (1H, s), 9.18 (1H, s).

Potassium (1Z)-1-(2-chloro-5-nitropyridin-4-yl)-3-ethoxy-3-oxoprop-1-en-2-olate (2.86 g, 9.20 mmol) was dissolved in acetic acid (140 mL) and iron powder (2.11 g, 37.7 mmol) was added. The mixture was heated at 60° C. for 6 h. The mixture was filtered through a pad of diatomaceous earth and washed with water followed by ethanol. The filtrate was concentrated to dryness. The residue was dissolved in 1:1 methylene chloride/methanol, filtered through a bed of silica gel and washed with 1:1 ethyl acetate/methylene chloride until the filtrate was no longer UV-active. Concentration of the filtrate provided ethyl 5-chloro-1H-pyrrolo[2,3-c]pyridine-2-carboxylate (0.39 g, 19%) as a brown solid: mp 170-175° C. dec.; $^1$H NMR (300 MHz, CD$_3$OD) δ1.42 (3H, t, J=7.1 Hz), 4.44 (2H, q, J=7.1 Hz), 7.17 (1H, s), 7.72 (1H, s), 8.60 (1H, s); ESI MS m/z 225 [C$_{10}$H$_9$ClN$_2$O$_2$+H]$^+$; HPLC (Method A) 94.9% (AUC), t$_R$=18.1 min.

Lithium aluminum hydride (105 mg, 2.77 mmol) was added in three portions to a solution of ethyl 5-chloro-1H-pyrrolo[2,3-c]pyridine-2-carboxylate (410 mg, 1.83 mmol) in tetrahydrofuran (15 mL) under stirring at 0° C. under a nitrogen atmosphere. The reaction mixture was warmed to room temperature and then heated to 60° C. for 3 h. The reaction mixture was quenched by the gradual addition of hydrated sodium sulfate. The sodium sulfate was removed by filtration and washed thoroughly with tetrahydrofuran to give a yellow filtrate, which was concentrated to a brown solid. After sonication in diethyl ether for 20 minutes, the solid was collected by filtration and dried to give (5-chloro-1H-pyrrolo[2,3-c]pyridin-2-yl)methanol (225 mg, 67%) as a brown solid: $^1$H NMR (300 MHz, Acetone-d$_6$) δ4.52-4.89 (3H, m), 6.38 (1H, s), 7.47 (1H, s), 8.49 (1H, s), 10.88 (1H, br s).

(5-Chloro-1H-pyrrolo[2,3-c]pyridin-2-yl)methanol (225 mg, 1.23 mmol) was dissolved in methylene chloride (25 mL). Manganese dioxide (1.07 g, 12.3 mmol) was added and the reaction mixture was stirred for 4 days. The reaction mixture was filtered through diatomaceous earth and the filter cake was washed several times with hot ethyl acetate. The filtrate was concentrated to give 5-chloro-1H-pyrrolo[2,3-c]pyridine-2-carboxaldehyde (156 mg, 70%) as a tan solid: $^1$H NMR (300 MHz, Acetone-d$_6$) δ7.43 (1H, s), 7.80 (1H, s), 8.77 (1H, s), 10.08 (1H, s), 11.49 (1H, br s).

To a solution of 5-chloro-1H-pyrrolo[2,3-c]pyridine-2-carboxaldehyde (156 mg, 0.86 mmol) in tetrahydrofuran (5 mL) was added 3.0 M phenylmagnesium bromide in diethyl ether (0.58 mL, 1.74 mmol) at −78° C. under a nitrogen atmosphere. The reaction mixture was slowly warmed to −15° C. After stirring for ca. 5 h, additional 3.0 M phenylmagnesium bromide in diethyl ether (0.15 mL, 0.45 mmol) was added. The reaction mixture was stirred for another 1 h, warming to 0° C. The reaction mixture was poured into a 2:1 solution of saturated ammonium chloride and water, and extracted with ethyl acetate (3×). The combined organic extracts were washed with water and brine, and dried over sodium sulfate. After filtration and concentration, the crude product was purified by Biotage chromatography (1 to 100% ethyl acetate in hexanes) to give (5-chloro-1H-pyrrolo[2,3-c]pyridin-2-yl)(phenyl)methanol (109 mg, 49%) as a yellow foam: $^1$H NMR (300 MHz, CDCl$_3$) 8.69 (1H, s), 6.23 (1H, s), 7.33-7.61 (6H, m), 8.49 (1H, s), 8.69 (1H, br s); ESI MS m/z 259 [C$_{14}$H$_{11}$ClN$_2$O+H]$^+$.

Example 141

7-(Dibenzylamino)-1H-pyrrolo[2,3-c]pyridine-2-carboxaldehyde

Ethyl 7-(dibenzylamino)-1H-pyrrolo[2,3-c]pyridine-2-carboxylate (Reference Example 3) (11.2 g, 29.0 mmol) was dissolved in tetrahydrofuran (150 mL) while stirring under N$_2$ at 0° C. Lithium aluminum hydride (1.65 g, 43.4 mmol) was added in three portions, while monitoring the gas evolution and temperature. After the final addition, the reaction mixture was stirred at room temperature for 3 h and then heated at 60° C. for 3 h. The reaction mixture was cooled to 0° C. and quenched with freshly prepared hydrated sodium sulfate. The solid was removed by filtration and washed thoroughly with tetrahydrofuran. Concentration of the filtrate provided [7-(dibenzylamino)-1H-pyrrolo[2,3-c]pyridin-2-yl]methanol (9.8 g, 99%) as a yellow solid: $^1$H NMR (300 MHz, CDCl$_3$) δ4.63 (2H, s), 4.78 (4H, s), 6.26 (1H, s), 6.98 (1H, d, J=5.54 Hz), 7.27-7.38 (10H, m), 7.84 (1H, d, J=5.7 Hz), 8.27 (1H, br s).

[7-(Dibenzylamino)-1H-pyrrolo[2,3-c]pyridin-2-yl]methanol (3.0 g, 8.74 mmol) was dissolved in methylene chlorine (175 mL). Manganese dioxide (8.0 g, 92 mmol) was added and the reaction mixture was stirred at room temperature for 20 h. The slurry was filtered through diatomaceous earth to remove the catalyst, and the filtrate was concentrated to a dark oil. Purification by Biotage chromatography (10-30% ethyl acetate in hexanes) provided 7-(dibenzylamino)-1H-pyrrolo[2,3-c]pyridine-2-carboxaldehyde (1.78 g, 60%) as a yellow oil: $^1$H NMR (300 MHz, CDCl$_3$) δ4.89 (4H, s), 7.06-7.12 (2H, m), 7.27-7.38 (10H, m), 7.93 (1H, d, J=5.7 Hz), 8.74 (1H, br s), 9.77 (1H, s).

Experimental Example 1 Determination of IKKβ Inhibitory Activity

To a reaction solution (37.5 μl, 25 mM HEPES (pH 7.5), 10 mM magnesium acetate) containing active IKKβ (10 ng) obtained in Reference Example 3A and 2.5 μg of IκBα substrate protein solution was added a test compound (2.5 μl) dissolved in DMSO, and the mixture was incubated at 30° C. for 5 min. To the obtained mixture was added 10 μl of ATP solution (2.5 μM ATP, 0.01 μCi [γ-$^{32}$P]ATP) and the mixture was allowed to react at 30° C. for 60 min. Then 20% TCA solution (50 μl) was added thereto to stop the reaction. The reaction solution was left standing at 4° C. for 20 min. and acid insoluble fraction was transferred to a GF/C filter (PACKARD JAPAN KK) using a cell harvester (PACKARD JAPAN KK) and washed with 250 mM phosphoric acid solution. The plate after washing was dried at 45° C. for 60 min., 40 μl of MicroSinti 0 (PACKARD JAPAN KK) was added and the radioactivity was determined using TopCount (PACKARD JAPAN KK). The concentration (IC$_{50}$) of the test compound necessary for 50% inhibition of the amount of $^{32}$P uptake by the acid insoluble fraction was calculated using PRISM 3.0 (GraphPad Software, Inc.). The results are shown in Table 1.

TABLE 1

| test compound (Example number) | IC$_{50}$ (μM) |
| --- | --- |
| 91 | 1.7 |

Formulation Example 1

Production of Capsules

| 1) Compound of Example 1 | 30 mg |
| --- | --- |
| 2) Finely divided cellulose | 10 mg |
| 3) Lactose | 19 mg |
| 4) Magnesium stearate | 1 mg |
| Total | 60 mg |

1), 2), 3) and 4) are admixed and filled into a gelatin capsule.

Formulation Example 2

Production of Tablets

| | |
|---|---|
| 1) Compound of Example 1 | 30 g |
| 2) Lactose | 50 g |
| 3) Corn starch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded together with water and the mixture, after vacuum drying, is granulated. The granular mixture is admixed with 14 g of 4) and 1 g of 5) and the resulting mixture is tableted using a tableting machine, to give 1000 tablets each containing 30 mg of compound of Example 1.

The structural formulas of the compounds obtained in the aforementioned Examples are shown in the following.

TABLE 2

| | Structure |
|---|---|
| Example 1 | [7-chloro-1H-pyrrolo[2,3-c]pyridin-2-yl]methanol |
| Example 2 | 7-chloro-N-benzyl-1H-pyrrolo[2,3-c]pyridine-2-carboxamide |
| Example 3 | (7-chloro-1H-pyrrolo[2,3-c]pyridin-2-yl)(morpholin-4-yl)methanone |
| Example 4 | 7-chloro-N-(pyridin-2-ylmethyl)-1H-pyrrolo[2,3-c]pyridine-2-carboxamide |
| Example 5 | 7-chloro-N-(pyridin-3-ylmethyl)-1H-pyrrolo[2,3-c]pyridine-2-carboxamide |
| Example 6 | 7-chloro-N-(pyridin-4-ylmethyl)-1H-pyrrolo[2,3-c]pyridine-2-carboxamide |
| Example 7 | 7-chloro-N-(furan-2-ylmethyl)-1H-pyrrolo[2,3-c]pyridine-2-carboxamide |
| Example 8 | 7-chloro-N-(thiophen-2-ylmethyl)-1H-pyrrolo[2,3-c]pyridine-2-carboxamide |
| Example 9 | N-{[(7-chloro-1H-pyrrolo[2,3-c]pyridin-2-yl)methyl]}ethylamine·HCl |
| Example 10 | N-{[(7-chloro-1H-pyrrolo[2,3-c]pyridin-2-yl)methyl]}methylamine·HCl |
| Example 11 | N-{[(7-chloro-1H-pyrrolo[2,3-c]pyridin-2-yl)methyl]}benzylamine·HCl |
| Example 12 | 1-(4-{(7-chloro-1H-pyrrolo[2,3-c]pyridin-2-yl)carbonyl}piperazin-1-yl)ethanone |
| Example 13 | (7-chloro-1H-pyrrolo[2,3-c]pyridin-2-yl)(pyrrolidin-1-yl)methanone |

TABLE 2-continued
| | Structure |
|---|---|
| Example 14 | 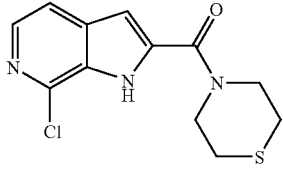 |
TABLE 3
| | Structure |
|---|---|
| Example 15 | 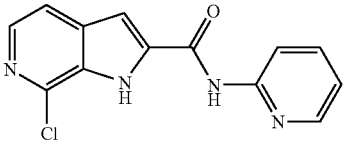 |
| Example 16 | 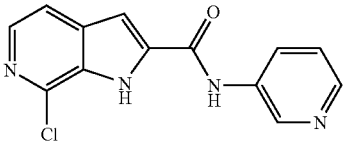 |
| Example 17 | 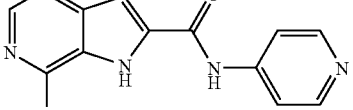 |
| Example 18 | 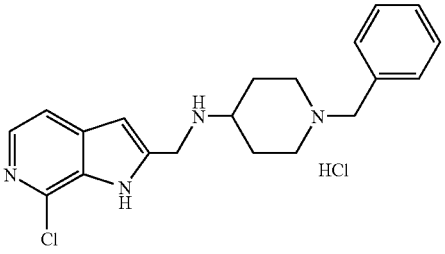 |
| Example 19 | 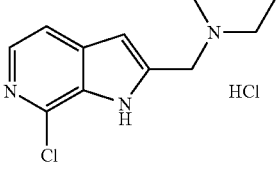 |
TABLE 3-continued
| | Structure |
|---|---|
| Example 20 | 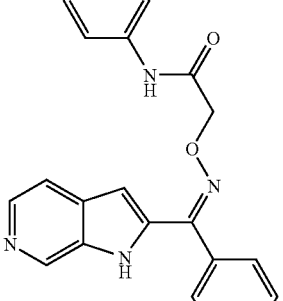 |
| Example 21 | 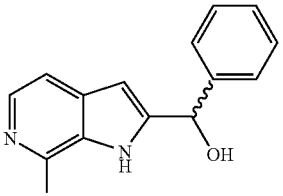 |
| Example 22 | 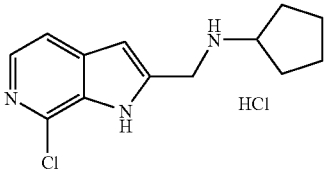 |
| Example 23 | 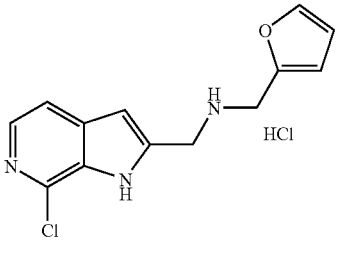 |
| Example 24 | 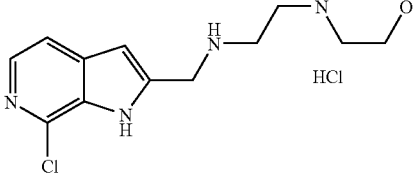 |
| Example 25 | 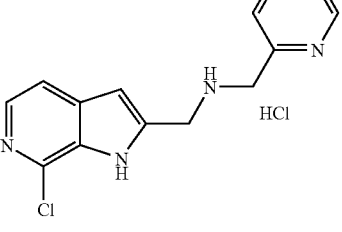 |
| Example 26 | 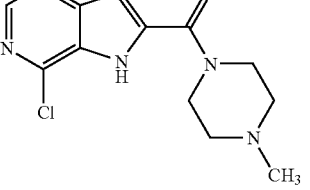 |

TABLE 4

| | Structure |
|---|---|
| Example 27 | (1H-pyrrolo[2,3-c]pyridine-2-carboxamide, N-(pyridin-2-ylmethyl)) |
| Example 28 | (1H-pyrrolo[2,3-c]pyridine-2-carboxamide, N-(pyridin-4-ylmethyl)) |
| Example 29 | (7-chloro-1H-pyrrolo[2,3-c]pyridin-2-yl)(phenyl)methanone |
| Example 30 | (1H-pyrrolo[2,3-c]pyridine-2-carboxamide, N-(pyridin-3-yl)) |
| Example 31 | ((1H-imidazol-2-yl)methyl oxime of phenyl(1H-pyrrolo[2,3-c]pyridin-2-yl)methanone), 2HCl |
| Example 32 | (1H-pyrrolo[2,3-c]pyridin-2-yl)(thiophen-3-yl)methanone |
| Example 33 | (1H-pyrrolo[2,3-c]pyridin-2-yl)(pyrrolidin-1-yl)methanone |

TABLE 4-continued

| | Structure |
|---|---|
| Example 34 | (N-benzyl-α-(7-chloro-1H-pyrrolo[2,3-c]pyridin-2-yl)benzylamine), 2HCl |
| Example 35 | (1H-pyrrolo[2,3-c]pyridin-2-yl)(phenyl)methanone |
| Example 36 | (O-(2-aminoethyl) oxime of furan-3-yl(1H-pyrrolo[2,3-c]pyridin-2-yl)methanone), 2HCl |
| Example 37 | (7-(dibenzylamino)-1H-pyrrolo[2,3-c]pyridine-2-carboxamide, N-(pyridin-3-ylmethyl)) |
| Example 38 | (7-(dibenzylamino)-1H-pyrrolo[2,3-c]pyridine-2-carboxamide, N-(thiophen-2-ylmethyl)) |

TABLE 5

| Structure |
|---|
| Example 39 |
| Example 40 |
| Example 41 |
| Example 42 |
| Example 43 |
| Example 44 |

TABLE 5-continued

| Structure |
|---|
| Example 45 |
| Example 46 |
| Example 47 |
| Example 48 |

TABLE 6

| | Structure |
|---|---|
| Example 49 | 6-azaindole-CH(Ph)-NH-C(O)-(4-pyridyl) |
| Example 50 | 6-azaindole-CH(Ph)-NH-C(O)-(2-pyridyl) |
| Example 51 | 6-azaindole-CH(Ph)-NH-C(O)-Ph |
| Example 52 | 6-azaindole-CH(OH)-Ph |
| Example 53 | 5-(N,N-dibenzylamino)-6-azaindole-2-CH(OH)-CH₃ |

TABLE 6-continued

| | Structure |
|---|---|
| Example 54 | [chemical structure: 5-(dibenzylamino)-2-[hydroxy(phenyl)methyl]-1H-pyrrolo[2,3-c]pyridine] |
| Example 55 | [chemical structure: 5-(dibenzylamino)-2-benzoyl-1H-pyrrolo[2,3-c]pyridine] |
| Example 56 | [chemical structure: 5-(dibenzylamino)-2-acetyl-1H-pyrrolo[2,3-c]pyridine] |
| Example 57 | [chemical structure: 5-amino-2-[hydroxy(phenyl)methyl]-1H-pyrrolo[2,3-c]pyridine] |
| Example 58 | [chemical structure: tert-butyl 2-{[(phenyl(1H-pyrrolo[2,3-c]pyridin-2-yl)methylene)amino]oxy}acetate] |

TABLE 6-continued
| | Structure |
|---|---|
| Example 59 | 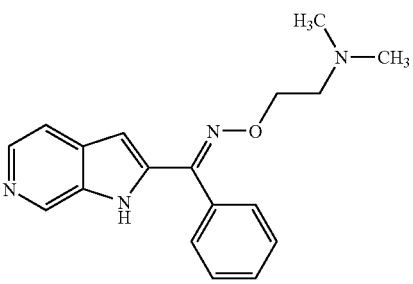 |
| Example 60 | 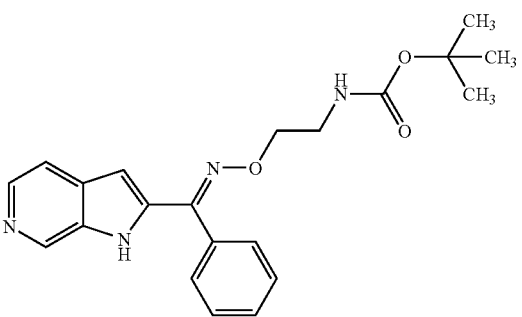 |
TABLE 7
| | Structure |
|---|---|
| Example 61 | 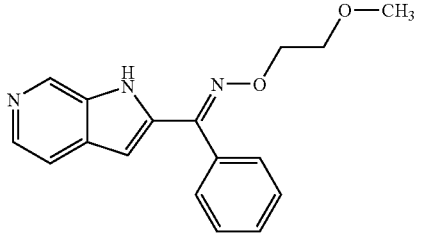 |
| Example 62 | 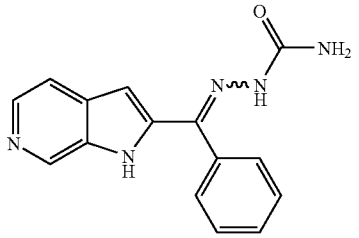 |
| Example 63 | 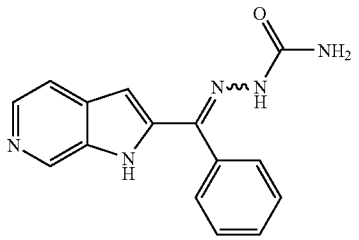 |

TABLE 7-continued
| | Structure |
|---|---|
| Example 64 | 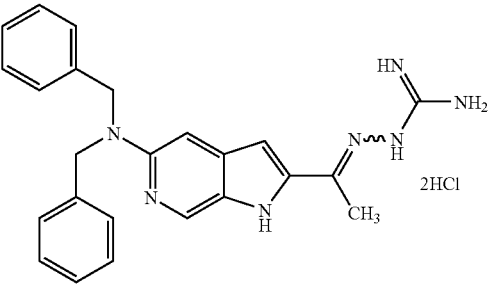 2HCl |
| Example 65 | 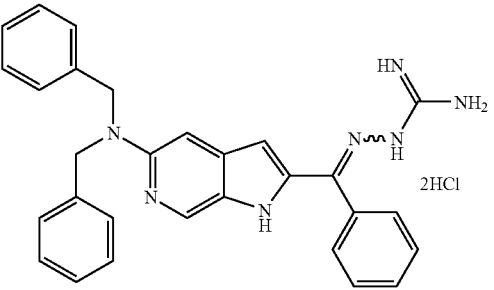 2HCl |
| Example 66 | 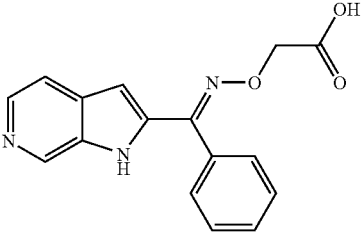 |
| Example 67 | 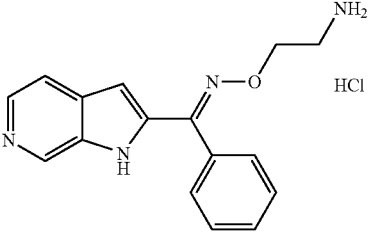 HCl |
| Example 68 | 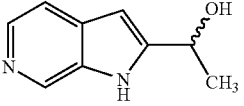 |
| Example 69 | 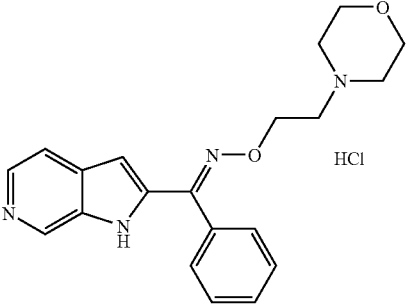 HCl |

TABLE 7-continued
| | Structure |
|---|---|
| Example 70 | 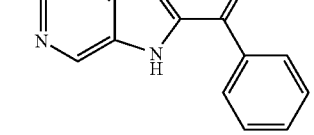 |
| Example 71 | 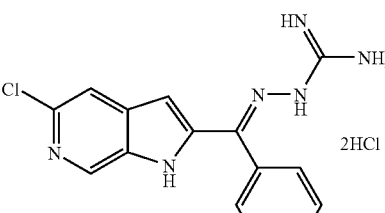 |
| Example 72 | 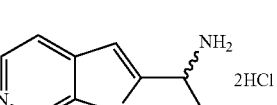 |
TABLE 8
| | Structure |
|---|---|
| Example 73 | 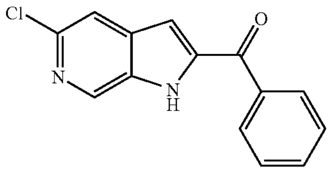 |
| Example 74 | 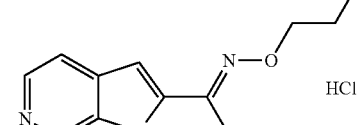 |
| Example 75 | 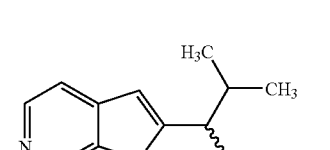 |
| Example 76 | 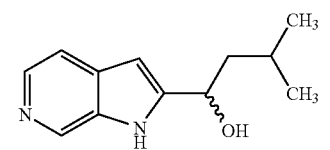 |
TABLE 8-continued
| | Structure |
|---|---|
| Example 77 | 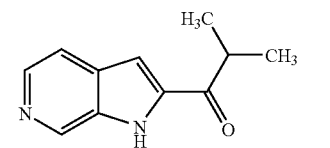 |
| Example 78 | 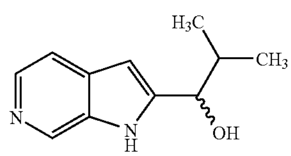 |
| Example 79 | 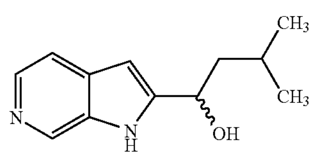 |
| Example 80 | 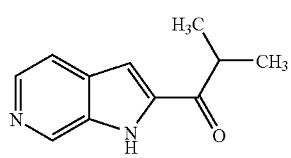 |
| Example 81 | 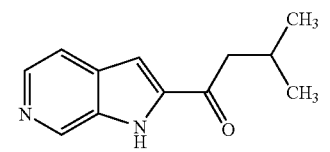 |

TABLE 8-continued
| Structure |
|---|
| Example 82 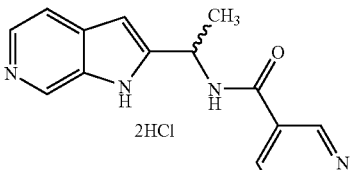 |
| Example 83 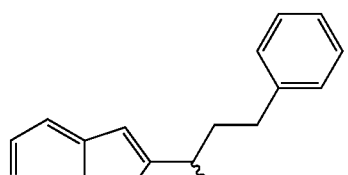 |
TABLE 8-continued
| Structure |
|---|
| Example 84 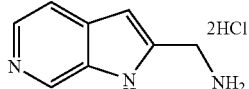 |
| Example 85 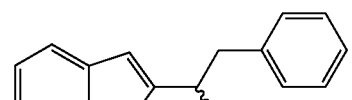 |
| Example 86 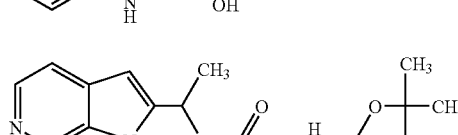 |
TABLE 9
| Structure |
|---|
| Example 87 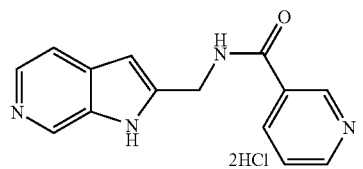 |
| Example 88 |
| Example 89 |

TABLE 9-continued
| Structure |
|---|
| Example 90 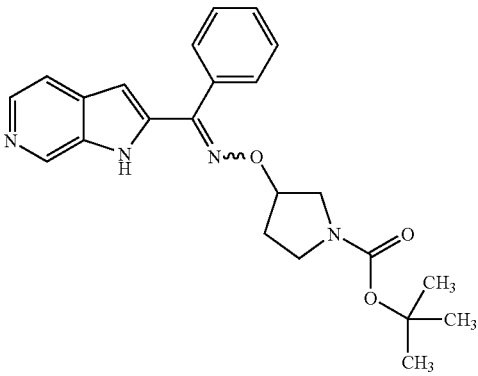 |
| Example 91 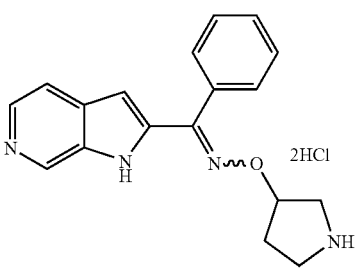 |
| Example 92 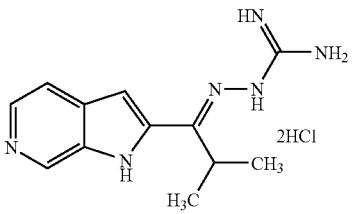 |
| Example 93 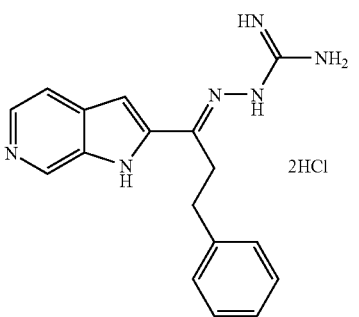 |
| Example 94 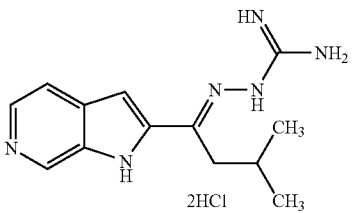 |

TABLE 9-continued

| | Structure |
|---|---|
| Example 95 | [Structure: 1H-pyrrolo[2,3-c]pyridine-2-yl with C(=N-O-CH2CH2-NH2)-phenyl, HCl salt] |
| Example 96 | [Structure: H2N-CH2CH2-O-N=C(phenyl)- attached to 1H-pyrrolo[2,3-c]pyridine-2-yl, 2CF3CO2H salt] |
| Example 97 | [Structure: 1H-pyrrolo[2,3-c]pyridine-3-yl-CH(OH)-phenyl] |
| Example 98 | [Structure: 1H-pyrrolo[2,3-c]pyridine-2-yl-CH(OH)-(4-methylphenyl)] |

TABLE 10

| | Structure |
|---|---|
| Example 99 | [Structure: 1H-pyrrolo[2,3-c]pyridine-2-yl-CH(OH)-(4-methoxyphenyl)] |
| Example 100 | [Structure: 1H-pyrrolo[2,3-c]pyridine-2-yl-C(=O)-(4-methylphenyl)] |

TABLE 10-continued
| | Structure |
|---|---|
| Example 101 | 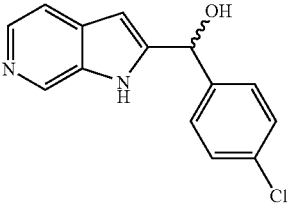 |
| Example 102 | 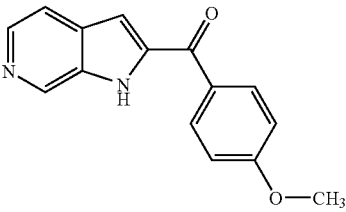 |
| Example 103 | 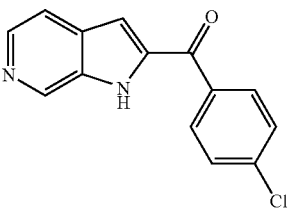 |
| Example 104 | 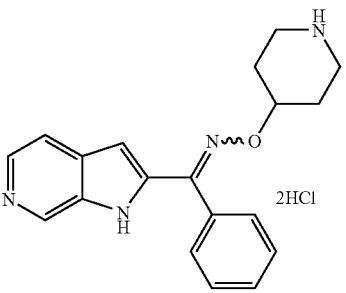 2HCl |
| Example 105 | 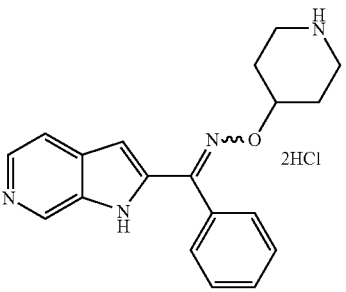 2HCl |
| Example 106 | 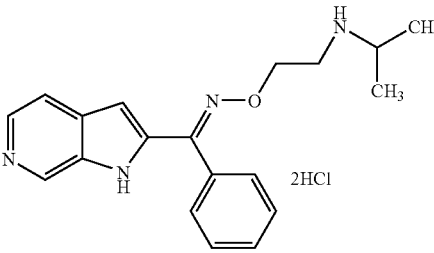 2HCl |

TABLE 10-continued
| Structure |
|---|
| Example 107 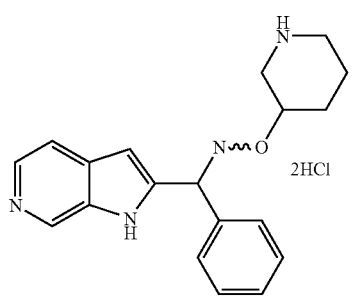 2HCl |
| Example 108 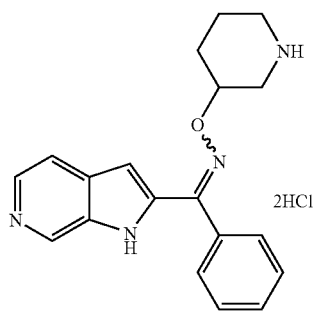 2HCl |
| Example 109 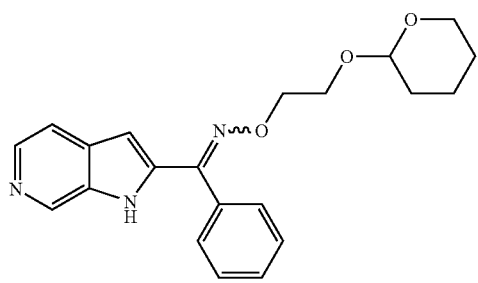 |
| Example 110 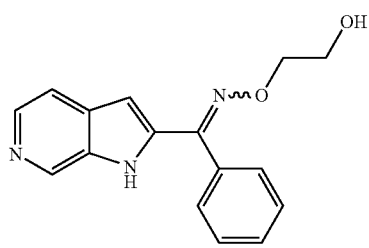 |

TABLE 11

| | Structure |
|---|---|
| Example 111 | [structure: tert-butyl carbamate-ethoxy-N=C(phenyl)-(1H-pyrrolo[2,3-c]pyridin-3-yl)] |
| Example 112 | [structure: H₂N-CH₂CH₂-O-N=C(phenyl)-(1H-pyrrolo[2,3-c]pyridin-3-yl)] |
| Example 113 | [structure: 1H-pyrrolo[2,3-c]pyridin-2-yl-CH(OH)-(3,4-dichlorophenyl)] |
| Example 114 | [structure: guanidinyl-N=C(phenyl)-(1H-pyrrolo[2,3-c]pyridin-3-yl), 2CF₃CO₂H] |
| Example 115 | [structure: 1H-pyrrolo[2,3-c]pyridin-2-yl-CH(phenyl)-N-O-CH₂-phenyl, HCl] |

TABLE 11-continued

| Structure |
| --- |

Example 116

Example 117

Example 118

Example 119

Example 120

TABLE 12

| | Structure |
|---|---|
| Example 121 | (6-azaindole)-C(=N-O-CH₃)-phenyl · HCl |
| Example 122 | (6-azaindole)-C(=O)-(2-pyridyl) |
| Example 123 | (6-azaindole)-C(=N-O-CH₂CH₂-NH₂)-(4-methoxyphenyl) · 2CF₃CO₂H |
| Example 124 | (6-azaindole)-C(=N-O-CH₂CH₂-NH₂)-(4-methoxyphenyl) · 2HCl |
| Example 125 | (6-azaindole)-C(=N-O-CH₂CH₂-NH₂)-(4-chlorophenyl) · 2CF₃CO₂H |
| Example 126 | (6-azaindole)-C(=N-O-CH₂CH₂-NH₂)-(4-chlorophenyl) · 2CF₃CO₂H |
| Example 127 | (6-azaindole)-C(=O)-(3,4-dichlorophenyl) |

TABLE 12-continued

| | Structure |
|---|---|
| Example 128 | (6-azaindole)-C(=N-O-CH₂CH₂-N(CH₃)-Boc)-phenyl |
| Example 129 | (6-azaindole)-C(=N-O-CH₂CH₂-N(CH₃)-Boc)-phenyl |
| Example 130 | (6-azaindole)-C(=N-O-CH₂-C(=O)NH₂)-phenyl |

TABLE 13

| | Structure |
|---|---|
| Example 131 | (6-azaindole)-C(=N-O-CH₂CH₂-NH-CH₃)-phenyl · 2HCl |

TABLE 13-continued

| | Structure |
|---|---|
| Example 132 | (6-azaindole with C(=N-O-CH2CH2-NHCH3)(phenyl) substituent at 2-position; 2HCl) |
| Example 133 | (6-azaindole with C(=N-O-CH2-C(=O)-NH-CH3)(phenyl) substituent at 2-position) |
| Example 134 | (6-azaindole with C(=N-O-CH2CH2-NH2)(3,4-dichlorophenyl) substituent at 2-position; 2CF3CO2H) |
| Example 135 | (6-azaindole with C(=N-O-CH2-imidazolyl)(phenyl) substituent at 2-position; 2HCl) |
| Example 136 | (6-azaindole with 3-pyridyl carbonyl substituent at 2-position) |
| Example 137 | (6-azaindole with 3-furyl carbonyl substituent at 2-position) |
| Example 138 | (7-chloro-6-azaindole-2-carbaldehyde) |
| Example 139 | (5-(dibenzylamino)-6-azaindole-2-carbaldehyde) |
| Example 140 | (5-chloro-6-azaindole with CH(OH)(phenyl) at 2-position) |
| Example 141 | (7-(dibenzylamino)-6-azaindole-2-carbaldehyde) |

INDUSTRIAL APPLICABILITY

The 6-azaindole compound of the present invention has a superior IκB kinase inhibitory activity, and is useful as a pharmaceutical agent such as an agent for preventing or treating diabetes and the like.

The invention claimed is:

1. A compound represented by the formula

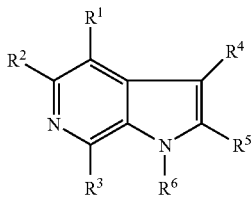

(I)

wherein
R$^1$, R$^2$, R$^3$ and R$^6$ are the same or different and each is a hydrogen atom, a halogen atom, an amino group, or a mono- or di-C$_{7-19}$ aralkylamino group;
R$^4$ is a hydrogen atom; and
R$^5$ is
1) a group represented by the formula: —C(=X)—R$^7$ wherein X is N—O—R$^8$ or N—NH—R$^9$
wherein R$^8$ and R$^9$ are the same or different and each is
(i) a hydrogen atom;
(ii) an amidino group;
(iii) a C$_{1-6}$ alkyl group optionally having 1 to 3 substituents selected from a hydroxy group, an optionally halogenated C$_{1-6}$ alkoxy group, a carboxyl group, an amino group, a mono-or di-C$_{1-6}$ alkylamino group, a 5- to 7-membered heterocyclic group, a C$_{1-6}$ alkoxy-carbonyl group, a carbamoyl group, a mono- or di-$C_{1-6}$ alkyl-carbamoyl group, a $C_{6-14}$ aryl-carbamoyl group, a $C_{1-6}$ alkoxy-carboxamido group and a 5- to 7-membered heterocyclic oxy group;
(iv) a $C_{7-19}$ aralkyl group;
(v) a heterocyclic group bonded via a carbon atom and optionally having 1 to 3 $C_{1-6}$ alkoxy-carbonyl groups; or
(vi) a carbamoyl group, and
$R^7$ is
(i) a hydrogen atom or
(ii) a $C_{1-6}$ alkyl group, a $C_{6-14}$ aryl group, a $C_{7-19}$ aralkyl group or a monocyclic aromatic heterocyclic group, each of which may have 1 to 3 substituents selected from a halogen atom, a $C_{1-6}$ alkyl group and an optionally halogenated $C_{1-6}$ alkoxy group;

2) a group represented by the formula: —C(=O)—$R^{10}$ wherein $R^{10}$
(i) a hydrogen atom;
(ii) a $C_{1-6}$ alkyl group;
(iii) $C_{6-14}$ aryl group optionally having 1 to 3 substituents selected from a halogen atom, a $C_{1-6}$ alkyl group and an optionally halogenated $C_{1-6}$ alkoxy group;
(iv) a $C_{7-19}$ aralkyl group; or
(v) a heterocyclic group bonded via a carbon atom;

3) a group represented by the formula: —CH(OH)—$R^{10}$ wherein $R^{10}$ is as defined above;

4) a group represented by the formula: —C(=O)—NH—$(CH_2)$n-Ar wherein n is 0, 1 or 2, and Ar is a $C_{6-14}$ aryl group or a 5 or 6-membered aromatic heterocyclic group;

5) a group represented by the formula: —C(=O)-Het wherein Het is 1-pyrrolidinyl, 1-piperazinyl, 4-morpholinyl or 4-thiomorpholinyl each optionally having 1 to 3 substituents selected from an optionally halogenated $C_{1-6}$ alkyl group and an optionally halogenated $C_{1-6}$ alkyl-carbonyl group; or 6) a group represented by the formula: —CH($R^{12}$)—N$R^{13}R^{14}$ wherein $R^{12}$ is a hydrogen atom, $C_{1-6}$ alkyl group or a $C_{6-14}$ aryl group;
$R^{13}$ and $R^{14}$ are the same or different and each is
(i) a hydrogen atom,
(ii) a $C_{1-6}$ alkyl group, a $C^{3-8}$ cycloalkyl group or a $C_{7-19}$ aralkyl group each optionally having one to three 5- to 7-membered heterocyclic groups,
(iii) a monocyclic non-aromatic heterocyclic group optionally having 1 to 3 $C_{7-19}$ aralkyl groups, or
(iv) a $C_{1-6}$ alkyl-carbonyl group, a $C_{6-14}$ aryl-carbonyl group or an aromatic heterocyclic carbonyl group each optionally having 1 to 3 $C_{1-6}$ alkoxy-carboxamido groups, or $R^{13}$ and $R^{14}$ form, together with the adjacent nitrogen atom, a nitrogen-containing heterocyclic group optionally having 1 to 3 substituents selected from a halogen atom, an optionally halogenated $C_{1-6}$ alkyl group and an optionally halogenated $C_{1-6}$ alkoxy group (provided that the nitrogen-containing heterocyclic group is not an oxopyrrolidinyl group or an oxopiperazinyl group), or a salt thereof.

2. The compound of claim 1, wherein $R^4$ is a hydrogen atom, and $R^5$ is a group represented by the formula: —C(=X)—$R^7$ wherein X and $R^7$ are as defined in claim 1.

3. The compound of claim 1, wherein $R^4$ is a hydrogen atom, and $R^5$ is a group represented by the formula: —C(=O)—$R^{10}$ wherein $R^{10}$ is as defined in claim 1.

4. The compound of claim 1, wherein $R^1$, $R^2$ and $R^3$ are each a hydrogen atom.

5. A pharmaceutical composition comprising a compound of claim 1 or a salt thereof and a pharmacologically acceptable carrier.

6. The compound of claim 1, wherein $R^1$, $R^2$, $R^3$ and $R^6$ are each a hydrogen atom.

7. The compound of claim 1,
wherein $R^1$, $R^2$, $R^3$ and $R^6$ are each a hydrogen atom;
$R^4$ is a hydrogen atom; and
$R^5$ a group represented by the formula: —C(=X)—$R^7$ wherein X and $R^7$ are as defined in claim 1.

8. The compound of claim 1,
wherein $R^1$, $R^2$, $R^3$ and $R^6$ are each a hydrogen atom;
$R^4$ is a hydrogen atom; and
$R^5$ is a group represented by the formula: —C(=O)—$R^{10}$ wherein $R^{10}$ is as defined in claim 1.

* * * * *

UNITED STATES PATENT AND TRADEMARK OFFICE
CERTIFICATE OF CORRECTION

PATENT NO. : 7,608,627 B2 Page 1 of 1
APPLICATION NO. : 11/547308
DATED : October 27, 2009
INVENTOR(S) : Horiguchi et al.

It is certified that error appears in the above-identified patent and that said Letters Patent is hereby corrected as shown below:

On title page after item (65) Prior Publication Data, please insert the following Item (60):
-- Related U.S. Application Data
(60) Provisional application No. 60/558,981, filed on April 5, 2004 --.

Signed and Sealed this

Sixteenth Day of March, 2010

David J. Kappos
*Director of the United States Patent and Trademark Office*